US008513222B2

(12) United States Patent
Kim et al.

(10) Patent No.: US 8,513,222 B2
(45) Date of Patent: Aug. 20, 2013

(54) METHODS OF TREATING FIBROSIS, CANCER AND VASCULAR INJURIES

(75) Inventors: Dae-Kee Kim, Seoul (KR); Yhun Yhong Sheen, Seoul (KR); Chenghua Jin, Seoul (KR); Chul-Yong Park, Seoul (KR); Domalapally Sreenu, Seoul (KR); Kota Sudhakar Rao, Seoul (KR); Maddeboina Krishnaiah, Seoul (KR); Vura Bala Subrahmanyam, Seoul (KR)

(73) Assignee: EWHA University—Industry Collaboration Foundation, Seoul (KR)

( * ) Notice: Subject to any disclaimer, the term of this patent is extended or adjusted under 35 U.S.C. 154(b) by 159 days.

(21) Appl. No.: 13/168,342

(22) Filed: Jun. 24, 2011

(65) Prior Publication Data

US 2011/0319408 A1 Dec. 29, 2011

Related U.S. Application Data

(63) Continuation-in-part of application No. 12/826,338, filed on Jun. 29, 2010, now Pat. No. 8,080,568.

(51) Int. Cl.
*A61K 31/437* (2006.01)
*C07D 471/04* (2006.01)

(52) U.S. Cl.
USPC ........................................ 514/119; 546/303

(58) Field of Classification Search
USPC ........................................ 514/303; 546/119
See application file for complete search history.

(56) References Cited

U.S. PATENT DOCUMENTS

| 7,407,958 | B2 | 8/2008 | Kim et al. |
| 2003/0149277 | A1 | 8/2003 | Gaster et al. |
| 2007/0142376 | A1 | 6/2007 | Fleenor et al. |
| 2008/0319012 | A1 | 12/2008 | Kim et al. |

FOREIGN PATENT DOCUMENTS

| WO | WO 00/61576 A | 10/2000 |
| WO | WO 01/62756 A | 8/2001 |
| WO | WO 02/055077 A | 7/2002 |
| WO | WO 03/087304 A | 10/2003 |
| WO | WO 2005/103028 A | 11/2005 |

OTHER PUBLICATIONS

Byfiled et al. Mol. Pharmacol. 2004, 65, 744-752.*
de Gouville et al., Drug News Perspect. 2006, 85-90.*
Neidle S. Cancer Drug Design and Discovery ed. (Elsevier/Academic Press, 2008) p. 427-431.*
Kottler, Ulrike B. et al.: "Comparative effects of TGF-β1 and TGF-β2 on extracellular matrix production, proliferation, migration, and collagen contraction of human Tenon's capsule fibroblasts in pseudoexfoliation and primary open-angle glaucoma", *Experimental Eye Research*, 80 (2005), pp. 121-134.
Picht, G. et al.: "Transforming growth factor β2 levels in the aqueous humor in different types of glaucoma and the relation to filtering bleb development", *Graefe's Arch Clin Exp Ophthalmol*, (2001) 239, pp. 199-207.
Wang, Qingjian et al.: "Reduction of bleomycin induced lung fibrosis by transforming growth factorβ soluble receptor in hamsters", *Thorax*, 1999; 54, pp. 805-812.
Wahab, Nadia Abdel et al.: "Expression of extracellular matrix molecules in human mesangial cells in response to prolonged hyperglycaemia", *Biochem J.*, (1996), 316, pp. 985-992.
Shah, Mamta et al.: "Neutralisation of TGF-$\beta_1$, and TGF-$\beta_2$ or exogenous addition of TGF-$\beta_3$ to cutaneous rat wounds reduces scarring", *Journal of Cell Science*, 108, 1995, pp. 985-1002.
Sanderson, Nancy et al.: "Hepatic expression of mature transforming growth factor β1 in transgenic mice results in multiple tissue lesions", *Proc. Natl. Acad. Sci. USA*, vol. 92, Mar. 1995, pp. 2572-2576.
Ryu, Md, Ji-Kan et al.: "IN-1130, a Novel Transforming Growth Factor-β Type I Receptor Kinase (Activin Receptor-like Kinase 5) Inhibitor, Promotes Regression of Fibrotic Plaque and Corrects Penile Curvature in a Rat Model of Peyronie's Disease",*J Sex Med*, 2009;6, pp. 1284-1296.
Rosendahl, Alexander et al.: "Activation of the TGF-β/Activin-Smad2 Pathway during Allergic Airway Inflammation", *Am J. Respir. Cell Mol. Biol.*, vol. 25, 2001, pp. 60-68.
Pawlowski, John E. et al.: "Stimulation of Activin A Expression in Rat Aortic Smooth Muscle Cells by Thrombin and Angiotensin II Correlates with Neointimal Formation in Vivo", *J. Clin. Invest.*, vol. 100, No. 3, Aug. 1997, pp. 639-648.
Munz, Barbara et al.: "Overexpression of activin A in the skin of transgenic mice reveals new activities of activin in epidermal morphogenesis, dermal fibrosis and wound repair", *The EMBO Journal*, vol. 18, No. 19, 1999, pp. 5205-5215.
Moon, J-A et al.: "IN-1130, a novel transforming growth factor-β type I receptor kinase (ALK5) inhibitor, suppresses renal fibrosis in obstructive nephropathy", *Kidney International*, 2006, 70, pp. 1234-1243.
McCaffrey, Timothy A. et al.: "Decreased Type II/Type I TGF-β Receptor Ratio in Cells Derived from Human Atherosclerotic Lesions", *J. Clin. Invest.*, vol. 96, Dec. 1995, pp. 2667-2675.
Matzuk, M.M. et al.: "Development of cancer cachexia-like syndrome and adrenal tumors in inhibin-deficient mice", *Proc. Natl. Acad. Sci. USA*, vol. 91, Sep. 1994, pp. 8817-8821.
Kim, MD, Jin Hyoung et al.: "IN-1233, an ALK-5 Inhibitor: Prevention of Granulation Tissue Formation after Bare Metallic Stent Placement in a Rat Urethal Model", *Radiology*, vol. 255; No. 1, Apr. 2010, pp. 75-82.
Luo, Jian et al.: "Glia-dependent TGF-β signaling, acting independently of the TH17 pathway, is critical for initiation of murine autoimmune encephalomyelitis", *The Journal of Clinical Investigation*, vol. 117, No. 11, Nov. 2007, pp. 3306-3315.
Long, MD, PHD, Lu et al.: "Altered Bone Morphogenetic Protein and Transforming Growth Factor-β Signaling in Rat Models of Pulmonary Hypertension", *Circulation*, Feb. 3, 2009, pp. 566-576.
Lee, Geun Taek et al.: "Effect of IN-1130, a Small Molecule Inhibitor of Transforming Growth Factor-β Type I Receptor/Activin Receptor-Like Kinase-5, on Prostate Cancer Cells", *The Journal of Urology*, vol. 180, Dec. 2008, pp. 2660-2667.

(Continued)

*Primary Examiner* — Jason M Nolan
(74) *Attorney, Agent, or Firm* — Frommer Lawrence & Haug LLP; Ronald R. Santucci

(57) ABSTRACT

This invention relates to use of inhibitors of the transforming growth factor-β (TGF-β) type I receptor (ALK5) and/or the activin type I receptor (ALK4) in treating, preventing, or reducing fibrosis, cancer, and vascular injuries.

6 Claims, 28 Drawing Sheets

(56) References Cited

OTHER PUBLICATIONS

Jagirdar, Jaishree et at.: "Immunohistochemical Localization of Transforming Growth Factor Beta Isoforms in Asbestos-Related Diseases", *Environmental Health Perspectives 105*, Supplement 5, Sep. 1997, 11 pages.

Hojo, Minoru et al.: "Cyclosporine induces cancer progression by a cell-autonomous mechanism", *Nature*, vol. 397, Feb. 11, 1999, pp. 530-534.

Dahly, Annette J et al.: "Antihypertensive effects of chronic anti-TGF-β antibody therapy in Dahl S rats", *Am. J. Physiol. Regul. Integr. Comp. Physiol.*, 283: 2002, pp. R757-R767.

Cipriano, Sherry C. et al.: "Follistatin Is a Modulator of Gonadal Tumor Progression and the Activin-Induced Wasting Syndrome in Inhibin-Deficient Mice", *Endocrinology*, vol. 141, No. 7, 2000, pp. 2319-2327.

Broekelmann, Thomas J. et al.: "Transforming growth factor$\beta_1$ is present at sites of extracellular matrix gene expression in human pulmonary fibrosis", *Proc. Natl. Acad. Sci. USA*, vol. 88, Aug. 1991, pp. 6642-6646.

Jordan, V.C.; Nature Reviews: *Drug Discovery*, 2, 2003, p. 205.

Dorwald, F. Zaragoza; "Side Reactions in Organic Synthesis: A guide to Successful Synthesis Design", Weinheim; Wiley-VCH Verlag GmbH & Co. KGaA, 2005, Preface.

Vippagunta et al.: *Advanced Drug Delivery Reviews*, 48, 2001, 18.

\* cited by examiner

Data represents the mean number of invaded cells per view field ± S.D. (n = 3).
†: significantly different from vehicle group ($p < 0.05$).
*: significantly different from TGF-β- treated group ($p < 0.05$).

Data represents the mean ± S.D. (n = 4).

Vehicle    13.6 mg/kg    27.3 mg/kg

Example 3

Data represents the mean ± S.E. (n = 8).

Data represents the mean ± S.E. (n = 7–10).

Vehicle     5 mg/kg     10 mg/kg 20 mg/kg     40 mg/kg

Example 2

Example 2

Data represents the mean ± S.E. (n = 9–10).
*: significantly different from vehicle group ($p < 0.05$).
**: significantly different from vehicle group ($p < 0.01$).

Vehicle | 43.6 mg/kg
Example 61

Data represents the mean ± S.D. (n = 8).
*: significantly different from vehicle group ($p < 0.05$).

Data represents the mean ± S.D. (n = 6).

Arrows indicate metastatic lesions in the lung.

Data represents the mean ± S.D. (n = 3).
*: significantly different from vehicle group ($p < 0.05$).

Data represents the mean ± S.D. (n = 3).

Data represents the mean ± S.D. (n = 6).
**: significantly different from vehicle group in lung ($p < 0.01$).

Data represents the mean ± S.E. (n = 7–10).
* : significantly different from vehicle group in lung ($p < 0.05$).

Data represents the mean ± S.E. (n = 5−8).
*: $p < 0.05$ vs. sham. **: $p < 0.01$ vs. sham.
: $p < 0.05$ vs. BDL. ##: $p < 0.01$ vs. BDL.

Data represents the mean ± S.E. (n = 5).
**: $p < 0.01$ vs. sham. ##: $p < 0.01$ vs. BDL.

Data represents the mean ± S.E. (n = 5).
**: $p < 0.01$ vs. sham. ##: $p < 0.01$ vs. BDL.

H&E staining

Data represents the mean ± S.E. (n = 5−8).
*: $p < 0.05$ vs. sham. **: $p < 0.01$ vs. sham.
: $p < 0.05$ vs. BDL.

Data represents the mean ± S.E. (n = 5).
**: $p < 0.01$ vs. sham. ##: $p < 0.01$ vs. BDL.

H&E staining sham

BLM

METHODS OF TREATING FIBROSIS, CANCER AND VASCULAR INJURIES

This application is a continuation-in-part of U.S. patent application Ser. No. 12/826,338 filed Jun. 29, 2010 entitled "2-Pyridyl Substituted Imidazoles as Therapeutic ALK5 and/or ALK 4 Inhibitors", the disclosure of which is incorporated herein by reference.

TECHNICAL FIELD OF THE INVENTION

This invention relates to use of inhibitors of the transforming growth factor-β (TGF-β) type I receptor (ALK5) and/or the activin type I receptor (ALK4) in treating, preventing, or reducing fibrosis, cancer, and vascular injuries.

BACKGROUND OF THE INVENTION

TGF-β denotes a family of proteins, TGF-β1, TGF-β2 and TGF-β3, which are pleiotropic modulators of cell proliferation and differentiation, wound healing, extracellular matrix production, and immunosuppression. Other members of this superfamily include activins, inhibins, bone morphogenetic proteins, growth and differentiation factors, and Müllerian inhibiting substance.

TGF-β1 transduces signals through two highly conserved single transmembrane serine/threonine kinases, the type I (ALK5) and type II TGF-β receptors. Upon ligand induced oligomerization, the type II receptor hyperphosphorylates serine/threonine residues in the GS region of the ALK5, which leads to activation of the ALK5 by creating a binding site for Smad proteins. The activated ALK5 in turn phosphorylates Smad2 and Smad3 proteins at the C-terminal SSXS-motif thereby causing their dissociation from the receptor and heteromeric complex formation with Smad4. Smad complexes translocate to the nucleus, assemble with specific DNA-binding co-factors and co-modulators to finally activate transcription of extracellular matrix components and inhibitors of matrix-degrading proteases.

Activins transduce signals in a manner similar to TGF-β. Activins bind to serine/thereonine kinase, the activin type II receptor (ActRIIB), and the activated type II receptor hyperphosphorylates serine/threonine residues in the GS region of the ALK4. The activated ALK4 in turn phosphorylates Smad2 and Smad3. The consequent formation of a hetero-Smad complex with Smad4 results in the activin-induced regulation of gene transcription.

Numerous experimental animal studies demonstrate an association between glomerular expression of TGF-β and fibrosis, including the Thy-1 rat model of proliferative glomerulonephritis, anti-GBM glomerulonephritis in rabbits, and the 5/6 nephrectomy rat model of focal segmental glomerulosclerosis, as has been reviewed recently (e.g., Bitzer, M. et al., *Kidney Blood Press. Res.* 21: 1-12 (1998)). Neutralizing antibody to TGF-β improves glomerular histology in the Thy-1 nephritis model (e.g., Border, W. A. et al., *Nature* 346: 371-374 (1990)).

Hyperglycemic conditions increase TGF-β mRNA and protein synthesis in both murine proximal tubule cells and human mesangial cells (e.g., Wahab, N. A. et al., *Biochem. J.* 316: 985-992 (1996); Rocco, M. V. et al., *Kidney Int.* 41: 107-114 (1992)). Diabetic patients with early kidney disease show increased accumulation of TGF-β mRNA and protein within the glomerulus (e.g., Yoshioka, K. et al., *Lab. Invest.* 68: 154-163 (1993)). In kidneys with chronic renal interstitial fibrosis, the hallmarks are thickened tubular basement membranes and an expanded interstitial compartment, with interstitial fibrosis characterized by an increase in collagens I, III, V, VII, and fibronectin (e.g., Eddy, A. A., *J. Am. Soc. Nephrol.* 7: 2495-2508 (1996)).

TGF-β gene expression and protein production are increased in a variety of animal models of pulmonary fibrosis including bleomycin, silica, asbestos, and radiation (e.g., Phan, S. H. and Kunkel, S. L., *Exp. Lung Res.* 18: 29-43 (1992); Williams, A. O. et al., *Am. J. Pathol.* 142: 1831-1840 (1993); Rube, C. E. et al., *Int. J. Radiat. Oncol. Biol. Phys.* 47: 1033-1042 (2000)). Coincident increase in TGF-β1 protein and collagen gene expression in adjacent tissue slices from idiopathic pulmonary fibrosis is observed in human pulmonary fibrotic disease (e.g., Broekelmann, T. J. et al., *Proc. Natl. Acad. Sci. USA* 88: 6642-6646 (1991)). Increased TGF-β production has been documented in patients with sarcoidosis, pneumoconiosis, asbestosis, and radiation-induced fibrosis (e.g., Khalil, N. et al., *Am. J. Respir. Cell. Mol. Biol.* 14: 131-138 (1996); Jagirdar, J. et al., *Environ. Health Perspect.* 105: 1197-1203 (1997)). Anti-TGF-β antibodies and TGF-β-soluble receptors could partially inhibit fibrosis in bleomycin-induced lung fibrosis rodent models (e.g., Giri, S. N. et al., *Thorax* 48: 959-966 (1993); Wang, Q. et al., *Thorax* 54: 805-812 (1999)). Tobacco smoke has been implicated as one of the most important factors that can cause small airway disease followed by chronic obstructive pulmonary disease (COPD) (e.g., Wright, J. M. et al., *Am. Rev. Respir. Dis.* 146: 240-262 (1992)). COPD is a slowly progressive and irreversible disorder characterized by the functional abnormality of airway obstruction. TGF-β has been hypothesized to be involved in airway remodeling found in chronic airway inflammatory disorders such as COPD (e.g., Takizawa, H. *Int. J. Mol. Med.* 1: 367-378 (1998); Ning, W. et al., *Proc. Natl. Acad. Sci. USA* 101: 14895-14900 (2004)).

Hepatic stellate cells (HSC) are the major source of extracellular matrix proteins in hepatic fibrosis. Extracellular matrix production by activated hepatic stellate cells is markedly increased through the action of TGF-β1 (e.g., Friedman, S. L., *Prog. Liver Dis.* 14: 101-130 (1996); Pietrangelo, A., *Semin. Liver Dis.* 16: 13-30 (1996)). Transgenic mice that overexpress TGF-β1 in the liver develop hepatic fibrosis as well as extrahepatic pathologies such as renal fibrosis (e.g., Sanderson, N. et al., *Proc. Natl. Acad. Sci. USA* 92: 2572-2576 (1995)).

TGF-β1 and its receptors are overexpressed in injured blood vessels and in fibroproliferative vascular lesions leading to overproduction of extracellular matrix (e.g., Saltis, J. et al., *Clin. Exp. Pharmacol. Physiol.* 23: 193-200 (1996); McCaffrey, T. A. et al., *J. Clin. Invest.* 96: 2667-2675 (1995)).

Anti-TGF-β antibodies reduce scar formation and improve the cytoarchitecture of the neodermis in rats (e.g., Shah, M., *J. Cell. Sci.* 108: 985-1002 (1995)), improve healing of corneal wounds in rabbits (e.g., Moller-Pedersen, T., *Curr. Eye Res.* 17: 736-747 (1998)), and accelerate wound healing of gastric ulcers in rats (e.g., Ernst, H., *Gut* 39: 172-175 (1996)).

Radiation fibrosis is a frequent sequel of therapeutic or accidental radiation overexposure in normal human tissues. TGF-β1 plays a central role in the initiation, development, and persistence of radiation fibrosis, as has been reviewed recently (e.g., Martin, M. et al., *Int. J. Radiat. Oncol. Biol. Phys.* 47: 277-290 (2000)).

Organ transplantation is complicated in many instances by chronic rejection and for some organs such as the kidney, it is the major forms of graft loss. In human patients, chronic rejection of lung and kidney transplants is associated with increased expression of TGF-β within the tissue (e.g., El- Gamel, A. et al., *Eur. J. Cardiothorac. Surg.* 13: 424-430 (1998); Shihab, F. S. et al., *J. Am. Soc. Nephrol.* 6: 286-294 (1995)).

TGF-β is implicated in peritoneal adhesions (e.g., Saed, G. M. et al., *Wound Repair Regen.* 7: 504-510 (1999)). The peritoneal and sub-dermal fibrotic adhesions could be prevented by inhibitors of ALK5 and/or ALK4.

TGF-β2 levels are increased in nearly half of the eyes with primary open-angle glaucoma (POAG) and in most of the eyes with juvenile glaucoma in the aqueous humor of eyes (e.g., Picht, G. et al., *Graefes Arch. Clin. Exp. Ophthalmol.* 239: 199-207 (2001)). Both TGF-β1 and TGF-β2 isoforms are reported to increase extracellular matrix production in cultured human Tenon's capsule fibroblasts derived from patients with pseudoexfoliation glaucoma and POAG (e.g., Kottler, U. B. et al., *Exp. Eye Res.* 80: 121-134 (2005)). US 2007/0142376 A1 discloses treatment of glaucoma and control of intraocular pressure using ALK5 modulating agents, and an ALK5 inhibitor reduces the level of fibronectin in TGF-β2-treated perfused human anterior segments and the levels of fibronectin, plasminogen activator inhibitor-1 (PAI-1), and pro-collagen type I C-peptide in TGF-β2-treated trabecular meshwork cell cultures.

The tumor cells and the stromal cells within the tumors in late stages of various cancers generally overexpress TGF-β. This leads to stimulation of angiogenesis and cell motility, suppression of the immune system, and increased interaction of tumor cells with the extracellular matrix (e.g., Hojo, M. et al., *Nature* 397: 530-534 (1999)). Consequently, the tumor cells become more invasive and metastasize to distant organs (e.g., Maehara, Y. et al., *J. Clin. Oncol.* 17: 607-614 (1999); Picon, A. et al., *Cancer Epidemiol. Biomarkers Prev.* 7: 497-504 (1998)).

PAI-1 is the major physiological inhibitor of both tissue-type plasminogen activator and urokinase-type plasminogen activator. Elevated levels of PAI-1 are associated with thrombosis and vascular disease, suggesting that high plasma PAI-1 may promote a hypercoagulable state by disrupting the natural balance between fibrinolysis and coagulation (e.g., Vaughan, D. E., *J. Invest. Med.* 46: 370-376 (1998)). It is known that TGF-β stimulates the expression of PAI-1 (e.g., Dennler, S. et al., *EMBO J.* 17: 3091-3100 (1998)). Accordingly, inhibition of the production of PAI-1 with an inhibitor of the TGF-β signaling pathway could produce a novel fibrinolytic therapy.

Activin signaling and overexpression of activin is linked to pathological disorders that involve extracellular matrix accumulation and fibrosis (e.g., Matsuse, T. et al., *Am. J. Respir. Cell Mol. Biol.* 13: 17-24 (1995); Inoue, S. et al., *Biochem. Biophys. Res. Comm.* 205: 441-448 (1994); Matsuse, T. et al., *Am. J. Pathol.* 148: 707-713 (1996); De Bleser et al., *Hepatology* 26: 905-912 (1997); Pawlowski, J. E., et al., *J. Clin. Invest.* 100: 639-648 (1997); Sugiyama, M. et al., *Gastroenterology* 114: 550-558 (1998); Munz, B. et al., *EMBO J.* 18: 5205-5215 (1999)), inflammatory responses (e.g., Rosendahl, A. et al., *Am. J. Respir. Cell Mol. Biol.* 25: 60-68 (2001), cachexia or wasting (Matzuk, M. M. et al., *Proc. Natl. Acd. Sci. USA* 91: 8817-8821 (1994); Coerver, K. A. et al., *Mol. Endocrinol.* 10: 534-543 (1996); Cipriano, S. C. et al., *Endocrinology* 141: 2319-2327 (2000)), diseases or pathological responses in the central nervous system (e.g., Logan, A. et al., *Eur. J. Neurosci.* 11: 2367-2374 (1999); Logan, A. et al., *Exp. Neurol.* 159: 504-510 (1999); Masliah, E. et al., *Neurochem. Int.* 39: 393-400 (2001); De Groot, C. J. A. et al., *J. Neuropathol. Exp. Neurol.* 58: 174-187 (1999); John, G. R. et al., *Nat. Med.* 8: 1115-1121 (2002)) and hypertension (e.g., Dahly, A. J. et al., *Am. J. Physiol. Regul. Integr. Comp. Physiol.* 283: R757-767 (2002)). Studies have shown that TGF-β and activin can act synergistically to induce extracellular matrix production (e.g., Sugiyama, M. et al., *Gastroenterology* 114; 550-558 (1998)).

Therefore, it becomes evident that inhibition of ALK5 and/or ALK4 phosphorylation of Smad2 and Smad3 by the preferred compounds of this invention could treat and prevent disorders involving these signaling pathways.

WO 00/61576 and US 2003/0149277 A1 disclose triarylimidazole derivatives and their use as ALK5 inhibitors. WO 01/62756 A1 discloses pyridinylimidazole derivatives and their use as ALK5 inhibitors. WO 02/055077 A1 discloses use of imidazolyl cyclic acetal derivatives as ALK5 inhibitors. WO 03/087304 A2 discloses tri-substituted heteroaryls and their use as ALK5 and/or ALK4 inhibitors. WO 2005/103028 A1 and U.S. Pat. No. 7,407,958 B2 disclose 2-pyridyl substituted imidazoles as ALK5 and/or ALK4 inhibitors. Especially, one of the representative compounds claimed in WO 2005/103028 A1 and U.S. Pat. No. 7,407,958 B2, IN-1130, demonstrates its use in several animal models as ALK5 and/or ALK4 inhibitors. IN-1130 effectively suppresses renal fibrosis induced by unilateral ureteral obstruction (UUO) in rats (Moon, J.-A. et al., *Kidney Int.* 70: 1234-1243 (2006)), ameliorates experimental autoimmune encephalomyelitis (EAE) in SBE-luc and GFAP-luc mice immunized with $MOG_{35-55}$ (Luo, J. et al., *J. Clin. Invest.* 117: 3306-3315 (2007)), lessens tunical fibrosis and corrects penile curvature in rats (Ryu, J.-K. et al., *J. Sex. Med.* 6: 1284-1296 (2009)), and dramatically reduces tumor volume with an enhanced immune response in mice treated with murine prostate cancer cell line Tramp C2 (Lee, G. T. et al., *J. Urol.* 180: 2660-2667 (2008)). And, also, US 2008/0319012 A1 discloses 2-pyridyl substituted imidazoles as ALK5 and/or ALK4 inhibitors. Especially, one of the representative compounds claimed in US 2008/0319012 A1, IN-1233, demonstrates its use in several animal models as ALK5 and/or ALK4 inhibitors. IN-1233 effectively prevents the development and progression of pulmonary arterial hypertension in the monocrotaline rat model through the inhibition of TGF-β signaling (Long, L. et al., *Circulation* 119: 566-576 (2009)) and also prevents granulation tissue formation after bare metallic stent placement in a rat urethral model (Kim, J. H. et al., *Radiology* 255: 75-82 (2010)).

SUMMARY

Surprisingly, it has now been discovered that a class of 2-pyridyl substituted imidazoles function as potent and selective inhibitors of ALK5 and/or ALK4 and, therefore, have utility in the treatment, prevention, and reduction of various disease states mediated by ALK5 and/or ALK4, such as glomerulonephritis, diabetic nephropathy, lupus nephritis, hypertension-induced nephropathy, renal interstitial fibrosis, renal fibrosis resulting from complications of drug exposure, HIV-associated nephropathy, transplant nephropathy, liver fibrosis due to all etiologies, hepatic dysfunction attributable to infections, alcohol-induced hepatitis, disorders of the biliary tree, cystic fibrosis, pulmonary fibrosis, interstitial lung disease, acute lung injury, adult respiratory distress syndrome, idiopathic pulmonary fibrosis, chronic obstructive pulmonary disease, pulmonary disease due to infectious or toxic agents, post-infarction cardiac fibrosis, congestive heart failure, dilated cardiomyopathy, myocarditis, intimal thickening, vascular stenosis, hypertension-induced vascular remodeling, pulmonary arterial hypertension, coronary restenosis, peripheral restenosis, carotid restenosis, stent-induced restenosis, atherosclerosis, ocular scarring, corneal scarring, proliferative vitreoretinopathy, glaucoma, intraocular pressure, excessive or hypertrophic scar or keloid formation in the dermis occurring during wound healing resulting from trauma or surgical wounds, peritoneal and sub-dermal adhesion, scleroderma, fibrosclerosis, progressive systemic sclerosis, dermatomyositis, polymyositis, arthritis, osteoporosis, ulcers, impaired neurological function, male erectile dysfunction, Peyronie's disease, Dupuytren's contracture, Alzheimer's disease, Raynaud's syndrome, radiation-induced fibrosis, thrombosis, tumor metastasis growth, multiple myeloma, melanoma, glioma, glioblastomas, leukemia, sarcomas, leiomyomas, mesothelioma, and carcinomas of lung, breast, colon, kidney, ovary, cervix, liver, biliary tract, gastrointestinal tract, pancreas, prostate, head, and neck.

BRIEF DESCRIPTION OF THE DRAWINGS

The aforementioned aspects and other features of the present invention will be explained in the following description, taken in conjunction with the accompanying drawings, wherein.

Figure 1:
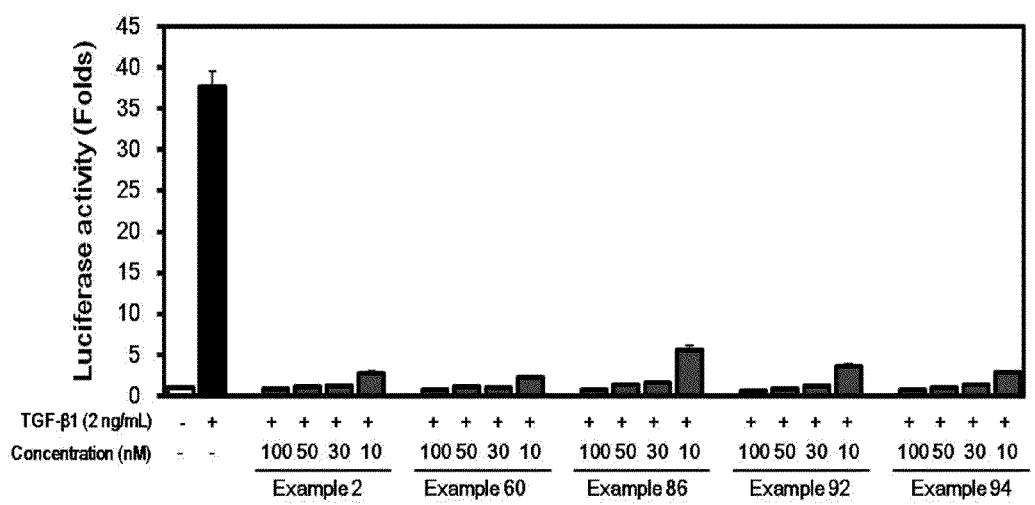
FIG. 1 shows effect of Examples 2, 60, 86, 92, and 94 on the TGF-β1-induced 3TP-Luc reporter activity in HaCaT-3TP-Luc cells.
Figure 2:
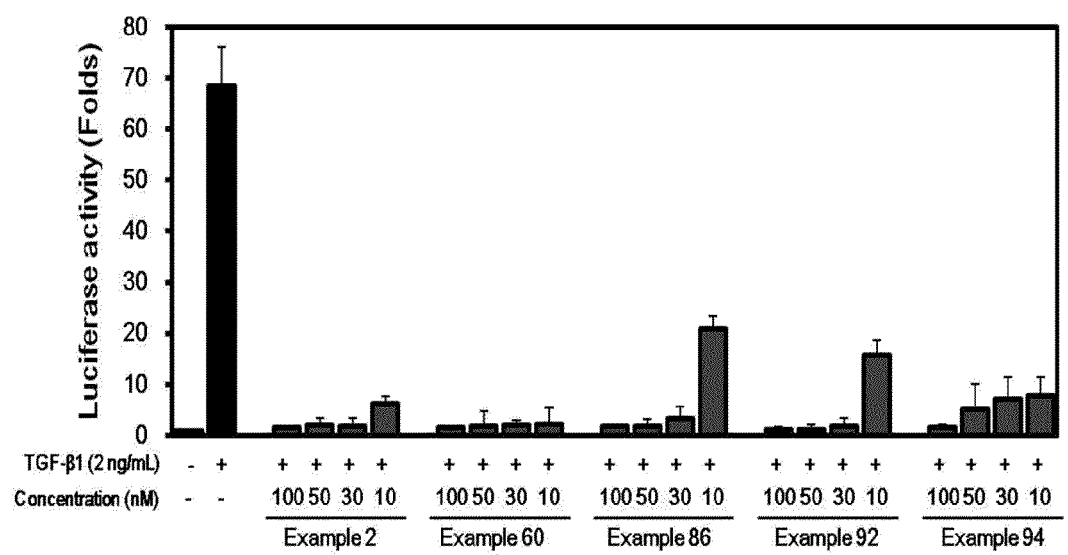
FIG. 2 shows effect of Examples 2, 60, 86, 92, and 94 on the TGF-β1-induced 3TP-Luc reporter activity in 4T1-3TP-Luc cells.
Figure 3:
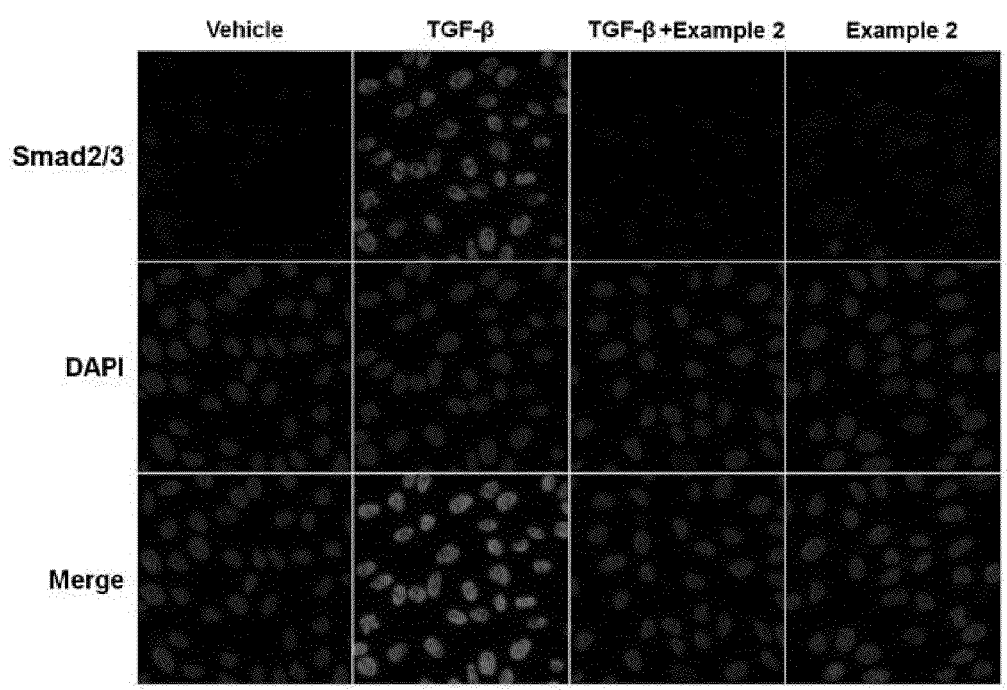
FIG. 3 shows effect of Example 2 on the TGF-β1-induced Smad2/3 nuclear translocation in MCF10A cells.
Figure 4:
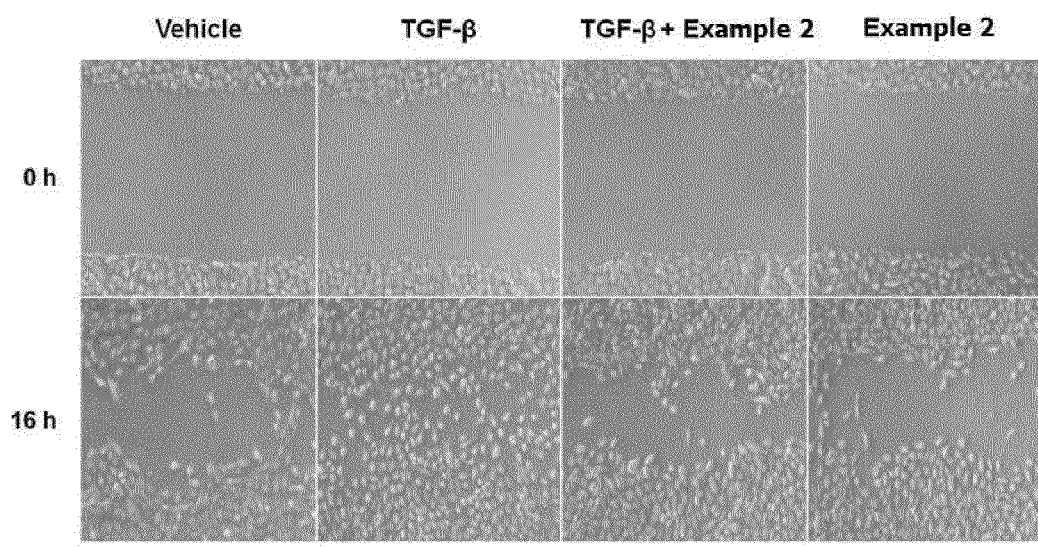
FIG. 4 shows effect of Example 2 on the TGF-β1-induced cell migration in MCF10A cells.
Figure 5A:
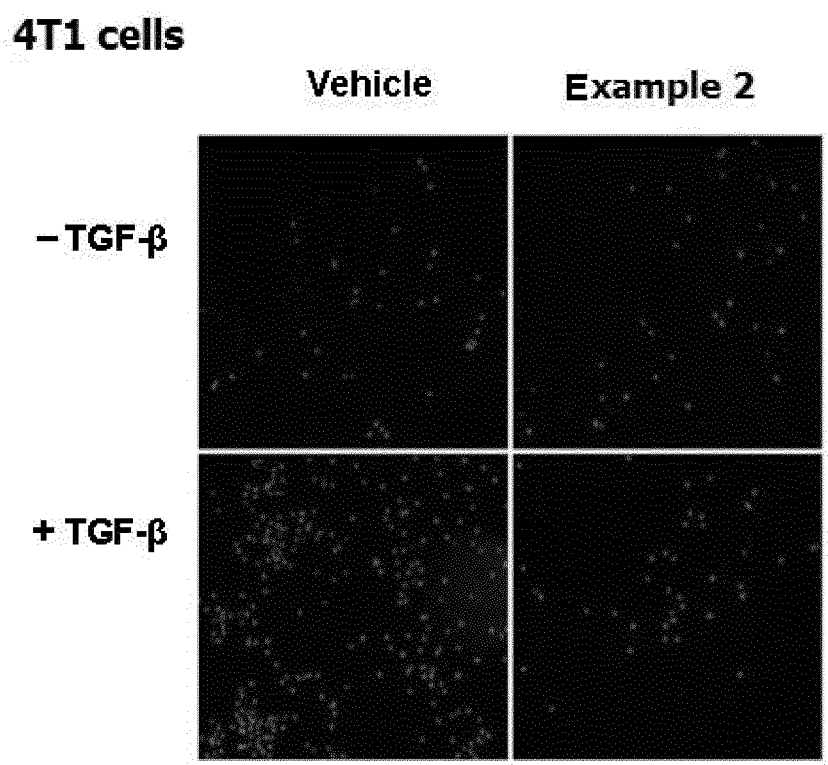
FIGS. 5A and 5B show effect of Example 2 on the TGF-β1-induced cell invasion in 4T1 cells. (5A). DAPI-stained cells remaining on the bottom surface. (5B). Average cell number per view field obtained from 5 random fields.
Figure 5B:
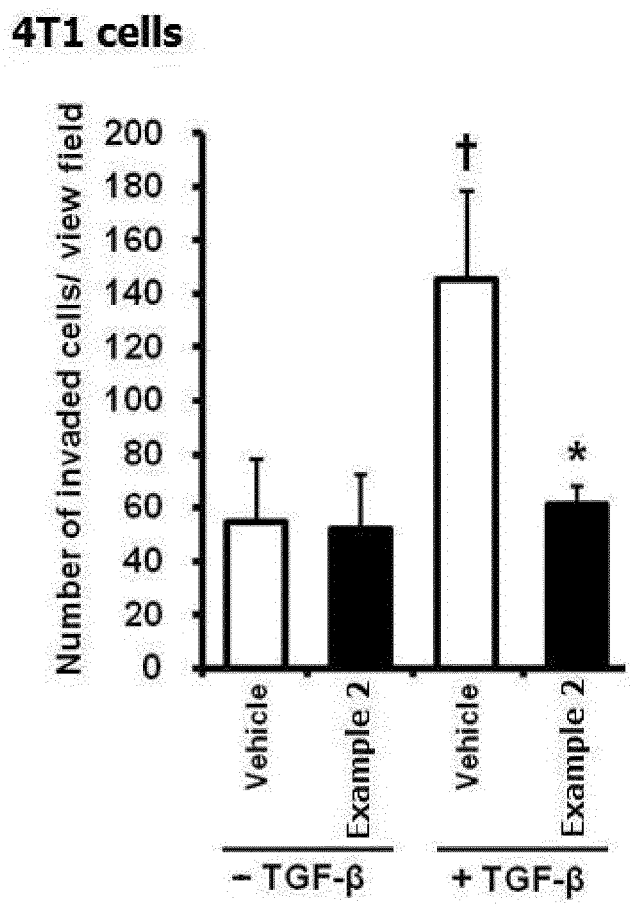
Figure 6:
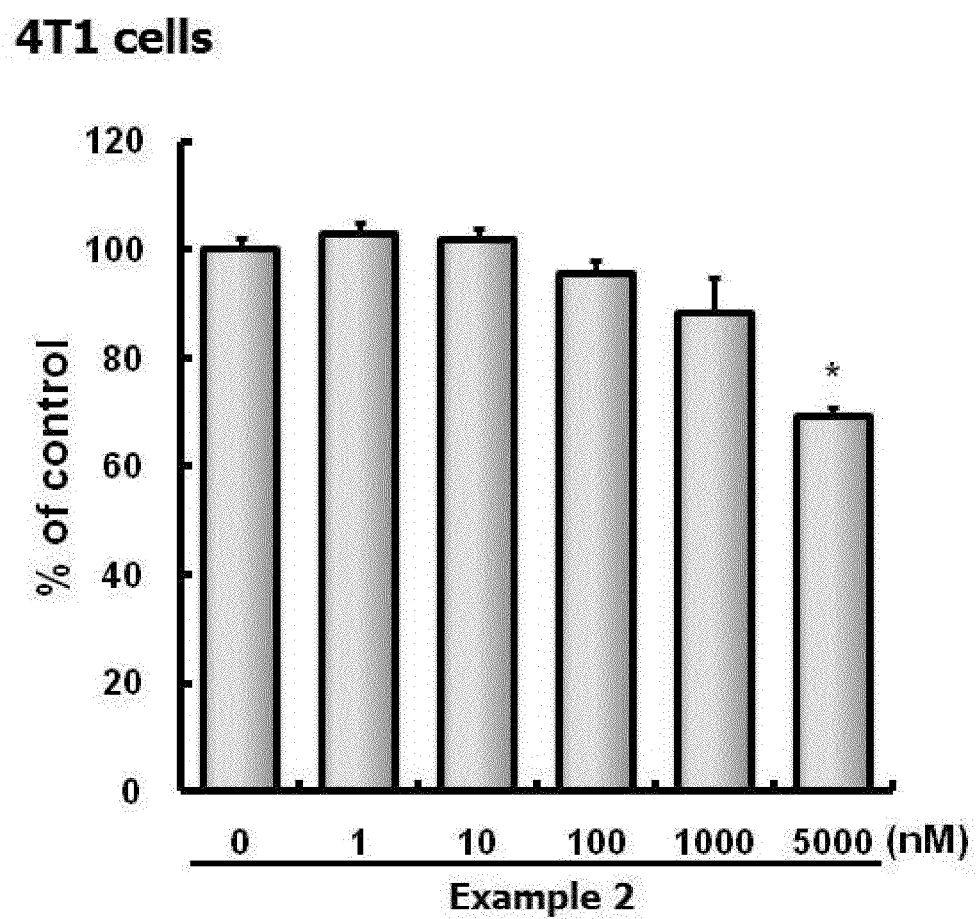
FIG. 6 shows effect of Example 2 on the cell growth of 4T1 cells.
Figure 7:
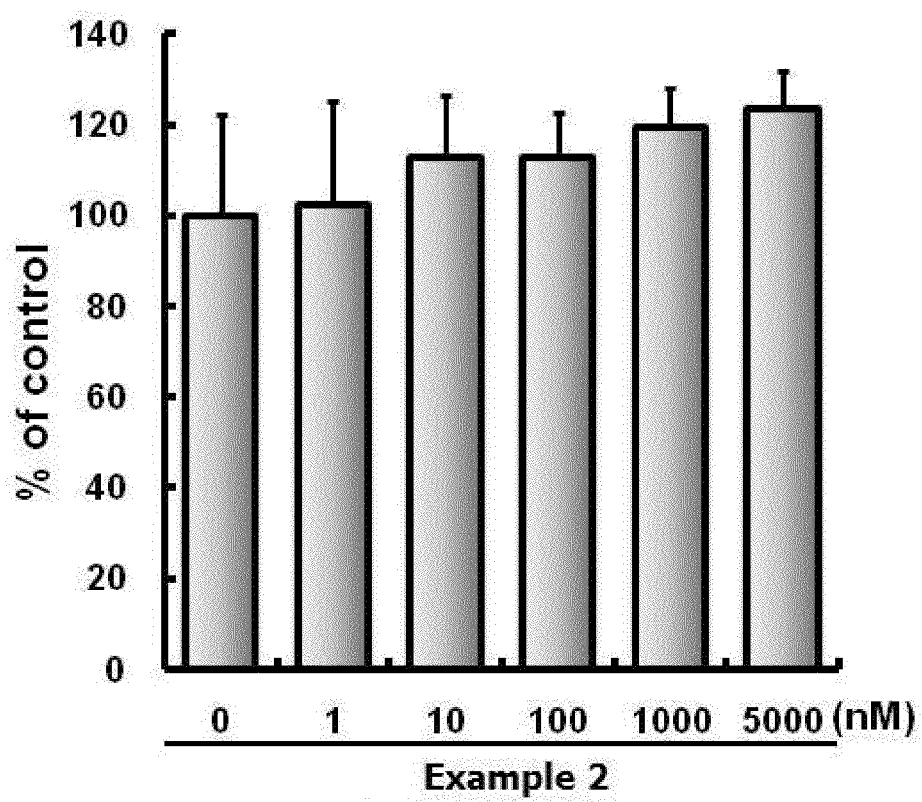
FIG. 7 shows effect of Example 2 on the cell growth of MCF10A cells.
Figure 8A:
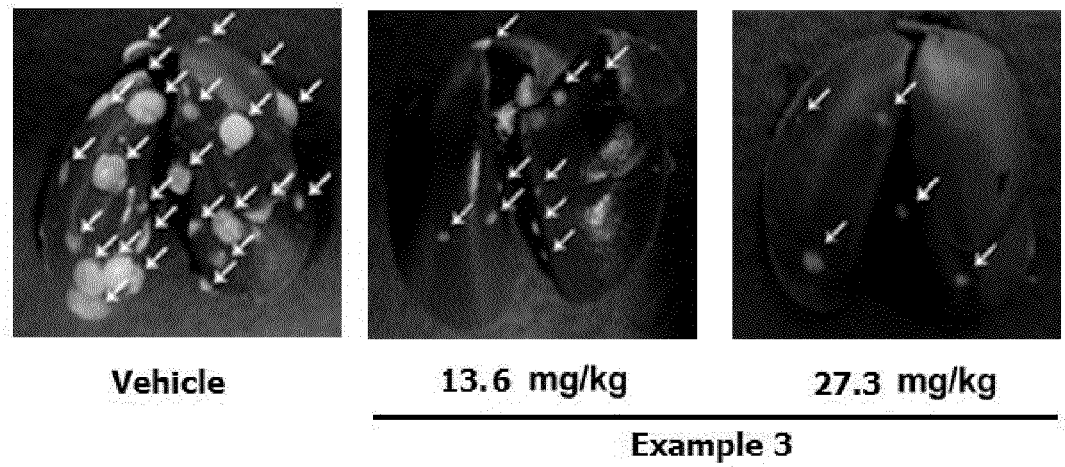
FIGS. 8A and 8B show effect of Example 3 on the breast tumor metastasis to the lung in BALB/c 4T1 xenografted mice. Example 3 (13.6 or 27.3 mg/kg) dissolved in water (vehicle) was given to mice orally BID five consecutive days per week for four weeks. (8A). White spots on the lung surface indicate metastastic nodules (white arrows). (8B). Number of metastastic nodules on whole lung surface.
Figure 8B:
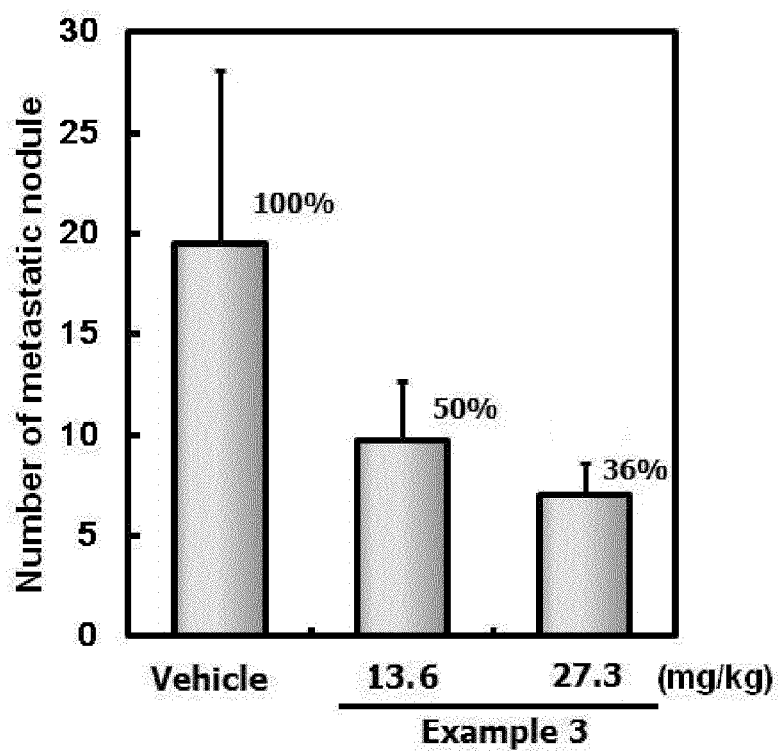
Figure 9A:
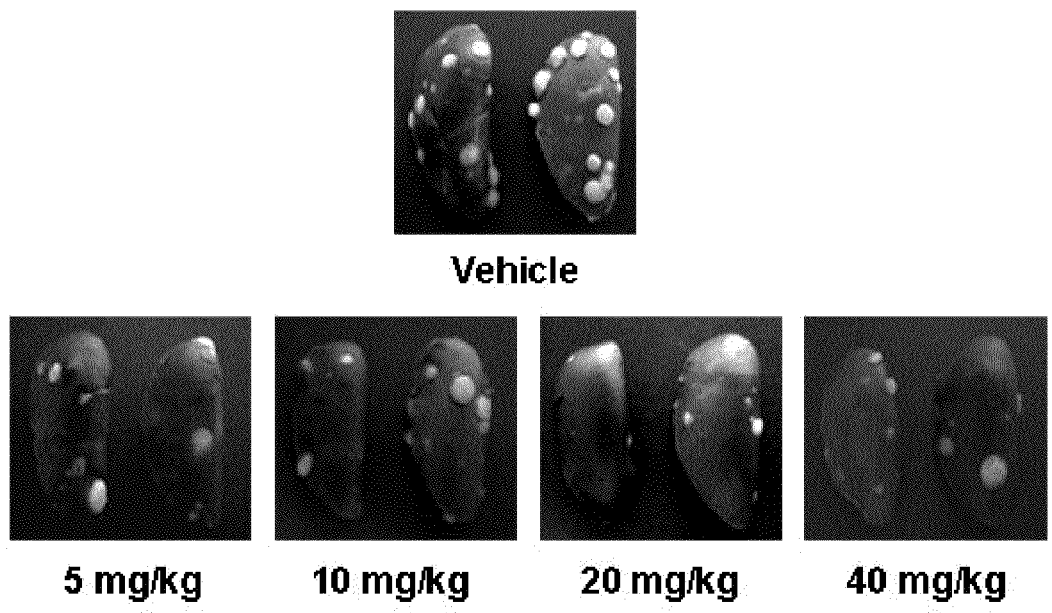
FIGS. 9A and 9B show effect of Example 2 on the breast tumor metastasis to the lung in BALB/c 4T1 xenografted mice. Example 2 (5, 10, 20, or 40 mg/kg) dissolved in artificial gastric fluid formulation (vehicle) was given to mice orally five consecutive days per week for three weeks. (9A). White spots on the lung surface indicate metastastic nodules. (9B). Number of metastastic nodules on surface of left lobe of lung.
Figure 9B:
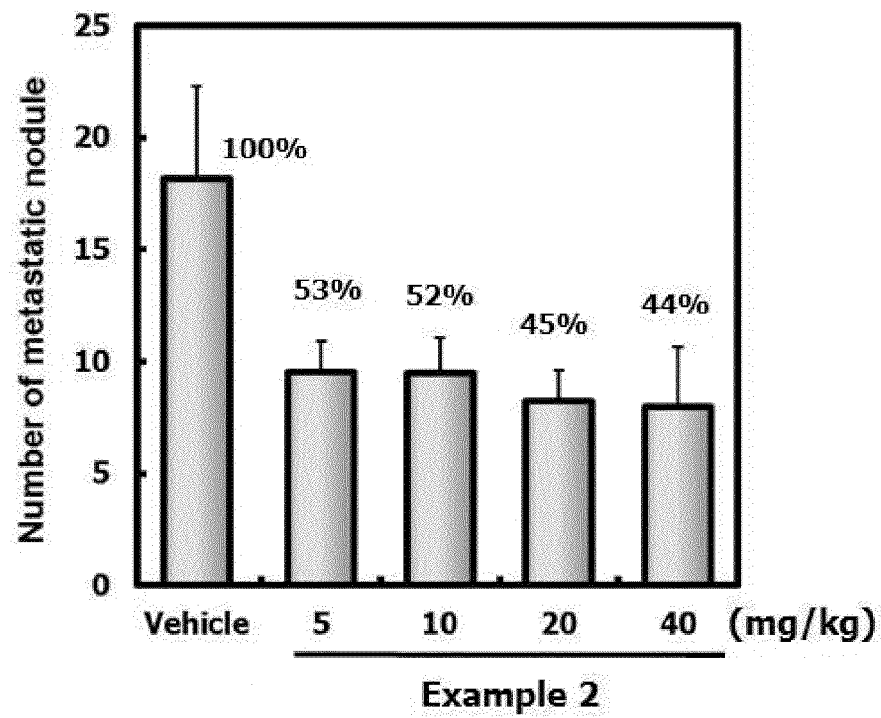
Figure 10A:
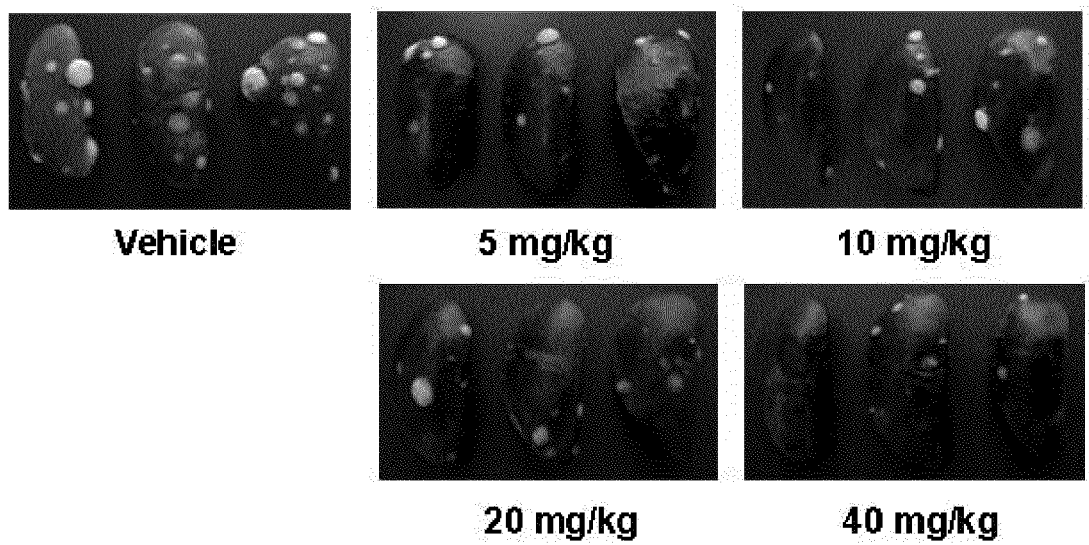
FIGS. 10A, 10B, and 10C show effect of Example 2 on the breast tumor metastasis to the lung in BALB/c 4T1 xenografted mice. Example 2 (5, 10, 20, or 40 mg/kg) dissolved in artificial gastric fluid formulation (vehicle) was given to mice orally every other day (three times per week) for 24 days. (10A). White spots on the lung surface indicate metastastic nodules. (10B). Number of metastastic nodules on surface of left lobe of lung. (10C). Effect on the TGF-β1-induced Smad2 phosphorylation in tumor tissues.
Figure 10B:
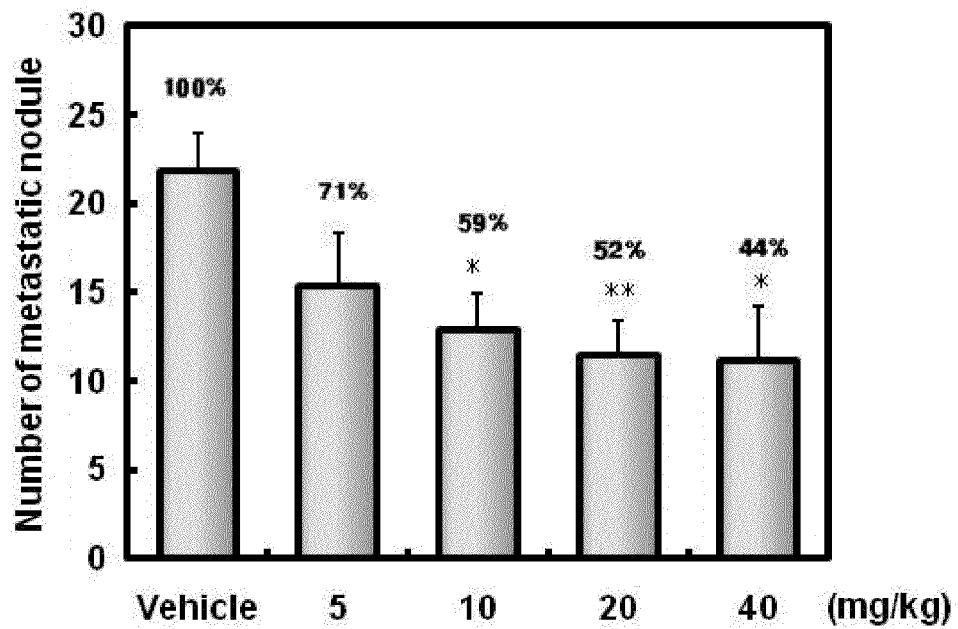
Figure 10C:
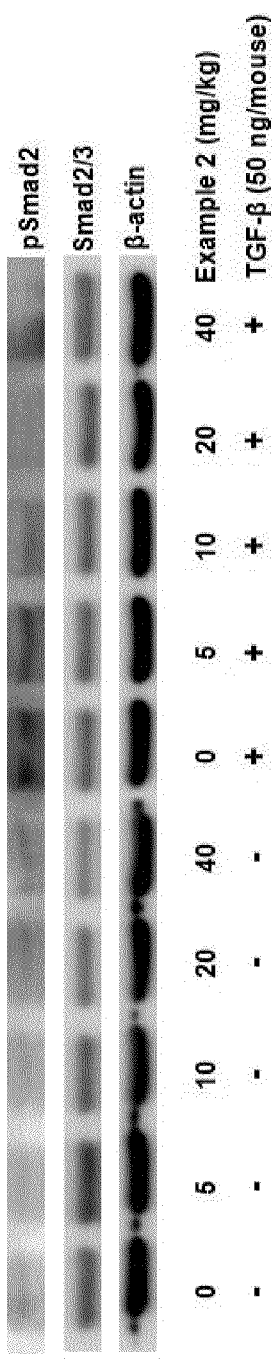
Figure 11A:
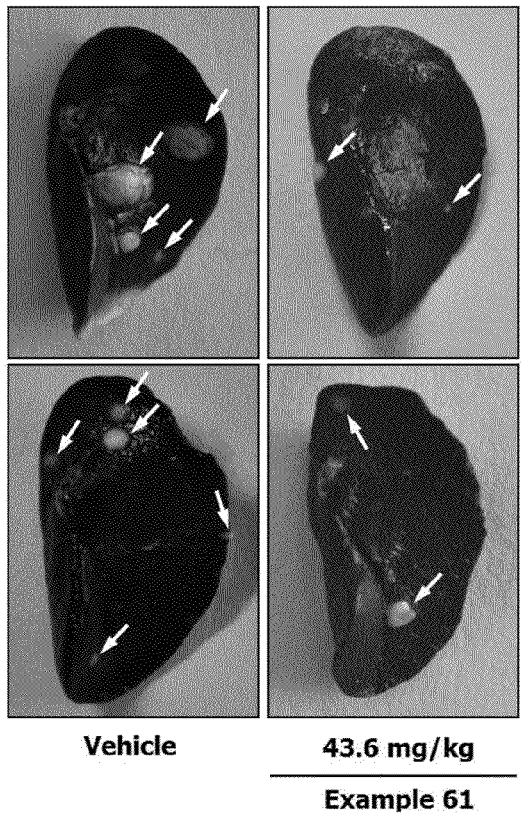
FIGS. 11A, 11B, and 11C show effect of Example 61 on the breast tumor metastasis to the lung in BALB/c 4T1 xenografted mice. Example 61 (43.6 mg/kg) dissolved in saline (vehicle) was given to mice intraperitoneally every other day (three times per week) for 2.5 weeks. (11A). White spots on the lung surface indicate metastastic nodules. (11B). Number of metastastic nodules on surface of left lobe of lung. (11C). Volume of primary tumor.
Figure 11B:
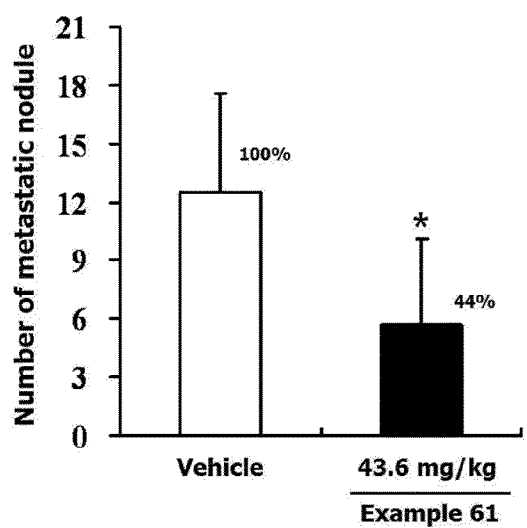
Figure 11C:
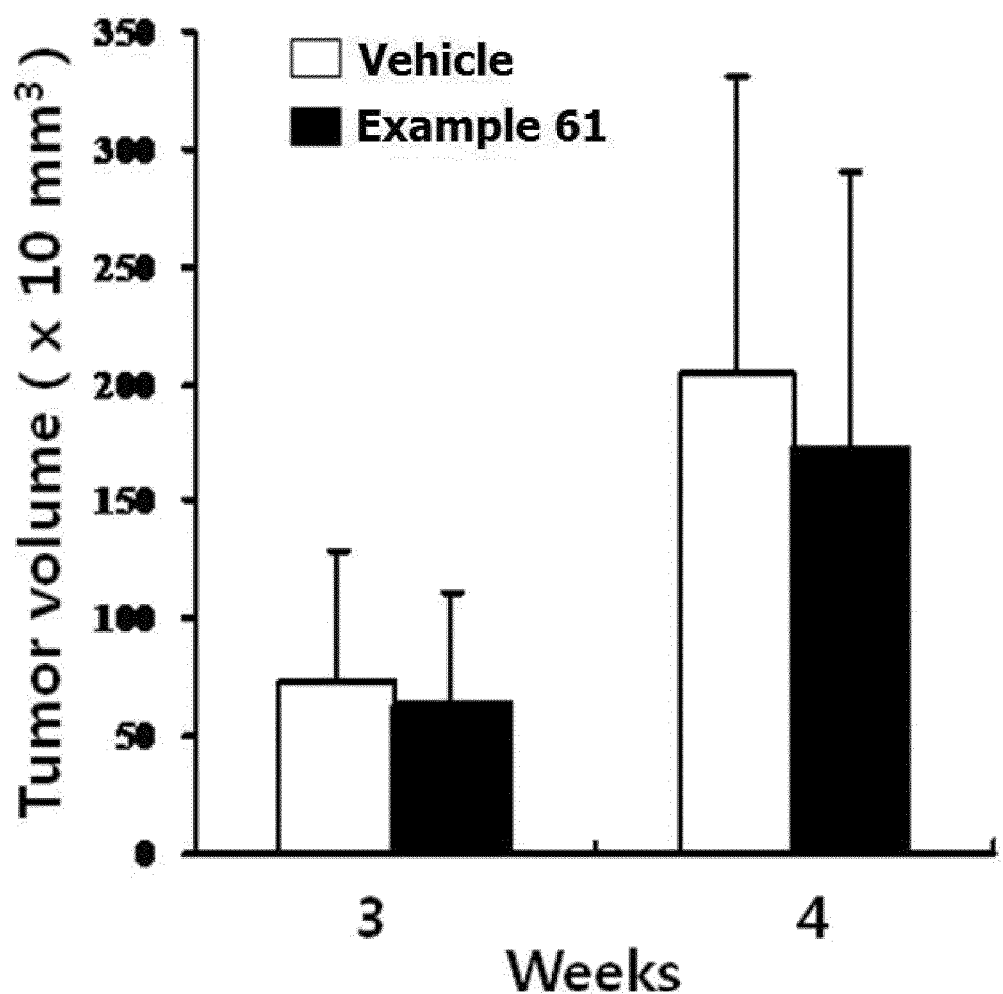
Figure 12A:
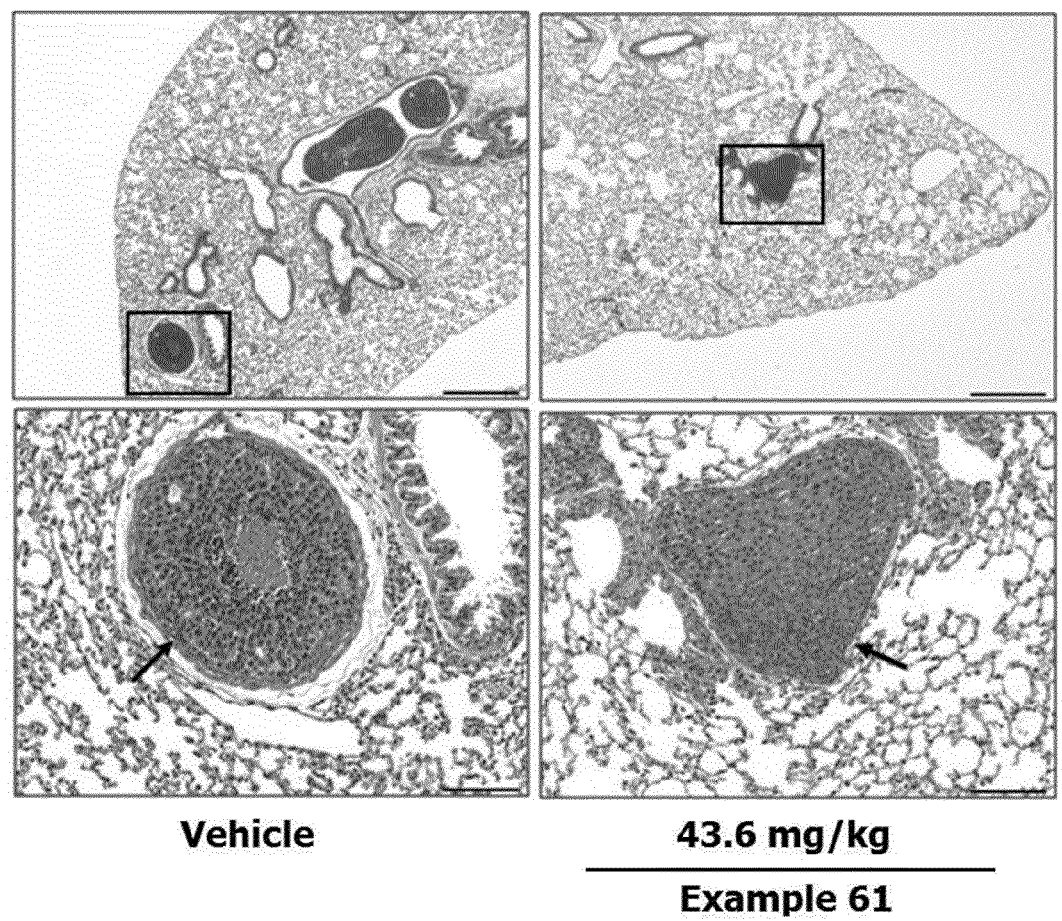
FIGS. 12A, 12B, 12C, and 12D show effect of Example 61 on the breast tumor metastasis to the lung in MMTV/c-Neu mice. Tumor-bearing MMTV/c-Neu mice were treated intraperitoneally with Example 61 (43.6 mg/kg) every other day for three weeks. (12A). Hematoxylin and eosin (H&E) staining of mammary tumor and lung tissues. (12B). Number of histologically detectable metastastic lesions in the lung. (12C). Volume of mammary tumor. (12D). β-Casein mRNA level.
Figure 12B:
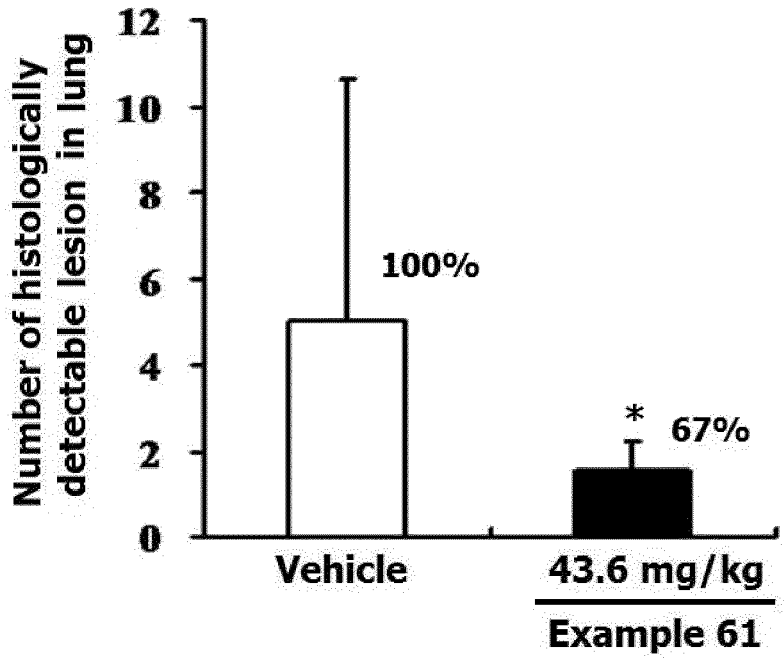
Figure 12C:
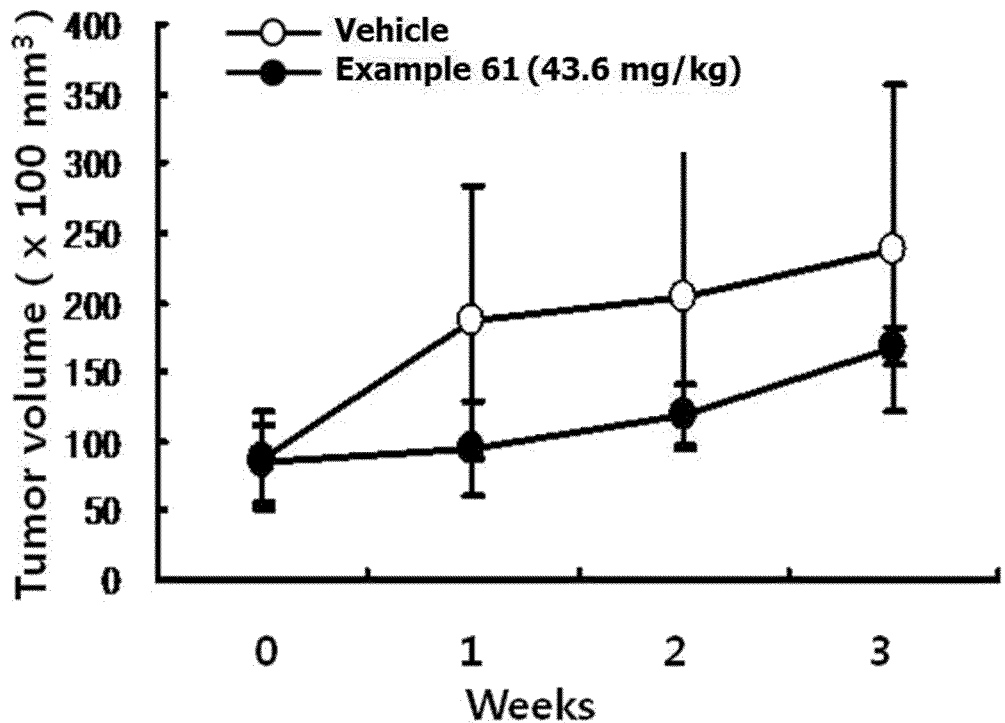
Figure 12D:
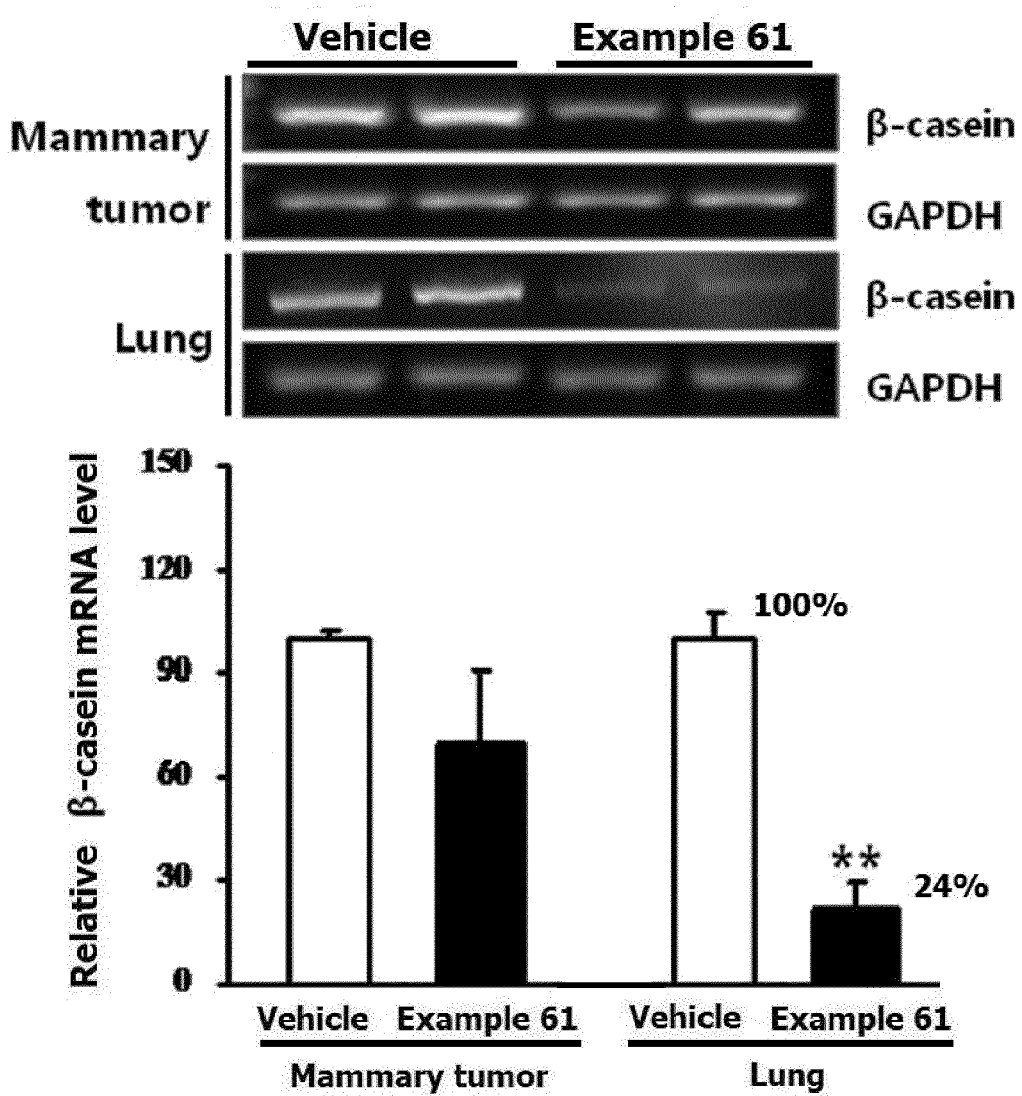
Figure 13A:
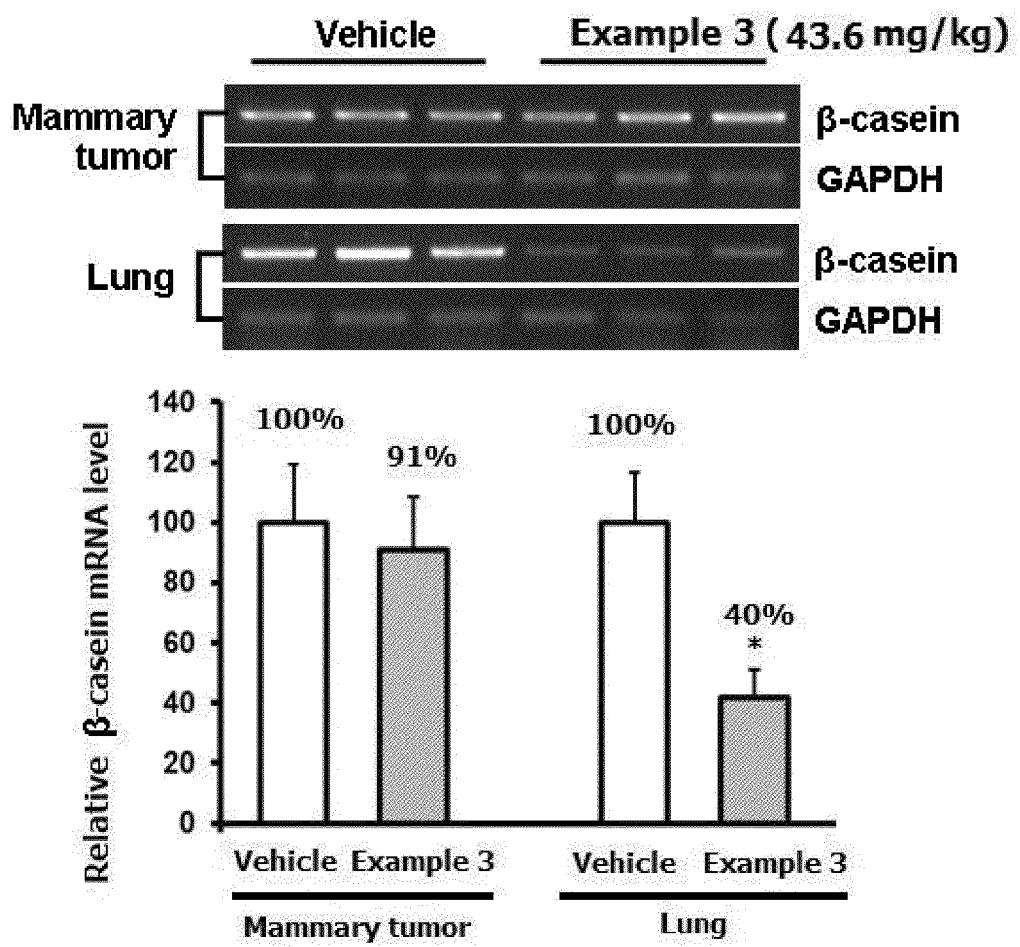
FIGS. 13A and 13B show effect of Example 3 on the breast tumor metastasis to the lung in MMTV/c-Neu mice. Tumor-bearing MMTV/c-Neu mice were treated intraperitoneally with Example 3 (43.6 mg/kg) every other day for ten weeks. (13A). β-Casein mRNA level. (13B). Activity of MMP-9 and MMP-2 in the primary mammary tumor.
Figure 13B:
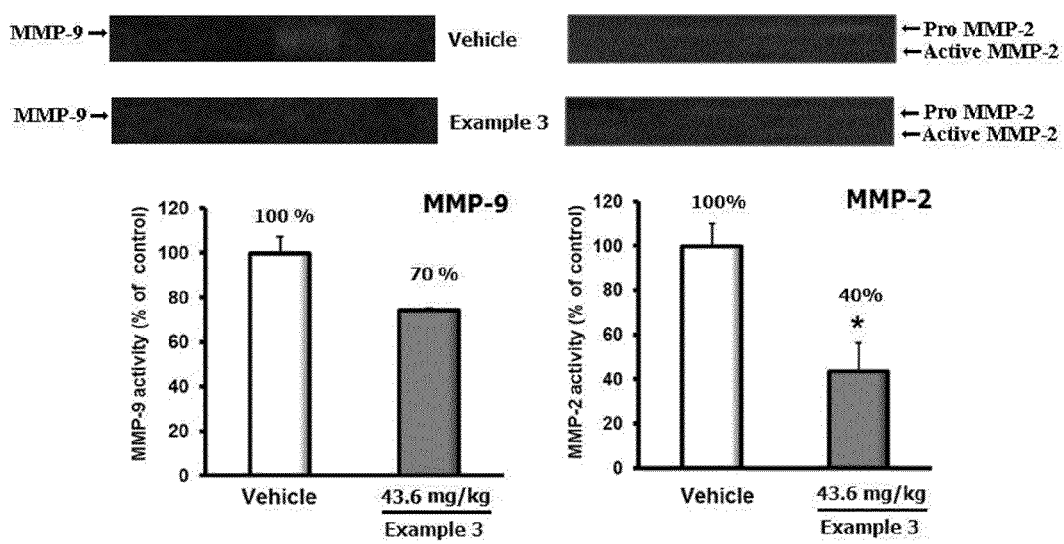
Figure 14A:
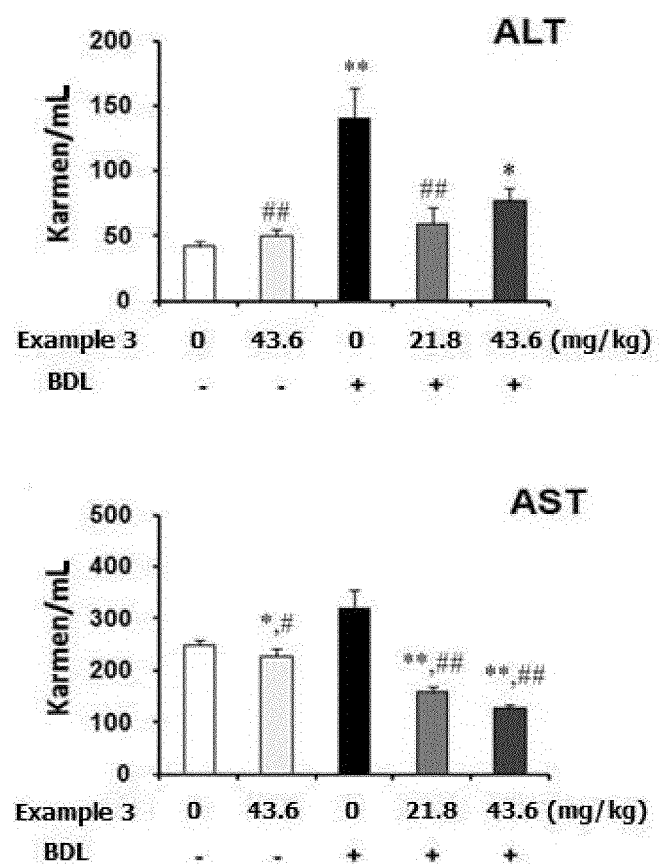
FIGS. 14A, 14B, 14C, and 14D show effect of Example 3 on the bile duct-ligated liver fibrosis in rats. Example 3 (21.8 or 43.6 mg/kg) dissolved in saline (vehicle) was given to rats orally three times per week for four weeks starting from BDL surgery. (14A). Activity of serum alanine aminotransferase (ALT) and aspartate aminotransferase (AST). (14B). Level of pSmad3 protein in the liver. (14C). Level of α-SMA, fibronectin, and vimentin proteins in the liver. (14D). Hematoxylin and eosin (H&E) staining of liver tissues.
Figure 14B:
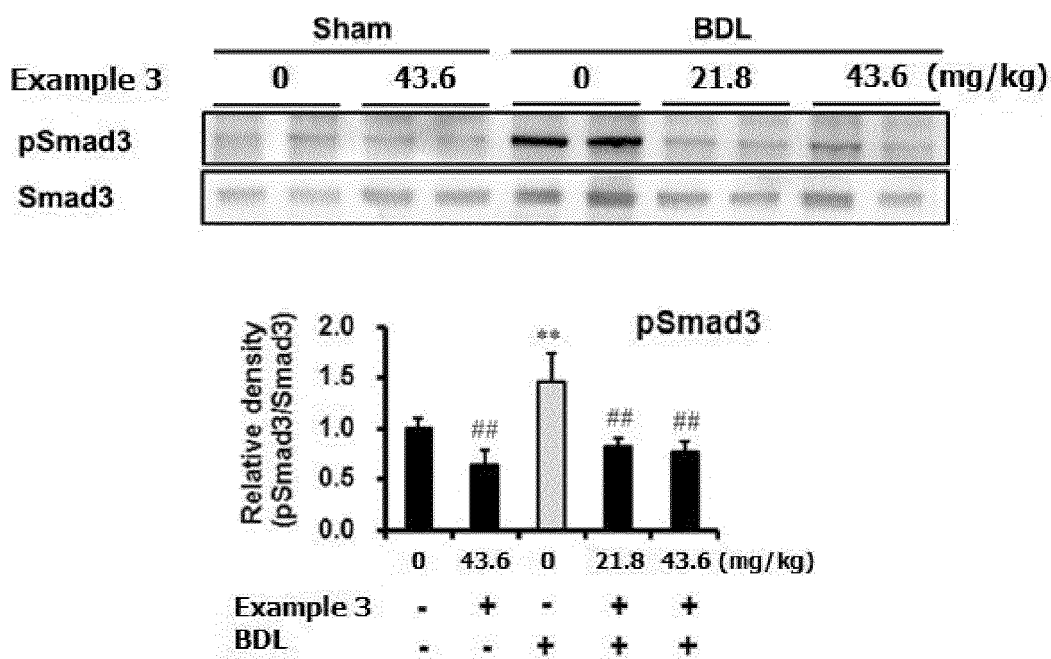
Figure 14C:
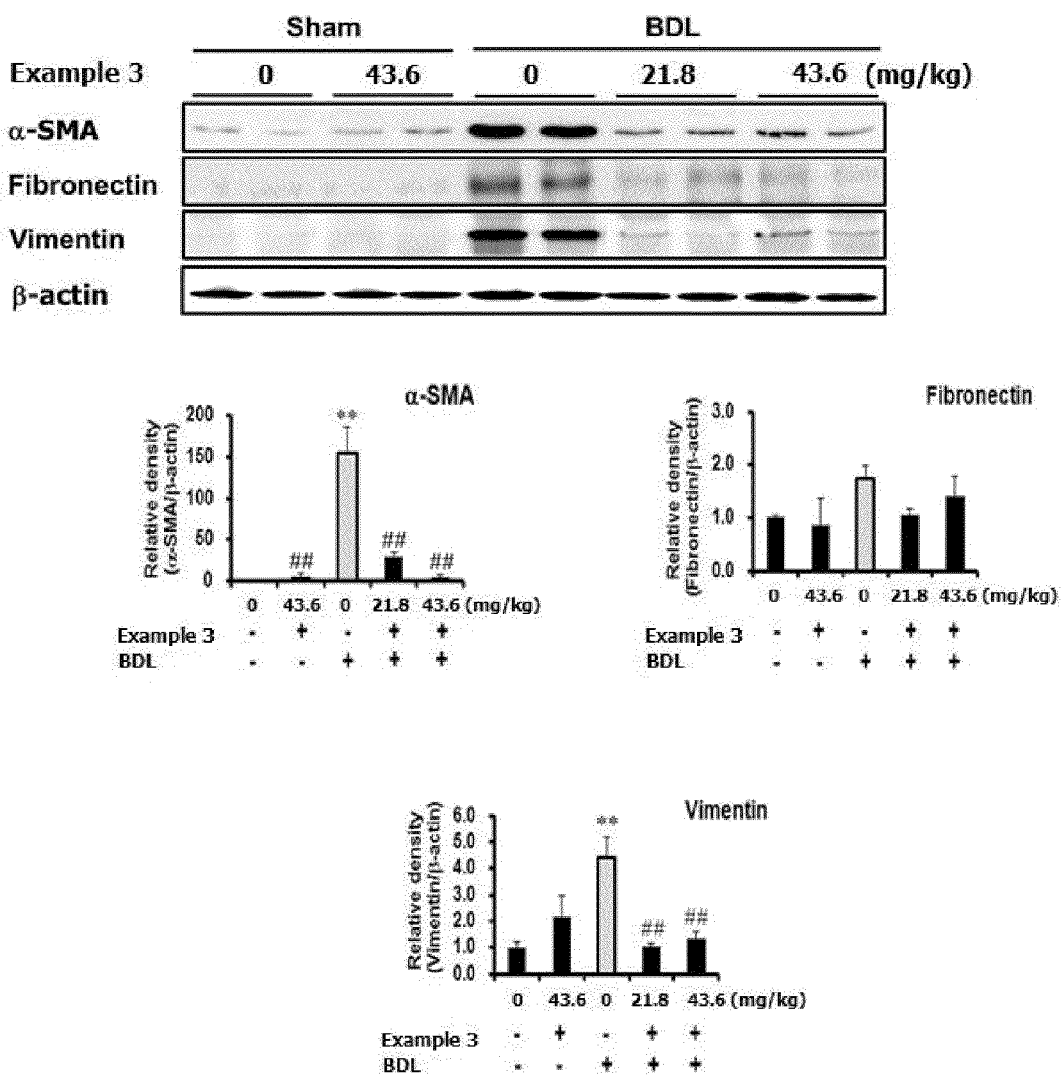
Figure 14D:
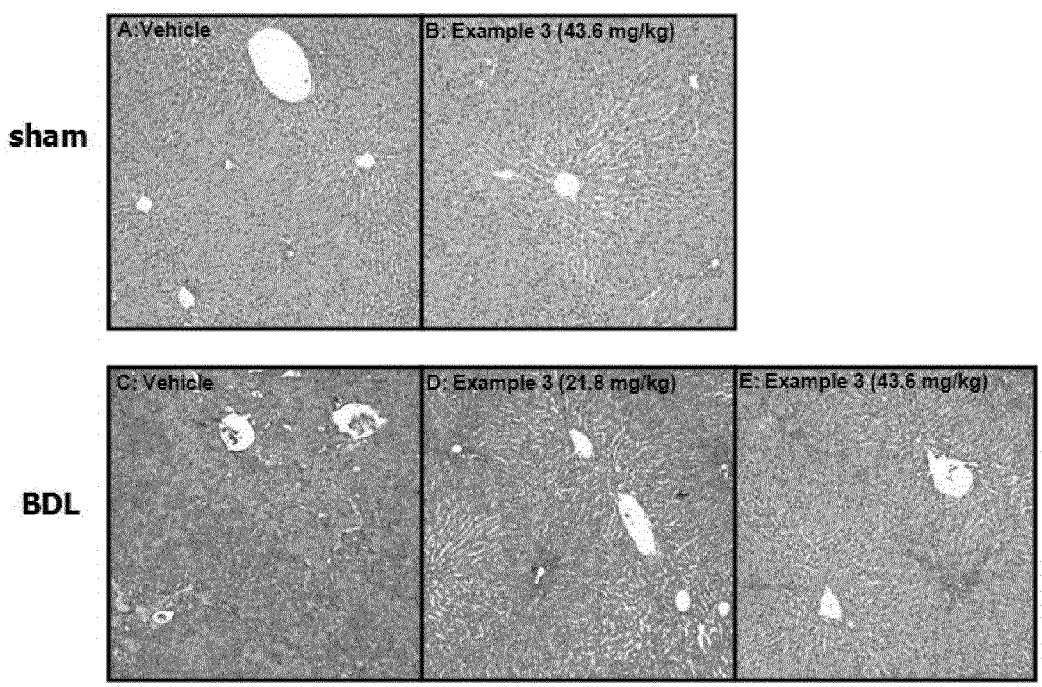
Figure 15A:
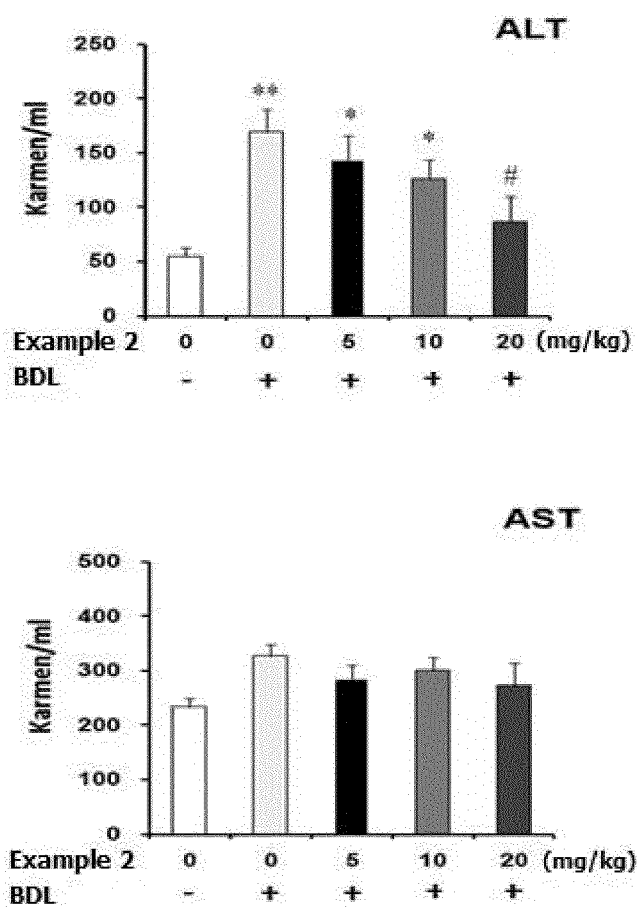
FIGS. 15A, 15B, and 15C show effect of Example 2 on the bile duct-ligated liver fibrosis in rats. Example 2 (5, 10, or 20 mg/kg) dissolved in artificial gastric fluid formulation (vehicle) was given to rats orally three times per week for four weeks starting from BDL surgery. (15A). Activity of ALT and AST. (15B). Level of α-SMA and fibronectin proteins in the liver. (15C). Hematoxylin and eosin (H&E) staining of liver tissues.
Figure 15B:
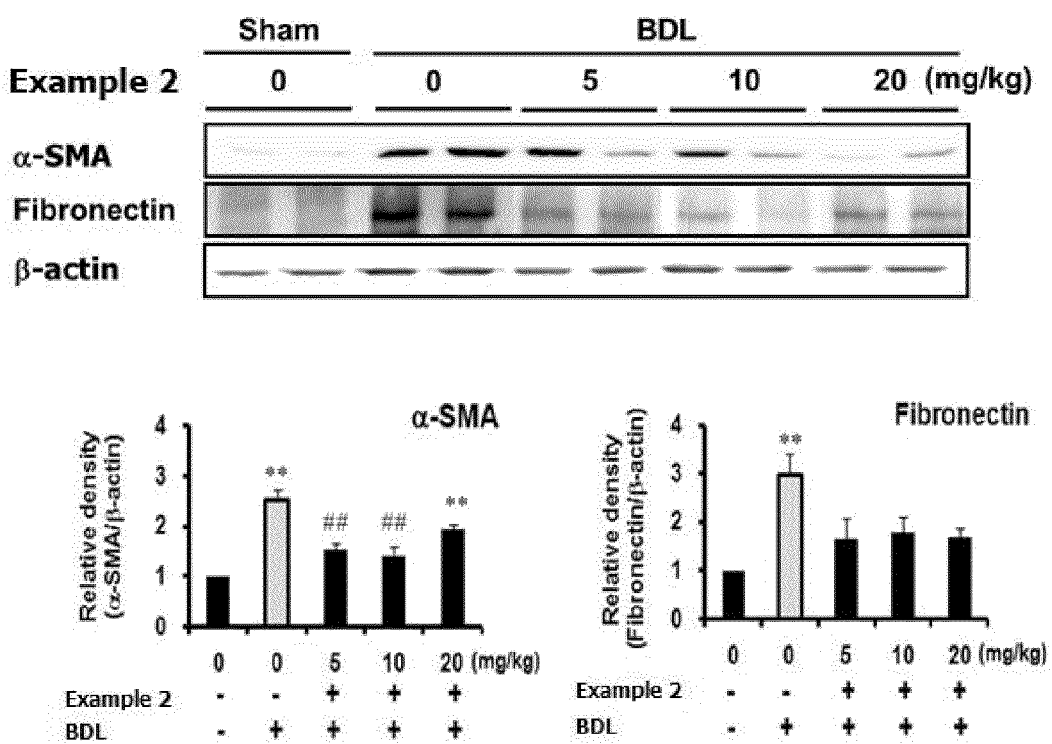
Figure 15C:
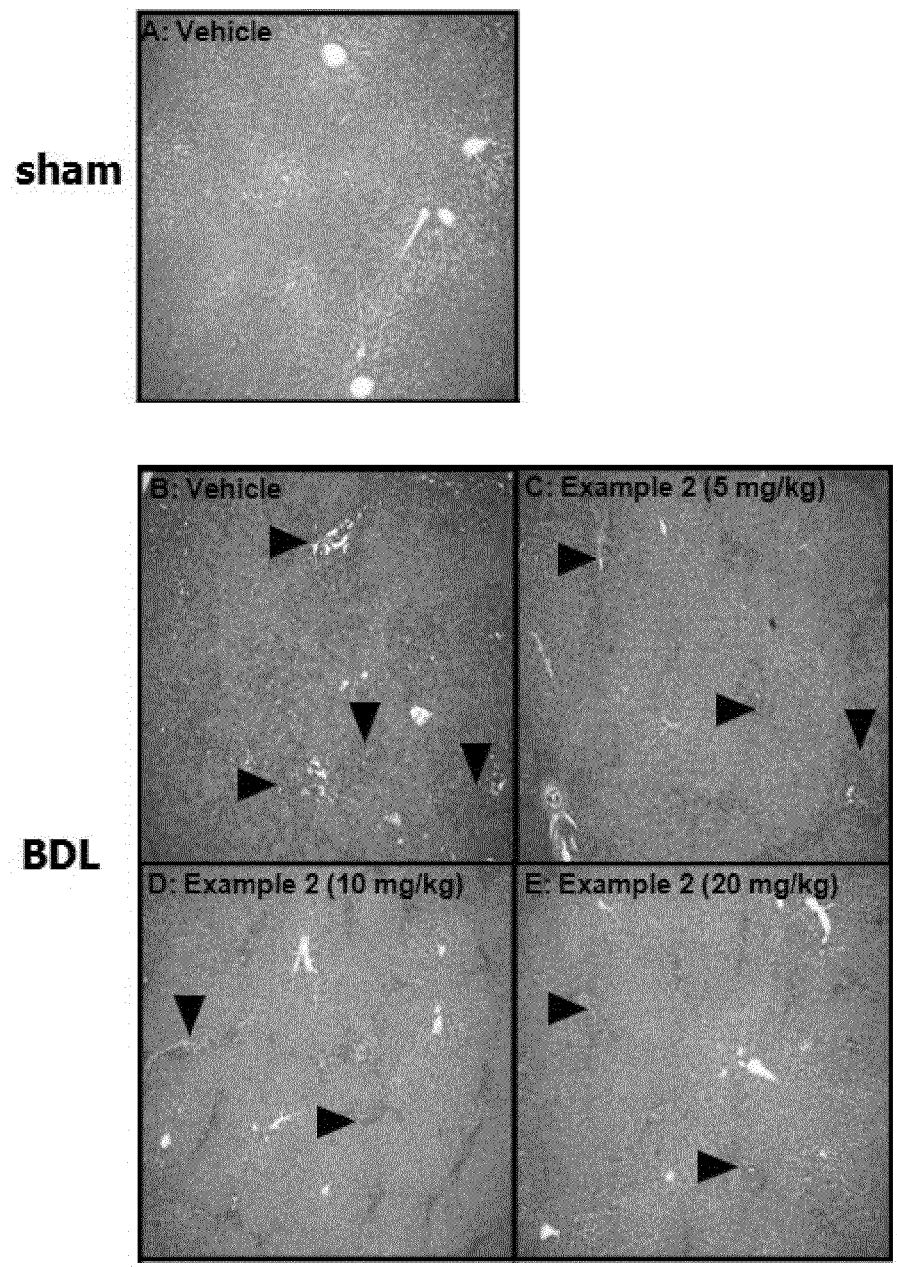
Figure 16A:
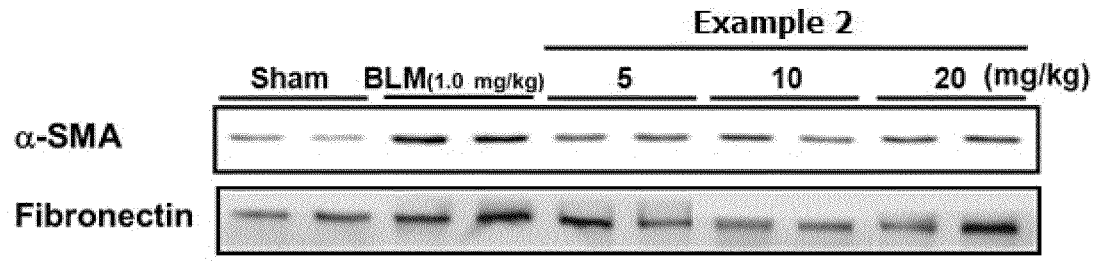
FIGS. 16A and 16B show effect of Example 2 on the bleomycin-induced lung fibrosis in mice. Example 2 (5, 10, or 20 mg/kg) dissolved in artificial gastric fluid formulation (vehicle) was given to mice orally five times per week for two weeks starting from day 7. (16A). Level of α-SMA and fibronectin proteins in the lung. (16B). Hematoxylin and eosin (H&E) staining of lung tissues.
Figure 16B:
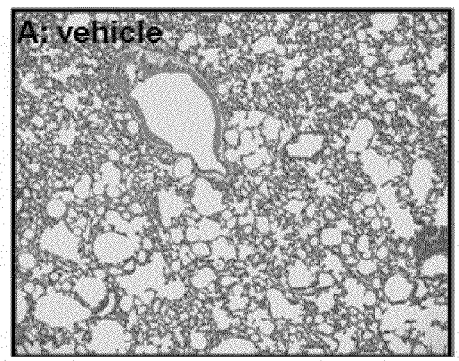
Figure 16B:
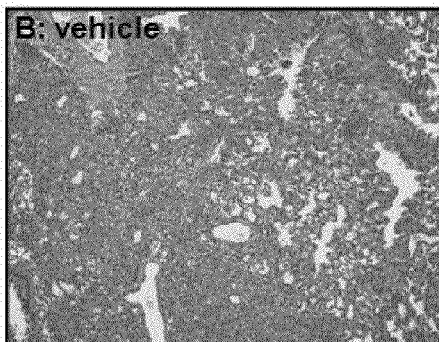
Figure 16B:
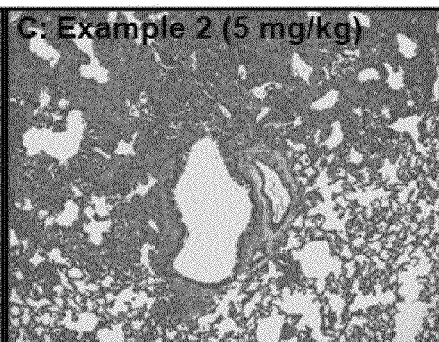
Figure 16B:
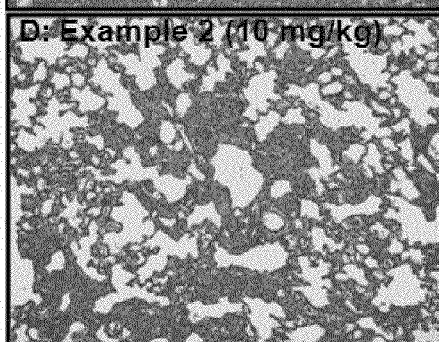
Figure 16B:
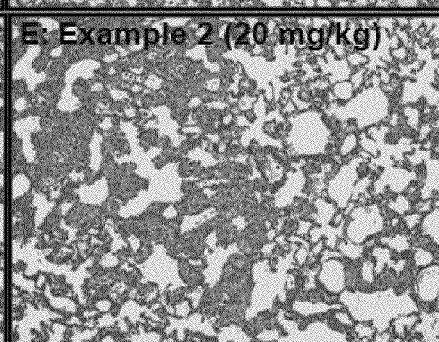

Table 1 shows structures and $^1$H NMR and MS spectral data of Examples 1-153,

Table 2 shows $IC_{50}$ values of selected Examples on ALK5 kinase phosphorylation, Table 3 shows either $IC_{50}$ values or % inhibition of Example 2 on various kinases phosphorylation, Table 4 shows effect of Example 3 on the body and organ weight changes in BDL rats, and Table 5 shows effect of Example 2 on the body and organ weight changes in BDL rats.

DETAILED DESCRIPTION OF PREFERRED EMBODIMENTS

In an embodiment of the present invention, there is provided a compound of formula (I) or a pharmaceutically acceptable salt thereof:

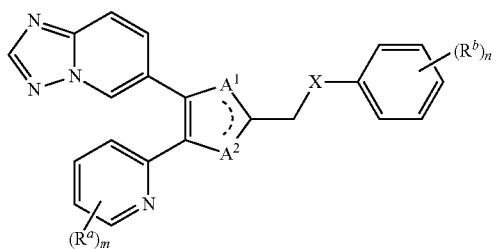

(I)

wherein each $R^a$ is independently H, halo, $C_{1-6}$alkyl, $C_{1-6}$haloalkyl, $C_{3-6}$cycloalkyl, OH, —O—$C_{1-6}$alkyl, —O—$C_{1-6}$halo alkyl, —O—$C_{3-6}$cycloalkyl, $NH_2$, —NH—$C_{1-6}$alkyl, —NH—$C_{1-6}$haloalkyl, —NH—$C_{3-6}$cycloalkyl, —S—$C_{1-6}$alkyl, —S—$C_{1-6}$haloalkyl, —S—$C_{3-6}$cycloalkyl, CN, or $NO_2$;

m is 0, 1, 2, 3, or 4;

one of $A^1$ and $A^2$ is N and the other is $NR^1$, wherein $R^1$ is H, OH, $C_{1-6}$alkyl, $C_{1-6}$ haloalkyl, or $C_{3-6}$cycloalkyl;

X is a bond, —$(CH_2)_p$—, —$NR^2$—, —O—, or —S—, wherein p is 0 or 1, and $R^2$ is H or $C_{1-3}$alkyl;

each $R^b$ is independently H, halo, $C_{1-6}$alkyl, $C_{1-6}$haloalkyl, $C_{3-6}$cycloalkyl, $C_{2-6}$alkenyl, $C_{2-6}$alkynyl, —$(CH_2)_q$—$OR^3$, —$(CH_2)_q$—$NR^3R^4$, —$(CH_2)_q$—$SR^3$, —$(CH_2)_q$—$NO_2$, —$(CH_2)_q$—CONHOH, —$(CH_2)_q$—CN, —$(CH_2)_q$—$COR^3$, —$(CH_2)_q$—$CO_2R^3$, —$(CH_2)_q$—$CONR^3R^4$, —$(CH_2)_q$-tetrazole, —$(CH_2)_q$—CH=CH—CN, —$(CH_2)_q$—CH=CH—$CO_2R^3$, —$(CH_2)_q$—CH=CH—$CONR^3R^4$, —$(CH_2)_q$—CH=CH-tetrazole, —$(CH_2)_q$—$NHCOR^3$, —$(CH_2)_q$—$NHCO_2R^3$, —$(CH_2)_q$—$CONHSO_2R^3$, —$(CH_2)_q$—$NHSO_2R^3$, —$(CH_2)_q$—C≡C—CN, —$(CH_2)_q$—C≡C—$CO_2R^3$, —$(CH_2)_q$—C≡C—$CONR^3R^4$, —$(CH_2)_q$—C≡C-tetrazole, —$(CH_2)_q$—$SOR^5$, —$(CH_2)_q$—$SO_2R^5$, or —$(CH_2)_r$—$(OR^3)_2$, wherein $R^3$ and $R^4$ are independently H, $C_{1-6}$alkyl, $C_{1-6}$haloalkyl, or $C_{3-6}$cycloalkyl; or taken together with the nitrogen atom to which they are attached form a mono-cyclic ring such as imidazole, pyrrolidine, piperidine, morpholine, piperazine and homopiperazine; $R^5$ is $C_{1-6}$alkyl, $C_{1-6}$haloalkyl, or $C_{3-6}$cycloalkyl; q is 0, 1, 2, 3, or 4; and r is 1, 2, 3, or 4;

n is 0, 1, 2, 3, 4, or 5.

As used herein, the double bond indicated by the dotted lines of formula (I), represent the possible tautomeric ring forms of the compounds falling within the scope of this invention, the double bond being to the unsubstituted nitrogen.

Preferably, $R^a$ is $C_{1-3}$alkyl or halo.

Preferably, m is 1 or 2.

Preferably, one of $A^1$ and $A^2$ is N and the other is $NR^1$, wherein $R^1$ is H.

Preferably, X is —$(CH_2)_p$— or —$NR^2$—, wherein p is 0 and $R^2$ is H.

Preferably, $R^b$ is halo, $C_{1-3}$alkyl, $C_{1-3}$haloalkyl, $C_{3-4}$cycloalkyl, $C_{2-4}$alkenyl, $C_{2-4}$alkynyl, $(CH_2)_q$—$OR^3$, —$(CH_2)_q$—$NR^3R^4$, —$(CH_2)_q$—$SR^3$, —$(CH_2)_q$—CN, —$(CH_2)_q$—$COR^3$, $(CH_2)_q$—$CO_2R^3$, —$(CH_2)_q$—$CONR^3R^4$, —$(CH_2)_q$—$NHCOR^3$, —$(CH_2)_q$—$NHSO_2R^3$, —$(CH_2)_q$—$SOR^5$, or —$(CH_2)_q$—$SO_2R^5$, wherein $R^3$ and $R^4$ are independently H, $C_{1-3}$alkyl, $C_{1-3}$haloalkyl, or $C_{3-4}$cycloalkyl; or taken together with the nitrogen atom to which they are attached form a mono-cyclic ring such as imidazole, pyrrolidine, piperidine, morpholine, piperazine and homopiperazine; $R^5$ is methyl; and q is 0, 1, or 2.

Preferably, n is 1, 2, or 3.

Specific compounds of the invention which may be mentioned include the following and pharmaceutically acceptable salts thereof:

N-((4-([1,2,4]triazolo[1,5-a]pyridin-6-yl)-5-(6-methylpyridin-2-yl)-1H-imidazol-2-yl)methyl)aniline;
N-((4-([1,2,4]triazolo[1,5-a]pyridin-6-yl)-5-(6-methylpyridin-2-yl)-1H-imidazol-2-yl)methyl)-2-fluoroaniline;
N-((4-([1,2,4]triazolo[1,5-a]pyridin-6-yl)-5-(6-methylpyridin-2-yl)-1H-imidazol-2-yl)methyl)-3-fluoroaniline;
N-((4-([1,2,4]triazolo[1,5-a]pyridin-6-yl)-5-(6-methylpyridin-2-yl)-1H-imidazol-2-yl)methyl)-4-fluoroaniline;
N-((4-([1,2,4]triazolo[1,5-a]pyridin-6-yl)-5-(6-methylpyridin-2-yl)-1H-imidazol-2-yl)methyl)-2,3-difluoroaniline;
N-((4-([1,2,4]triazolo[1,5-a]pyridin-6-yl)-5-(6-methylpyridin-2-yl)-1H-imidazol-2-yl)methyl)-3,4-difluoroaniline;
N-((4-([1,2,4]triazolo[1,5-a]pyridin-6-yl)-5-(6-methylpyridin-2-yl)-1H-imidazol-2-yl)methyl)-3,5-difluoroaniline;
N-((4-([1,2,4]triazolo[1,5-a]pyridin-6-yl)-5-(6-methylpyridin-2-yl)-1H-imidazol-2-yl)methyl)-2-chloroaniline;
N-((4-([1,2,4]triazolo[1,5-a]pyridin-6-yl)-5-(6-methylpyridin-2-yl)-1H-imidazol-2-yl)methyl)-3-chloroaniline;
N-((4-([1,2,4]triazolo[1,5-a]pyridin-6-yl)-5-(6-methylpyridin-2-yl)-1H-imidazol-2-yl)methyl)-4-chloroaniline;
N-((4-([1,2,4]triazolo[1,5-a]pyridin-6-yl)-5-(6-methylpyridin-2-yl)-1H-imidazol-2-yl)methyl)-2,3-dichloroaniline;
N-((4-([1,2,4]triazolo[1,5-a]pyridin-6-yl)-5-(6-methylpyridin-2-yl)-1H-imidazol-2-yl)methyl)-3,4-dichloroaniline;
N-((4-([1,2,4]triazolo[1,5-a]pyridin-6-yl)-5-(6-methylpyridin-2-yl)-1H-imidazol-2-yl)methyl)-3,5-dichloroaniline;
N-((4-([1,2,4]triazolo[1,5-a]pyridin-6-yl)-5-(6-methylpyridin-2-yl)-1H-imidazol-2-yl)methyl)-2-bromoaniline;
N-((4-([1,2,4]triazolo[1,5-a]pyridin-6-yl)-5-(6-methylpyridin-2-yl)-1H-imidazol-2-yl)methyl)-3-bromoaniline;
N-((4-([1,2,4]triazolo[1,5-a]pyridin-6-yl)-5-(6-methylpyridin-2-yl)-1H-imidazol-2-yl)methyl)-4-bromoaniline;
N-((4-([1,2,4]triazolo[1,5-a]pyridin-6-yl)-5-(6-methylpyridin-2-yl)-1H-imidazol-2-yl)methyl)-2-methylaniline;
N-((4-([1,2,4]triazolo[1,5-a]pyridin-6-yl)-5-(6-methylpyridin-2-yl)-1H-imidazol-2-yl)methyl)-3-methylaniline;
N-((4-([1,2,4]triazolo[1,5-a]pyridin-6-yl)-5-(6-methylpyridin-2-yl)-1H-imidazol-2-yl)methyl)-4-methylaniline;
N-((4-([1,2,4]triazolo[1,5-a]pyridin-6-yl)-5-(6-methylpyridin-2-yl)-1H-imidazol-2-yl)methyl)-2,3-dimethylaniline;
N-((4-([1,2,4]triazolo[1,5-a]pyridin-6-yl)-5-(6-methylpyridin-2-yl)-1H-imidazol-2-yl)methyl)-3,4-dimethylaniline;
N-((4-([1,2,4]triazolo[1,5-a]pyridin-6-yl)-5-(6-methylpyridin-2-yl)-1H-imidazol-2-yl)methyl)-3,5-dimethylaniline;
N-((4-([1,2,4]triazolo[1,5-a]pyridin-6-yl)-5-(6-methylpyridin-2-yl)-1H-imidazol-2-yl)methyl)-2-ethylaniline;
N-((4-([1,2,4]triazolo[1,5-a]pyridin-6-yl)-5-(6-methylpyridin-2-yl)-1H-imidazol-2-yl)methyl)-3-ethylaniline;
N-((4-([1,2,4]triazolo[1,5-a]pyridin-6-yl)-5-(6-methylpyridin-2-yl)-1H-imidazol-2-yl)methyl)-2-isopropylaniline;
N-((4-([1,2,4]triazolo[1,5-a]pyridin-6-yl)-5-(6-methylpyridin-2-yl)-1H-imidazol-2-yl)methyl)-3-isopropylaniline;
N-((4-([1,2,4]triazolo[1,5-a]pyridin-6-yl)-5-(6-methylpyridin-2-yl)-1H-imidazol-2-yl)methyl)-4-isopropylaniline;
N-((4-([1,2,4]triazolo[1,5-a]pyridin-6-yl)-5-(6-methylpyridin-2-yl)-1H-imidazol-2-yl)methyl)-2-vinylaniline;
N-((4-([1,2,4]triazolo[1,5-a]pyridin-6-yl)-5-(6-methylpyridin-2-yl)-1H-imidazol-2-yl)methyl)-3-vinylaniline;
N-((4-([1,2,4]triazolo[1,5-a]pyridin-6-yl)-5-(6-methylpyridin-2-yl)-1H-imidazol-2-yl)methyl)-4-vinylaniline;
N-((4-([1,2,4]triazolo[1,5-a]pyridin-6-yl)-5-(6-methylpyridin-2-yl)-1H-imidazol-2-yl)methyl)-3-ethynylaniline;
N-((4-([1,2,4]triazolo[1,5-a]pyridin-6-yl)-5-(6-methylpyridin-2-yl)-1H-imidazol-2-yl)methyl)-2-methoxyaniline;

N-((4-([1,2,4]triazolo[1,5-a]pyridin-6-yl)-5-(6-methylpyridin-2-yl)-1H-imidazol-2-yl)methyl)-3-methoxyaniline;
N-((4-([1,2,4]triazolo[1,5-a]pyridin-6-yl)-5-(6-methylpyridin-2-yl)-1H-imidazol-2-yl)methyl)-4-methoxyaniline;
N-((4-([1,2,4]triazolo[1,5-a]pyridin-6-yl)-5-(6-methylpyridin-2-yl)-1H-imidazol-2-yl)methyl)-2,3-dimethoxyaniline;
N-((4-([1,2,4]triazolo[1,5-a]pyridin-6-yl)-5-(6-methylpyridin-2-yl)-1H-imidazol-2-yl)methyl)-3,4-dimethoxyaniline;
N-((4-([1,2,4]triazolo[1,5-a]pyridin-6-yl)-5-(6-methylpyridin-2-yl)-1H-imidazol-2-yl)methyl)-3,5-dimethoxyaniline;
N-((4-([1,2,4]triazolo[1,5-a]pyridin-6-yl)-5-(6-methylpyridin-2-yl)-1H-imidazol-2-yl)methyl)-2-(methoxymethyl)aniline;
N-((4-([1,2,4]triazolo[1,5-a]pyridin-6-yl)-5-(6-methylpyridin-2-yl)-1H-imidazol-2-yl)methyl)-3-(methoxymethyl)aniline;
N-((4-([1,2,4]triazolo[1,5-a]pyridin-6-yl)-5-(6-methylpyridin-2-yl)-1H-imidazol-2-yl)methyl)-4-(methoxymethyl)aniline;
N-((4-([1,2,4]triazolo[1,5-a]pyridin-6-yl)-5-(6-methylpyridin-2-yl)-1H-imidazol-2-yl)methyl)-2-(trifluoromethoxy)aniline;
N-((4-([1,2,4]triazolo[1,5-a]pyridin-6-yl)-5-(6-methylpyridin-2-yl)-1H-imidazol-2-yl)methyl)-3-(trifluoromethoxy)aniline;
N-((4-([1,2,4]triazolo[1,5-a]pyridin-6-yl)-5-(6-methylpyridin-2-yl)-1H-imidazol-2-yl)methyl)-4-(trifluoromethoxy)aniline;
N-((4-([1,2,4]triazolo[1,5-a]pyridin-6-yl)-5-(6-methylpyridin-2-yl)-1H-imidazol-2-yl)methyl)-2-(methylthio)aniline;
N-((4-([1,2,4]triazolo[1,5-a]pyridin-6-yl)-5-(6-methylpyridin-2-yl)-1H-imidazol-2-yl)methyl)-3-(methylthio)aniline;
N-((4-([1,2,4]triazolo[1,5-a]pyridin-6-yl)-5-(6-methylpyridin-2-yl)-1H-imidazol-2-yl)methyl)-4-(methylthio)aniline;
2-((4-([1,2,4]triazolo[1,5-a]pyridin-6-yl)-5-(6-methylpyridin-2-yl)-1H-imidazol-2-yl)methylamino)benzonitrile;
3-((4-([1,2,4]triazolo[1,5-a]pyridin-6-yl)-5-(6-methylpyridin-2-yl)-1H-imidazol-2-yl)methylamino)benzonitrile;
4-((4-([1,2,4]triazolo[1,5-a]pyridin-6-yl)-5-(6-methylpyridin-2-yl)-1H-imidazol-2-yl)methylamino)benzonitrile;
3-((4-([1,2,4]triazolo[1,5-a]pyridin-6-yl)-5-(6-methylpyridin-2-yl)-1H-imidazol-2-yl)methylamino)phthalonitrile;
2-((4-([1,2,4]triazolo[1,5-a]pyridin-6-yl)-5-(6-methylpyridin-2-yl)-1H-imidazol-2-yl)methylamino)benzamide;
3-((4-([1,2,4]triazolo[1,5-a]pyridin-6-yl)-5-(6-methylpyridin-2-yl)-1H-imidazol-2-yl)methylamino)benzamide;
4-((4-([1,2,4]triazolo[1,5-a]pyridin-6-yl)-5-(6-methylpyridin-2-yl)-1H-imidazol-2-yl)methylamino)benzamide;
2-(3-((4-([1,2,4]triazolo[1,5-a]pyridin-6-yl)-5-(6-methylpyridin-2-yl)-1H-imidazol-2-yl)methylamino)phenyl)acetonitrile;
2-(4-((4-([1,2,4]triazolo[1,5-a]pyridin-6-yl)-5-(6-methylpyridin-2-yl)-1H-imidazol-2-yl)methylamino)phenyl)acetonitrile;
1-(3-((4-([1,2,4]triazolo[1,5-a]pyridin-6-yl)-5-(6-methylpyridin-2-yl)-1H-imidazol-2-yl)methylamino)phenyl)ethanone;
1-(4-((4-([1,2,4]triazolo[1,5-a]pyridin-6-yl)-5-(6-methylpyridin-2-yl)-1H-imidazol-2-yl)methylamino)phenyl)ethanone;
Methyl 3-((4-([1,2,4]triazolo[1,5-a]pyridin-6-yl)-5-(6-methylpyridin-2-yl)-1H-imidazol-2-yl)methylamino)benzoate;
Methyl 4-((4-([1,2,4]triazolo[1,5-a]pyridin-6-yl)-5-(6-methylpyridin-2-yl)-1H-imidazol-2-yl)methylamino)benzoate;
N-(2-((4-([1,2,4]triazolo[1,5-a]pyridin-6-yl)-5-(6-methylpyridin-2-yl)-1H-imidazol-2-yl)methylamino)phenyl)acetamide;
N-(3-((4-([1,2,4]triazolo[1,5-a]pyridin-6-yl)-5-(6-methylpyridin-2-yl)-1H-imidazol-2-yl)methylamino)phenyl)acetamide;
N-(4-((4-([1,2,4]triazolo[1,5-a]pyridin-6-yl)-5-(6-methylpyridin-2-yl)-1H-imidazol-2-yl)methylamino)phenyl)acetamide;
N-(2-((4-([1,2,4]triazolo[1,5-a]pyridin-6-yl)-5-(6-methylpyridin-2-yl)-1H-imidazol-2-yl)methylamino)phenyl)methanesulfonamide;
N-(3-((4-([1,2,4]triazolo[1,5-a]pyridin-6-yl)-5-(6-methylpyridin-2-yl)-1H-imidazol-2-yl)methylamino)phenyl)methanesulfonamide;
N-(4-((4-([1,2,4]triazolo[1,5-c]pyridin-6-yl)-5-(6-methylpyridin-2-yl)-1H-imidazol-2-yl)methylamino)phenyl)methanesulfonamide;
$N^1$-((4-([1,2,4]triazolo[1,5-c]pyridin-6-yl)-5-(6-methylpyridin-2-yl)-1H-imidazol-2-yl)methyl)-$N^2,N^2$-dimethylbenzene-1,2-diamine;
$N^1$-((4-([1,2,4]triazolo[1,5-c]pyridin-6-yl)-5-(6-methylpyridin-2-yl)-1H-imidazol-2-yl)methyl)-$N^3,N^3$-dimethylbenzene-1,3-diamine;
N-((4-([1,2,4]triazolo[1,5-c]pyridin-6-yl)-5-(6-methylpyridin-2-yl)-1H-imidazol-2-yl)methyl)-2-(pyrrolidin-1-yl)aniline;
N-((4-([1,2,4]triazolo[1,5-c]pyridin-6-yl)-5-(6-methylpyridin-2-yl)-1H-imidazol-2-yl)methyl)-2-morpholinoaniline;
N-((4-([1,2,4]triazolo[1,5-c]pyridin-6-yl)-5-(6-methylpyridin-2-yl)-1H-imidazol-2-yl)methyl)-3-morpholinoaniline;
$N^3$-((4-([1,2,4]triazolo[1,5-c]pyridin-6-yl)-5-(6-methylpyridin-2-yl)-1H-imidazol-2-yl)methyl)-4-fluoro-$N^1,N^1$-dimethylbenzene-1,3-diamine;
3-((4-([1,2,4]triazolo[1,5-c]pyridin-6-yl)-5-(6-methylpyridin-2-yl)-1H-imidazol-2-yl)methylamino)-5-(dimethylamino)benzonitrile;
3-((4-([1,2,4]triazolo[1,5-c]pyridin-6-yl)-5-(6-methylpyridin-2-yl)-1H-imidazol-2-yl)methylamino)-4-(dimethylamino)benzonitrile;
N-((4-([1,2,4]triazolo[1,5-c]pyridin-6-yl)-5-(6-methylpyridin-2-yl)-1H-imidazol-2-yl)methyl)-2-((dimethylamino)methyl)aniline;
N-((4-([1,2,4]triazolo[1,5-c]pyridin-6-yl)-5-(6-methylpyridin-2-yl)-1H-imidazol-2-yl)methyl)-3-((dimethylamino)methyl)aniline;
N-((4-([1,2,4]triazolo[1,5-c]pyridin-6-yl)-5-(6-methylpyridin-2-yl)-1H-imidazol-2-yl)methyl)-2-(pyrrolidin-1-ylmethyl)aniline;
N-((4-([1,2,4]triazolo[1,5-c]pyridin-6-yl)-5-(6-methylpyridin-2-yl)-1H-imidazol-2-yl)methyl)-3-(pyrrolidin-1-ylmethyl)aniline;
N-((4-([1,2,4]triazolo[1,5-c]pyridin-6-yl)-5-(6-methylpyridin-2-yl)-1H-imidazol-2-yl)methyl)-2-(morpholinomethyl)aniline;
N-((4-([1,2,4]triazolo[1,5-c]pyridin-6-yl)-5-(6-methylpyridin-2-yl)-1H-imidazol-2-yl)methyl)-3-(morpholinomethyl)aniline;

N-((4-([1,2,4]triazolo[1,5-c]pyridin-6-yl)-5-(6-methylpyridin-2-yl)-1H-imidazol-2-yl)methyl)-5-((dimethylamino)methyl)-2-fluoroaniline;
N-((4-([1,2,4]triazolo[1,5-a]pyridin-6-yl)-5-(6-methylpyridin-2-yl)-1H-imidazol-2-yl)methyl)-3-((dimethylamino)methyl)-2-fluoroaniline;
N-((4-([1,2,4]triazolo[1,5-a]pyridin-6-yl)-5-(6-methylpyridin-2-yl)-1H-imidazol-2-yl)methyl)-2-fluoro-3-(pyrrolidin-1-ylmethyl)aniline;
N-((4-([1,2,4]triazolo[1,5-a]pyridin-6-yl)-5-(6-methylpyridin-2-yl)-1H-imidazol-2-yl)methyl)-2-fluoro-3-(morpholinomethyl)aniline;
3-((4-([1,2,4]triazolo[1,5-a]pyridin-6-yl)-5-(6-methylpyridin-2-yl)-1H-imidazol-2-yl)methylamino)-4-((dimethylamino)methyl)benzonitrile;
3-((4-([1,2,4]triazolo[1,5-a]pyridin-6-yl)-5-(6-methylpyridin-2-yl)-1H-imidazol-2-yl)methylamino)-2-((dimethylamino)methyl)benzonitrile;
3-((4-([1,2,4]triazolo[1,5-a]pyridin-6-yl)-5-(6-methylpyridin-2-yl)-1H-imidazol-2-yl)methylamino)-5-((dimethylamino)methyl)benzonitrile;
3-((4-([1,2,4]triazolo[1,5-a]pyridin-6-yl)-5-(6-methylpyridin-2-yl)-1H-imidazol-2-yl)methylamino)-4-(pyrrolidin-1-ylmethyl)benzonitrile;
3-((4-([1,2,4]triazolo[1,5-a]pyridin-6-yl)-5-(6-methylpyridin-2-yl)-1H-imidazol-2-yl)methylamino)-2-(pyrrolidin-1-ylmethyl)benzonitrile;
3-((4-([1,2,4]triazolo[1,5-a]pyridin-6-yl)-5-(6-methylpyridin-2-yl)-1H-imidazol-2-yl)methylamino)-5-(pyrrolidin-1-ylmethyl)benzonitrile;
3-((4-([1,2,4]triazolo[1,5-a]pyridin-6-yl)-5-(6-methylpyridin-2-yl)-1H-imidazol-2-yl)methylamino)-4-(morpholinomethyl)benzonitrile;
3-((4-([1,2,4]triazolo[1,5-a]pyridin-6-yl)-5-(6-methylpyridin-2-yl)-1H-imidazol-2-yl)methylamino)-2-(morpholinomethyl)benzonitrile;
3-((4-([1,2,4]triazolo[1,5-a]pyridin-6-yl)-5-(6-methylpyridin-2-yl)-1H-imidazol-2-yl)methylamino)-5-(morpholinomethyl)benzonitrile;
N-((4-([1,2,4]triazolo[1,5-a]pyridin-6-yl)-5-(6-methylpyridin-2-yl)-1H-imidazol-2-yl)methyl)-2-(2-(dimethylamino)ethyl)aniline;
N-((4-([1,2,4]triazolo[1,5-a]pyridin-6-yl)-5-(6-methylpyridin-2-yl)-1H-imidazol-2-yl)methyl)-3-(2-(dimethylamino)ethyl)aniline;
3-((4-([1,2,4]triazolo[1,5-a]pyridin-6-yl)-5-(6-ethylpyridin-2-yl)-1H-imidazol-2-yl)methylamino)benzonitrile;
N-((4-([1,2,4]triazolo[1,5-a]pyridin-6-yl)-5-(6-ethylpyridin-2-yl)-1H-imidazol-2-yl)methyl)-2-fluoroaniline;
N-((4-([1,2,4]triazolo[1,5-a]pyridin-6-yl)-5-(6-methylpyridin-2-yl)-1H-imidazol-2-yl)methyl)-2-fluoro-N-methylaniline;
3-((4-([1,2,4]triazolo[1,5-a]pyridin-6-yl)-5-(6-methylpyridin-2-yl)-1H-imidazol-2-yl)methyl)(methyl)amino)benzonitrile;
3-((4-([1,2,4]triazolo[1,5-a]pyridin-6-yl)-5-(6-methylpyridin-2-yl)-1H-imidazol-2-yl)methyl)(methyl)amino)benzamide;
6-(2-benzyl-5-(6-methylpyridin-2-yl)-1H-imidazol-4-yl)-[1,2,4]triazolo[1,5-a]pyridine;
6-(2-(2-fluorobenzyl)-5-(6-methylpyridin-2-yl)-1H-imidazol-4-yl)-[1,2,4]triazolo[1,5-a]pyridine;
3-((4-([1,2,4]triazolo[1,5-a]pyridin-6-yl)-5-(6-methylpyridin-2-yl)-1H-imidazol-2-yl)methyl)benzonitrile;
3-((4-([1,2,4]triazolo[1,5-a]pyridin-6-yl)-5-(6-methylpyridin-2-yl)-1H-imidazol-2-yl)methyl)benzamide;
6-(5-(6-methylpyridin-2-yl)-2-(phenoxymethyl)-1H-imidazol-4-yl)-[1,2,4]triazolo[1,5-a]pyridine;
6-(2-((2-fluorophenoxy)methyl)-5-(6-methylpyridin-2-yl)-1H-imidazol-4-yl)-[1,2,4]triazolo[1,5-a]pyridine;
3-((4-([1,2,4]triazolo[1,5-a]pyridin-6-yl)-5-(6-methylpyridin-2-yl)-1H-imidazol-2-yl)methoxy)benzonitrile;
3-((4-([1,2,4]triazolo[1,5-a]pyridin-6-yl)-5-(6-methylpyridin-2-yl)-1H-imidazol-2-yl)methoxy)benzamide;
6-(5-(6-methylpyridin-2-yl)-2-(phenylthiomethyl)-1H-imidazol-4-yl)-[1,2,4]triazolo[1,5-a]pyridine;
6-(2-((2-fluorophenylthio)methyl)-5-(6-methylpyridin-2-yl)-1H-imidazol-4-yl)-[1,2,4]triazolo[1,5-a]pyridine.

The compounds of the present invention typically are small organic molecules (non-peptide small molecules), generally less than about 1,000 daltons in size. Preferred non-peptide small molecules have molecular weights of less than about 750 daltons, more preferably less than about 500 daltons.

Compounds of formula (I) may also be supplied in the form of a "prodrug" which is designed to release compound of formula (I) when administered to a subject. Prodrug formed designs are well known in the art, and depend on the substituents contained in compound of formula (I). For example, a substituent containing hydroxyl could be coupled to a carrier which renders the compound biologically inactive until it is removed by endogenous enzymes or, for example, by enzymes targeted to a particular receptor or location in the subject.

A compound of formula (I) that is acidic in nature (e.g., having a carboxyl or phenolic hydroxyl group) can form a pharmaceutically acceptable salt such as a sodium, potassium, calcium, or gold salt. Also within the scope of the invention are salts formed with pharmaceutically acceptable amines such as ammonia, alkyl amines, hydroxyalkylamines, and N-methylglycamine. A compound of formula (I) can be treated with an acid to form acid addition salts. Examples of such acids include hydrochloric acid, hydrobromic acid, hydroiodic acid, sulfuric acid, methanesulfonic acid, phosphoric acid, p-bromophenylsulfonic acid, carbonic acid, succinic acid, citric acid, benzoic acid, oxalic acid, malonic acid, salicyclic acid, malic acid, fumaric acid, ascorbic acid, maleic acid, acetic acid, and other mineral and organic acids well known to those skilled in the art. The acid addition salts can be prepared by treating a compound of formula (I) in its free base form with a sufficient amount of an acid (e.g., hydrochloric acid) to produce an acid addition salt (e.g., a hydrochloride salt). The acid addition salt can be converted back to its free base form by treating the salt with a suitable dilute aqueous basic solution (e.g., sodium hydroxide, sodium bicarbonate, potassium carbonate, or ammonia).

Some of the compounds of this invention may be crystallized or recrystallized from solvents such as aqueous and organic solvents. In such cases solvates may be formed. This invention includes within its scope stoichiometric solvates including hydrates as well as compounds containing variable amounts of water that may be produced by processes such as lyophilization.

Compounds of formula (I) may contain one or more asymmetric centers and thus can exist as enantiomers or diastereomers. It is to be understood that the invention includes both mixtures and separate individual isomers of compounds of the formula (I). Furthermore, certain compounds of formula (I) which contain alkenyl groups may exist as cis- or trans-isomers. In each instance, the invention includes both mixtures and separate individual isomers.

Compounds of formula (I) may also exist in tautomeric forms and the invention includes both mixtures and separate individual tautomers thereof.

Also included in the invention are radiolabelled derivatives of compounds of formula (I) which are suitable for biological studies.

As used herein, the term "alkyl" group refers to a saturated aliphatic hydrocarbon group containing 1-6 carbon atoms. An alkyl group can be straight or branched. Examples of an alkyl group include, but are not limited to, methyl, ethyl, propyl, isopropyl, butyl, isobutyl, sec-butyl, tert-butyl, n-pentyl, and n-hexyl. An alkyl group can be optionally substituted with one or more substituents such as alkoxy, cycloalkoxy, amino, nitro, carboxy, cyano, halo, hydroxyl, sulfo, or mercapto.

As used herein, the term "cycloalkyl" group refers to an aliphatic carbocyclic ring of 3-6 carbon atoms. Examples of cycloalkyl groups include cyclopropyl, cyclobutyl, cyclopentyl, and cyclohexyl.

As used herein, the term "haloalkyl" group refers to an alkyl group containing one or more halogen atoms. Examples of haloalkyl groups include fluoromethyl, chloromethyl, bromomethyl, and trifluoromethyl.

As used herein, the term "halo" group refers to fluorine, chlorine, bromine, or iodine.

As used herein, the term "alkenyl" group refers to an aliphatic carbon group that contains 2-6 carbon atoms and at least one double bond. Like an alkyl group, an alkenyl group can be straight or branched. Examples of an alkenyl group include, but are not limited to, vinyl, allyl, isoprenyl, 2-butenyl, and 2-hexenyl. An alkenyl group can be optionally substituted with one or more substituents such as alkoxy, cycloalkoxy, amino, nitro, carboxy, cyano, halo, hydroxyl, sulfo, or mercapto.

As used herein, the term "alkynyl" group refers to an aliphatic carbon group that contains 2-6 carbon atoms and has at least one triple bond. An alkynyl group can be straight or branched. Examples of an alkynyl group include, but are not limited to, ethynyl, propargyl, and butynyl. An alkynyl group can be optionally substituted with one or more substituents such as alkoxy, cycloalkoxy, amino, nitro, carboxy, cyano, halo, hydroxyl, sulfo, or mercapto.

As used herein, the term "ALK5 and/or ALK4 inhibitor" refers to a compound, other than inhibitory Smads, e.g. Smad6 and Smad7, which selectively inhibits the ALK5 and/or ALK4 receptors preferentially over p38 or type II receptors.

As used herein, the term "ALK5 and/or ALK4-mediated disease state" refers to any disease state which is mediated (or modulated) by ALK5 and/or ALK4, for example, a disease which is modulated by the inhibition of the phosphorylation of Smad2 and Smad3 in the TGF-β and/or activin signaling pathways.

As used herein, the term "ulcers" is used to include, but not to be limited to, diabetic ulcers, chronic ulcers, gastric ulcers, and duodenal ulcers.

The invention provides a compound of formula (I), or a pharmaceutically acceptable salt or solvate thereof, or a pharmaceutical composition containing either entity, for use in therapy.

The invention further provides the use of a compound of formula (I), or a pharmaceutically acceptable salt or solvate thereof, or a pharmaceutical composition containing either entity, for the manufacture of a medicament for the treatment of a disease, mediated by the ALK5 and/or ALK4 receptors in mammals.

ALK5- and/or ALK4-mediated disease states include, but are not limited to, glomerulonephritis, diabetic nephropathy, lupus nephritis, hypertension-induced nephropathy, renal interstitial fibrosis, renal fibrosis resulting from complications of drug exposure, HIV-associated nephropathy, transplant nephropathy, liver fibrosis due to all etiologies, hepatic dysfunction attributable to infections, alcohol-induced hepatitis, disorders of the biliary tree, cystic fibrosis, pulmonary fibrosis, interstitial lung disease, acute lung injury, adult respiratory distress syndrome, idiopathic pulmonary fibrosis, chronic obstructive pulmonary disease, pulmonary disease due to infectious or toxic agents, post-infarction cardiac fibrosis, congestive heart failure, dilated cardiomyopathy, myocarditis, intimal thickening, vascular stenosis, hypertension-induced vascular remodeling, pulmonary arterial hypertension, coronary restenosis, peripheral restenosis, carotid restenosis, stent-induced restenosis, atherosclerosis, ocular scarring, corneal scarring, proliferative vitreoretinopathy, glaucoma, intraocular pressure, excessive or hypertrophic scar or keloid formation in the dermis occurring during wound healing resulting from trauma or surgical wounds, peritoneal and sub-dermal adhesion, scleroderma, fibrosclerosis, progressive systemic sclerosis, dermatomyositis, polymyositis, arthritis, osteoporosis, ulcers, impaired neurological function, male erectile dysfunction, Peyronie's disease, Dupuytren's contracture, Alzheimer's disease, Raynaud's syndrome, radiation-induced fibrosis, thrombosis, tumor metastasis growth, multiple myeloma, melanoma, glioma, glioblastomas, leukemia, sarcomas, leiomyomas, mesothelioma, and carcinomas of lung, breast, colon, kidney, ovary, cervix, liver, biliary tract, gastrointestinal tract, pancreas, prostate, head, and neck.

The invention further provides a method of inhibiting the TGF-β and/or activin signaling pathways in human, for example, inhibiting the phosphorylation of Smad2 or Smad3 by ALK5 and/or ALK4.

The invention further provides a method of reducing the accumulation of excess extracellular matrix in human by inhibiting the TGF-β and/or activin signaling pathways, for example, inhibiting the phosphorylation of Smad2 or Smad3 by ALK5 and/or ALK4.

The invention further provides a method of inhibiting metastasis of tumor cells in human by inhibiting the TGF-β signaling pathway.

The invention further provides a method of treating carcinomas mediated by an overexpression of TGF-β in human by inhibiting the TGF-β signaling pathway.

The present invention is further illustrated in the following Examples, which should not be taken to limit the scope of the invention described in the claims.

TABLE 1

| Example | Structure | $^1$H NMR (ppm) | MS (ESI) m/z (MH$^+$) |
|---|---|---|---|
| 1 | 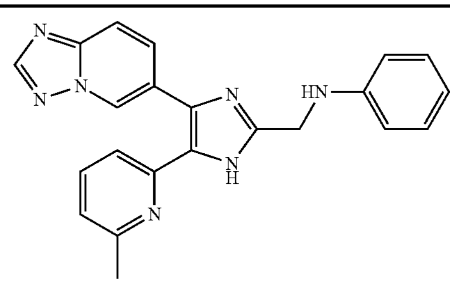 | (400 MHz, CDCl$_3$) δ 10.43 (br s, 1 H), 8.96 (s, 1 H), 8.37 (s, 1 H), 7.82 (dd, 1 H, J = 9.2, 1.6 Hz), 7.77 (dd, 1 H, J = 9.2, 0.8 Hz), 7.45 (t, 1 H, J = 7.6 Hz), 7.25-7.19 (m, 3 H), 7.01 (d, 1 H, J = 7.6 Hz), 6.80 (tt, 1 H, J = 8.0, 1.2 Hz), 6.74-6.72 (m, 2 H), 4.55 (s, 2 H), 2.53 (s, 3 H) | 382.19 |

TABLE 1-continued

| Example | Structure | $^1$H NMR (ppm) | MS (ESI) m/z (MH$^+$) |
|---|---|---|---|
| 2 | 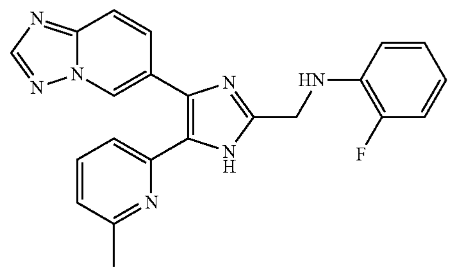 | (400 MHz, CDCl$_3$) δ 11.34 (br s, 1 H), 8.96 (dd, 1 H, J = 1.6, 0.8 Hz), 8.35 (s, 1 H), 7.81 (dd, 1 H, J = 9.2, 1.6 Hz), 7.74 (dd, 1 H, J = 9.2, 0.8 Hz), 7.45 (t, 1 H, J = 7.6 Hz), 7.23 (d, 1 H, J = 7.6 Hz), 6.97-6.90 (m, 2 H), 6.94 (dd, 1 H, J = 8.0, 1.2 Hz), 6.72 (td, 1 H, J = 8.4, 1.6 Hz), 6.69-6.63 (m, 1 H), 4.51 (s, 2 H), 2.35 (s, 3 H). | 400.18 |
| 3 | ·HCl | (400 MHz, DMSO-d$_6$) δ 9.44 (d, 1 H, J = 0.8 Hz), 8.62 (s, 1 H), 7.96 (dd, 1 H, J = 9.2, 0.8 Hz), 7.83 (t, 1 H, J = 8.0 Hz), 7.80 (dd, 1 H, J = 9.2, 1.6 Hz), 7.53 (d, 1 H, J = 8.0 Hz), 7.38 (d, 1 H, J = 7.6 Hz), 7.10 (ddd, 1 H, J = 12.0, 8.0, 1.2 Hz), 7.01 (td, 1 H, J = 7.6, 1.2 Hz), 6.88 (br t, 1 H, J = 8.6 Hz), 6.70-6.64 (m, 1 H), 4.75 (s, 2 H), 2.54 (s, 3 H) | |
| 4 | ·H$_2$SO$_4$ | (400 MHz, DMSO-d$_6$) δ 9.40 (dd, 1 H, J = 2.0, 0.8 Hz), 8.64 (s, 1 H), 7.99 (dd, 1 H, J = 9.2, 0.8 Hz), 7.85 (t, 1 H, J = 8.0 Hz), 7.77 (dd, 1 H, J = 9.2, 2.0 Hz), 7.42 (pseudo t, 2 H, J = 7.4 Hz), 7.11 (ddd, 1 H, J = 12.0, 8.0, 1.2 Hz), 7.02 (td, 1 H, J = 7.6, 1.2 Hz), 6.82 (td, 1 H, J = 8.0, 1.2 Hz), 6.71-6.65 (m, 1 H), 4.73 (s, 2 H), 2.59 (s, 3 H) | |
| 5 | 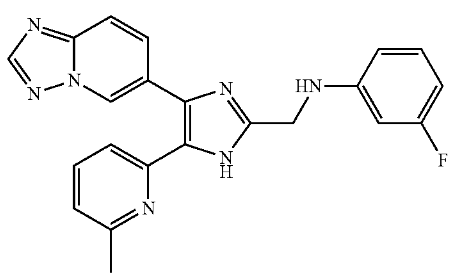 [SMILES: Cc1cccc(-c2[nH]c(CNc3cccc(F)c3)nc2-c2ccc3ncnn3c2)n1] | (400 MHz, CDCl$_3$) δ 8.94 (t, 1 H, J = 1.4 Hz), 8.36 (s, 1 H), 7.79 (dd, 1 H, J = 9.2, 1.6 Hz), 7.75 (dd, 1 H, J = 9.2, 0.8 Hz), 7.46 (t, 1 H, J = 7.8 Hz), 7.23 (d, 1 H, J = 8.0 Hz), 7.13-7.07 (m, 1 H), 7.01 (d, 1 H, J = 7.6 Hz), 6.47-6.41 (m, 2 H), 6.37 (dt, 1 H, J = 8.8, 2.4 Hz), 4.49 (s, 2 H), 2.49 (s, 3 H) | 400.19 |
| 6 | 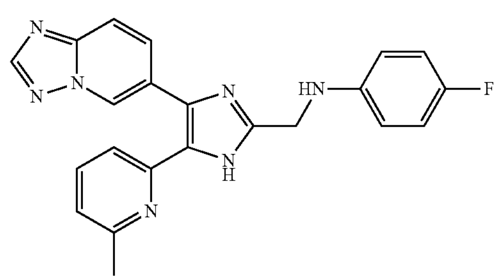 [SMILES: Cc1cccc(-c2[nH]c(CNc3ccc(F)cc3)nc2-c2ccc3ncnn3c2)n1] | (400 MHz, CDCl$_3$) δ 8.95 (dd, 1 H, J = 1.6, 1.2 Hz), 8.37 (s, 1 H), 7.80 (dd, 1 H, J = 9.2, 1.6 Hz), 7.76 (dd, 1 H, J = 9.2, 1.2 Hz), 7.46 (t, 1 H, J = 7.6 Hz), 7.23 (d, 1 H, J = 7.6 Hz), 7.01 (d, 1 H, J = 7.6 Hz), 6.92-6.88 (m, 2 H), 6.65-6.62 (m, 2 H), 4.49 (s, 2 H), 2.51 (s, 3 H) | 400.19 |

TABLE 1-continued

| Example | Structure | ¹H NMR (ppm) | MS (ESI) m/z (MH⁺) |
|---|---|---|---|
| 7 | 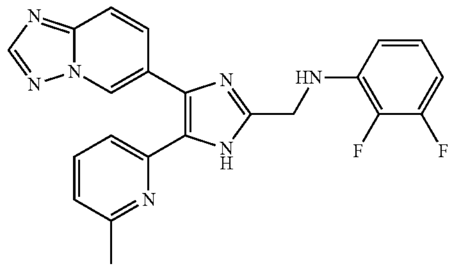 [SMILES: Cc1cccc(-c2[nH]c(CNc3cccc(F)c3F)nc2-c2ccc3ncnn3c2)n1] | (400 MHz, CDCl₃) δ 8.96 (br s, 1 H), 8.38 (s, 1 H), 7.82 (dd, 1 H, J = 9.2, 1.6 Hz), 7.78 (dd, 1 H, J = 9.2, 0.8 Hz), 7.47 (t, 1 H, J = 7.6 Hz), 7.24 (d, 1 H, J = 7.6 Hz), 7.02 (dd, 1 H, J = 7.6, 0.4 Hz), 6.94-6.88 (m, 1 H), 6.60-6.51 (m, 2 H), 4.71 (br s, 1 H), 4.58 (d, 2 H, J = 3.6 Hz), 2.51 (s, 3 H) | 418.18 |
| 8 | 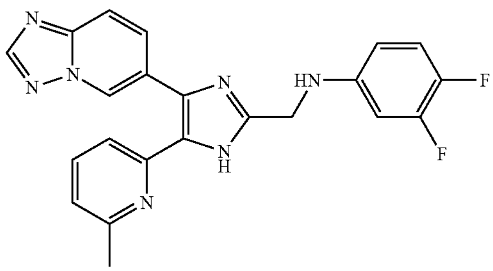 [SMILES: Cc1cccc(-c2[nH]c(CNc3ccc(F)c(F)c3)nc2-c2ccc3ncnn3c2)n1] | (400 MHz, CDCl₃) δ 8.94 (t, 1 H, J = 1.4 Hz), 8.38 (s, 1 H), 7.81 (dd, 1 H, overlapped, J = 9.2, 1.6 Hz), 7.78 (dd, 1 H, overlapped, J = 9.2, 1.2 Hz), 7.47 (t, 1 H, J = 7.8 Hz), 7.24 (d, 1 H, J = 8.0 Hz), 7.03 (d, 1 H, J = 7.6 Hz), 7.04-6.95 (m, 1 H), 6.52 (ddd, 1 H, J = 12.4, 6.8, 2.8 Hz), 6.42-6.37 (m, 1 H), 4.48 (s, 2 H), 2.55 (s, 3 H) | 418.18 |
| 9 | 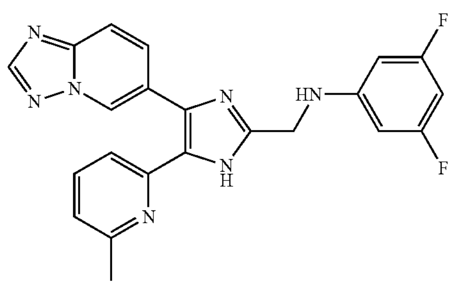 [SMILES: Cc1cccc(-c2[nH]c(CNc3cc(F)cc(F)c3)nc2-c2ccc3ncnn3c2)n1] | (400 MHz, CDCl₃) δ 8.94 (t, 1 H, J = 1.2 Hz), 8.38 (s, 1 H), 7.81 (dd, 1 H, overlapped, J = 9.2, 1.6 Hz), 7.79 (dd, 1 H, overlapped, J = 9.2, 1.2 Hz), 7.47 (t, 1 H, J = 7.8 Hz), 7.24 (d, 1 H, J = 8.0 Hz), 7.03 (d, 1 H, J = 7.6 Hz), 6.24-6.19 (m, 3 H), 4.71 (br s, 1 H), 4.50 (s, 2 H), 2.55 (s, 3 H) | 418.18 |
| 10 | 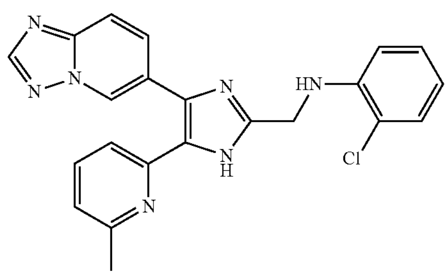 [SMILES: Cc1cccc(-c2[nH]c(CNc3ccccc3Cl)nc2-c2ccc3ncnn3c2)n1] | (400 MHz, CDCl₃) δ 8.97 (br s, 1 H), 8.37 (s, 1 H), 7.82 (dd, 1 H, J = 9.2, 1.6 Hz), 7.77 (dd, 1 H, J = 9.2, 1.0 Hz), 7.46 (t, 1 H, J = 7.6 Hz), 7.29 (dd, 1 H, J = 7.6, 1.6 Hz), 7.23 (br d, 1 H, J = 7.6 Hz), 7.14 (td, 1 H, J = 8.4, 1.6 Hz), 7.01 (dd, 1 H, J = 7.6, 0.4 Hz), 6.75 (dd, 1 H, J = 8.8, 1.4 Hz), 6.72 (td, 1 H, J = 8.4, 1.6 Hz), 5.01 (br s, 1 H), 4.60 (br s, 2 H), 2.50 (s, 3 H) | 416.16 |
| 11 | 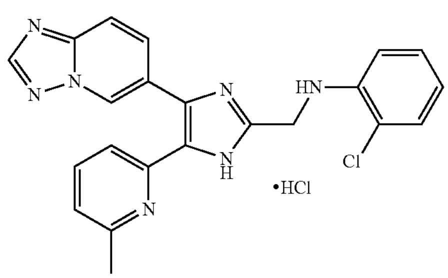 [SMILES: Cc1cccc(-c2[nH]c(CNc3ccccc3Cl)nc2-c2ccc3ncnn3c2)n1 ; Cl] | (400 MHz, DMSO-d₆) δ 9.43 (s, 1 H), 8.61 (s, 1 H), 7.95 (dd, 1 H, J = 9.2, 0.8 Hz), 7.82 (t, 1 H, overlapped, J = 7.8 Hz), 7.81 (dd, 1 H, overlapped, J = 9.2, 2.0 Hz), 7.49 (d, 1 H, J = 8.0 Hz), 7.36 (d, 1 H, J = 7.6 Hz), 7.32 (dd, 1 H, J = 7.8, 1.4 Hz), 7.17 (td, 1 H, J = 8.4, 1.2 Hz), 6.87 (dd, 1 H, J = 8.4, 1.2 Hz), 6.69 (td, 1 H, J = 7.8, 1.4 Hz), 6.15 (br s, 1 H), 4.76 (s, 2 H), 2.55 (s, 3 H) | |

TABLE 1-continued

| Example | Structure | ¹H NMR (ppm) | MS (ESI) m/z (MH⁺) |
|---|---|---|---|
| 12 | 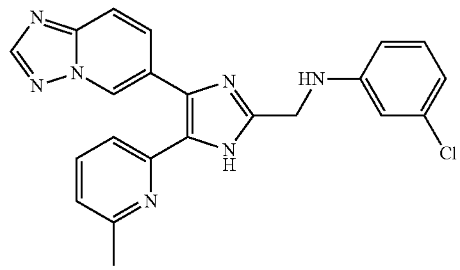 [SMILES: Cc1cccc(-c2[nH]c(CNc3cccc(Cl)c3)nc2-c2ccc3ncnn3c2)n1] | (400 MHz, CDCl₃) δ 8.95 (t, 1 H, J = 1.6 Hz), 8.37 (s, 1 H), 7.81 (dd, 1 H, J = 9.2, 1.6 Hz), 7.77 (dd, 1 H, J = 9.2, 1.2 Hz), 7.47 (t, 1 H, J = 7.8 Hz), 7.24 (d, 1 H, J = 8.0 Hz), 7.10 (t, 1 H, J = 8.0 Hz), 7.02 (d, 1 H, J = 7.6 Hz), 6.75 (ddd, 1 H, J = 8.0, 2.0, 0.8 Hz), 6.69 (t, 1 H, J = 2.0 Hz), 6.57 (ddd, 1 H, J = 8.0, 2.4, 0.8 Hz), 4.51 (s, 2 H), 2.52 (s, 3 H) | 416.16 |
| 13 | ·HCl | (400 MHz, DMSO-d₆) δ 9.45 (dd, 1 H, J = 1.6, 0.8 Hz), 8.63 (s, 1 H), 7.97 (dd, 1 H, J = 9.2, 0.8 Hz), 7.85 (t, 1 H, J = 8.0 Hz), 7.81 (dd, 1 H, J = 9.2, 1.6 Hz), 7.56 (d, 1 H, J = 8.4 Hz), 7.39 (d, 1 H, J = 7.6 Hz), 7.15 (t, 1 H, J = 8.0 Hz), 6.80 (t, 1 H, J = 2.2 Hz), 6.71-6.65 (m, 2 H), 4.71 (s, 2 H), 2.54 (s, 3 H) | |
| 14 | 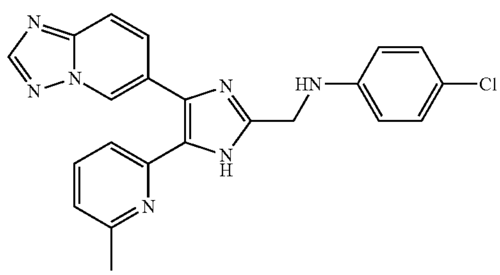 [SMILES: Cc1cccc(-c2[nH]c(CNc3ccc(Cl)cc3)nc2-c2ccc3ncnn3c2)n1] | (400 MHz, CDCl₃) δ 8.95 (t, 1 H, J = 1.4 Hz), 8.38 (s, 1 H), 7.81 (dd, 1 H, overlapped, J = 9.2, 1.4 Hz), 7.78 (dd, 1 H, overlapped, J = 9.2, 1.2 Hz), 7.47 (t, 1 H, J = 7.6 Hz), 7.23 (br d, 1 H, J = 7.6 Hz), 7.16 (m, 2 H), 7.02 (br d, 1 H, J = 7.6 Hz), 6.65 (m, 2 H), 4.51 (s, 2 H), 2.54 (s, 3 H) | 416.16 |
| 15 | 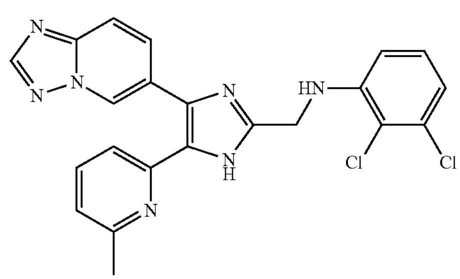 [SMILES: Cc1cccc(-c2[nH]c(CNc3cccc(Cl)c3Cl)nc2-c2ccc3ncnn3c2)n1] | (400 MHz, CDCl₃) δ 11.02 (br s, 1 H), 8.97 (s, 1 H), 8.36 (s, 1 H), 7.81 (dd, 1 H, J = 9.2, 1.6 Hz), 7.75 (dd, 1 H, J = 9.2, 0.8 Hz), 7.46 (t, 1 H, J = 8.0 Hz), 7.24 (d, 1 H, J = 8.0 Hz), 7.03 (t, 1 H, overlapped, J = 8.0 Hz), 7.00 (d, 1 H, overlapped, J = 8.0 Hz), 6.85 (dd, 1 H, J = 8.0, 1.6 Hz), 6.63 (dd, 1 H, J = 8.0, 1.6 Hz), 5.15 (t, 1 H, J = 5.6 Hz), 4.57 (d, 2 H, J = 5.6 Hz), 2.43 (s, 3 H) | 450.12 |
| 16 | 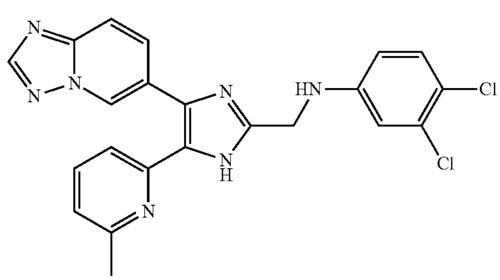 [SMILES: Cc1cccc(-c2[nH]c(CNc3ccc(Cl)c(Cl)c3)nc2-c2ccc3ncnn3c2)n1] | (400 MHz, CDCl₃) δ 8.94 (t, 1 H, J = 1.2 Hz), 8.37 (s, 1 H), 7.80 (dd, 1 H, overlapped, J = 9.2, 1.6 Hz), 7.77 (dd, 1 H, overlapped, J = 9.2, 1.2 Hz), 7.47 (t, 1 H, J = 8.0 Hz), 7.24 (br d, 1 H, J = 8.0 Hz), 7.20 (d, 1 H, J = 8.8 Hz), 7.03 (d, 1 H, J = 8.0 Hz), 6.77 (d, 1 H, J = 2.8 Hz), 6.53 (dd, 1 H, J = 8.8, 2.8 Hz), 4.47 (s, 2 H), 2.51 (s, 3 H) | 450.12 |

TABLE 1-continued

| Example | Structure | ¹H NMR (ppm) | MS (ESI) m/z (MH⁺) |
|---|---|---|---|
| 17 | 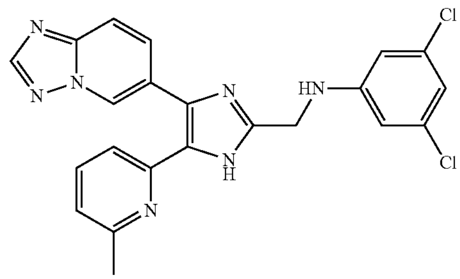 [SMILES: Cc1cccc(-c2[nH]c(CNc3cc(Cl)cc(Cl)c3)nc2-c2ccc3ncnn3c2)n1] | (400 MHz, CDCl₃/CD₃OD) δ 8.90 (s, 1 H), 8.24 (s, 1 H), 7.71 (dd, 1 H, J = 9.2, 1.6 Hz), 7.64 (dd, 1 H, J = 9.2, 0.8 Hz), 7.45 (t, 1 H, J = 7.6 Hz), 7.16 (br d, 1 H, J = 7.6 Hz), 6.99 (d, 1 H, J = 7.6 Hz), 6.57 (t, 1 H, J = 1.6 Hz), 6.51 (d, 2 H, J = 1.6 Hz), 4.36 (s, 2 H), 2.45 (s, 3 H) | 450.12 |
| 18 | 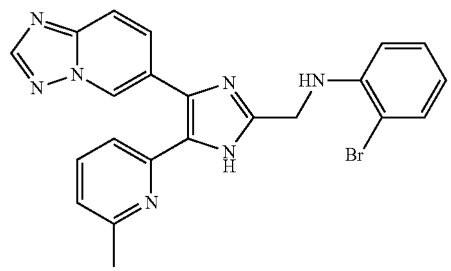 | (400 MHz, CDCl₃) δ 10.94 (br s, 1 H), 8.97 (br s, 1 H), 8.36 (s, 1 H), 7.82 (d, 1 H, J = 9.2 Hz), 7.75 (d, 1 H, J = 9.2 Hz), 7.45 (t, 1 H, overlapped, J = 7.8 Hz), 7.43 (dd, 1 H, J = 8.0, 1.6 Hz), 7.21 (d, 1 H, J = 8.0 Hz), 7.16 (td, 1 H, J = 8.4, 1.2 Hz), 6.99 (d, 1 H, J = 7.6 Hz), 6.71 (dd, 1 H, J = 8.4, 1.2 Hz), 6.63 (td, 1 H, J = 8.0, 1.6 Hz), 4.99 (t, 1 H, J = 5.6 Hz), 4.57 (d, 2 H, J = 5.6 Hz), 2.44 (s, 3 H) | 460.11 |
| 19 | 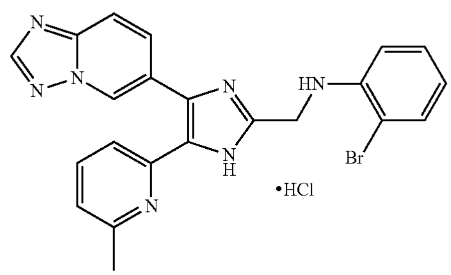 | (400 MHz, DMSO-d₆) δ 9.43 (dd, 1 H, J = 1.6, 0.8 Hz), 8.62 (s, 1 H), 7.96 (dd, 1 H, J = 9.2, 0.8 Hz), 7.83 (t, 1 H, J = 7.6 Hz), 7.80 (dd, 1 H, J = 9.2, 1.6 Hz), 7.50 (d, 1 H, J = 7.6 Hz), 7.48 (dd, 1 H, J = 8.0, 1.6 Hz), 7.37 (d, 1 H, J = 7.6 Hz), 7.21 (td, 1 H, J = 7.6, 1.6 Hz), 6.87 (dd, 1 H, J = 8.0, 1.2 Hz), 6.63 (td, 1 H, J = 7.6, 1.2 Hz), 6.04 (br s 1 H), 4.78 (s, 2 H), 2.55 (s, 3 H) | |
| 20 | 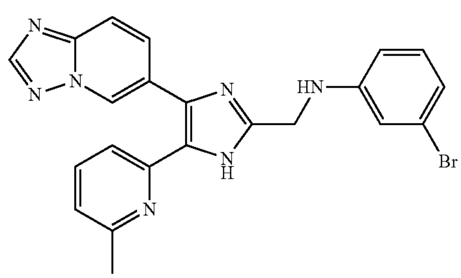 [SMILES: Cc1cccc(-c2[nH]c(CNc3cccc(Br)c3)nc2-c2ccc3ncnn3c2)n1] | (400 MHz, CDCl₃) δ 8.89 (br s, 1 H), 8.30 (s, 1 H), 7.75 (dd, 1 H, J = 9.2, 1.6 Hz), 7.69 (d, 1 H, J = 9.2 Hz), 7.44 (br t, 1 H, J = 7.6 Hz), 7.12 (br d, 1 H, J = 7.6 Hz), 7.00 (d, 1 H, J = 8.0 Hz), 6.97 (t, 1 H, overlapped, J = 8.0 Hz), 6.82-6.78 (m, 2 H), 6.58 (ddd, 1 H, J = 8.2, 2.4, 0.8 Hz), 4.41 (s, 2 H), 2.49 (s, 3 H) | 460.11 |
| 21 | 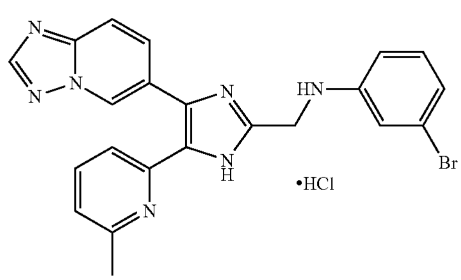 [SMILES: Cc1cccc(-c2[nH]c(CNc3cccc(Br)c3)nc2-c2ccc3ncnn3c2)n1 ; Cl] | (400 MHz, DMSO-d₆) δ 9.44 (d, 1 H, J = 0.8 Hz), 8.61 (s, 1 H), 7.95 (dd, 1 H, J = 9.2, 0.8 Hz), 7.83 (t, 1 H, J = 7.8 Hz), 7.82 (dd, 1 H, J = 9.2, 1.6 Hz), 7.50 (d, 1 H, J = 8.0 Hz), 7.37 (d, 1 H, J = 7.6 Hz), 7.08 (t, 1 H, J = 8.0 Hz), 6.94 (t, 1 H, J = 2.0 Hz), 6.79 (ddd, 1 H, J = 7.6, 2.0, 0.8 Hz), 6.71 (ddd, 1 H, J = 8.4, 2.0, 0.8 Hz), 4.63 (s, 2 H), 2.55 (s, 3 H) | |

TABLE 1-continued

| Example | Structure | ¹H NMR (ppm) | MS (ESI) m/z (MH⁺) |
|---|---|---|---|
| 22 | 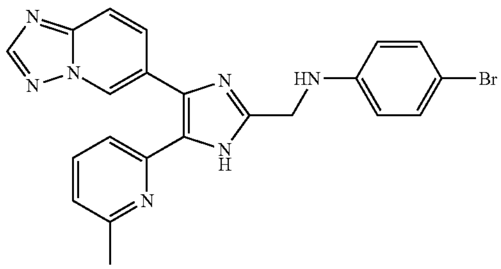 | (400 MHz, CDCl₃) δ 8.94 (br s, 1 H), 8.38 (s, 1 H), 7.82-7.77 (m, 2 H), 7.46 (t, 1 H, J = 7.6 Hz), 7.29 (m, 2 H), 7.21 (d, 1 H, J = 7.6 Hz), 7.02 (d, 1 H, J = 7.6 Hz), 6.61 (m, 2 H), 4.51 (s, 2 H), 4.44 (br s, 1 H), 2.54 (s, 3 H) | 460.11 |
| 23 | 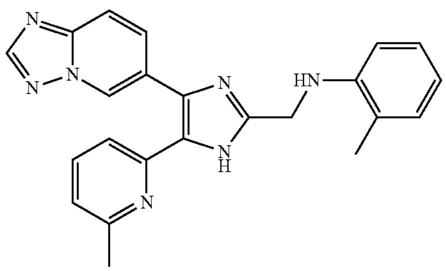 | (400 MHz, CDCl₃) δ 8.97 (s, 1 H), 8.37 (s, 1 H), 7.83 (dd, 1 H, J = 9.2, 1.6 Hz), 7.78 (dd, 1 H, J = 9.2, 0.8 Hz), 7.46 (t, 1 H, J = 7.8 Hz), 7.23 (br d, 1 H, J = 7.6 Hz), 7.14 (t, 1 H, overlapped, J = 8.0 Hz), 7.12 (d, 1 H, overlapped, J = 7.6 Hz), 7.01 (d, 1 H, J = 8.0 Hz), 6.76 (td, 1 H, J = 7.6, 0.8 Hz), 6.69 (d, 1 H, J = 7.6 Hz), 4.61 (s, 2 H), 2.54 (s, 3 H), 2.26 (s, 3 H) | 396.21 |
| 24 | 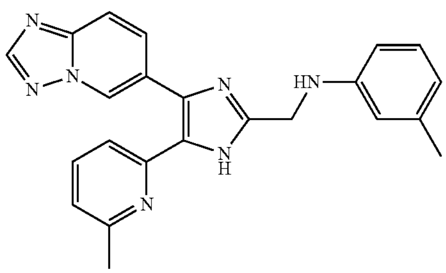 [SMILES: Cc1cccc(NCc2nc(-c3ccc4ncnn4c3)c(-c3cccc(C)n3)[nH]2)c1] | (400 MHz, CDCl₃) δ 8.96 (dd, 1 H, J = 1.6, 1.2 Hz), 8.37 (s, 1 H), 7.82 (dd, 1 H, J = 9.2, 1.6 Hz), 7.78 (dd, 1 H, J = 9.2, 1.2 Hz), 7.46 (t, 1 H, J = 7.8 Hz), 7.22 (br d, 1 H, J = 8.0 Hz), 7.11 (t, 1 H, J = 7.8 Hz), 7.01 (d, 1 H, J = 1.6 Hz), 6.63 (dt, 1 H, J = 7.6, 0.8 Hz), 6.57-6.53 (m, 2 H), 4.55 (s, 2 H), 2.54 (s, 3 H), 2.29 (s, 3 H) | 396.21 |
| 25 | 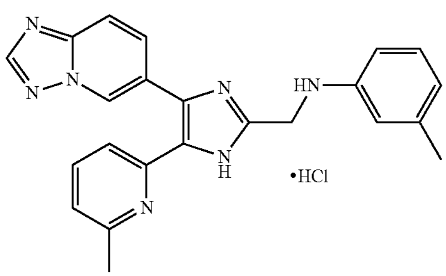 [SMILES: Cc1cccc(NCc2nc(-c3ccc4ncnn4c3)c(-c3cccc(C)n3)[nH]2)c1 ; Cl] | (400 MHz, DMSO-d₆) δ 9.45 (dd, 1 H, J = 1.6, 0.8 Hz), 8.63 (s, 1 H), 7.97 (dd, 1 H, J = 9.2, 0.8 Hz), 7.83 (t, 1H, J = 8.0 Hz), 7.81 (dd, 1 H, J = 9.2, 1.6 Hz), 7.56 (d, 1 H, J = 8.0 Hz), 7.37 (d, 1 H, J = 8.0 Hz), 7.02 (t, 1 H, J = 7.8 Hz), 6.60 (s, 1 H), 6.54 (dd, 1 H, J = 8.0, 2.0 Hz), 6.49 (d, 1 H, J = 7.6 Hz), 4.69 (s, 2 H), 2.52 (s, 3 H), 2.21 (s, 3 H) | |
| 26 | 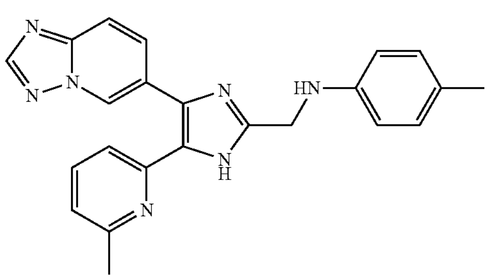 [SMILES: Cc1ccc(NCc2nc(-c3ccc4ncnn4c3)c(-c3cccc(C)n3)[nH]2)cc1] | (400 MHz, CDCl₃) δ 8.96 (t, 1 H, J = 1.2 Hz), 8.37 (s, 1 H), 7.82 (d d, 1 H, J = 9.2, 1.6 Hz), 7.77 (dd, 1 H, J = 9.2, 0.8 Hz), 7.45 (t, 1 H, J = 7.8 Hz), 7.22 (br d, 1 H, J = 8.0 Hz), 7.03 (m, 2 H), 7.02 (d, 1 H, overlapped, J = 7.6 Hz), 6.65 (m, 2 H), 4.53 (s, 2 H), 2.53 (s, 3 H), 2.25 (s, 3 H) | 396.21 |

TABLE 1-continued

| Example | Structure | $^1$H NMR (ppm) | MS (ESI) m/z (MH$^+$) |
|---|---|---|---|
| 27 | 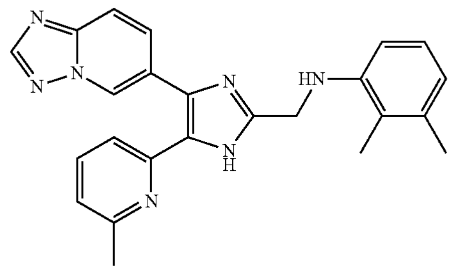 [SMILES: Cc1cccc(-c2[nH]c(CNc3cccc(C)c3C)nc2-c2ccc3ncnn3c2)n1] | (400 MHz, CDCl$_3$) δ 8.97 (s, 1 H), 8.37 (s, 1 H), 7.83 (dd, 1 H, J = 9.2, 1.6 Hz), 7.78 (dd, 1 H, J = 9.2, 0.8 Hz), 7.45 (t, 1 H, J = 7.8 Hz), 7.22 (br d, 1 H, J = 7.6 Hz), 7.03 (t, 1 H, overlapped, J = 7.8 Hz), 7.02 (d, 1 H, overlapped, J = 8.0 Hz), 6.69 (d, 1 H, J = 7.6 Hz), 6.58 (d, 1 H, J = 8.0 Hz), 4.59 (s, 2 H), 2.54 (s, 3 H), 2.31 (s, 3 H), 2.17 (s, 3 H) | 410.23 |
| 28 | 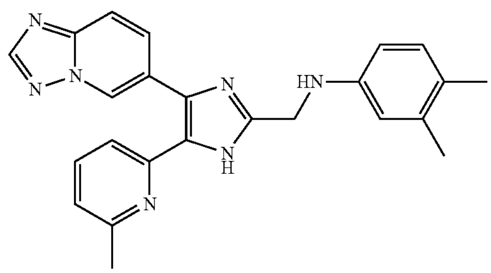 [SMILES: Cc1cccc(-c2[nH]c(CNc3ccc(C)c(C)c3)nc2-c2ccc3ncnn3c2)n1] | (400 MHz, CDCl$_3$) δ 8.96 (d, 1 H, J = 1.2 Hz), 8.37 (s, 1 H), 7.82 (dd, 1 H, J = 9.2, 1.6 Hz), 7.77 (dd, 1 H, J = 9.2, 0.8 Hz), 7.45 (t, 1 H, J = 7.6 Hz), 7.22 (br d, 1 H, J = 8.0 Hz), 7.00 (d, 1 H, J = 7.6 Hz), 6.98 (d, 1 H, J = 8.0 Hz), 6.57 (d, 1 H, J = 2.4 Hz), 6.50 (dd, 1 H, J = 8.0, 2.4 Hz), 4.53 (s, 2 H), 2.54 (s, 3 H), 2.20 (s, 3 H), 2.16 (s, 3 H) | 410.23 |
| 29 | 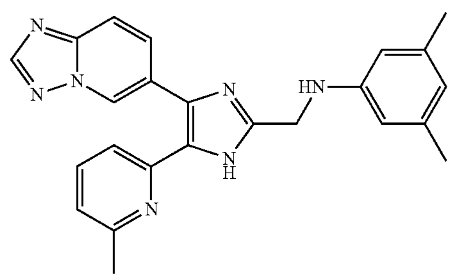 [SMILES: Cc1cc(C)cc(NCc2nc(-c3ccc4ncnn4c3)c(-c3cccc(C)n3)[nH]2)c1] | (400 MHz, CDCl$_3$) δ 8.95 (dd, 1 H, J = 1.6, 1.2 Hz), 8.36 (s, 1 H), 7.79 (dd, 1 H, J = 9.2, 1.6 Hz), 7.74 (dd, 1 H, J = 9.2, 1.2 Hz), 7.45 (t, 1 H, J = 7.8 Hz), 7.22 (d, 1 H, J = 8.0 Hz), 6.99 (d, 1 H, J = 7.6 Hz), 6.44 (br s, 1 H), 6.31 (s, 2 H), 4.49 (s, 2 H), 2.48 (s, 3 H), 2.21 (s, 6 H) | 410.23 |
| 30 | 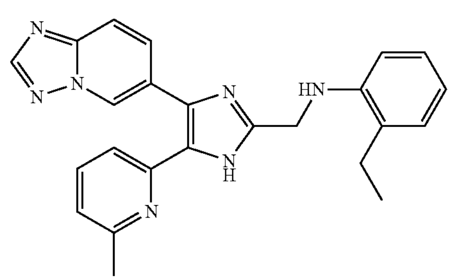 [SMILES: CCc1ccccc1NCc1nc(-c2ccc3ncnn3c2)c(-c2cccc(C)n2)[nH]1] | (400 MHz, CDCl$_3$) δ 8.97 (br s, 1 H), 8.37 (s, 1 H), 7.83 (dd, 1 H, J = 9.2, 1.6 Hz), 7.78 (dd, 1 H, J = 9.2, 0.8 Hz), 7.46 (t, 1 H, J = 7.8 Hz), 7.23 (br d, 1 H, J = 7.6 Hz), 7.16-7.11 (m, 2 H), 7.01 (d, 1 H, J = 7.6 Hz), 6.80 (td, 1 H, J = 7.6, 1.2 Hz), 6.71 (dd, 1 H, J = 8.4, 1.2 Hz), 4.60 (s, 2 H), 2.60 (q, 2 H, J = 7.6 Hz), 2.52 (s, 3 H), 1.32 (t, 3 H, J = 7.6 Hz) | 410.23 |
| 31 | 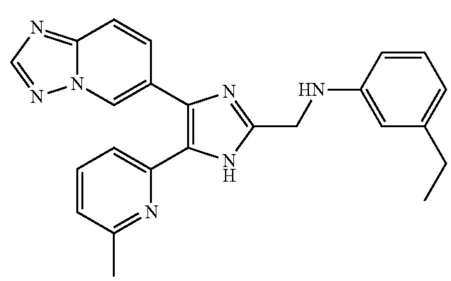 [SMILES: CCc1cccc(NCc2nc(-c3ccc4ncnn4c3)c(-c3cccc(C)n3)[nH]2)c1] | (400 MHz, CDCl$_3$) δ 8.96 (d, 1 H, J = 1.2 Hz), 8.37 (s, 1 H), 7.82 (dd, 1 H, J = 9.2, 1.6 Hz), 7.77 (dd, 1 H, J = 9.2, 1.2 Hz), 7.45 (t, 1 H, J = 7.8 Hz), 7.22 (br d, 1 H, J = 8.0 Hz), 7.14 (t, 1 H, J = 7.8 Hz), 7.01 (d, 1 H, J = 7.6 Hz), 6.66 (dd, 1 H, J = 7.6, 0.8 Hz), 6.58 (d, 1 H, J = 2.0 Hz), 6.55 (dd, 1 H, J = 7.6, 2.0 Hz), 4.55 (s, 2 H), 2.58 (q, 2 H, J = 7.6 Hz), 2.53 (s, 3 H), 1.21 (t, 3 H, J = 7.6 Hz) | 410.23 |

TABLE 1-continued

| Example | Structure | $^1$H NMR (ppm) | MS (ESI) m/z (MH$^+$) |
|---|---|---|---|
| 32 | 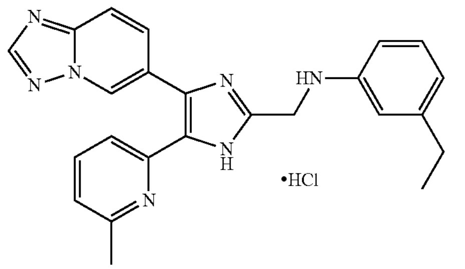 | (400 MHz, DMSO-d$_6$) δ 9.45 (dd, 1 H, J = 1.6, 0.8 Hz), 8.63 (s, 1 H), 7.97 (dd, 1 H, J = 9.2, 0.8 Hz), 7.83 (t, 1 H, J = 8.0 Hz), 7.81 (dd, 1 H, J = 9.2, 1.6 Hz), 7.57 (d, 1 H, J = 8.0 Hz), 7.37 (d, 1 H, J = 8.0 Hz), 7.05 (t, 1 H, J = 7.6 Hz), 6.64 (d, 1 H, J = 1.6 Hz), 6.57-6.52 (m, 2 H), 4.71 (s, 2 H), 2.53 (s, 3 H), 2.50 (q, 2 H, J = 7.6 Hz), 1.14 (t, 3 H, J = 7.6 Hz) | |
| 33 | 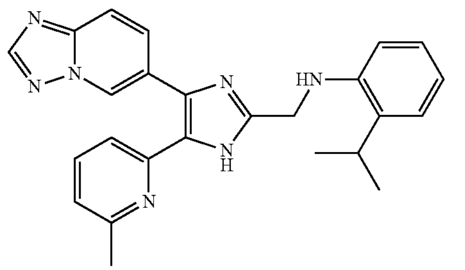 | (400 MHz, CDCl$_3$) δ 8.97 (br s, 1 H), 8.37 (s, 1 H), 7.82 (dd, 1 H, J = 9.2, 1.6 Hz), 7.76 (dd, 1 H, J = 9.2, 0.8 Hz), 7.45 (t, 1 H, J = 7.8 Hz), 7.23 (br d, 1 H, overlapped, J = 8.0 Hz), 7.21 (dd, 1 H, overlapped, J = 7.6, 1.6 Hz), 7.12 (td, 1 H, J = 7.6, 1.6 Hz), 7.00 (d, 1 H, J = 7.6 Hz), 6.83 (td, 1 H, J = 7.6, 1.2 Hz), 6.71 (dd, 1 H, J = 8.0, 1.2 Hz), 4.58 (s, 2 H), 3.00 (heptet, 1 H, J = 6.8 Hz), 2.50 (s, 3 H), 1.31 (d, 6 H, J = 6.8 Hz) | 424.24 |
| 34 | 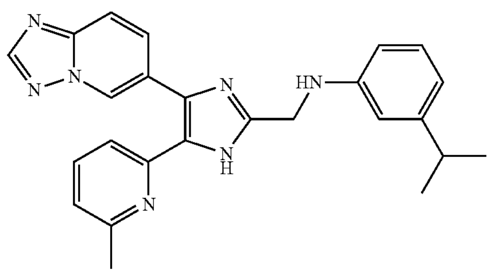 [SMILES: Cc1cccc(-c2[nH]c(CNc3cccc(C(C)C)c3)nc2-c2ccc3ncnn3c2)n1] | (400 MHz, CDCl$_3$) δ 8.96 (dd, 1 H, J = 1.4, 0.8 Hz), 8.35 (s, 1 H), 7.79 (dd, 1 H, J = 9.2, 1.4 Hz), 7.73 (dd, 1 H, J = 9.2, 0.8 Hz), 7.44 (t, 1 H, J = 7.8 Hz), 7.21 (d, 1 H, J = 7.6 Hz), 7.11 (t, 1 H, J = 7.8 Hz), 6.99 (dd, 1 H, J = 7.8, 0.4 Hz), 6.67 (d, 1 H, J = 7.6 Hz), 6.57 (t, 1 H, J = 2.4 Hz), 6.50 (ddd, 1 H, J = 8.0, 2.4, 0.8 Hz), 4.51 (s, 2 H), 2.80 (heptet, 1 H, J = 6.8 Hz), 2.47 (s, 3 H), 1.20 (d, 6 H, J = 6.8 Hz) | 424.24 |
| 35 | 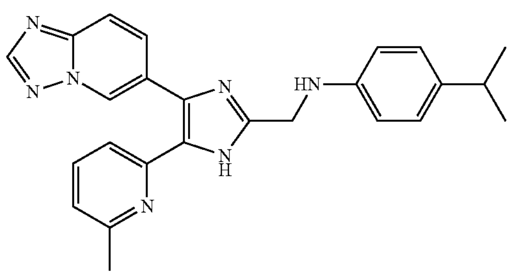 [SMILES: Cc1cccc(-c2[nH]c(CNc3ccc(C(C)C)cc3)nc2-c2ccc3ncnn3c2)n1] | (400 MHz, CDCl$_3$) δ 8.96 (t, 1 H, J = 1.2 Hz), 8.36 (s, 1 H), 7.81 (dd, 1 H, J = 9.2, 1.6 Hz), 7.75 (d, 1 H, J = 9.2 Hz), 7.44 (t, 1 H, J = 7.8 Hz), 7.21 (d, 1 H, J = 8.0 Hz), 7.06 (m, 2 H), 6.99 (d, 1 H, J = 7.6 Hz), 6.64 (m, 2 H), 4.50 (s, 2 H), 2.80 (heptet, 1 H, J = 6.8 Hz), 2.48 (s, 3 H), 1.19 (d, 6 H, J = 6.8 Hz) | 424.24 |
| 36 | 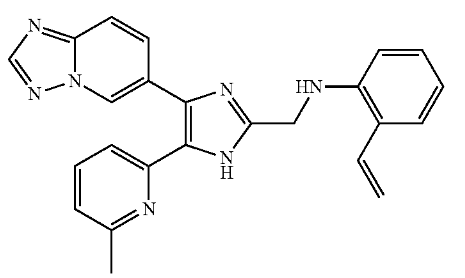 | (400 MHz. CDCl$_3$) δ 8.96 (br s, 1 H), 8.35 (s, 1 H), 7.80 (dd, 1 H, J = 9.2, 1.6 Hz), 7.73 (dd, 1 H, J = 9.2, 0.8 Hz), 7.44 (t, 1 H, J = 7.8 Hz), 7.28 (dd, 1 H, J = 7.6, 1.2 Hz), 7.22 (br d, 1 H, J = 8.0 Hz), 7.15 (td, 1 H, J = 7.8, 1.2 Hz), 6.99 (d, 1 H, J = 7.6 Hz), 6.79 (dd, 1 H, overlapped, J = 17.2, 11.2 Hz), 6.78 (td, 1 H, overlapped, J = 7.6, 0.8 Hz), 6.68 (dd, 1 H, J = 8.2, 1.0 Hz), 5.62 (dd, 1 H, J = 17.2, 1.4 Hz), 5.34 (dd, 1 H, J = 11.2, 1.4 Hz), 4.53 (s, 2 H), 2.45 (s, 3 H) | 408.21 |

TABLE 1-continued

| Example | Structure | $^1$H NMR (ppm) | MS (ESI) m/z (MH$^+$) |
|---|---|---|---|
| 37 | 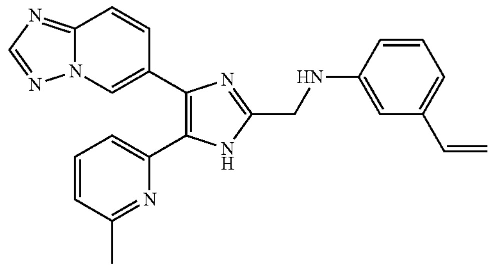 [SMILES: C=Cc1cccc(NCc2nc(-c3ccc4ncnn4c3)c(-c3cccc(C)n3)[nH]2)c1] | (400 MHz, CDCl$_3$) δ 10.59 (br s, 1 H), 8.94 (s, 1 H), 8.37 (s, 1 H), 7.81 (d, 1 H, J = 9.2 Hz), 7.77 (d, 1 H, J = 9.2 Hz), 7.45 (t, 1 H, J = 7.8 Hz), 7.20 (br d, 1 H, overlapped, J = 7.6 Hz), 7.15 (t, 1 H, overlapped, J = 7.8 Hz), 7.00 (d, 1 H, J = 8.0 Hz), 6.86 (d, 1 H, J = 7.6 Hz), 6.75 (t, 1 H, J = 2.0 Hz), 6.63 (dd, 1 H, overlapped, J = 17.6, 10.8 Hz), 6.61 (dd, 1 H, overlapped, J = 8.0, 2.0 Hz), 5.69 (dd, 1 H, J = 17.6, 0.8 Hz), 5.21 (dd, 1 H, J = 10.8, 0.8 Hz), 4.55 (s, 2 H), 4.39 (br s, 1 H), 2.51 (s, 3 H) | 408.21 |
| 38 | ·HCl | (400 MHz, DMSO-d$_6$) δ 9.49 (dd, 1 H, J = 1.6, 0.8 Hz), 8.65 (s, 1 H), 7.97 (dd, 1 H, J = 9.2, 0.8 Hz), 7.86 (dd, 1 H, overlapped, J = 9.2, 1.6 Hz), 7.85 (t, 1 H, overlapped, J = 7.8 Hz), 7.65 (d, 1 H, J = 8.0 Hz), 7.38 (d, 1 H, J = 7.6 Hz), 7.12 (t, 1 H, J = 7.8 Hz), 6.91 (t, 1 H, J = 1.6 Hz), 6.79 (d, 1 H, J = 7.6 Hz), 6.71 (dd, 1 H, J = 8.0, 1.6 Hz), 6.64 (dd, 1 H, J = 17.6, 11.2 Hz), 5.80 (dd, 1 H, J = 17.6, 0.8 Hz), 5.20 (dd, 1 H, J = 11.2, 0.8 Hz), 4.79 (s, 2 H), 2.51 (s, 3 H) | |
| 39 | ·H$_2$SO$_4$ | (400 MHz, DMSO-d$_6$) δ 9.40 (dd, 1 H, J = 1.6, 0.8 Hz), 8.63 (s, 1 H), 7.98 (dd, 1 H, J = 9.2, 0.8 Hz), 7.84 (t, 1 H, J = 8.0 Hz), 7.76 (dd, 1 H, J = 9.2, 1.6 Hz), 7.43 (d, 1 H, J = 7.6 Hz), 7.40 (d, 1 H, J = 8.0 Hz), 7.13 (t, 1 H, J = 7.8 Hz), 6.80 (br s, 1 H), 6.79 (d, 1 H, overlapped, J = 7.6 Hz), 6.64 (dd, 1 H, overlapped, J = 17.6, 11.2 Hz), 6.63 (dd, 1 H, overlapped, J = 7.6, 2.0 Hz), 5.74 (dd, 1 H, J = 17.6, 0.8 Hz), 5.21 (dd, 1 H, J = 11.2, 0.8 Hz), 4.68 (s, 2 H), 2.58 (s, 3 H) | |
| 40 | 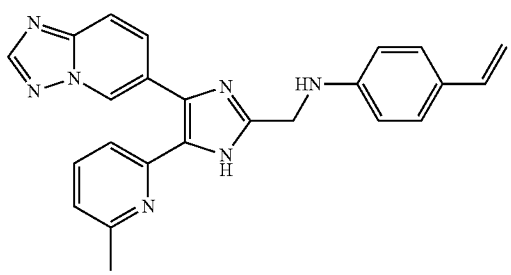 [SMILES: C=Cc1ccc(NCc2nc(-c3ccc4ncnn4c3)c(-c3cccc(C)n3)[nH]2)cc1] | (400 MHz, CDCl$_3$) δ 10.39 (br s, 1 H), 8.96 (s, 1 H), 8.37 (s, 1 H), 7.82 (dd, 1 H, J = 9.2, 1.6 Hz), 7.78 (dd, 1 H, J = 9.2, 0.8 Hz), 7.45 (t, 1 H, J = 7.6 Hz), 7.28 (m, 2 H), 7.22 (br d, 1 H, J = 7.6 Hz), 7.01 (d, 1 H, J = 7.6 Hz), 6.69 (m, 2 H), 6.61 (dd, 1 H, J = 17.6, 10.8 Hz), 5.55 (dd, 1 H, J = 17.6, 0.8 Hz), 5.05 (dd, 1 H, J = 10.8, 0.8 Hz), 4.56, (s, 2 H), 2.53 (s, 3 H) | 408.21 |
| 41 | 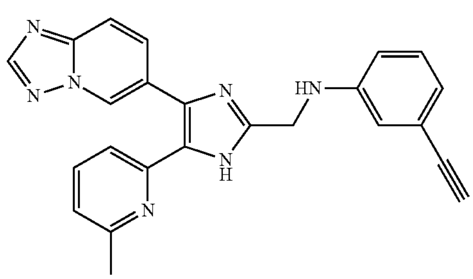 [SMILES: C#Cc1cccc(NCc2nc(-c3ccc4ncnn4c3)c(-c3cccc(C)n3)[nH]2)c1] | (400 MHz, CDCl$_3$) δ 8.94 (t, 1 H, J = 1.2 Hz), 8.35 (s, 1 H), 7.77 (dd, 1 H, J = 9.2, 1.2 Hz), 7.72 (d, 1 H, J = 9.2 Hz), 7.46 (t, 1 H, J = 7.8 Hz), 7.23 (d, 1 H, J = 8.0 Hz), 7.07 (t, 1 H, J = 7.8 Hz), 6.99 (d, 1 H, J = 7.6 Hz), 6.86 (d, 1 H, J = 7.6 Hz), 6.73 (br s, 1 H), 6.61 (br d, 1 H, J = 8.0 Hz), 4.45 (s, 2 H), 2.98 (s, 1 H), 2.42 (s, 3 H) | 406.18 |

TABLE 1-continued

| Example | Structure | ¹H NMR (ppm) | MS (ESI) m/z (MH⁺) |
|---|---|---|---|
| 42 | 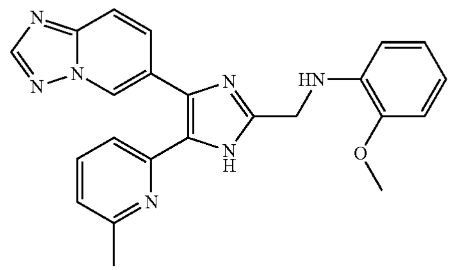 | (400 MHz, CDCl₃) δ 8.98 (br s, 1 H), 8.37 (s, 1 H), 7.83 (dd, 1 H, J = 9.2, 1.6 Hz), 7.78 (dd, 1 H, J = 9.2, 0.8 Hz), 7.45 (t, 1 H, J = 7.6 Hz), 7.22 (br d, 1 H, J = 7.6 Hz), 7.00 (d, 1 H, J = 7.6 Hz), 6.87 (td, 1 H, J = 7.6, 1.6 Hz), 6.84 (dd, 1 H, J = 8.0, 1.6 Hz), 6.77 (td, 1 H, J = 7.8, 1.6 Hz), 6.69 (dd, 1 H, J = 7.8, 1.6 Hz), 4.58 (s, 2 H), 3.91 (s, 3 H), 2.53 (s, 3 H) | 412.21 |
| 43 | 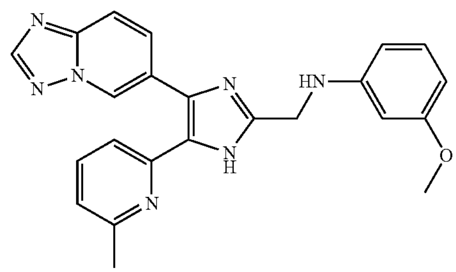 [SMILES: COc1cccc(NCc2nc(-c3ccc4ncnn4c3)c(-c3cccc(C)n3)[nH]2)c1] | (400 MHz, CDCl₃) 8.95 (br s, 1 H), 8.37 (s, 1 H), 7.81 (dd, 1 H, J = 9.2, 1.6 Hz), 7.76 (dd, 1 H, J = 9.2, 0.8 Hz), 7.45 (t, 1 H, J = 7.6 Hz), 7.22 (d, 1 H, J = 7.6 Hz), 7.11 (t, 1 H, J = 8.0 Hz), 7.01 (d, 1 H, J = 7.6 Hz), 6.36-6.31 (m, 2 H), 6.27 (t, 1 H, J = 2.4 Hz), 4.52 (s, 2 H), 3.75 (s, 3 H), 2.51 (s, 3 H) | 412.21 |
| 44 | 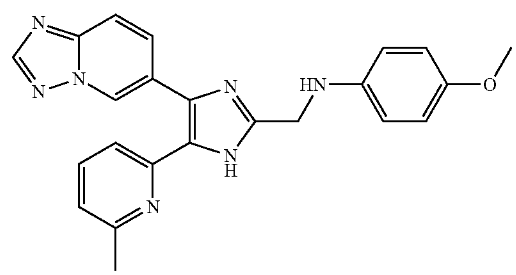 | (400 MHz. CDCl₃) δ 8.96 (br s, 1 H), 8.37 (s, 1 H), 7.82 (dd, 1 H, J = 9.2, 1.6 Hz), 7.77 (dd, 1 H, J = 9.2, 0.8 Hz), 7.45 (t, 1 H, J = 7.8 Hz), 7.22 (br d, 1 H, J = 7.6 Hz), 7.01 (br d, 1 H, J = 8.0 Hz), 6.80 (m, 2 H), 6.70 (m, 2 H), 4.50 (s, 2 H), 3.74 (s, 3 H), 2.53 (s, 3 H) | 412.21 |
| 45 | 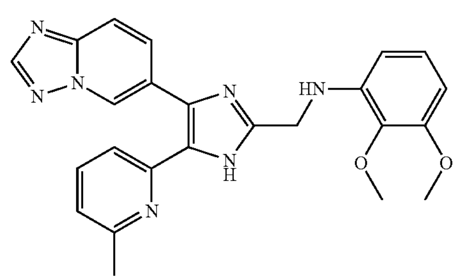 [SMILES: COc1cccc(NCc2nc(-c3ccc4ncnn4c3)c(-c3cccc(C)n3)[nH]2)c1OC] | (400 MHz, CDCl₃) δ 8.96 (br s, 1 H), 8.34 (s, 1 H), 7.80 (dd, 1 H, J = 9.2, 1.6 Hz), 7.72 (d, 1 H, J = 9.2 Hz), 7.42 (t, 1 H, J = 7.6 Hz), 7.20 (br d, 1 H, J = 7.6 Hz), 6.96 (d, 1 H, J = 7.6 Hz), 6.88 (td, 1 H, J = 8.2, 0.4 Hz), 6.36 (d, 1 H, overlapped, J = 8.0 Hz), 6.34 (d, 1 H, overlapped, J = 8.2 Hz), 4.52 (s, 2 H), 3.84 (s, 3 H), 3.81 (s, 3 H), 2.43 (s, 3 H) | 442.22 |
| 46 | 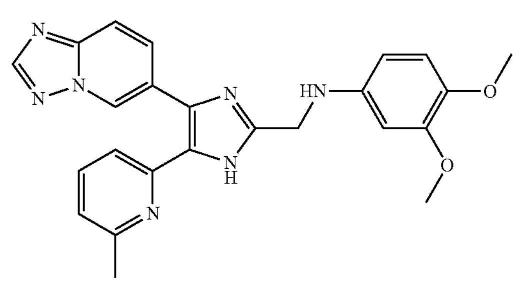 [SMILES: COc1ccc(NCc2nc(-c3ccc4ncnn4c3)c(-c3cccc(C)n3)[nH]2)cc1OC] | (400 MHz, CDCl₃) δ 8.94 (dd, 1 H, J = 1.6, 0.8 Hz), 8.34 (s, 1 H), 7.78 (dd, 1 H, J = 9.2, 1.6 Hz), 7.72 (dd, 1 H, J = 9.2, 0.8 Hz), 7.44 (t, 1 H, J = 8.0 Hz), 7.21 (br d, 1 H, J = 8.0 Hz), 6.99 (d, 1 H, J = 8.0 Hz), 6.71 (d, 1 H, J = 8.4 Hz), 6.30 (d, 1 H, J = 2.4 Hz), 6.19 (dd, 1 H, J = 8.4, 2.4 Hz), 4.46 (s, 2 H), 3.78 (s, 3 H), 3.76 (s, 3 H), 2.47 (s, 3 H) | 442.22 |

TABLE 1-continued

| Example | Structure | $^1$H NMR (ppm) | MS (ESI) m/z (MH$^+$) |
|---|---|---|---|
| 47 | 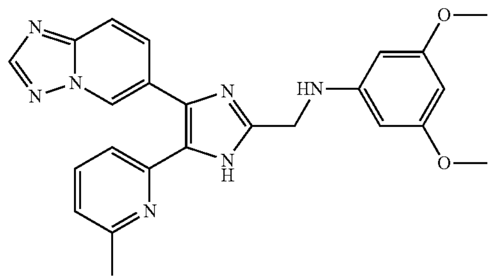 [SMILES: COc1cc(NCc2nc(-c3ccc4ncnn4c3)c(-c3cccc(C)n3)[nH]2)cc(OC)c1] | (400 MHz, CDCl$_3$) δ 10.43 (br s, 1 H), 8.94 (s, 1 H), 8.37 (s, 1 H), 7.81 (d, 1 H, J = 9.2 Hz), 7.77 (d, 1 H, J = 9.2 Hz), 7.45 (t, 1 H, J = 7.6 Hz), 7.20 (d, 1 H, J = 7.6 Hz), 7.01 (d, 1 H, J = 7.6 Hz), 5.96 (t, 1 H, J = 2.0 Hz), 5.92 (d, 2 H, J = 2.0 Hz), 4.52 (d, 2 H, J = 2.8 Hz), 4.41 (br s, 1 H), 3.75 (s, 6 H), 2.54 (s, 3 H) | 442.22 |
| 48 | 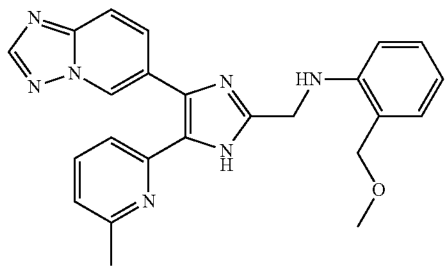 [SMILES: COCc1ccccc1NCc1nc(-c2ccc3ncnn3c2)c(-c2cccc(C)n2)[nH]1] | (400 MHz, CDCl$_3$) δ 8.97 (br s, 1 H), 8.37 (s, 1 H), 7.83 (dd, 1 H, J = 9.2, 1.6 Hz), 7.77 (dd, 1 H, J = 9.2, 0.8 Hz), 7.45 (t, 1 H, J = 7.6 Hz), 7.23 (td, 1 H, overlapped, J = 7.6, 1.6 Hz), 7.22 (br d, 1 H, overlapped, J = 7.6 Hz) 7.12 (dd, 1 H, J = 7.6, 1.6 Hz), 7.01 (d, 1 H, J = 8.0 Hz), 6.77-6.73 (m, 2 H), 4.63 (s, 2 H), 4.60 (s, 2 H), 3.42 (s, 3 H), 2.53 (s, 3 H) | 426.22 |
| 49 | 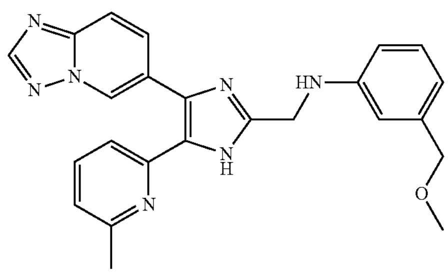 [SMILES: COCc1cccc(NCc2nc(-c3ccc4ncnn4c3)c(-c3cccc(C)n3)[nH]2)c1] | (400 MHz, CDCl$_3$) δ 8.96 (br s, 1 H), 8.37 (s, 1 H), 7.82 (dd, 1 H, J = 9.2, 1.6 Hz), 7.78 (dd, 1 H, J = 9.2, 0.8 Hz), 7.45 (t, 1 H, J = 7.6 Hz), 7.21 (t, 1 H, overlapped, J = 8.0 Hz), 7.20 (br d, 1 H, overlapped, J = 7.6 Hz), 7.01 (d, 1 H, J = 7.6 Hz), 6.76 (d, 1 H, overlapped, J = 8.0 Hz), 6.75 (d, 1 H, overlapped, J = 1.6 Hz), 6.67-6.64 (m, 1 H), 4.56 (s, 2 H), 4.40 (s, 2 H), 3.38 (s, 3 H), 2.54 (s, 3 H) | 426.22 |
| 50 | 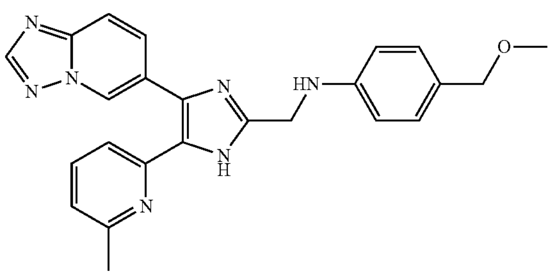 [SMILES: COCc1ccc(NCc2nc(-c3ccc4ncnn4c3)c(-c3cccc(C)n3)[nH]2)cc1] | (400 MHz, CDCl$_3$) δ 10.36 (br s, 1 H), 8.95 (s, 1 H), 8.37 (s, 1 H), 7.82 (br d, 1 H, J = 9.2 Hz), 7.78 (br d, 1 H, J = 9.2 Hz), 7.45 (t, 1 H, J = 7.6 Hz), 7.20 (br d, 1 H, overlapped, J = 7.6 Hz), 7.19 (d, 2 H, overlapped, J = 8.4 Hz), 7.01 (d, 1 H, J = 7.6 Hz), 6.71 (d, 2 H, J = 8.4 Hz), 4.55 (s, 2 H), 4.40 (br s, 1 H), 4.34 (s, 2 H), 3.34 (s, 3 H), 2.53 (s, 3 H) | 426.22 |
| 51 | 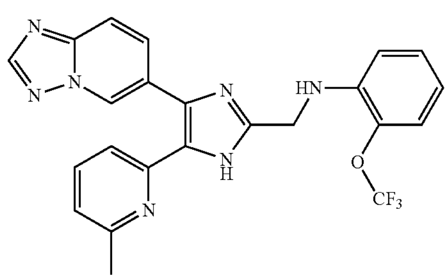 | (400 MHz, CDCl$_3$) δ 10.42 (br s, 1 H), 8.96 (br s, 1 H), 8.37 (s, 1 H), 7.82 (d, 1 H, J = 9.2 Hz), 7.78 (d, 1 H, J = 9.2 Hz), 7.45 (t, 1 H, J = 7.8 Hz), 7.25-7.18 (m, 2 H), 7.15 (td, 1 H, J = 7.8, 1.2 Hz), 7.01 (d, 1 H, J = 7.6 Hz), 6.81 (dd, 1 H, J = 8.0, 1.2 Hz), 6.76 (td, 1 H, J = 7.8, 1.6 Hz), 4.85 (t, 1 H, J = 5.6 Hz), 4.61 (d, 2 H, J = 5.6 Hz), 2.52 (s, 3 H) | 466.18 |

TABLE 1-continued

| Example | Structure | ¹H NMR (ppm) | MS (ESI) m/z (MH⁺) |
|---|---|---|---|
| 52 | 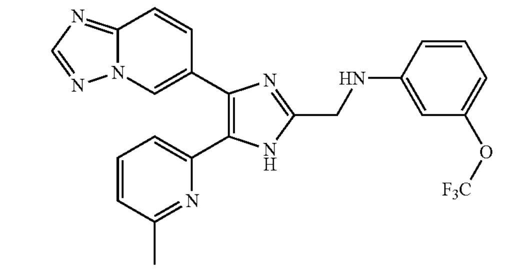 [SMILES: Cc1cccc(-c2[nH]c(CNc3cccc(OC(F)(F)F)c3)nc2-c2ccc3ncnn3c2)n1] | (400 MHz, CDCl₃) δ 8.94 (br s, 1 H), 8.37 (s, 1 H), 7.80 (dd, 1 H, J = 9.2, 1.6 Hz), 7.77 (dd, 1 H, J = 9.2, 0.8 Hz), 7.46 (t, 1 H, J = 7.8 Hz), 7.23 (br d, 1 H, J = 8.0 Hz), 7.19 (t, 1 H, J = 8.2 Hz), 7.02 (d, 1 H, J = 7.6 Hz), 6.64-6.60 (m, 2 H), 6.55 (br s, 1 H), 4.62 (br s, 1 H), 4.52 (s, 2 H), 2.52 (s, 3 H) | 466.18 |
| 53 | 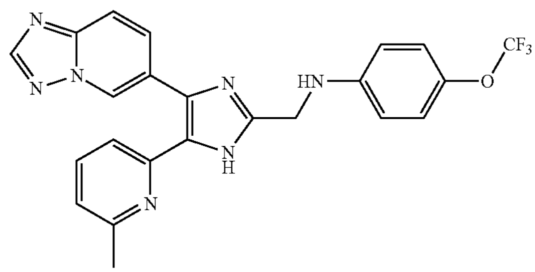 [SMILES: Cc1cccc(-c2[nH]c(CNc3ccc(OC(F)(F)F)cc3)nc2-c2ccc3ncnn3c2)n1] | (400 MHz, CDCl₃) δ 8.95 (s, 1 H), 8.38 (s, 1 H), 7.81 (dd, 1 H, J = 9.2, 1.6 Hz), 7.78 (dd, 1 H, J = 9.2, 0.8 Hz), 7.46 (t, 1 H, J = 7.8 Hz), 7.23 (d, 1 H, J = 8.0 Hz), 7.08 (m, 2 H), 7.02 (d, 1 H, J = 7.6 Hz), 6.70 (m, 2 H), 4.53 (s, 2 H), 2.54 (s, 3 H) | 466.18 |
| 54 | 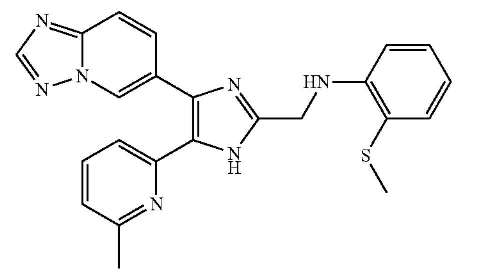 | (400 MHz, CDCl₃) δ 11.34 (br s, 1 H), 8.99 (s, 1 H), 8.34 (s, 1 H), 7.83 (br d, 1 H, J = 9.2 Hz), 7.72 (br d, 1 H, J = 9.2 Hz), 7.43 (t, 1 H, J = 7.8 Hz), 7.35 (dd, 1 H, J = 7.6, 1.6 Hz), 7.21 (br d, 1 H, J = 7.8, 1.6 Hz), 6.95 (d, 1 H, J = 8.0 Hz), 6.70 (td, 1 H, J = 7.6, 1.2 Hz), 6.65 (dd, 1 H, J = 8.0, 1.2 Hz), 5.49 (br t, 1 H, J = 4.8 Hz), 4.55 (d, 2 H, J = 4.8 Hz), 2.33 (s, 3 H), 2.32 (s, 3 H) | 428.18 |
| 55 | 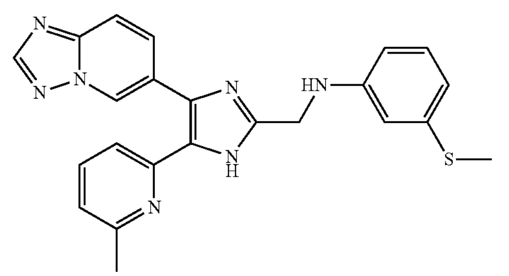 [SMILES: CSc1cccc(NCc2nc(-c3ccc4ncnn4c3)c(-c3cccc(C)n3)[nH]2)c1] | (400 MHz, CDCl₃) δ 11.06 (br s, 1 H), 8.94 (s, 1 H), 8.35 (s, 1 H), 7.78 (dd, 1 H, J = 9.2, 1.2 Hz), 7.74 (d, 1 H, J = 9.2 Hz), 7.45 (t, 1 H, J = 7.8 Hz), 7.21 (br d, 1 H, J = 8.0 Hz), 7.07 (t, 1 H, J = 7.8 Hz), 6.99 (d, 1 H, J = 7.6 Hz), 6.64 (dd, 1 H, J = 7.6, 2.0 Hz), 6.54 (t, 1 H, J = 1.6 Hz), 6.42 (dd, 1 H, J = 8.0, 1.6 Hz), 4.47 (s, 2 H) 4.42 (br s, 1 H), 2.45 (s, 3 H), 2.40 (s, 3 H) | 428.19 |
| 56 | 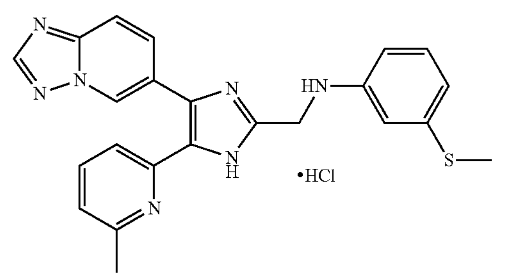 [SMILES: CSc1cccc(NCc2nc(-c3ccc4ncnn4c3)c(-c3cccc(C)n3)[nH]2)c1 ; Cl] | (400 MHz, DMSO-d₆) δ 9.43 (br s, 1 H), 8.62 (s, 1 H), 7.97 (dd, 1 H, J = 9.2, 0.8 Hz), 7.84 (t, 1 H, J = 7.6 Hz), 7.80 (dd, 1 H, J = 9.2, 1.6 Hz), 7.51 (d, 1 H, J = 7.6 Hz), 7.38 (d, 1 H, J = 7.6 Hz), 7.08 (t, 1 H, J = 7.8 Hz), 6.62 (t, 1 H, J = 2.0 Hz), 6.55 (d, 1 H, J = 7.6 Hz), 6.51 (dd, 1 H, J = 8.0, 2.0 Hz), 4.68 (s, 2 H), 2.55 (s, 3 H), 2.41 (s, 3 H) | |

TABLE 1-continued

| Example | Structure | ¹H NMR (ppm) | MS (ESI) m/z (MH⁺) |
|---|---|---|---|
| 57 | 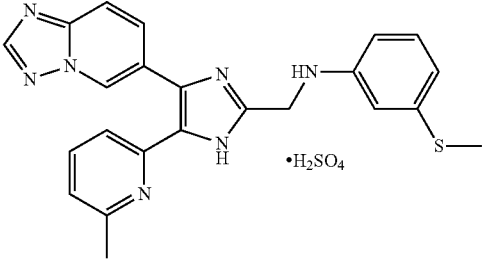 | (400 MHz, DMSO-d₆) δ 9.40 (dd, 1 H, J = 1.6, 0.8 Hz), 8.63 (s, 1 H), 7.98 (d, 1 H, J = 9.6 Hz), 7.84 (t, 1 H, J = 7.6 Hz), 7.77 (dd, 1 H, J = 9.6, 1.6 Hz), 7.43 (d, 1 H, J = 7.6 Hz), 7.40 (d, 1 H, J = 7.6 Hz), 7.08 (t, 1 H, J = 8.0 Hz), 6.60 (t, 1 H, J = 2.0 Hz), 6.56 (d, 1 H, J = 8.0 Hz), 6.48 (dd, 1 H, J = 8.0, 2.0 Hz), 4.65 (s, 2 H), 2.58 (s, 3 H), 2.40 (s, 3 H) | |
| 58 | 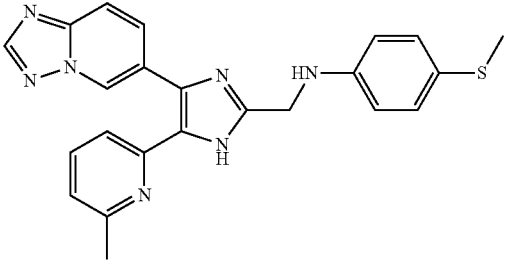 [SMILES: CSc1ccc(NCc2nc(-c3ccc4ncnn4c3)c(-c3cccc(C)n3)[nH]2)cc1] | (400 MHz, CDCl₃) δ 11.08 (br s, 1 H), 8.94 (s, 1 H), 8.35 (s, 1 H), 7.78 (dd, 1 H, J = 9.2, 1.6 Hz), 7.73 (d, 1 H, J = 9.2 Hz), 7.45 (t, 1 H, J = 7.8 Hz), 7.21 (br d, 1 H, J = 8.0 Hz), 7.17 (m, 2 H), 6.99 (d, 1 H, J = 7.6 Hz), 6.60 (m, 2 H), 4.46 (s, 2 H), 2.45 (s, 3 H), 2.37 (s, 3 H) | 428.18 |
| 59 | 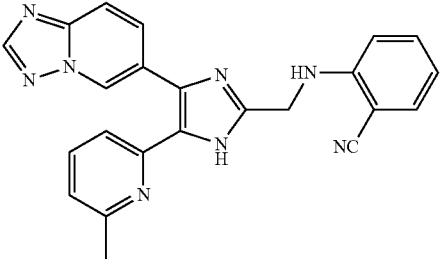 | (400 MHz, CDCl₃) δ 8.98 (br s, 1 H), 8.36 (s, 1 H), 7.83 (dd, 1 H, J = 9.2, 1.6 Hz), 7.76 (dd, 1 H, J = 9.2, 0.8 Hz), 7.47 (t, 1 H, J = 7.8 Hz), 7.40 (br d, 1 H, overlapped, J = 7.6 Hz), 7.38 (t, 1 H, J = 7.8 Hz), 7.25 (br d, 1 H, J = 8.0 Hz), 7.00 (d, 1 H, J = 7.6), 6.80 (d, 1 H, J = 8.4 Hz), 6.75 (td, 1 H, J = 8.0, 0.8 Hz), 5.32 (br t, 1 H, J = 5.6 Hz), 4.62 (d, 2 H, J = 5.6 Hz), 2.41 (s, 3 H) | 407.19 |
| 60 | 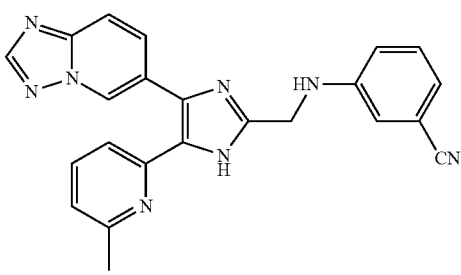 | (400 MHz, CDCl₃) δ 8.94 (t, 1 H, J = 1.2 Hz), 8.38 (s, 1 H), 7.80 (dd, 1 H, J = 9.2, 0.8 Hz), 7.77 (dd, 1 H, J = 9.2, 1.6 Hz), 7.55 (t, 1 H, J = 8.0 Hz), 7.31 (d, 1 H, J = 8.0 Hz), 7.25 (t, 1 H, J = 8.0 Hz), 7.08 (d, 1 H, J = 8.0 Hz), 7.02 (dt, 1 H, J = 7.6, 1.2 Hz), 6.96-6.92 (m, 2 H), 4.56 (s, 2 H), 2.62 (s, 3 H) | 407.19 |
| 61 | 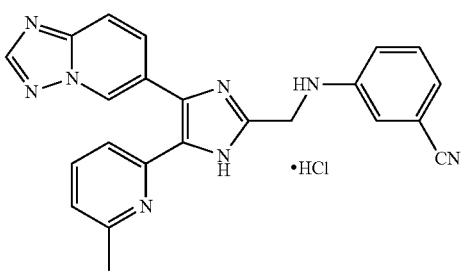 | (400 MHz, DMSO-d₆) δ 9.47 (d, 1 H, J = 0.8 Hz), 8.66 (s, 1 H), 7.97 (dd, 1 H, J = 9.2, 0.8 Hz), 7.87 (t, 1 H, overlapped, J = 7.8 Hz), 7.85 (dd, 1 H, overlapped, J = 9.2, 1.6 Hz), 7.63 (d, 1 H, J = 7.6 Hz), 7.40 (d, 1 H, J = 8.0 Hz), 7.33 (t, 1 H, J = 7.8 Hz), 7.16 (t, 1 H, J = 1.6 Hz), 7.11 (dd, 1 H, J = 8.4, 1.6 Hz), 7.06 (br d, 1 H, J = 7.6 Hz), 4.79 (s, 2 H), 2.53 (s, 3 H) | |

TABLE 1-continued

| Example | Structure | $^1$H NMR (ppm) | MS (ESI) m/z (MH$^+$) |
|---|---|---|---|
| 62 | (structure: [1,2,4]triazolo[1,5-a]pyridine-imidazole with 6-methylpyridine and (3-cyanophenyl)aminomethyl, ·H$_2$SO$_4$) | (400 MHz, DMSO-d$_6$) δ 9.39 (br s, 1 H), 8.64 (s, 1 H), 7.99 (d, 1 H, J = 9.2 Hz), 7.87 (t, 1 H, J = 7.6 Hz), 7.77 (dd, 1 H, J = 9.2, 1.6 Hz), 7.45 (d, 1 H, overlapped, J = 7.6 Hz), 7.44 (d, 1 H, overlapped, J = 7.6 Hz), 7.34 (t, 1 H, J = 8.0 Hz), 7.10 (d, 1 H, J = 2.0 Hz), 7.07 (d, 1 H, overlapped, J = 7.6 Hz), 7.04 (dd, 1 H, overlapped, J = 8.0, 2.0 Hz), 4.70 (s, 2 H), 2.60 (s, 3 H) | |
| 63 | (structure: with 4-cyanophenyl amino) | (400 MHz, CDCl$_3$) δ 8.93 (t, 1 H, J = 1.2 Hz), 8.37 (s, 1 H), 7.79 (dd, 1 H, overlapped, J = 9.2, 1.6 Hz), 7.76 (dd, 1 H, overlapped, J = 9.2, 0.8 Hz), 7.48 (t, 1 H, J = 7.8 Hz), 7.43 (m, 2 H), 7.24 (d, 1 H, J = 8.0 Hz), 7.03 (d, 1 H, J = 7.6 Hz), 6.68 (m, 2 H), 5.12 (br s, 1 H), 4.54 (d, 2 H, J = 4.0 Hz), 2.51 (s, 3 H) | 407.19 |
| 64 | (structure: with 2,3-dicyanophenyl amino) | (400 MHz, CDCl$_3$) δ 8.99 (br s, 1 H), 8.35 (s, 1 H), 7.84 (dd, 1 H, J = 9.2, 1.6 Hz), 7.74 (dd, 1 H, J = 9.2, 0.8 Hz), 7.50 (t, 1 H, J = 7.8 Hz), 7.37 (t, 1 H, J = 8.2 Hz), 7.27 (br d, 1 H, J = 7.6 Hz), 7.05 (d, 1 H, J = 8.8 Hz), 7.01 (d, 1 H, J = 8.0 Hz), 6.98 (d, 1 H, overlapped, J = 7.6 Hz), 5.94 (br t, 1 H, J = 5.6 Hz), 4.66 (d, 2 H, J = 5.6 Hz), 2.30 (s, 3 H) | 432.19 |
| 65 | (structure: with 2-carbamoylphenyl amino) | (400 MHz, CDCl$_3$) δ 9.04 (dd, 1 H, J = 1.6, 0.8 Hz), 8.48 (br s, 1 H), 8.33 (s, 1 H), 7.84 (dd, 1 H, J = 9.2, 1.6 Hz), 7.72 (d, 1 H, J = 9.2 Hz), 7.41 (t, 1 H, J = 7.8 Hz), 7.37 (dd, 1 H, J = 7.6, 1.2 Hz), 7.29 (td, 1 H, J = 8.4, 1.2 Hz), 7.21 (br d, 1 H, J = 8.0 Hz), 6.92 (d, 1 H, J = 7.6 Hz), 6.83 (d, 1 H, J = 8.4 Hz), 6.62 (td, 1 H, J = 8.0, 1.0 Hz), 6.25 (br s, 2 H), 4.59 (d, 2 H, J = 5.2 Hz), 2.32 (s, 3 H) | 425.20 |
| 66 | (structure: with 3-carbamoylphenyl amino) | (400 MHz, CD$_3$OD) δ 9.06 (br s, 1 H), 8.34 (s, 1 H), 7.83 (br d, 1 H, J = 9.2 Hz), 7.71 (d, 1 H, J = 9.2 Hz), 7.59-7.55 (m, 2 H), 7.22-7.18 (m, 2 H), 7.15 (dt, 1 H, J = 7.6, 2.0 Hz), 7.10 (dd, 1 H, J = 8.4, 0.8 Hz), 6.86 (ddd, 1 H, J = 7.6, 2.0, 0.8 Hz), 4.51 (s, 2 H), 2.50 (s, 3 H) | 425.20 |

TABLE 1-continued

| Example | Structure | ¹H NMR (ppm) | MS (ESI) m/z (MH+) |
|---|---|---|---|
| 67 | 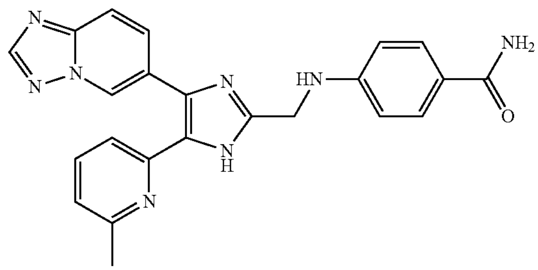 [SMILES: Cc1cccc(-c2[nH]c(CNc3ccc(C(N)=O)cc3)nc2-c2ccc3ncnn3c2)n1] | (400 MHz, CDCl₃/CD₃OD) δ 9.03 (br s, 1 H), 8.32 (s, 1 H), 7.81 (dd, 1 H, J = 9.2, 1.6 Hz), 7.70 (dd, 1 H, J = 9.2, 0.8 Hz), 7.67 (m, 2 H), 7.55 (t, 1 H, J = 7.6 Hz), 7.26 (br d, 1 H, J = 7.6 Hz), 7.09 (d, 1 H, J = 7.6 Hz), 6.71 (m, 2 H), 4.52 (s, 2 H), 2.51 (s, 3 H) | 425.20 |
| 68 | 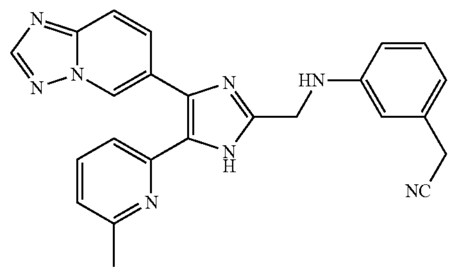 [SMILES: Cc1cccc(-c2[nH]c(CNc3cccc(CC#N)c3)nc2-c2ccc3ncnn3c2)n1] | (400 MHz, CDCl₃) δ 10.76 (br s, 1 H), 8.94 (br s, 1 H), 8.37 (s, 1 H), 7.81 (br d, 1 H, J = 9.2 Hz), 7.76 (br d, 1 H, J = 9.2 Hz), 7.46 (t, 1 H, J = 7.6 Hz), 7.21 (br d, 1 H, J = 7.6 Hz), 7.20-7.15 (m, 1 H), 7.01 (d, 1 H, J = 7.6 Hz), 6.69 (dd, 1 H, J = 7.6, 0.8 Hz), 6.62-6.40 (m, 2 H), 4.53 (br s, 1 H, overlapped), 4.52 (br s, 2 H, overlapped), 3.65 (s, 2 H), 2.50 (s, 3 H) | 421.21 |
| 69 | 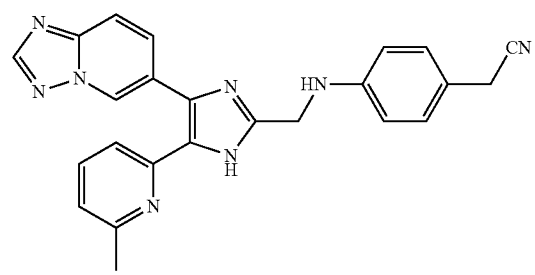 [SMILES: Cc1cccc(-c2[nH]c(CNc3ccc(CC#N)cc3)nc2-c2ccc3ncnn3c2)n1] | (400 MHz, CDCl₃) δ 10.78 (br s, 1 H), 8.94 (br s, 1 H), 8.36 (s, 1 H), 7.80 (dd, 1 H, J = 9.2, 1.2 Hz), 7.76 (d, 1 H, J = 9.2 Hz), 7.46 (t, 1 H, J = 7.8 Hz), 7.22 (br d, 1 H, J = 7.6 Hz), 7.11 (d, 2 H, J = 8.4 Hz), 7.01 (d, 1 H, J = 8.0 Hz), 6.67 (d, 2 H, J = 8.4 Hz), 4.50 (br s, 3 H), 3.61 (s, 2 H), 2.49 (s, 3 H) | 421.21 |
| 70 | 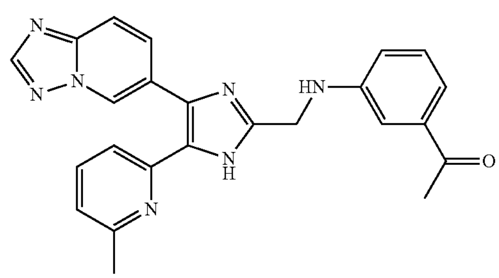 [SMILES: CC(=O)c1cccc(NCc2nc(-c3ccc4ncnn4c3)c(-c3cccc(C)n3)[nH]2)c1] | (400 MHz, CDCl₃) δ 11.09 (br s, 1 H), 8.92 (s, 1 H), 8.35 (s, 1 H), 7.79 (d, 1 H, J = 9.2 Hz), 7.74 (d, 1 H, J = 9.2 Hz), 7.44 (t, 1 H, J = 7.8 Hz), 7.30 (d, 1 H, J = 7.6 Hz), 7.26-7.24 (m, 1 H), 7.23 (t, 1 H, overlapped, J = 7.8 Hz), 7.19 (br d, 1 H, J = 8.0 Hz), 7.00 (d, 1 H, J = 8.0 Hz), 6.86 (dd, 1 H, J = 8.0, 1.8 Hz), 4.68 (br s, 1 H), 4.52 (d, 2 H, J = 5.2 Hz), 2.53 (s, 3 H), 2.47 (s, 3 H) | 424.21 |
| 71 | 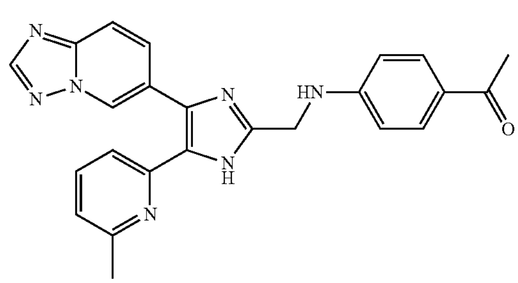 [SMILES: CC(=O)c1ccc(NCc2nc(-c3ccc4ncnn4c3)c(-c3cccc(C)n3)[nH]2)cc1] | (400 MHz, CDCl₃) δ 8.96 (t, 1 H, J = 1.4 Hz), 8.37 (s, 1 H), 7.81 (d, 2 H, J = 8.8 Hz), 7.79-7.76 (m, 2 H), 7.54 (t, 1 H, J = 7.8 Hz), 7.30 (d, 1 H, J = 8.0 Hz), 7.07 (d, 1 H, J = 7.6 Hz), 6.70 (d, 2 H, J = 8.8 Hz), 4.63 (s, 2 H), 2.59 (s, 3 H), 2.48 (s, 3 H) | 424.21 |

TABLE 1-continued

| Example | Structure | ¹H NMR (ppm) | MS (ESI) m/z (MH⁺) |
|---|---|---|---|
| 72 | 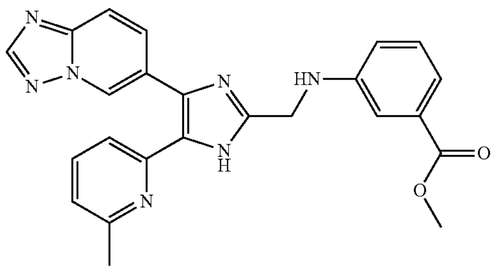 [SMILES: COC(=O)c1cccc(NCc2nc(-c3ccc4ncnn4c3)c(-c3cccc(C)n3)[nH]2)c1] | (400 MHz, CDCl₃) δ 8.94 (br s, 1 H), 8.34 (s, 1 H), 7.77 (dd, 1 H, J = 9.2, 1.6 Hz), 7.72 (dd, 1 H, J = 9.2, 0.8 Hz), 7.44 (t, 1 H, J = 7.8 Hz), 7.39 (dt, 1 H, J = 7.6, 1.2 Hz), 7.32 (dd, 1 H, J = 2.4, 1.6 Hz), 7.22 (d, 1 H, overlapped, J = 8.0 Hz), 7.19 (t, 1 H, overlapped, J = 8.0 Hz), 6.98 (d, 1 H, J = 7.6 Hz), 6.81 (ddd, 1 H, J = 8.0, 2.4, 0.8 Hz), 4.49 (s, 2 H), 3.84 (s, 3 H), 2.43 (s, 3 H) | 440.20 |
| 73 | 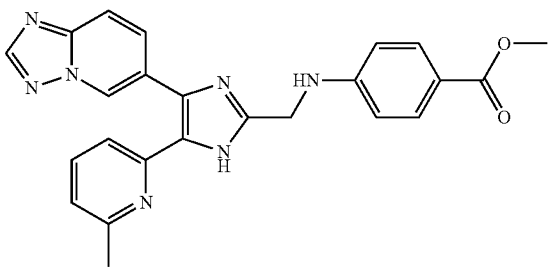 [SMILES: COC(=O)c1ccc(NCc2nc(-c3ccc4ncnn4c3)c(-c3cccc(C)n3)[nH]2)cc1] | (400 MHz, CDCl₃) δ 10.52 (br s, 1 H), 8.94 (s, 1 H), 8.37 (s, 1 H), 7.89 (m, 2 H), 7.81 (br d, 1 H, J = 9.6 Hz), 7.78 (br d, 1 H, J = 9.6 Hz), 7.46 (t, 1 H, J = 8.0 Hz), 7.21 (d, 1 H, J = 8.0 Hz), 7.02 (d, 1 H, J = 8.0 Hz), 6.68 (m, 2 H), 4.90 (t, 1 H, J = 5.6 Hz), 4.58 (d, 2 H, J = 5.6 Hz), 3.85 (s, 3 H), 2.51 (s, 3 H) | 440.20 |
| 74 | 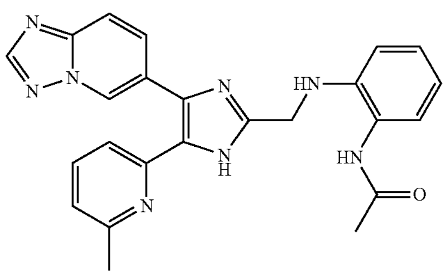 [SMILES: CC(=O)Nc1ccccc1NCc1nc(-c2ccc3ncnn3c2)c(-c2cccc(C)n2)[nH]1] | (400 MHz, DMSO-d₆) δ 12.56 (br s, 1 H), 9.36 (s, 1 H), 9.58 (s, 1 H), 8.50 (s, 1 H), 8.00 (br d, 1 H, J = 9.2 Hz), 7.82 (d, 1 H, J = 9.2 Hz), 7.71 (t, 1 H, J = 7.8 Hz), 7.44 (br s, 1 H), 7.16 (d, 1 H, overlapped, J = 8.0 Hz), 7.15 (d, 1 H, overlapped, J = 7.6 Hz), 7.03 (td, 1 H, J = 7.6, 1.2 Hz), 6.81 (d, 1 H, J = 7.6 Hz), 6.61 (td, 1 H, J = 7.6, 1.2 Hz), 5.65 (t, 1 H, J = 6.0 Hz), 4.45 (d, 2 H, J = 6.0 Hz), 2.47 (br s, 3 H), 2.09 (s, 3 H) | 439.22 |
| 75 | 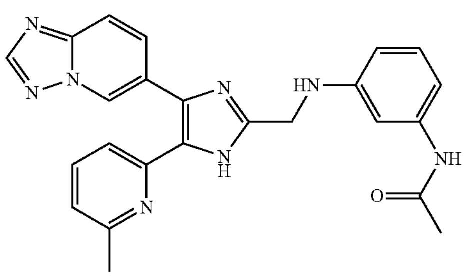 [SMILES: CC(=O)Nc1cccc(NCc2nc(-c3ccc4ncnn4c3)c(-c3cccc(C)n3)[nH]2)c1] | (400 MHz, DMSO-d₆) δ 8.97 (br s, 1 H), 8.35 (s, 1 H), 7.79 (dd, 1 H, J = 9.2, 1.6 Hz), 7.73 (d, 1 H, J = 9.2 Hz), 7.46 (t, 1 H, J = 7.8 Hz), 7.38 (br s, 1 H), 7.24 (d, 1 H, J = 8.0 Hz), 7.15 (br s, 1 H), 7.09 (t, 1 H, J = 8.0 Hz), 7.01 (d, 1 H, J = 7.6 Hz), 6.69 (br d, 1 H, J = 8.0 Hz), 6.41 (dd, 1 H, J = 8.0, 1.6 Hz), 4.50 (s, 2 H), 2.51 (s, 3 H), 2.13 (s, 3 H) | 439.22 |
| 76 | 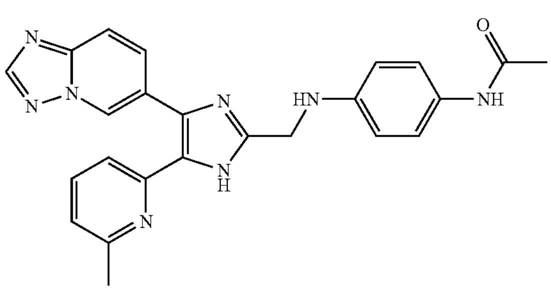 [SMILES: CC(=O)Nc1ccc(NCc2nc(-c3ccc4ncnn4c3)c(-c3cccc(C)n3)[nH]2)cc1] | (400 MHz, DMSO-d₆) δ 8.96 (br s, 1 H), 8.37 (s, 1 H), 7.81 (dd, 1 H, J = 9.2, 1.6 Hz), 7.76 (dd, 1 H, J = 9.2, 0.8 Hz), 7.46 (t, 1 H, J = 7.8 Hz), 7.27 (m, 2 H), 7.23 (d, 1 H, J = 8.0 Hz), 7.10 (br s, 1 H), 7.01 (d, 1 H, J = 7.6 Hz), 6.66 (m, 2 H), 4.50 (s, 2 H), 2.53 (s, 3 H), 2.13 (s, 3 H) | 439.22 |

TABLE 1-continued

| Example | Structure | $^1$H NMR (ppm) | MS (ESI) m/z (MH$^+$) |
|---|---|---|---|
| 77 | 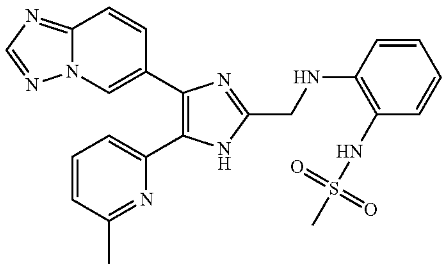 [SMILES: Cc1cccc(-c2[nH]c(CNc3ccccc3NS(C)(=O)=O)nc2-c2ccc3ncnn3c2)n1] | (400 MHz, CD$_3$OD) δ 9.18 (dd, 1 H, J = 1.6, 0.8 Hz), 8.41 (s, 1 H), 7.87 (dd, 1 H, J = 9.2, 1.6 Hz), 7.75 (dd, 1 H, J = 9.2, 0.8 Hz), 7.66 (t, 1 H, J = 7.8 Hz), 7.38 (br d, 1 H, J = 7.6 Hz), 7.20 (dd, 1 H, J = 7.8, 1.4 Hz), 7.16 (d, 1 H, overlapped, J = 7.6 Hz), 7.15 (td, 1 H, overlapped, J = 8.0, 1.6 Hz), 6.82 (dd, 1 H, J = 8.0, 1.2 Hz), 6.71 (td, 1 H, J = 8.0, 1.4 Hz), 4.59 (s, 2 H), 3.05 (s, 3 H), 2.48 (s, 3 H) | 475.19 |
| 78 | 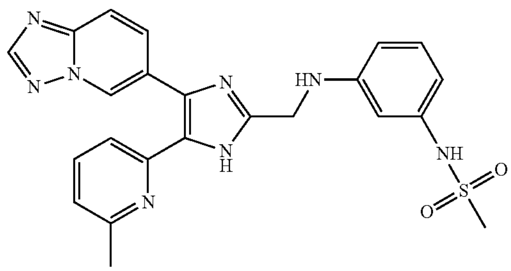 [SMILES: Cc1cccc(-c2[nH]c(CNc3cccc(NS(C)(=O)=O)c3)nc2-c2ccc3ncnn3c2)n1] | (400 MHz, CDCl$_3$) δ 8.92 (br s, 1 H), 8.35 (s, 1 H), 7.78 (dd, 1 H, J = 9.2, 1.6 Hz), 7.73 (dd, 1 H, J = 9.2, 0.8 Hz), 7.46 (t, 1 H, J = 7.6 Hz), 7.21 (br d, 1 H, J = 7.6 Hz), 7.11 (t, 1 H, overlapped, J = 8.2 Hz), 7.10 (br s, 1 H, overlapped), 7.01 (d, 1 H, J = 7.6 Hz), 6.58 (t, 1 H, J = 2.0 Hz), 6.54 (ddd, 1 H, J = 8.2, 2.0, 0.8 Hz), 6.49 (ddd, 1 H, J = 8.2, 2.0, 0.8 Hz), 4.50 (s, 2 H), 2.94 (s, 3 H), 2.51 (s, 3 H) | 475.19 |
| 79 | 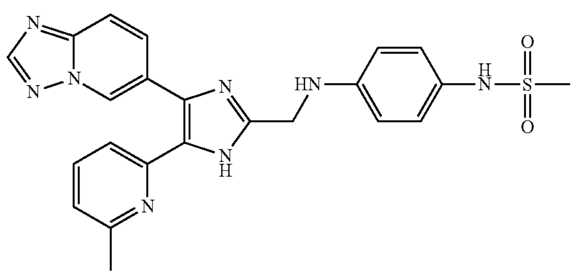 [SMILES: Cc1cccc(-c2[nH]c(CNc3ccc(NS(C)(=O)=O)cc3)nc2-c2ccc3ncnn3c2)n1] | (400 MHz, CDCl$_3$) δ 8.93 (br s, 1 H), 8.38 (s, 1 H), 7.80 (dd, 1 H, J = 9.2, 1.6 Hz), 7.76 (d, 1 H, J = 9.2 Hz), 7.46 (t, 1 H, J = 7.8 Hz), 7.22 (br d, 1 H, J = 8.0 Hz), 7.09 (d, 2 H, J = 8.8 Hz), 7.02 (d, 1 H, J = 7.6 Hz), 6.67 (d, 2 H, J = 8.8 Hz), 6.34 (br s, 1 H), 4.52 (br s, 3 H), 2.93 (s, 3 H), 2.54 (s, 3 H) | 475.19 |
| 80 | 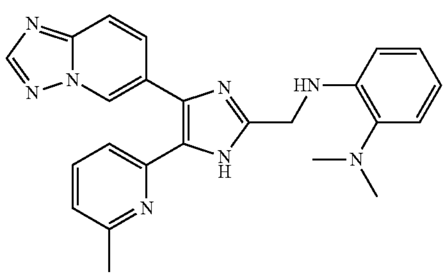 | (400 MHz, CDCl$_3$) δ 8.99 (s, 1 H), 8.36 (s, 1 H), 7.83 (dd, 1 H, J = 9.2, 1.6 Hz), 7.77 (dd, 1 H, J = 9.2, 0.8 Hz), 7.45 (t, 1 H, J = 7.8 Hz), 7.23 (br d, 1 H, J = 7.6 Hz), 7.10 (dd, 1 H, J = 8.0, 1.2 Hz), 7.02 (td, 1 H, overlapped, J = 7.6 Hz), 7.00 (d, 1 H, overlapped, J = 8.0 Hz), 6.78 (td, 1 H, J = 7.6, 1.2 Hz), 6.72 (dd, 1 H, J = 8.0, 1.2 Hz), 4.58 (s, 2 H), 2.73 (s, 6 H), 2.50 (s, 3 H) | 425.20 |
| 81 | 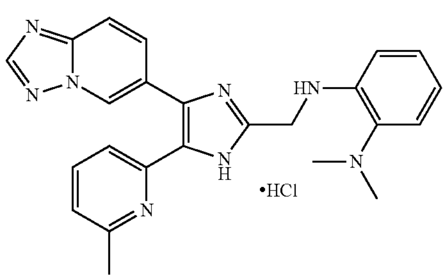 | (400 MHz, DMSO-d$_6$) δ 9.47 (dd, 1 H, J = 1.6, 0.8 Hz), 8.63 (s, 1 H), 7.97 (dd, 1 H, J = 9.2, 0.8 Hz), 7.87 (t, 1 H, J = 7.8 Hz), 7.84 (dd, 1 H, J = 9.2, 1.6 Hz), 7.59 (br d, 1 H, overlapped, J = 8.0 Hz), 7.58 (d, 1 H, J = 7.6 Hz), 7.41 (d, 1 H, J = 7.6 Hz), 7.29 (t, 1 H, J = 7.4 Hz), 6.99 (dd, 1 H, J = 7.6. 0.8 Hz), 6.89 (t, 1 H, J = 7.4 Hz), 4.81 (s, 2 H), 3.10 (s, 6 H), 2.56 (s, 3 H) | |

TABLE 1-continued

| Example | Structure | $^1$H NMR (ppm) | MS (ESI) m/z (MH$^+$) |
|---|---|---|---|
| 82 | 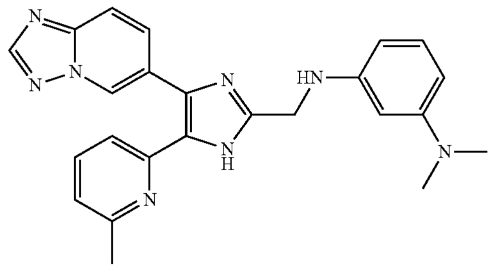 [SMILES: Cc1cccc(-c2[nH]c(CNc3cccc(N(C)C)c3)nc2-c2ccc3ncnn3c2)n1] | (400 MHz, CDCl$_3$) δ 8.97 (s, 1 H), 8.36 (s, 1 H), 7.80 (dd, 1 H, J = 9.2, 1.6 Hz), 7.75 (d, 1 H, J = 9.2 Hz), 7.45 (t, 1 H, J = 7.8 Hz), 7.23 (d, 1 H, J = 8.0 Hz), 7.07 (t, 1 H, J = 8.2 Hz), 7.00 (d, 1 H, J = 7.6 Hz), 6.24 (d, 1 H, J = 8.0 Hz), 6.14 (br s, 2 H), 4.55 (s, 2 H), 2.90 (s, 6 H), 2.52 (s, 3 H) | 425.21 |
| 83 | 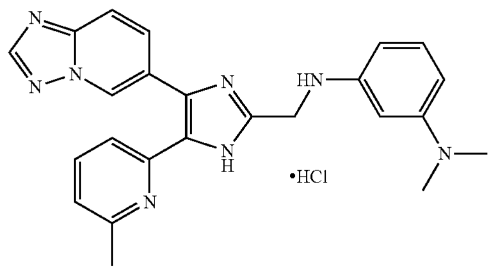 [SMILES: Cc1cccc(-c2[nH]c(CNc3cccc(N(C)C)c3)nc2-c2ccc3ncnn3c2)n1 ; Cl] | (400 MHz, DMSO-d$_6$) δ 9.48 (dd, 1 H, J = 1.6, 0.8 Hz), 8.64 (s, 1 H), 7.97 (dd, 1 H, J = 9.2, 0.8 Hz), 7.86 (t, 1 H, overlapped, J = 7.8 Hz), 7.85 (dd, 1 H, overlapped, J = 9.2, 1.6 Hz), 7.62 (d, 1 H, J = 8.0 Hz), 7.39 (d, 1 H, J = 7.6 Hz), 7.28 (t, 1 H, J = 8.2 Hz), 7.17 (br s, 1 H), 6.98 (br d, 1 H, J = 8.0 Hz), 6.81 (br d, 1 H, J = 8.4 Hz), 4.78 (s, 2 H), 3.09 (s, 6 H), 2.52 (s, 3 H) | |
| 84 | 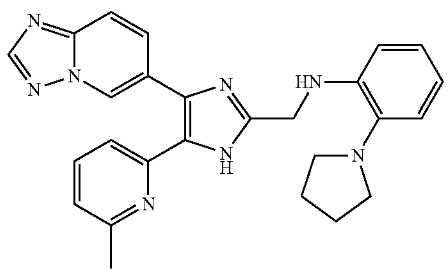 [SMILES: Cc1cccc(-c2[nH]c(CNc3ccccc3N3CCCC3)nc2-c2ccc3ncnn3c2)n1] | (400 MHz, CDCl$_3$) δ 10.41 (br s, 1 H), 8.99 (s, 1 H), 8.36 (s, 1 H), 7.84 (dd, 1 H, J = 9.2, 1.2 Hz), 7.76 (d, 1 H, J = 9.2 Hz), 7.45 (t, 1 H, J = 7.8 Hz), 7.23 (br s, 1 H), 7.10 (dd, 1 H, J = 7.6, 1.2 Hz), 7.00 (td, 1 H, overlapped, J = 7.6, 1.2 Hz), 6.99 (d, 1 H, overlapped, J = 7.6 Hz), 6.77 (td, 1 H, J = 7.6, 1.2 Hz), 6.72 (d, 1 H, J = 8.0 Hz), 4.58 (s, 2 H), 3.12 (br s, 4 H), 2.51 (s, 3 H), 1.98 (br s, 4 H) | 451.22 |
| 85 | 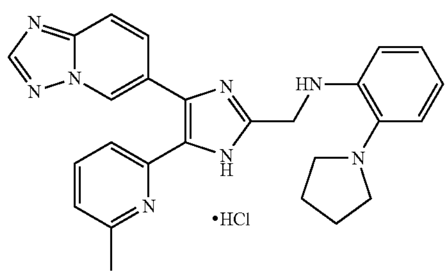 [SMILES: Cc1cccc(-c2[nH]c(CNc3ccccc3N3CCCC3)nc2-c2ccc3ncnn3c2)n1 ; Cl] | (400 MHz, DMSO-d$_6$) δ 9.47 (dd, 1 H, J = 2.0, 0.8 Hz), 8.63 (s, 1 H), 7.97 (dd, 1 H, J = 9.2, 0.8 Hz), 7.87 (t, 1 H, J = 7.8 Hz), 7.84 (dd, 1 H, J = 9.2, 2.0 Hz), 7.60 (d, 1 H, J = 8.0 Hz), 7.57 (d, 1 H, J = 8.0 Hz), 7.41 (d, 1 H, J = 7.6 Hz), 7.30 (td, 1 H, J = 7.8, 0.8 Hz), 7.02 (dd, 1 H, J = 7.8, 1.2 Hz), 6.88 (td, 1 H, J = 8.0, 1.2 Hz), 4.82 (s, 2 H), 3.72 (br s, 4 H), 2.55 (s, 3 H), 2.17 (m, 4 H) | |
| 86 | 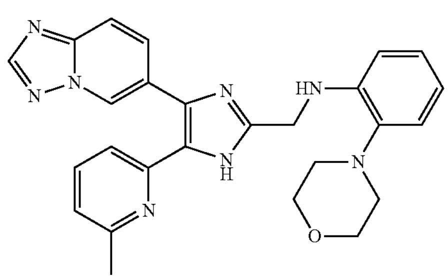 [SMILES: Cc1cccc(-c2[nH]c(CNc3ccccc3N3CCOCC3)nc2-c2ccc3ncnn3c2)n1] | (400 MHz, CDCl$_3$) δ 8.96 (s, 1 H), 8.37 (s, 1 H), 7.82 (dd, 1 H, J = 9.2, 1.6 Hz), 7.78 (dd, 1 H, J = 9.2, 1.2 Hz), 7.48 (t, 1 H, J = 7.6 Hz), 7.25 (br d, 1 H, J = 7.6 Hz), 7.09 (dd, 1 H, J = 8.0, 1.6 Hz), 7.05 (td, 1 H, overlapped, J = 7.6, 1.6 Hz), 7.02 (d, 1 H, overlapped, J = 7.6 Hz), 6.80 (td, 1 H, J = 7.6, 1.2 Hz), 6.71 (dd, 1 H, J = 8.0, 1.2 Hz), 4.57 (s, 2 H), 3.90 (br t, 4 H, J = 4.6 Hz), 2.96 (br t, 4 H, J = 4.6 Hz), 2.54 (s, 3 H) | 467.22 |

TABLE 1-continued

| Example | Structure | ¹H NMR (ppm) | MS (ESI) m/z (MH⁺) |
|---|---|---|---|
| 87 | 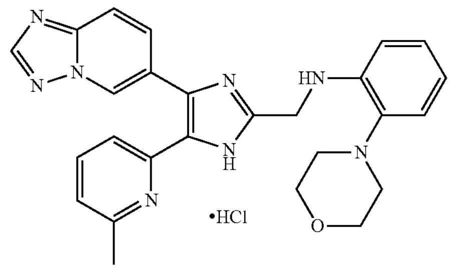 [SMILES: Cc1cccc(-c2[nH]c(CNc3ccccc3N3CCOCC3)nc2-c2ccc3ncnn3c2)n1 ; Cl] | (400 MHz, DMSO-d₆) δ 9.46 (dd, 1 H, J = 1.6, 0.8 Hz), 8.64 (s, 1 H), 7.98 (dd, 1 H, J = 9.2, 0.8 Hz), 7.84 (t, 1 H, J = 7.8 Hz), 7.82 (dd, 1 H, J = 9.2, 1.6 Hz), 7.57 (d, 1 H, J = 8.0 Hz), 7.38 (d, 1 H, J = 7.6 Hz), 7.06 (dd, 1 H, J = 7.6, 1.2 Hz), 6.98 (td, 1 H, J = 7.8, 1.2 Hz), 6.82 (dd, 1 H, J = 7.8, 1.2 Hz), 6.70 (td, 1 H, J = 7.6, 1.2 Hz), 4.80 (s, 2 H), 3.84 (br t, 4 H, J = 4.4 Hz), 2.89 (br t, 4 H, J = 4.4 Hz), 2.53 (s, 3 H) | |
| 88 | 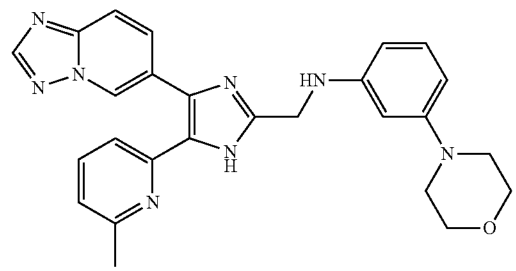 [SMILES: Cc1cccc(-c2[nH]c(CNc3cccc(N4CCOCC4)c3)nc2-c2ccc3ncnn3c2)n1] | (400 MHz, CDCl₃) δ 8.96 (t, 1 H, J = 1.2 Hz), 8.37 (s, 1 H), 7.82-7.76 (m, 2 H), 7.48 (t, 1 H, J = 7.6 Hz), 7.24 (br d, 1 H, J = 7.6 Hz), 7.12 (t, 1 H, J = 8.0 Hz), 7.03 (d, 1 H, J = 7.6 Hz), 6.39 (dd, 1 H, J = 8.0, 1.6 Hz), 6.34 (t, 1 H, J = 2.0 Hz), 6.29 (dd, 1 H, J = 8.0, 2.0 Hz), 4.56 (s, 2 H), 3.85-3.82 (m, 4 H), 3.15-3.12 (m, 4 H), 2.56 (s, 3 H) | 467.23 |
| 89 | 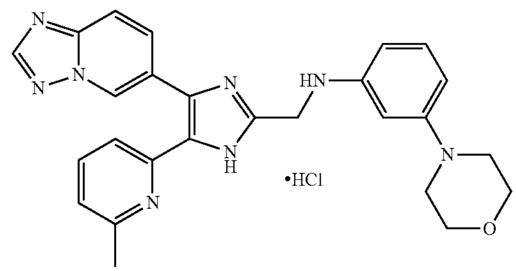 [SMILES: Cc1cccc(-c2[nH]c(CNc3cccc(N4CCOCC4)c3)nc2-c2ccc3ncnn3c2)n1 ; Cl] | (400 MHz, DMSO-d₆) δ 9.47 (dd, 1 H, J = 1.6, 0.8 Hz), 8.64 (s, 1 H), 7.97 (dd, 1 H, J = 9.2, 0.8 Hz), 7.85 (t, 1 H, J = 8.0 Hz), 7.84 (dd, 1 H, J = 9.2, 1.6 Hz), 7.60 (d, 1 H, J = 8.0 Hz), 7.39 (d, 1 H, J = 8.0 Hz), 7.17 (t, 1 H, J = 8.0 Hz), 6.86 (br s, 1 H), 6.76 (br s, 1 H), 6.59 (br d, 1 H, J = 7.6 Hz), 4.76 (s, 2 H), 3.92 (br s, 4 H), 3.34 (br s, 4 H), 2.52 (s, 3 H) | |
| 90 | 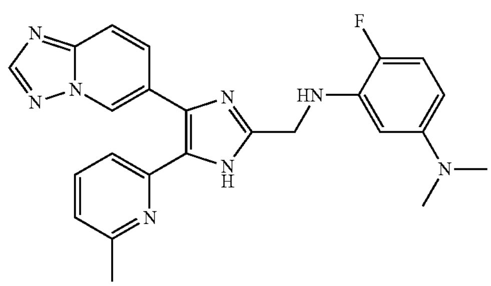 [SMILES: Cc1cccc(-c2[nH]c(CNc3cc(N(C)C)ccc3F)nc2-c2ccc3ncnn3c2)n1] | (400 MHz, CDCl₃) δ 8.95 (t, 1 H, J = 1.2 Hz), 8.35 (s, 1 H), 7.78 (dd, 1 H, J = 9.2, 1.6 Hz), 7.70 (dd, 1 H, J = 9.2, 1.2 Hz), 7.43 (t, 1 H, J = 7.8 Hz), 7.21 (d, 1 H, J = 8.0 Hz), 6.94 (d, 1 H, J = 7.6 Hz), 6.80-6.73 (m, 1 H), 6.14 (br d, 1 H, J = 7.6 Hz), 6.00-5.95 (m, 1 H), 4.49 (s, 2 H), 2.79 (s, 6 H), 2.31 (s, 3 H) | 443.21 |
| 91 | 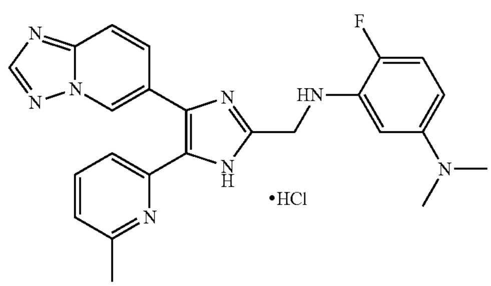 [SMILES: Cc1cccc(-c2[nH]c(CNc3cc(N(C)C)ccc3F)nc2-c2ccc3ncnn3c2)n1 ; Cl] | (400 MHz, DMSO-d₆) δ 9.49 (dd, 1 H, J = 1.6, 0.8 Hz), 8.63 (s, 1 H), 7.97 (dd, 1 H, J = 9.2, 0.8 Hz), 7.85 (dd, 1 H, overlapped, J = 9.2, 1.6 Hz), 7.84 (t, 1 H, overlapped, J = 8.0 Hz), 7.60 (d, 1 H, J = 8.0 Hz), 7.39 (br s, 1 H, overlapped), 7.38 (d, 1 H, overlapped, J = 8.0 Hz), 7.24 (pseudo t, 1 H, J = 9.8 Hz), 6.97 (br s, 1 H), 4.86 (s, 2 H), 3.10 (s, 6 H), 2.52 (s, 3 H) | |

TABLE 1-continued

| Example | Structure | $^1$H NMR (ppm) | MS (ESI) m/z (MH$^+$) |
|---|---|---|---|
| 92 | 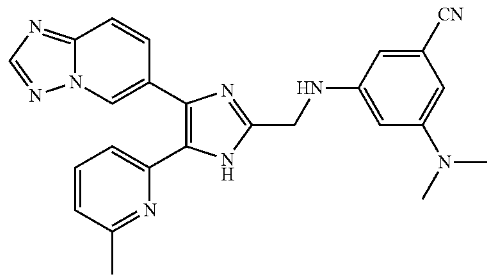 [SMILES: Cc1cccc(-c2[nH]c(CNc3cc(C#N)cc(N(C)C)c3)nc2-c2ccc3ncnn3c2)n1] | (400 MHz, CDCl$_3$) δ 8.94 (t, 1 H, J = 1.2 Hz), 8.38 (s, 1 H), 7.80 (dd, 1 H, overlapped, J = 9.2, 1.6 Hz), 7.78 (dd, 1 H, overlapped, J = 9.2, 1.2 Hz), 7.49 (t, 1 H, J = 7.6 Hz), 7.25 (d, 1 H, J = 7.6 Hz), 7.04 (d, 1 H, J = 7.6 Hz), 6.38 (dd, 1 H, J = 2.4, 1.2 Hz), 6.30 (t, 1 H, J = 1.6 Hz), 6.18 (t, 1 H, J = 2.2 Hz), 4.53 (s, 2 H), 2.92 (s, 6 H), 2.56 (s, 3 H) | 450.21 |
| 93 | •HCl | (400 MHz, DMSO-d$_6$) δ 9.44 (dd, 1 H, J = 2.0, 0.8 Hz), 8.63 (s, 1 H), 7.97 (dd, 1 H, J = 9.2, 0.8 Hz), 7.85 (t, 1 H, J = 7.8 Hz), 7.81 (dd, 1 H, J = 9.2, 2.0 Hz), 7.55 (d, 1 H, J = 8.0 Hz), 7.40 (d, 1 H, J = 7.6 Hz), 6.47 (s, 2 H), 6.37 (br s, 1 H), 4.73 (s, 2 H), 2.90 (s, 6 H), 2.55 (s, 3 H) | |
| 94 | 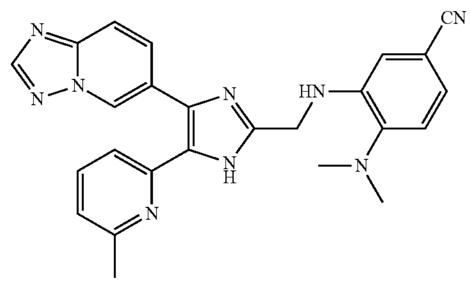 [SMILES: Cc1cccc(-c2[nH]c(CNc3cc(C#N)ccc3N(C)C)nc2-c2ccc3ncnn3c2)n1] | (400 MHz, CDCl$_3$) δ 8.96 (t, 1 H, J = 1.6 Hz), 8.38 (s, 1 H), 7.82 (dd, 1 H, J = 9.2, 1.6 Hz), 7.79 (dd, 1 H, J = 9.2, 0.8 Hz), 7.53 (t, 1 H, J = 7.8 Hz), 7.31 (d, 1 H, J = 8.0 Hz), 7.08-7.03 (m, 3 H), 6.87 (d, 1 H, J = 1.6 Hz), 5.44 (br s, 1 H), 4.55 (s, 2 H), 2.74 (s, 6 H), 2.58 (s, 3 H) | 450.21 |
| 95 | •HCl | (400 MHz, DMSO-d$_6$) δ 9.44 (dd, 1 H, J = 1.6, 0.8 Hz), 8.64 (s, 1 H), 7.99 (dd, 1 H, J = 9.2, 0.8 Hz), 7.84 (t, 1 H, overlapped, J = 7.8 Hz), 7.82 (dd, 1 H, J = 9.2, 0.8 Hz), 7.51 (d, 1 H, J = 8.0 Hz), 7.39 (d, 1 H, J = 7.6 Hz), 7.15 (dd, 2 H, overlapped, J = 7.6, 0.8 Hz), 7.14 (d, 1 H, overlapped, J = 1.2 Hz), 4.79 (s, 2 H), 2.71 (s, 6 H), 2.56 (s, 3 H) | |
| 96 | 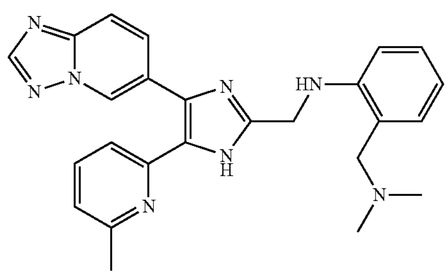 [SMILES: Cc1cccc(-c2[nH]c(CNc3ccccc3CN(C)C)nc2-c2ccc3ncnn3c2)n1] | (400 MHz, CDCl$_3$) δ 10.57 (br s, 1 H), 8.97 (s, 1 H), 8.34 (s, 1 H), 7.82 (dd, 1 H, J = 9.2, 1.2 Hz), 7.74 (d, 1 H, J = 9.2 Hz), 7.43 (t, 1 H, J = 7.8 Hz), 7.21 (br s, 1 H, overlapped), 7.17 (td, 1 H, J = 8.0, 1.6 Hz), 7.01 (dd, 1 H, J = 7.6, 1.6 Hz), 6.98 (d, 1 H, J = 7.6 Hz), 6.72-6.66 (m, 2 H), 4.61 (s, 2 H), 3.54 (s, 2 H), 2.51 (s, 3 H), 2.28 (s, 6 H) | 439.23 |

TABLE 1-continued

| Example | Structure | ¹H NMR (ppm) | MS (ESI) m/z (MH⁺) |
|---|---|---|---|
| 97 | 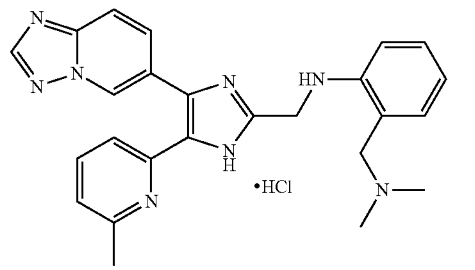 [SMILES: Cc1cccc(-c2[nH]c(CNc3ccccc3CN(C)C)nc2-c2ccc3ncnn3c2)n1 ; Cl] | (400 MHz, DMSO-d₆) δ 10.03 (br s, 1 H), 9.48 (dd, 1 H, J = 1.6, 0.8 Hz), 8.62 (s, 1 H), 7.95 (dd, 1 H, J = 9.2, 0.8 Hz), 7.87-7.82 (m, 2 H), 7.64 (d, 1 H, J = 7.6 Hz), 7.38 (d, 1 H, J = 7.6 Hz), 7.33-7.27 (m, 2 H), 6.95 (br s, 1 H), 6.78-6.74 (m, 2 H), 4.81 (s, 2 H), 4.43 (s, 2 H), 2.77 (s, 6 H), 2.52 (s, 3 H) | |
| 98 | 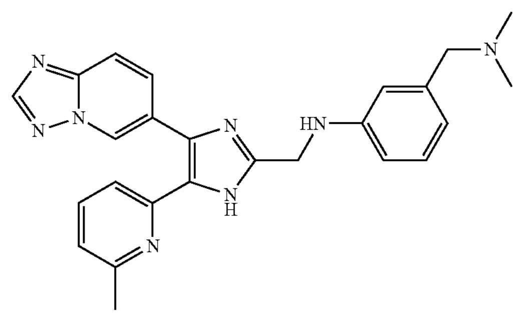 [SMILES: Cc1cccc(-c2[nH]c(CNc3cccc(CN(C)C)c3)nc2-c2ccc3ncnn3c2)n1] | (400 MHz, CDCl₃) δ 9.02 (br s, 1 H), 8.35 (s, 1 H), 7.82 (dd, 1 H, J = 9.2, 1.6 Hz), 7.74 (dd, 1 H, J = 9.2, 0.8 Hz), 7.46 (t, 1 H, J = 7.6 Hz), 7.27 (br d, 1 H, J = 7.6 Hz), 7.13 (t, 1 H, J = 7.8 Hz), 7.00 (d, 1 H, J = 7.6 Hz), 6.90 (br s, 1 H), 6.67 (d, 1 H, J = 7.6 Hz), 6.61 (dd, 1 H, J = 8.0. 2.0 Hz), 4.54 (s, 2 H), 3.48 (s, 2 H), 2.51 (s, 3 H), 2.30 (s, 6H) | 439.23 |
| 99 | 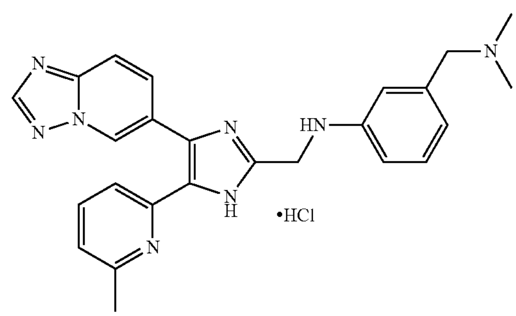 [SMILES: Cc1cccc(-c2[nH]c(CNc3cccc(CN(C)C)c3)nc2-c2ccc3ncnn3c2)n1 ; Cl] | (400 MHz, DMSO-d₆) δ 10.69 (br s, 1 H), 9.48 (dd, 1 H, J = 1.6, 0.8 Hz), 8.63 (s, 1 H), 7.96 (dd, 1 H, J = 9.2, 0.8 Hz), 7.84 (t, 1 H, J = 8.0 Hz), 7.83 (dd, 1 H, J = 9.2, 1.6 Hz), 7.61 (d, 1 H, J = 8.0 Hz), 7.37 (d, 1 H, J = 8.0 Hz), 7.21 (t, 1 H, J = 8.2 Hz), 7.09 (br s, 1 H), 6.85 (dd, 1 H, overlapped, J = 8.4, 2.2 Hz), 6.82 (d, 1 H, J = 8.0 Hz), 4.76 (s, 2 H), 4.16 (d, 1 H, J = 4.8 Hz), 2.66 (d, 6 H, J = 4.4 Hz), 2.51 (s, 3 H) | |
| 100 | 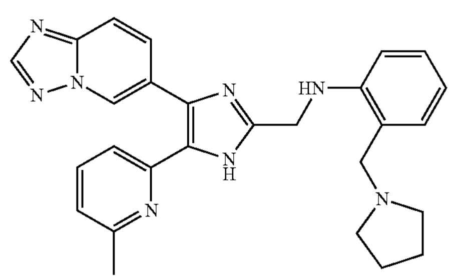 [SMILES: Cc1cccc(-c2[nH]c(CNc3ccccc3CN3CCCC3)nc2-c2ccc3ncnn3c2)n1] | (400 MHz, CDCl₃) δ 10.40 (br s, 1 H), 8.98 (s, 1 H), 8.35 (s, 1 H), 7.83 (d, 1 H, J = 9.2 Hz), 7.75 (d, 1 H, J = 9.2 Hz), 7.43 (t, 1 H, J = 7.6 Hz), 7.20 (br s, 1 H, overlapped), 7.15 (td, 1 H, J = 8.0, 1.6 Hz), 7.04 (d, 1 H, J = 8.0 Hz), 6.98 (d, 1 H, J = 7.6 Hz), 6.69 (pseudo t, 2 H, J = 7.2 Hz), 4.58 (s, 2 H), 3.72 (s, 2 H), 2.56 (br s, 4 H), 2.50 (s, 3 H), 1.80 (br s, 4 H) | 465.25 |
| 101 | 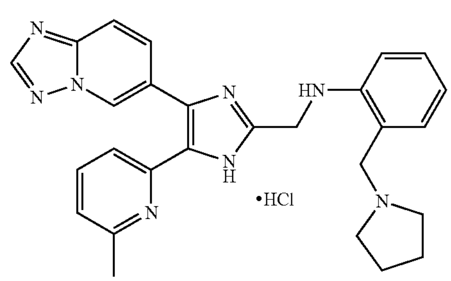 [SMILES: Cc1cccc(-c2[nH]c(CNc3ccccc3CN3CCCC3)nc2-c2ccc3ncnn3c2)n1 ; Cl] | (400 MHz, DMSO-d₆) δ 10.29 (br s, 1 H), 9.47 (t, 1 H, J = 0.8 Hz), 8.62 (s, 1 H), 7.95 (d, 1 H, J = 9.2 Hz), 7.87-7.83 (m, 2 H), 7.65 (d. 1 H, J = 8.0 Hz), 7.38 (br d, 2 H, J = 7.6 Hz), 7.27 (td, 1 H, J = 8.0, 1.2 Hz), 6.75 (t, 1 H, overlapped, J = 7.6 Hz), 6.72 (d, 1 H, overlapped, J = 7.6 Hz), 4.82 (s, 2 H), 4.47 (s, 2 H), 3.44 (br s, 2 H), 3.17 (br s, 2 H), 2.52 (s, 3 H), 2.04 (br s, 2 H), 1.94 (br s, 2 H) | |

TABLE 1-continued

| Example | Structure | ¹H NMR (ppm) | MS (ESI) m/z (MH⁺) |
|---|---|---|---|
| 102 | 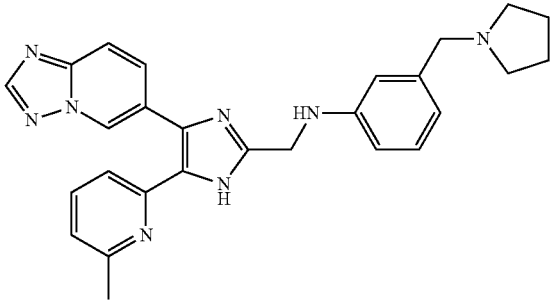 [SMILES: Cc1cccc(-c2[nH]c(CNc3cccc(CN4CCCC4)c3)nc2-c2ccc3ncnn3c2)n1] | (400 MHz, CDCl₃) δ 9.04 (s, 1 H), 8.35 (s, 1 H), 7.83 (dd, 1 H, J = 9.2, 1.6 Hz), 7.73 (d, 1 H, J = 9.2 Hz), 7.47 (t, 1 H, J = 7.8 Hz), 7.28 (br d, 1 H, J = 7.6 Hz), 7.11 (t, 1 H, J = 7.8 Hz), 7.00 (d, 1 H, J = 8.0 Hz), 6.95 (br s, 1 H), 6.68 (d, 1 H, J = 7.6 Hz), 6.60 (dd, 1 H, J = 8.0. 2.0 Hz), 4.54 (s, 2 H), 3.65 (s, 2 H), 2.61 (br s, 4 H), 2.51 (s, 3 H), 1.78-1.75 ( m, 4 H) | 465.25 |
| 103 | 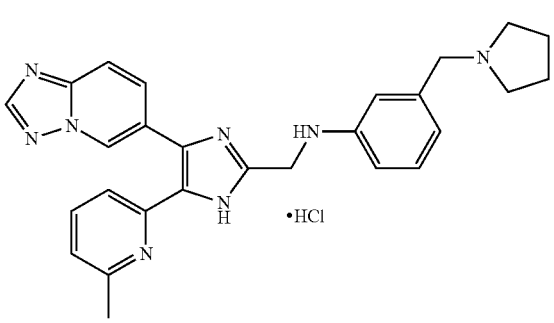 [SMILES: Cc1cccc(-c2[nH]c(CNc3cccc(CN4CCCC4)c3)nc2-c2ccc3ncnn3c2)n1 ; Cl] | (400 MHz, DMSO-d₆) δ 10.93 (br s, 1 H), 9.48 (dd, 1 H, J = 1.2, 1.6 Hz), 8.63 (s, 1 H), 7.96 (dd, 1 H, J = 9.2, 0.8 Hz), 7.86-7.81 (m, 2 H), 7.61 (d, 1 H, J = 8.0 Hz), 7.37 (d, 1 H, J = 7.6 Hz), 7.19 (t, 1 H, J = 7.8 Hz), 7.15 (br s, 1 H), 6.86-6.81 (m, 2 H), 4.76 (s, 2 H), 4.22 (d, 2 H, J = 5.6 Hz), 3.29 (m, 2 H), 3.00 (m, 2 H), 2.51 (s, 3 H), 1.92 (m, 2 H), 1.82 (m, 2 H) | |
| 104 | 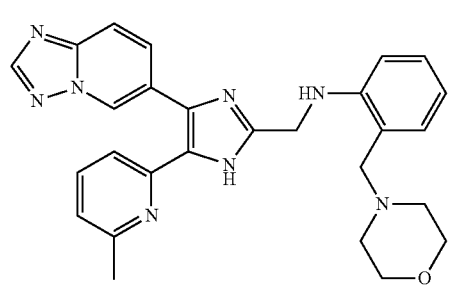 [SMILES: Cc1cccc(-c2[nH]c(CNc3ccccc3CN3CCOCC3)nc2-c2ccc3ncnn3c2)n1] | (400 MHz, CDCl₃) δ 10.35 (br s, 1 H), 8.97 (s, 1 H), 8.36 (s, 1 H), 7.83 (d, 1 H, J = 9.2 Hz), 7.76 (d, 1 H, J = 9.2 Hz), 7.44 (t, 1 H, J = 7.6 Hz), 7.21 (br s, 1 H, overlapped), 7.19 (td, 1 H, J = 7.6, 1.6 Hz), 7.04 (dd, 1 H, J = 7.6, 1.6 Hz), 6.99 (d, 1 H, J = 7.6 Hz), 6.73-6.68 (m, 2 H), 4.57 (s, 2 H), 3.71 (br s, 4 H), 3.63 (s, 2 H), 2.50 (br s, 7 H) | 481.25 |
| 105 | 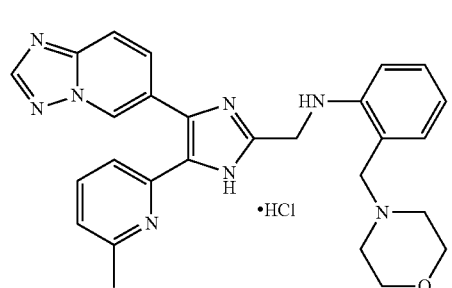 | (400 MHz, DMSO-d₆) δ 9.46 (s, 1 H), 8.62 (s, 1 H), 7.96 (dd, 1 H, J = 9.2, 0.8 Hz), 7.85 (t, 1 H, overlapped, J = 8.0 Hz), 7.83 (dd, 1 H, overlapped, J = 9.2, 1.6 Hz), 7.60 (d, 1 H, J = 8.0 Hz), 7.38 (br d, 2 H, J = 8.0 Hz), 7.29 (td, 1 H, J = 8.0, 1.2 Hz), 6.75 (t 1 H, overlapped, J = 8.0 Hz), 6.74 (d, 1 H, overlapped, J = 8.0 Hz), 4.82 (s, 2 H), 4.45 (s, 2 H), 3.93 (br s, 4 H), 3.34 (br s, 4 H), 2.53 (s, 3 H) | |
| 106 | 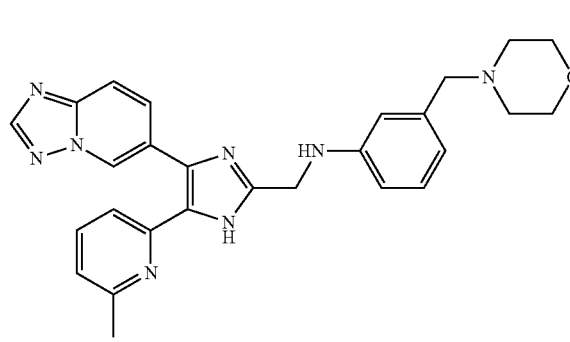 | (400 MHz, CDCl₃) δ 10.78 (br s, 1 H), 8.97 (s, 1 H), 8.35 (s, 1 H), 7.81 (dd, 1 H, J = 9.2, 1.6 Hz), 7.74 (d, 1 H, J = 9.2 Hz), 7.45 (t, 1 H, J = 7.8 Hz), 7.23 (br s, 1 H ), 7.13 (t, 1 H, J = 7.8 Hz), 7.00 (d, 1 H, J = 7.6 Hz), 6.79 (br s, 1 H), 6.71 (d, 1 H, J = 7.6 Hz), 6.59 (dd, 1 H, J = 8.0, 1.6 Hz), 4.53 (s, 2 H), 4.44 (br s, 1 H), 3.66 (m, 4 H), 3.45 (s, 2 H), 2.49 (s, 3 H), 2.44 (br s, 4 H) | 481.25 |

TABLE 1-continued

| Example | Structure | ¹H NMR (ppm) | MS (ESI) m/z (MH⁺) |
|---|---|---|---|
| 107 | 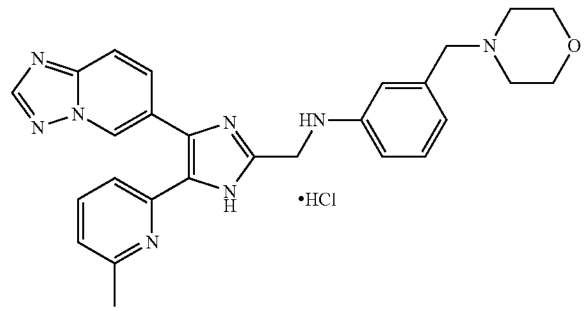 [SMILES: Cc1cccc(-c2[nH]c(CNc3cccc(CN4CCOCC4)c3)nc2-c2ccc3ncnn3c2)n1 ; Cl] | (400 MHz, DMSO-d₆/D₂O) δ 9.36 (dd, 1 H, J = 1.8, 1.0 Hz), 8.62 (s, 1 H), 7.95 (dd, 1 H, J = 9.4, 1.0 Hz), 7.87 (t, 1 H, J = 7.8 Hz), 7.82 (dd, 1 H, J = 9.4, 1.8 Hz), 7.48 (d, 1 H, J = 8.0 Hz), 7.42 (d, 1 H, J = 7.6 Hz), 7.28 (t, 1 H, J = 7.8 Hz), 6.90 (br s, 1 H), 6.86-6.82 (m, 2 H), 4.68 (s, 2 H Hz), 4.23 (s, 2 H), 3.70 (br s, 4 H), 3.22 (br s, 2 H), 3.14 (br s, 2 H), 2.58 (s, 3 H) | |
| 108 | 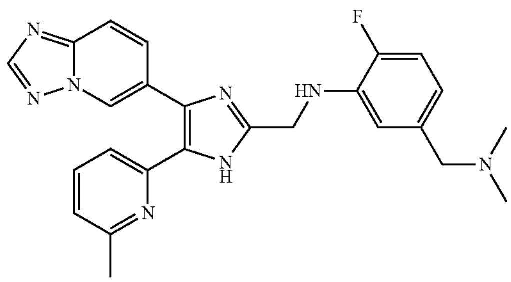 [SMILES: Cc1cccc(-c2[nH]c(CNc3cc(CN(C)C)ccc3F)nc2-c2ccc3ncnn3c2)n1] | (400 MHz, CDCl₃) δ 9.06 (s, 1 H), 8.34 (s, 1 H), 7.84 (dd, 1 H, J = 9.2, 1.6 Hz), 7.72 (d, 1 H, J = 9.2 Hz), 7.48 (t, 1 H, J = 7.6 Hz), 7.32 (br s, 1 H ), 7.18 (br s, 1 H), 7.00 (d, 1 H, J = 7.6 Hz), 6.90 (dd, 1 H, J = 11.2, 8.0 Hz), 6.55-6.51 (m, 1 H), 4.78 (br s, 1 H), 4.59 (d, 2 H, J = 6.4 Hz), 3.54 (s, 2 H), 2.50 (s, 3 H), 2.34 (s, 6 H) | 457.22 |
| 109 | 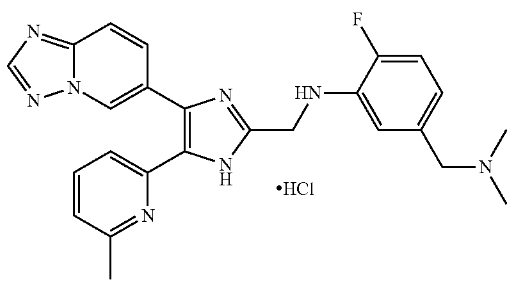 [SMILES: Cc1cccc(-c2[nH]c(CNc3cc(CN(C)C)ccc3F)nc2-c2ccc3ncnn3c2)n1 ; Cl] | (400 MHz, DMSO-d₆) δ 10.73 (br s, 1 H), 9.46 (t, 1 H, J = 1.2 Hz), 8.62 (s, 1 H), 7.96 (dd, 1 H, J = 9.2, 0.8 Hz), 7.84 (dd, 1 H, overlapped, J = 9.2, 1.6 Hz), 7.82 (t, 1 H, overlapped, J = 7.8 Hz), 7.55 (d, 1 H, J = 8.0 Hz), 7.37 (dd, 1 H, overlapped, J = 8.2, 2.0 Hz), 7.36 (d, 1 H, J = 7.6 Hz), 7.18 (dd, 1 H, J = 11.8, 8.2 Hz), 6.82-6.78 (m, 1 H), 4.79 (s, 2 H), 4.17 (br s, 2 H), 2.64 (d, 6 H, J = 1.6 Hz), 2.52 (s, 3 H) | |
| 110 | 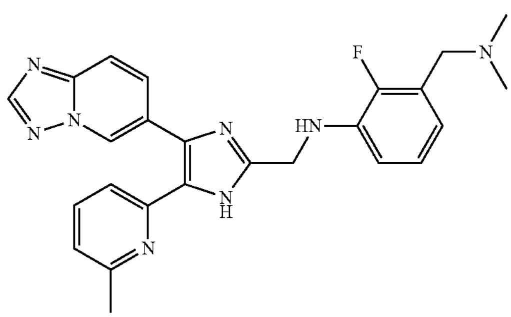 [SMILES: Cc1cccc(-c2[nH]c(CNc3cccc(CN(C)C)c3F)nc2-c2ccc3ncnn3c2)n1] | (400 MHz, CDCl₃) δ 8.99 (br s, 1 H), 8.36 (s, 1 H), 7.83 (dd, 1 H, J = 9.2, 1.6 Hz), 7.76 (d, 1 H, J = 9.2 Hz), 7.46 (t, 1 H, J = 7.8 Hz), 7.24 (br s, 1 H), 6.99 (d, 1 H, overlapped, J = 8.0 Hz), 6.95 (t, 1 H, overlapped, J = 8.0 Hz), 6.76-6.70 (m, 2 H), 4.73 (br s, 1 H), 4.56 (d, 2 H, J = 5.6 Hz), 3.60 (s, 2 H), 2.50 (s, 3 H), 2.36 (s, 6 H) | 457.23 |
| 111 | 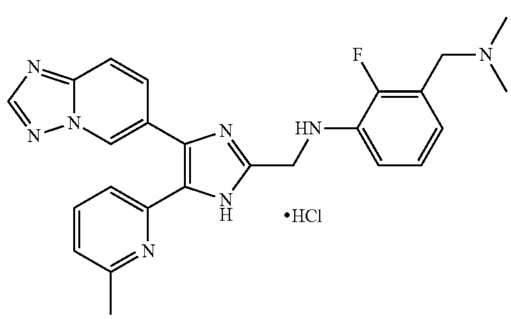 | (400 MHz, DMSO-d₆) δ 10.62 (br s, 1 H), 9.46 (s, 1 H), 8.62 (s, 1 H), 7.96 (d, 1 H, J = 9.2 Hz), 7.84 (t, 1 H, overlapped, J = 8.0 Hz), 7.83 (d, 1 H, overlapped, J = 9.2 Hz), 7.57 (d, 1 H, J = 8.0 Hz), 7.37 (d, 1 H, J = 8.0 Hz), 7.10 (t, 1 H, J = 7.6 Hz), 7.02 (t, 1 H, J = 7.6 Hz), 6.93 (pseudo t, 1 H, J = 6.6 Hz), 4.78 (s, 2 H), 4.30 (d, 2 H, J = 4.8 Hz), 2.72 (d, 6 H, J = 4.4 Hz), 2.53 (s, 3 H) | |

TABLE 1-continued

| Example | Structure | $^1$H NMR (ppm) | MS (ESI) m/z (MH$^+$) |
|---|---|---|---|
| 112 | 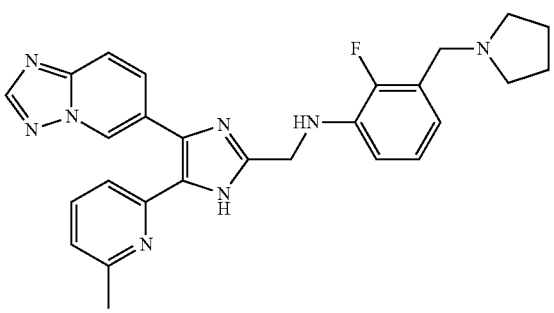 [SMILES: Cc1cccc(-c2[nH]c(CNc3cccc(CN4CCCC4)c3F)nc2-c2ccc3ncnn3c2)n1] | (400 MHz, CDCl$_3$) δ 11.11 (br s, 1 H), 8.98 (s, 1 H), 8.35 (s, 1 H), 7.81 (dd, 1 H, J = 9.2, 1.6 Hz), 7.73 (d, 1 H, J = 9.2 Hz), 7.44 (t, 1 H, J = 7.8 Hz), 7.23 (br s, 1 H), 6.97 (d, 1 H, J = 8.0 Hz), 6.91 (t, 1 H, J = 8.0 Hz), 6.75 (td, 1 H, J = 8.0, 1.2 Hz), 6.65 (td, 1 H, J = 8.0, 1.2 Hz), 4.66 (br s, 1 H), 4.51 (d, 2 H, J = 5.6 Hz), 3.66 (s, 2 H), 2.59 (br s, 4 H), 2.42 (s, 3 H), 1.81-1.75 (m, 4 H) | 483.24 |
| 113 | 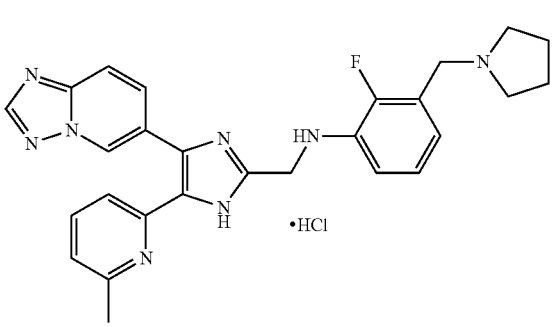 | (400 MHz, DMSO-d$_6$) δ 10.84 (br s, 1 H), 9.46 (s, 1 H), 8.62 (s, 1 H), 7.95 (d, 1 H, J = 9.2 Hz), 7.84 (t, 1 H, J = 7.8 Hz), 7.83 (dd, 1 H, J = 9.2, 1.6 Hz), 7.57 (d, 1 H, J = 8.0 Hz), 7.36 (d, 1 H, J = 7.6 Hz), 7.08 (t, 1 H, J = 7.8 Hz), 7.03-6.96 (m, 2 H), 4.77 (s, 2 H), 4.36 (d, 2 H, J = 5.2 Hz), 3.39 (m, 2 H), 3.07 (m, 2 H), 2.53 (s, 3 H), 2.03-1.87 (m, 4 H) | |
| 114 | 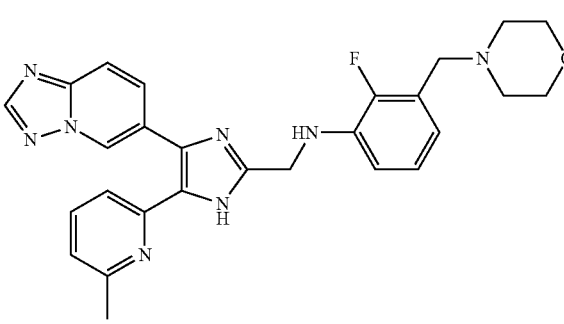 | (400 MHz, CDCl$_3$) δ 8.97 (s, 1 H), 8.36 (s, 1 H), 7.82 (dd, 1 H, J = 9.2, 2.0 Hz), 7.76 (dd, 1 H, J = 9.2, 0.8 Hz), 7.46 (t, 1 H, J = 7.6 Hz), 7.23 (br d, 1 H, J = 7.6 Hz), 7.00 (d, 1 H, J = 7.6 Hz), 6.95 (t, 1 H, J = 8.0 Hz), 6.76 (t, 1 H, J = 7.6 Hz), 6.70 (td, 1 H, J = 8.0, 1.6 Hz), 4.67 (br s, 1 H), 4.54 (d, 2 H, J = 4.8 Hz), 3.73 (m, 4 H), 3.59 (s, 2 H), 2.53 (br s, 4 H), 2.47 (s, 3 H) | 499.24 |
| 115 | 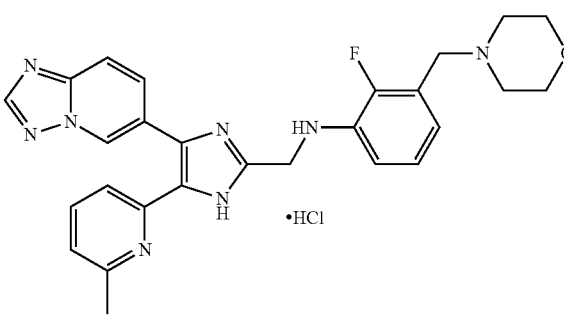 | (400 MHz, DMSO-d$_6$) δ 11.18 (br s, 1 H), 9.46 (dd, 1 H, J = 1.6, 1.2 Hz), 8.62 (s, 1 H), 7.96 (dd, 1 H, J = 9.2, 0.8 Hz), 7.84 (t, 1 H, overlapped, J = 7.8 Hz), 7.83 (dd, 1 H, overlapped, J = 9.2, 1.6 Hz), 7.57 (d, 1 H, J = 7.6 Hz), 7.37 (d, 1 H, J = 8.0 Hz), 7.10 (t, 1 H, J = 7.8 Hz), 7.05-6.99 (m, 2 H), 4.78 (s, 2 H), 4.34 (s, 2 H), 3.93 (br s, 2 H), 3.81 (br t, 2 H, J = 11.8 Hz) 3.29 (br s, 2 H), 3.13 (br s, 2 H), 2.53 (s, 3 H) | |
| 116 | 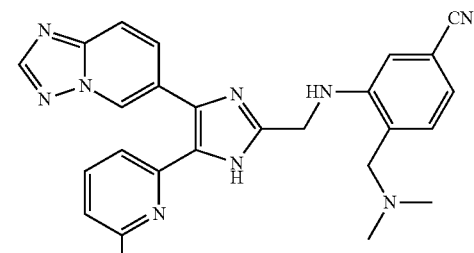 | (400 MHz, CDCl$_3$) δ 8.99 (s, 1 H), 8.36 (s, 1 H), 7.86 (dd, 1 H, J = 9.2, 1.6 Hz), 7.78 (dd, 1 H, J = 9.2, 0.8 Hz), 7.47 (t, 1 H, J = 7.6 Hz), 7.23 (br d, 1 H, J = 7.6 Hz), 7.09 (d, 1 H, J = 7.6 Hz), 7.01 (d, 1 H, J = 7.6 Hz), 6.98 (dd, 1 H, J = 7.6, 1.6 Hz), 6.93 (br s, 1 H), 4.59 (s, 2 H), 3.63 (s, 2 H), 2.53 (s, 3 H), 2.33 (s, 6 H) | 464.23 |

TABLE 1-continued

| Example | Structure | ¹H NMR (ppm) | MS (ESI) m/z (MH⁺) |
|---|---|---|---|
| 117 | 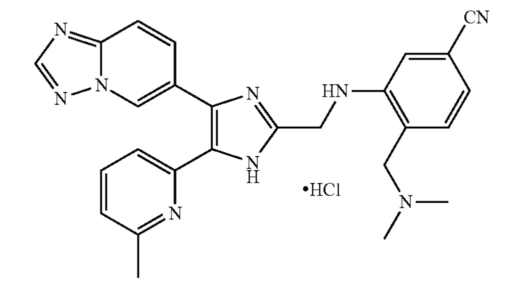 [SMILES: Cc1cccc(-c2[nH]c(CNc3cc(C#N)ccc3CN(C)C)nc2-c2ccc3ncnn3c2)n1 ; Cl] | (400 MHz, DMSO-d₆) δ 9.45 (dd, 1 H, J = 1.6, 0.8 Hz), 8.60 (s, 1 H), 7.94 (dd, 1 H, J = 9.2, 0.8 Hz), 7.85 (t, 1 H, overlapped, J = 7.6 Hz), 7.84 (dd, 1 H, overlapped, J = 9.2, 1.6 Hz), 7.57 (d, 1 H, J = 7.6 Hz), 7.52 (d, 1 H, J = 8.0 Hz), 7.39 (d, 1 H, J = 7.6 Hz), 7.30 (br s, 1 H), 7.19-7.17 (m, 2 H), 4.79 (s, 2 H), 4.48 (s, 2 H), 2.78 (s, 6 H), 2.55 (s, 3 H) | |
| 118 | 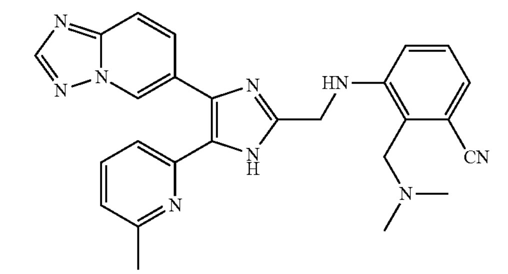 [SMILES: Cc1cccc(-c2[nH]c(CNc3cccc(C#N)c3CN(C)C)nc2-c2ccc3ncnn3c2)n1] | (400 MHz, DMSO-d₆) δ 12.70 (br s, 1 H), 9.54 (s, 1 H), 8.50 (s, 1 H), 7.99 (dd, 1 H, J = 9.2, 2.0 Hz), 7.83 (dd, 1 H, J = 9.2, 0.8 Hz), 7.72 (t, 1 H, J = 7.8 Hz), 7.52 (br s, 1 H), 7.32 (t, 1 H, J = 7.6 Hz), 7.17-7.13 (m, 2 H), 7.07 (d, 1 H, J = 8.0 Hz), 7.02 (dd, 1 H, J = 7.6, 0.8 Hz), 4.48 (d, 2 H, J = 5.6 Hz), 3.68 (s, 2 H), 2.47 (s, 3 H), 2.23 (s, 6 H) | 464.23 |
| 119 | 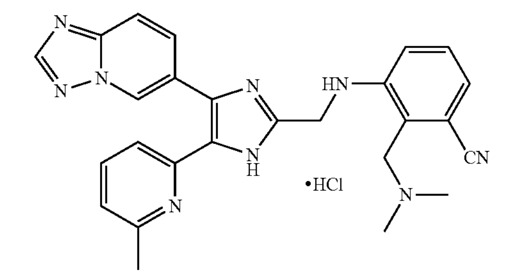 [SMILES: Cc1cccc(-c2[nH]c(CNc3cccc(C#N)c3CN(C)C)nc2-c2ccc3ncnn3c2)n1 ; Cl] | (400 MHz, DMSO-d₆) δ 9.48 (t, 1 H, J = 1.2 Hz), 8.60 (s, 1 H), 7.92 (dd, 1 H, J = 9.2, 1.2 Hz), 7.86 (dd, 1 H, overlapped, J = 9.2, 1.6 Hz), 7.85 (t, 1 H, overlapped, J = 8.0 Hz), 7.64 (d, 1 H, J = 8.0 Hz), 7.49 (t, 1 H, J = 7.8 Hz), 7.37 (d, 1 H, J = 8.0 Hz), 7.24 (dd, 1 H, J = 7.6, 0.8 Hz), 7.10 (dd, 1 H, J = 8.0, 0.8 Hz), 4.81 (s, 2 H), 4.61 (s, 2 H), 2.89 (s, 6 H), 2.52 (s, 3 H) | |
| 120 | 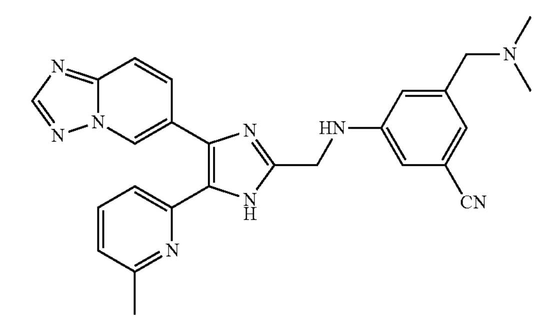 [SMILES: Cc1cccc(-c2[nH]c(CNc3cc(C#N)cc(CN(C)C)c3)nc2-c2ccc3ncnn3c2)n1] | (400 MHz, CDCl₃) δ 9.01 (s, 1 H), 8.36 (s, 1 H), 7.83 (dd, 1 H, J = 9.2, 1.6 Hz), 7.76 (dd, 1 H, J = 9.2, 0.8 Hz), 7.49 (t, 1 H, J = 1.6 Hz), 7.28 (br d, 1 H, J = 7.6 Hz), 7.15 (br s, 1 H), 7.03 (d, 1 H, J = 7.6 Hz), 6.94 (s, 1 H), 6.82 (dd, 1 H, J = 2.0, 1.2 Hz), 4.86 (br s, 1 H), 4.55 (d, 2 H, J = 5.6 Hz), 3.48 (s, 2 H), 2.54 (s, 3 H), 2.32 (s, 6 H) | 464.23 |
| 121 | 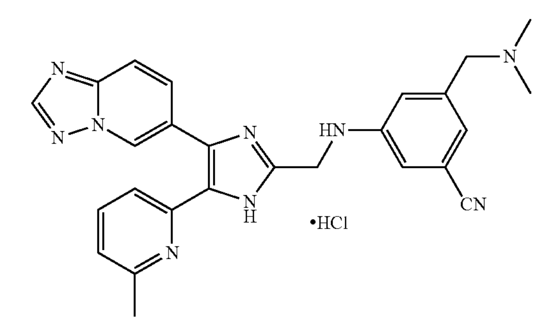 [SMILES: Cc1cccc(-c2[nH]c(CNc3cc(C#N)cc(CN(C)C)c3)nc2-c2ccc3ncnn3c2)n1 ; Cl] | (400 MHz, DMSO-d₆) δ 10.77 (br s, 1 H), 9.46 (dd, 1 H, J = 1.6, 0.8 Hz), 8.60 (s, 1 H), 7.94 (dd, 1 H, J = 9.2, 0.8 Hz), 7.85 (dd, 1 H, overlapped, J = 9.2, 1.6 Hz), 7.84 (t, 1 H, overlapped, J = 7.8 Hz), 7.55 (d, 1 H, J = 7.6 Hz), 7.36 (d, 1 H, overlapped, J = 8.0 Hz), 7.35 (s, 1 H, overlapped), 7.23 (br s, 2 H), 4.71 (s, 2 H), 4.22 (s, 2 H), 2.67 (s, 6 H), 2.53 (s, 3 H) | |

TABLE 1-continued

| Example | Structure | $^1$H NMR (ppm) | MS (ESI) m/z (MH$^+$) |
|---|---|---|---|
| 122 | 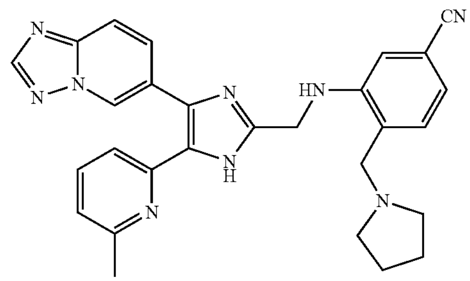 [SMILES: Cc1cccc(-c2[nH]c(CNc3cc(C#N)ccc3CN3CCCC3)nc2-c2ccc3ncnn3c2)n1] | (400 MHz, CDCl$_3$) δ 10.40 (br s, 1 H), 8.96 (s, 1 H), 8.36 (s, 1 H), 7.84 (dd, 1 H, J = 9.2, 1.6 Hz), 7.77 (d, 1 H, J = 9.2 Hz), 7.46 (t, 1 H, J = 7.6 Hz), 7.24 (br d, 1 H, J = 7.6 Hz), 7.09 (d, 1 H, J = 7.6 Hz), 7.00 (d, 1 H, J = 7.6 Hz), 6.96 (dd, 1 H, J = 7.6, 1.6 Hz), 6.86 (br s, 1 H), 4.55 (s, 2 H), 3.74 (s, 2 H), 2.54 (br s, 4 H), 2.51 (s, 3 H), 1.81 (br s, 4 H) | 490.25 |
| 123 | 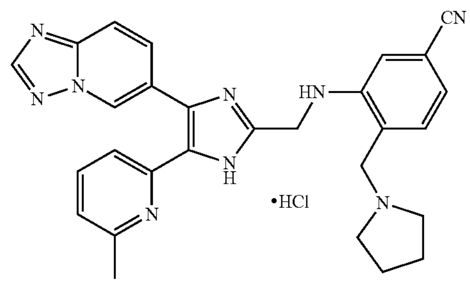 [SMILES: Cc1cccc(-c2[nH]c(CNc3cc(C#N)ccc3CN3CCCC3)nc2-c2ccc3ncnn3c2)n1 ; Cl] | (400 MHz. DMSO-d$_6$) δ 10.47 (br s, 2 H), 9.46 (s, 1 H), 8.61 (s, 1 H), 7.95 (dd, 1 H, J = 9.2, 0.4 Hz), 7.86 (t, 1 H, overlapped, J = 7.6 Hz), 7.85 (dd, 1 H, overlapped, J = 9.2, 1.2 Hz), 7.60 (d, 1 H, J = 7.6 Hz), 7.59 (d, 1 H, J = 8.0 Hz), 7.39 (d, 1 H, J = 7.6 Hz), 7.32 (br s, 1 H), 7.18 (dd, 1 H, J = 7.6, 1.6 Hz), 7.14 (d, 1 H, J = 1.6 Hz), 4.82 (s, 2 H), 4.53 (s, 2 H), 3.23 (br s, 4 H), 2.55 (s, 3 H), 1.99 (br s, 4 H) | |
| 124 | 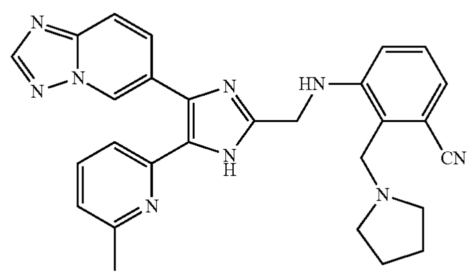 [SMILES: Cc1cccc(-c2[nH]c(CNc3cccc(C#N)c3CN3CCCC3)nc2-c2ccc3ncnn3c2)n1] | (400 MHz, DMSO-d$_6$) δ 12.71 (br s, 1 H), 9.52 (s, 1 H), 8.50 (s, 1 H), 7.98 (dd, 1 H, J = 9.2, 1.6 Hz), 7.83 (d, 1 H, J = 9.2 Hz), 7.71 (t, 1 H, J = 7.8 Hz), 7.51 (brs, 1 H), 7.37 (t, 1 H, J = 5.2 Hz), 7.31 (t, 1 H, J = 8.0 Hz), 7.16 (d, 1 H, J = 1.6 Hz), 7.05 (d, 1 H, J = 8.0 Hz), 7.00 (dd, 1 H, J = 8.0, 1.2 Hz), 4.47 (d, 2 H, J = 5.2 Hz), 3.87 (s, 2 H), 2.51 (br s, 4 H), 2.47 (s, 3 H), 1.74 (br s, 4 H) | 490.25 |
| 125 | 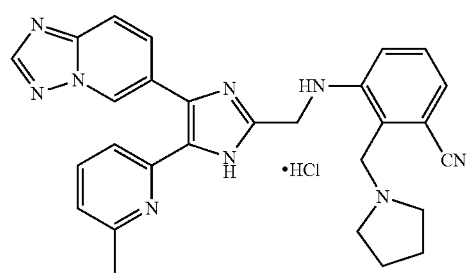 [SMILES: Cc1cccc(-c2[nH]c(CNc3cccc(C#N)c3CN3CCCC3)nc2-c2ccc3ncnn3c2)n1 ; Cl] | (400 MHz, DMSO-d$_6$/D$_2$O) δ 9.41 (dd, 1 H, J = 1.6, 0.8 Hz), 8.61 (s, 1 H), 7.94 (dd, 1 H, J = 9.2, 0.8 Hz), 7.89 (t, 1 H, J = 7.8 Hz), 7.84 (dd, 1 H, J = 9.2, 1.6 Hz), 7.55 (d, 1 H, J = 8.0 Hz), 7.50 (t, 1 H, J = 7.6 Hz), 7.42 (d, 1 H, J = 7.6 Hz), 7.25 (dd, 1 H, J = 7.6, 0.8 Hz), 7.09 (d, 1 H, J = 7.6 Hz), 4.78 (s, 2 H), 4.64 (s, 2 H), 3.45 (br s, 4 H), 2.58 (s, 3 H), 2.06 (br s, 4 H) | |
| 126 | 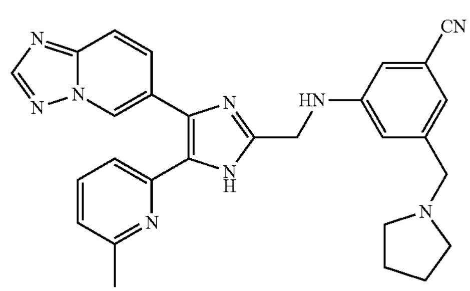 [SMILES: Cc1cccc(-c2[nH]c(CNc3cc(C#N)cc(CN4CCCC4)c3)nc2-c2ccc3ncnn3c2)n1] | (400 MHz, CDCl$_3$) δ 8.99 (s, 1 H), 8.36 (s, 1 H), 7.82 (dd, 1 H, J = 9.2, 1.6 Hz), 7.77 (d, 1 H, J = 9.2 Hz), 7.48 (t, 1 H, J = 7.6 Hz), 7.27 (br d, 1 H, J = 7.6 Hz), 7.13 (br s, 1 H), 7.03 (d, 1 H, J = 7.6 Hz), 6.97 (br s, 1 H), 6.81 (dd, 1 H, J = 2.4, 1.2 Hz), 4.81 (br s, 1 H), 4.54 (d, 2 H, J = 5.6 Hz), 3.62 (s, 2 H), 2.57 (br s, 4 H), 2.54 (s, 3 H), 1.79 (br s, 4 H) | 490.25 |

TABLE 1-continued

| Example | Structure | ¹H NMR (ppm) | MS (ESI) m/z (MH⁺) |
|---|---|---|---|
| 127 | 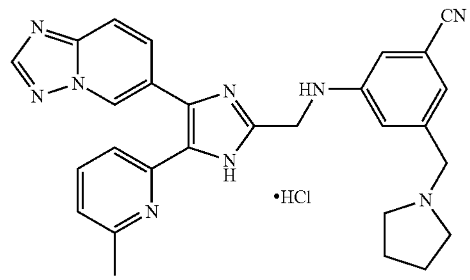 [SMILES: Cc1cccc(-c2[nH]c(CNc3cc(C#N)cc(CN4CCCC4)c3)nc2-c2ccc3ncnn3c2)n1 ; Cl] | (400 MHz, DMSO-d₆) δ 10.96 (br s 1 H), 9.45 (dd, 1 H, J = 1.6, 0.8 Hz), 8.60 (s, 1 H), 7.94 (dd, 1 H, J = 9.2, 0.8 Hz), 7.84 (dd, 1 H, overlapped, J = 9.2, 1.6 Hz), 7.83 (t, 1 H, overlapped, J = 7.8 Hz), 7.54 (d, 1 H, J = 8.0 Hz), 7.39 (br s, 1 H), 7.36 (d, 1 H, J = 7.6 Hz), 7.26 (s, 1 H), 7.21 (dd, 1 H, J = 2.0, 1.6 Hz), 4.72 (s, 2 H), 4.29 (s, 2 H), 3.02 (br s, 4 H), 2.53 (s, 3 H), 1.95 (br s, 2 H), 1.84 (br s, 2 H) | |
| 128 | 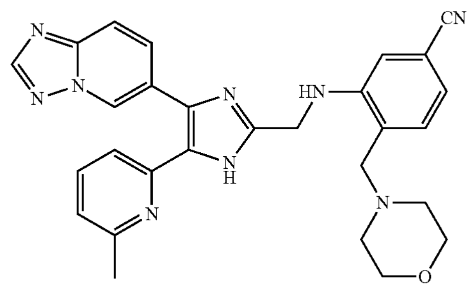 [SMILES: Cc1cccc(-c2[nH]c(CNc3cc(C#N)ccc3CN3CCOCC3)nc2-c2ccc3ncnn3c2)n1] | (400 MHz, CDCl₃) δ 8.97 (s, 1 H), 8.37 (s, 1 H), 7.84 (dd, 1 H, J = 9.2, 1.6 Hz), 7.79 (dd, 1 H, J = 9.2, 1.2 Hz), 7.49 (t, 1 H, J = 7.8 Hz), 7.29 (br d, 1 H, J = 8.0 Hz), 7.12 (d, 1 H, J = 7.6 Hz), 7.03 (d, 1 H, J = 7.6 Hz), 6.99 (dd, 1 H, J = 7.6, 1.6 Hz), 6.93 (br s, 1 H), 4.57 (s, 2 H), 3.75 (br s, 4 H, overlapped), 3.72 (s, 2 H, overlapped), 2.55 (br s, 7 H) | 506.25 |
| 129 | 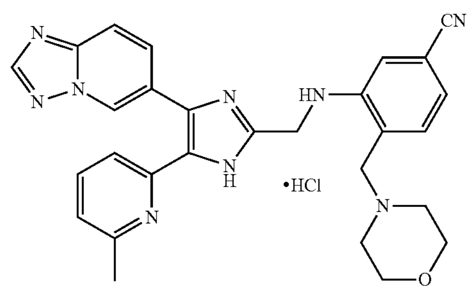 [SMILES: Cc1cccc(-c2[nH]c(CNc3cc(C#N)ccc3CN3CCOCC3)nc2-c2ccc3ncnn3c2)n1 ; Cl] | (400 MHz, DMSO-d₆) δ 9.45 (d, 1 H, J = 0.4 Hz), 8.61 (s, 1 H), 7.96 (d, 1 H, J = 9.2 Hz), 7.86 (t, 1 H, overlapped, J = 8.0 Hz), 7.85 (dd, 1 H, overlapped, J = 9.2, 1.6 Hz), 7.60 (d, 1 H, J = 8.0 Hz), 7.39 (d, 1 H, J = 8.0 Hz), 7.19 (s, 1 H), 7.17 (dd, 1 H, overlapped, J = 8.0, 1.2 Hz), 4.82 (s, 2 H), 4.52 (s, 2 H), 3.91 (br s, 4 H), 3.32 (br s, 4 H), 2.55 (s, 3 H) | |
| 130 | 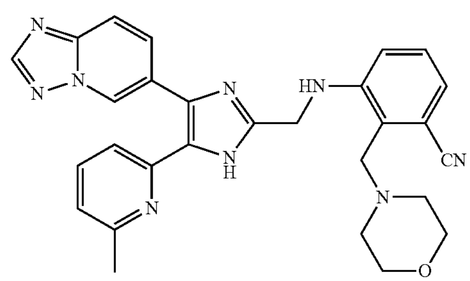 [SMILES: Cc1cccc(-c2[nH]c(CNc3cccc(C#N)c3CN3CCOCC3)nc2-c2ccc3ncnn3c2)n1] | (400 MHz, DMSO-d₆) δ 12.70 (br s, 1 H), 9.48 (br s, 1 H), 8.50 (s, 1 H), 7.95 (dd, 1 H, J = 9.2, 1.6 Hz), 7.84 (d, 1 H, J = 9.2 Hz), 7.71 (t, 1 H, J = 7.6 Hz), 7.44 (br s, 1 H), 7.34 (t, 1 H, J = 8.0 Hz), 7.28 (t, 1 H, J = 5.6 Hz), 7.16 (d, 1 H, J = 7.6 Hz), 7.07 (d, 1 H, J = 8.4 Hz), 7.03 (dd, 1 H, J = 7.6, 1.2 Hz), 4.49 (d, 2 H, J = 5.6 Hz), 3.76 (s, 2 H), 3.58 (m, 4 H), 2.48 (s, 3 H), 2.41 (br s, 4 H) | 506.24 |
| 131 | 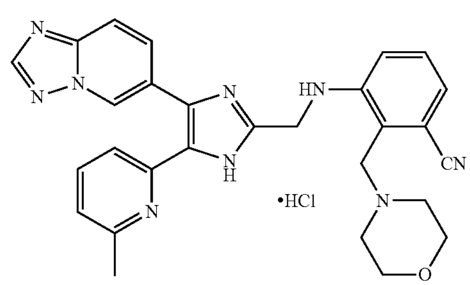 [SMILES: Cc1cccc(-c2[nH]c(CNc3cccc(C#N)c3CN3CCOCC3)nc2-c2ccc3ncnn3c2)n1 ; Cl] | (400 MHz, DMSO-d₆) δ 9.46 (d, 1 H, J = 0.8 Hz), 8.60 (s, 1 H), 7.94 (dd, 1 H, J = 9.2, 0.8 Hz), 7.85 (t, 1 H, overlapped, J = 7.6 Hz), 7.84 (dd, 1 H, overlapped, J = 9.2, 1.6 Hz), 7.60 (d, 1 H, J = 7.6 Hz), 7.47 (t, 1 H, J = 8.0 Hz), 7.37 (d, 1 H, J = 8.0 Hz), 7.22 (dd, 1 H, J = 7.6, 0.8 Hz), 7.08 (d, 1 H, J = 8.0 Hz), 4.82 (s, 2 H), 4.57 (s, 2 H), 3.95 (br t, 4 H, J = 4.4 Hz), 3.40 (br s, 4 H), 2.53 (s, 3 H) | |

TABLE 1-continued

| Example | Structure | $^1$H NMR (ppm) | MS (ESI) m/z (MH$^+$) |
|---|---|---|---|
| 132 | 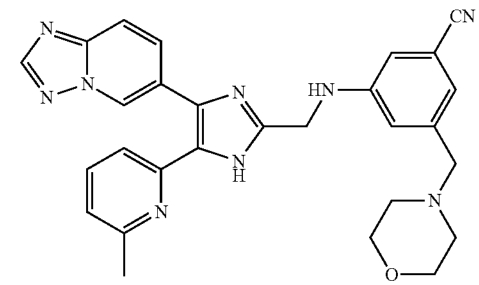 [SMILES: Cc1cccc(-c2[nH]c(CNc3cc(C#N)cc(CN4CCOCC4)c3)nc2-c2ccc3ncnn3c2)n1] | (400 MHz, CDCl$_3$) δ 8.97 (s, 1 H), 8.38 (s, 1 H), 7.82 (dd, 1 H, J = 9.2, 1.6 Hz), 7.78 (dd, 1 H, J = 9.2, 0.8 Hz), 7.48 (t, 1 H, J = 7.6 Hz), 7.28 (br d, 1 H, J = 7.6 Hz), 7.06 (br s, 1 H, overlapped), 7.04 (d, 1 H, J = 7.6 Hz), 7.01 (s, 1 H), 6.84 (dd, 1 H, J = 2.0, 1.2 Hz), 4.79 (br s, 1 H), 4.54 (d, 2 H, J = 7.6 Hz), 3.70 (m, 4 H), 3.48 (s, 2 H), 2.55 (s, 3 H), 2.47 (br s, 4 H) | 506.24 |
| 133 | 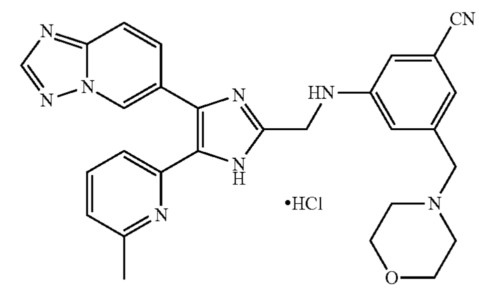 [SMILES: Cc1cccc(-c2[nH]c(CNc3cc(C#N)cc(CN4CCOCC4)c3)nc2-c2ccc3ncnn3c2)n1 ; Cl] | (400 MHz, DMSO-d$_6$) δ 9.45 (dd, 1 H, J = 1.6, 0.8 Hz), 8.61 (s, 1 H), 7.95 (dd, 1 H, J = 9.2, 0.8 Hz), 7.85 (t, 1 H, overlapped, J = 7.6 Hz), 7.84 (dd, 1 H, overlapped, J = 9.2, 1.6 Hz), 7.54 (d, 1 H, J = 7.6 Hz), 7.43 (br s, 1 H), 7.37 (d, 1 H, J = 7.6 Hz), 7.28 (s, 1 H), 7.23 (dd, 1 H, J = 2.2, 1.4 Hz), 4.74 (s, 2 H), 4.28 (s, 2 H), 3.83 (br s, 4 H), 3.81 (br s, 2 H), 3.08 (br s, 2 H), 2.54 (s, 3 H) | |
| 134 | 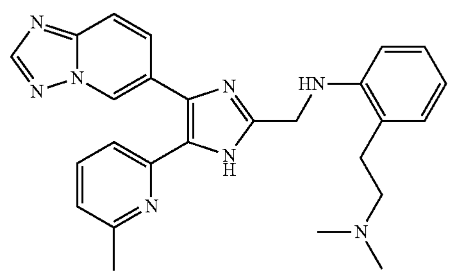 [SMILES: Cc1cccc(-c2[nH]c(CNc3ccccc3CCN(C)C)nc2-c2ccc3ncnn3c2)n1] | (400 MHz, CDCl$_3$) δ 8.98 (s, 1 H), 8.36 (s, 1 H), 7.83 (dd, 1 H, J = 9.2, 1.6 Hz), 7.76 (dd, 1 H, J = 9.2, 0.8 Hz), 7.45 (t, 1 H, J = 7.8 Hz), 7.23 (br d, 1 H, J = 7.6 Hz), 7.13 (td, 1 H, J = 8.0, 1.2 Hz), 7.04 (dd, 1 H, J = 8.0, 1.2 Hz), 6.99 (d, 1 H, J = 8.0 Hz), 6.72 (d, 1 H, overlapped, J = 7.6 Hz), 6.71 (td, 1 H, overlapped, J = 8.0, 1.2 Hz), 4.56 (s, 2 H), 2.81 (t, 2 H, J = 6.4 Hz), 2.63 (t, 2 H, J = 6.4 Hz), 2.52 (s, 3 H), 2.36 (s, 6 H) | 453.25 |
| 135 | 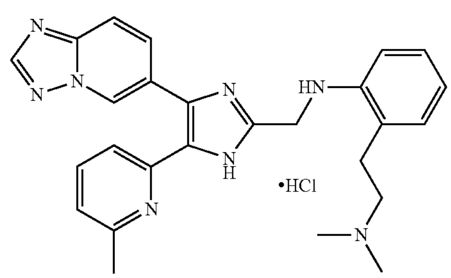 [SMILES: Cc1cccc(-c2[nH]c(CNc3ccccc3CCN(C)C)nc2-c2ccc3ncnn3c2)n1 ; Cl] | (400 MHz, DMSO-d$_6$/D$_2$O) δ 9.40 (dd, 1 H, J = 1.8, 0.8 Hz), 8.63 (s, 1 H), 7.96 (dd, 1 H, J = 9.2, 0.8 Hz), 7.86 (t, 1 H, J = 7.8 Hz), 7.82 (dd, 1 H, J = 9.2, 1.8 Hz), 7.48 (d, 1 H, J = 8.0 Hz), 7.41 (d, 1 H, J = 7.6 Hz), 7.17-7.12 (m, 2 H), 6.75-671 (m, 2 H), 4.73 (s, 2 H), 3.32 (br t, 2 H, J = 8.4 Hz), 3.02 (br t, 2 H, J = 8.4 Hz), 2.90 (s, 6 H), 2.58 (s, 3 H) | |
| 136 | 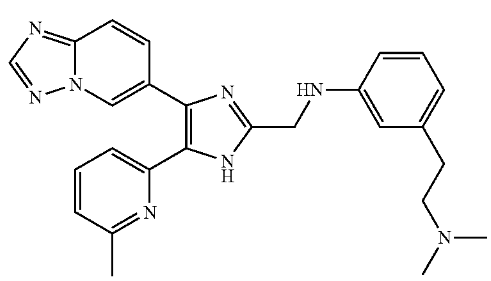 [SMILES: Cc1cccc(-c2[nH]c(CNc3cccc(CCN(C)C)c3)nc2-c2ccc3ncnn3c2)n1] | (400 MHz, CDCl$_3$) δ 9.08 (s, 1 H), 8.32 (s, 1 H), 7.83 (dd, 1 H, J = 9.2, 1.6 Hz), 7.68 (d, 1 H, J = 9.2 Hz), 7.47 (t, 1 H, J = 7.6 Hz), 7.34 (br d, 1 H, J = 7.6 Hz), 7.04 (t, 1 H, J = 7.6 Hz), 6.99 (dd, 1 H, J = 7.6, 0.4 Hz), 6.66 (br s, 1 H), 6.53-6.49 (m, 2 H), 4.48 (s, 2 H), 2.89-2.83 (m 4 H), 2.56 (s, 6 H), 2.48 (s, 3 H) | 453.25 |

TABLE 1-continued

| Example | Structure | ¹H NMR (ppm) | MS (ESI) m/z (MH⁺) |
|---|---|---|---|
| 137 | 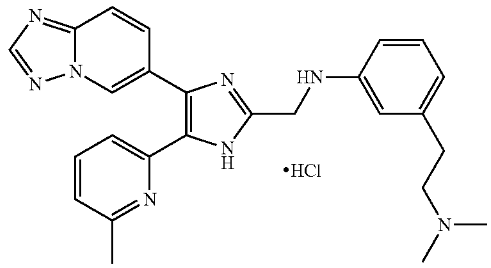 [SMILES: Cc1cccc(-c2[nH]c(CNc3cccc(CCN(C)C)c3)nc2-c2ccc3ncnn3c2)n1 ; Cl] | (400 MHz, DMSO-d₆) δ 10.47 (br s, 1 H), 9.49 (t, 1 H, J = 0.8 Hz), 8.63 (s, 1 H), 7.97 (dd, 1 H, J = 9.2, 0.8 Hz), 7.85 (dd, 1 H, overlapped, J = 9.2, 1.2 Hz), 7.84 (t, 1 H, overlapped, J = 7.8 Hz), 7.64 (d, 1 H, J = 8.0 Hz), 7.37 (d, 1 H, J = 7.6 Hz), 7.10 (t, 1 H, J = 8.0 Hz), 6.81 (br s, 1 H), 6.66 (dd, 1 H, J = 8.0, 1.6 Hz), 6.58 (d, 1 H, J = 8.0 Hz), 4.75 (s, 2 H), 3.30-3.25 (m, 2 H), 2.94-2.89 (m, 2 H), 2.77 (d, 6 H, J = 4.8 Hz), 2.51 (s, 3 H) | |
| 138 | 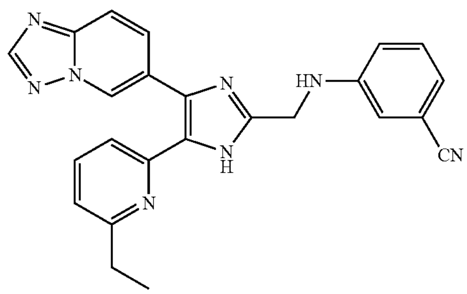 [SMILES: CCc1cccc(-c2[nH]c(CNc3cccc(C#N)c3)nc2-c2ccc3ncnn3c2)n1] | (400 MHz, CDCl₃) δ 10.40 (br s, 1 H), 8.94 (s, 1 H), 8.38 (s, 1 H), 7.83 (dd, 1 H, J = 9.2, 1.2 Hz), 7.80 (dd, 1 H, J = 9.2, 0.8 Hz), 7.49 (t, 1 H, J = 7.8 Hz), 7.30-7.27 (m, 1 H), 7.24 (d, 1 H, J = 8.0 Hz), 7.06 (dt, 1 H, overlapped, J = 7.6, 1.2 Hz), 7.05 (d, 1 H, overlapped, J = 7.6 Hz), 6.94-6.93 (m, 2 H), 4.72 (t, 1 H, J = 5.2 Hz), 4.54 (d, 2 H, J = 5.2 Hz), 2.82 (q, 2 H, J = 7.6 Hz), 1.31 (t, 3 H, J = 7.6 Hz) | 421.21 |
| 139 | 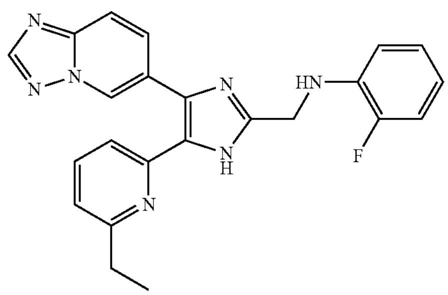 [SMILES: CCc1cccc(-c2[nH]c(CNc3ccccc3F)nc2-c2ccc3ncnn3c2)n1] | (400 MHz, CDCl₃) δ 10.37 (br s, 1 H), 8.96 (s, 1 H), 8.38 (s, 1 H), 7.84 (dd, 1 H, J = 9.2, 1.2 Hz), 7.79 (dd, 1 H, J = 9.2, 0.8 Hz), 7.48 (t, 1 H, J = 7.8 Hz), 7.22 (d, 1 H, J = 8.0 Hz), 7.06-7.00 (m, 3 H), 6.80 (td, 1 H, J = 8.0, 1.2 Hz), 6.76-6.70 (m, 1 H), 4.62 (br s, 1 H, overlapped), 4.60 (s, 2 H), 2.80 (q, 2 H, J = 7.6 Hz), 1.29 (t, 3 H, J = 7.6 Hz) | 414.20 |
| 140 | 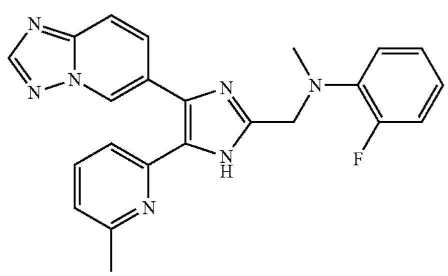 [SMILES: Cc1cccc(-c2[nH]c(CN(C)c3ccccc3F)nc2-c2ccc3ncnn3c2)n1] | (400 MHz, CDCl₃) δ 8.97 (br s, 1 H), 8.37 (s, 1 H), 7.82 (dd, 1 H, J = 9.2, 1.6 Hz), 7.78 (dd, 1 H, J = 9.2, 1.2 Hz), 7.49 (t, 1 H, J = 7.8 Hz), 7.25 (br d, 1 H, J = 7.6 Hz), 7.14-7.06 (m, 3 H), 7.04 (d, 1 H, J = 7.6 Hz), 7.00-6.94 (m, 1 H), 4.44 (s, 2 H), 2.91 (s, 3 H), 2.58 (s, 3 H) | 414.20 |
| 141 | 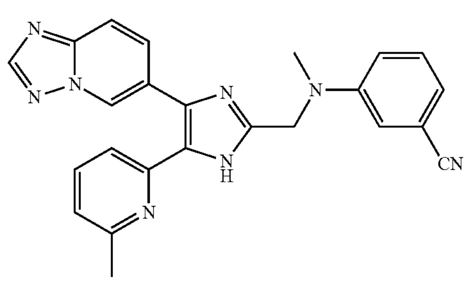 [SMILES: Cc1cccc(-c2[nH]c(CN(C)c3cccc(C#N)c3)nc2-c2ccc3ncnn3c2)n1] | (400 MHz, CDCl₃) δ 8.93 (s, 1 H), 8.37 (s, 1 H), 7.80-7.78 (m, 2 H), 7.48 (t, 1 H, J = 7.6 Hz), 7.35-7.30 (m, 1 H), 7.24 (br d, 1 H, J = 8.0 Hz), 7.08-7.05 (m, 3 H), 7.02 (d, 1 H, J = 7.6 Hz), 4.67 (s, 2 H), 3.14 (s, 3 H), 2.50 (s, 3 H) | 421.20 |

TABLE 1-continued

| Example | Structure | ¹H NMR (ppm) | MS (ESI) m/z (MH⁺) |
|---|---|---|---|
| 142 | 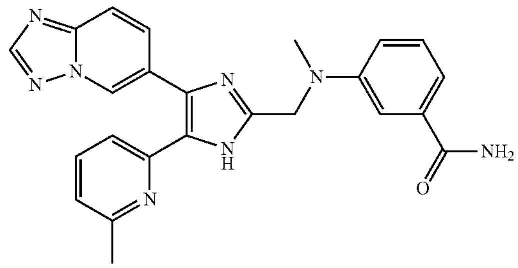 [SMILES: Cc1cccc(-c2[nH]c(CN(C)c3cccc(C(N)=O)c3)nc2-c2ccc3ncnn3c2)n1] | (400 MHz, CDCl₃/CD₃OD) δ 8.86 (dd, 1 H, J = 1.6, 1.2 Hz), 8.18 (s, 1 H), 7.62 (dd, 1 H, J = 9.2, 1.6 Hz), 7.57 (dd, 1 H, J = 9.2, 1.2 Hz), 7.43 (t, 1 H, J = 8.0 Hz), 7.24 (dd, 1 H, J = 2.4, 1.6 Hz), 7.14 (t, 1 H, overlapped, J = 8.0 Hz), 7.13 (d, 1 H, overlapped, J = 8.0 Hz), 7.04 (ddd, 1 H, J = 8.0, 1.2, 0.8 Hz), 6.97 (d, 1 H, J = 7.6 Hz), 6.83 (ddd, 1 H, J = 8.0, 2.4, 0.8 Hz), 4.54 (s, 2 H), 2.99 (s, 3 H), 2.38 (s, 3 H) | 439.22 |
| 143 | 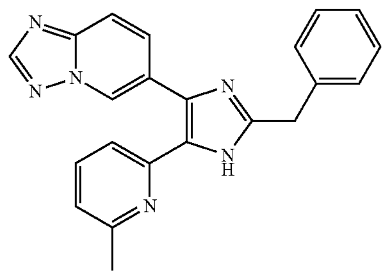 [SMILES: Cc1cccc(-c2[nH]c(Cc3ccccc3)nc2-c2ccc3ncnn3c2)n1] | (400 MHz, CDCl₃) δ 8.94 (br s, 1 H), 8.36 (s, 1 H), 7.81 (dd, 1 H, J = 9.2, 1.6 Hz), 7.77 (dd, 1 H, J = 9.2, 0.8 Hz), 7.44 (t, 1 H, J = 7.8 Hz), 7.40-7.28 (m, 5 H), 7.20 (br d, 1 H, J = 8.0 Hz), 6.99 (d, 1 H, J = 7.6 Hz), 4.21 (s, 2 H), 2.51 (s, 3 H) | 367.18 |
| 144 | 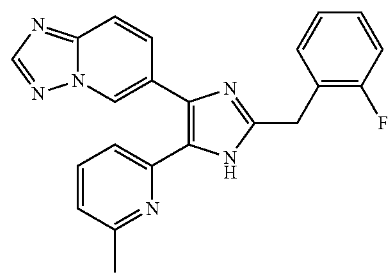 [SMILES: Cc1cccc(-c2[nH]c(Cc3ccccc3F)nc2-c2ccc3ncnn3c2)n1] | (400 MHz, CDCl₃) δ 8.93 (t, 1 H, J = 1.2 Hz), 8.37 (s, 1 H), 7.80 (dd, 1 H, overlapped, J = 9.2, 1.6 Hz), 7.77 (dd, 1 H, overlapped, J = 9.2, 0.8 Hz), 7.46 (t, 1 H, J = 7.8 Hz), 7.39 (td, 1 H, J = 7.6, 1.6 Hz), 7.31-7.25 (m, 1 H), 7.21 (br d, 1 H, J = 8.0 Hz), 7.14 (td, 1 H, overlapped, J = 7.6, 1.2 Hz), 7.10 (dd, 1 H, J = 8.4, 1.2 Hz), 7.02 (br d, 1 H, J = 7.6 Hz), 4.24 (s, 2 H), 2.55 (s, 3 H) | 385.17 |
| 145 | 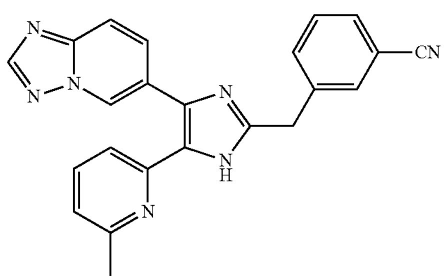 [SMILES: Cc1cccc(-c2[nH]c(Cc3cccc(C#N)c3)nc2-c2ccc3ncnn3c2)n1] | (400 MHz, DMSO-d₆) δ 12.70 (br s, 1 H), 9.53 (br s, 1 H), 8.49 (s, 1 H), 7.96 (dd, 1 H, J = 9.2, 1.8 Hz), 7.84 (d, 1 H, J = 2.0 Hz), 7.82 (d, 1 H, J = 9.2 Hz), 7.74-7.71 (m, 2 H), 7.69 (t, 1 H, overlapped, J = 7.6 Hz), 7.56 (t, 1 H, J = 7.8 Hz), 7.47 (br s, 1 H), 7.15 (d, 1 H, J = 7.6 Hz), 4.18 (s, 2 H), 2.47 (s, 3 H) | 392.18 |
| 146 | 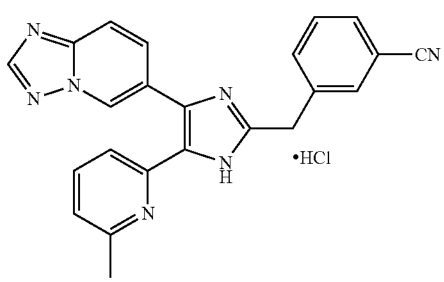 [SMILES: Cc1cccc(-c2[nH]c(Cc3cccc(C#N)c3)nc2-c2ccc3ncnn3c2)n1 ; Cl] | (400 MHz, DMSO-d₆) δ 9.51 (dd, 1 H, J = 1.6, 0.8 Hz), 8.65 (s, 1 H), 8.08 (br s, 1 H), 7.97 (dd, 1 H, overlapped, J = 9.2, 0.8 Hz), 7.95 (br d, overlapped, 1 H, J = 8.0 Hz), 7.87 (dd, 1 H, J = 9.2, 1.6 Hz), 7.85-7.79 (m, 2 H), 7.63 (dd, 1 H, overlapped, J = 7.6, 1.2 Hz), 7.61 (t, 1 H, overlapped, J = 7.6 Hz), 7.36 (d, 1 H, J = 7.6 Hz), 4.55 (s, 2 H), 2.50 (s, 3 H) | |

TABLE 1-continued

| Example | Structure | ¹H NMR (ppm) | MS (ESI) m/z (MH⁺) |
|---|---|---|---|
| 147 | 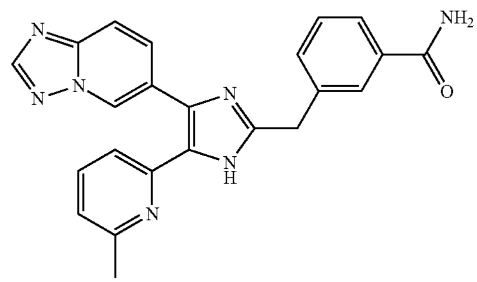 [SMILES: Cc1cccc(-c2[nH]c(Cc3cccc(C(N)=O)c3)nc2-c2ccc3ncnn3c2)n1] | (400 MHz, CDCl₃) δ 8.93 (br s, 1 H), 8.32 (s, 1 H), 7.77 (s, 1 H). 7.76 (dd, 1 H, overlapped, J = 9.2, 1.6 Hz), 7.69 (d, 1 H, J = 9.2 Hz), 7.56 (d, 1 H, J = 8.0 Hz), 7.44 (t, 1 H, J = 7.6 Hz), 7.39 (d, 1 H, J = 7.6 Hz), 7.26 (t, 1 H, J = 8.0 Hz), 7.21 (d, 1 H, J = 7.6 Hz), 6.98 (d, 1 H, J = 7.6 Hz), 6.60 (br s, 1 H), 6.27 (br s, 1 H), 4.15 (s, 2 H), 2.44 (s, 3 H) | 410.19 |
| 148 | 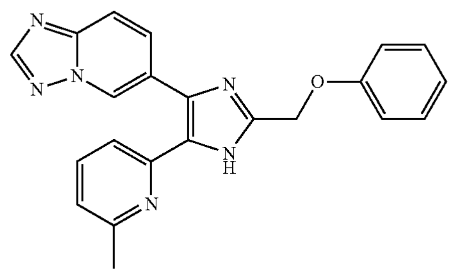 [SMILES: Cc1cccc(-c2[nH]c(COc3ccccc3)nc2-c2ccc3ncnn3c2)n1] | (400 MHz, CDCl₃) δ 8.94 (s, 1 H), 8.37 (s, 1 H), 7.77-7.72 (m, 2 H), 7.51 (t, 1 H, J = 7.6 Hz), 7.32-7.25 (m, 3 H), 7.06 (d, 1 H, J = 7.6 Hz), 7.00 (t, 1 H, overlapped, J = 7.6 Hz), 6.97 (d, 2 H, overlapped, J = 8.0 Hz), 5.22 (s, 2 H), 2.54 (s, 3 H) | 383.17 |
| 149 | 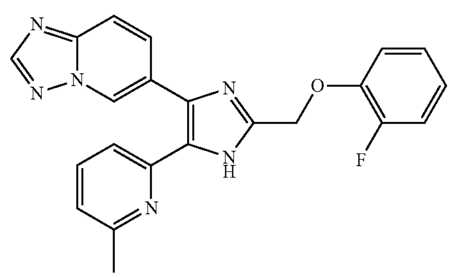 [SMILES: Cc1cccc(-c2[nH]c(COc3ccccc3F)nc2-c2ccc3ncnn3c2)n1] | (400 MHz, CDCl₃) δ 8.95 (t, 1 H, J = 1.2 Hz), 8.38 (s, 1 H), 7.80 (dd, 1 H, J = 9.2, 0.8 Hz), 7.77 (dd, 1 H, J = 9.2, 1.2 Hz), 7.56 (t, 1 H, J = 8.0 Hz), 7.31 (d, 1H, J = 7.6 Hz), 7.19 (td, 1 H, J = 8.0, 1.6 Hz), 7.14-7.06 (m, 3 H), 7.01-6.95 (m, 1 H), 5.34 (s, 2 H), 2.64 (s, 3 H) | 401.17 |
| 150 | 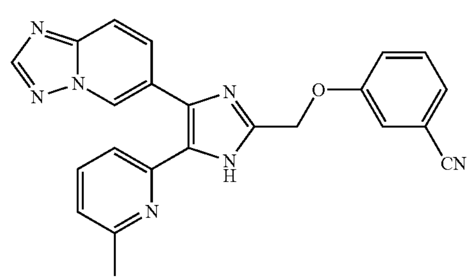 [SMILES: Cc1cccc(-c2[nH]c(COc3cccc(C#N)c3)nc2-c2ccc3ncnn3c2)n1] | (400 MHz, CDCl₃/CD₃OD) δ 8.94 (dd, 1 H, J = 1.6, 1.2 Hz), 8.32 (s, 1 H), 7.78 (dd, 1 H, J = 9.2, 1.6 Hz), 7.73 (dd, 1 H, J = 9.2, 1.2 Hz), 7.52 (t, 1 H, J = 7.8 Hz), 7.42-7.37 (m, 1 H), 7.31-7.26 (m, 3 H), 7.25 (br d, 1 H, overlapped, J = 8.0 Hz), 7.07 (d, 1 H, J = 7.6 Hz), 5.23 (s, 2 H), 2.55 (s, 3 H) | 408.17 |
| 151 | 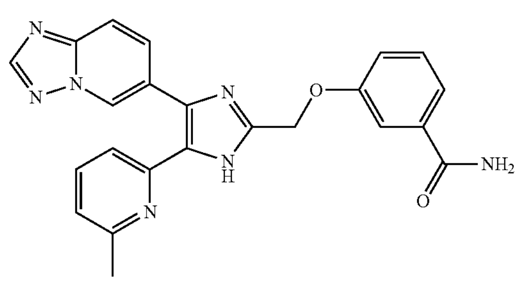 [SMILES: Cc1cccc(-c2[nH]c(COc3cccc(C(N)=O)c3)nc2-c2ccc3ncnn3c2)n1] | (400 MHz, CDCl₃/CD₃OD) δ 8.94 (t, 1 H, J = 1.6 Hz), 8.31 (s, 1 H), 7.76 (dd, 1 H, J = 9.2, 1.6 Hz), 7.70 (dd, 1 H, J = 9.2, 0.8 Hz), 7.51-7.47 (m, 2 H), 7.42 (ddd, 1 H, J = 8.0, 2.4, 1.2 Hz), 7.31 (t, 1 H, J = 8.0 Hz), 7.23 (d, 1 H, J = 7.6 Hz), 7.12 (ddd, 1 H, J = 8.0, 2.4, 0.8 Hz), 7.04 (d, 1 H, J = 7.6 Hz), 5.22 (s, 2 H), 2.51 (s, 3 H) | 426.18 |

TABLE 1-continued

| Example | Structure | ¹H NMR (ppm) | MS (ESI) m/z (MH+) |
|---|---|---|---|
| 152 | 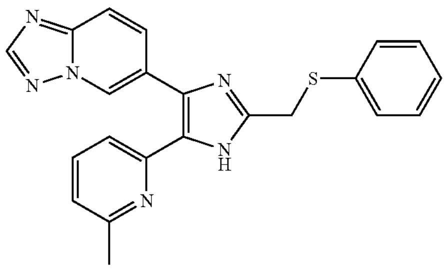 | (400 MHz, CDCl₃) δ 8.89 (t, 1 H, J = 1.4 Hz), 8.35 (s, 1 H), 7.76-7.19 (m, 2 H), 7.45 (t, 1 H, J = 7.8 Hz), 7.39-7.36 (m, 2 H), 7.30-7.26 (m, 2 H), 7.23-7.19 (m, 2 H), 7.01 (d, 1 H, J = 7.6 Hz), 4.26 (s, 2 H), 2.49 (s, 3 H) | 399.15 |
| 153 | 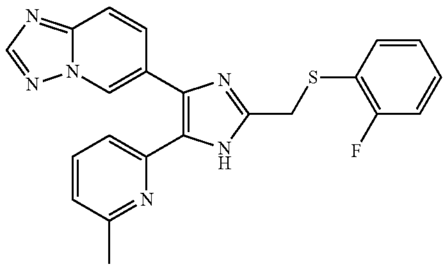 [SMILES: Cc1cccc(-c2[nH]c(CSc3ccccc3F)nc2-c2ccc3ncnn3c2)n1] | (400 MHz, CDCl₃) δ 8.86 (br s, 1 H), 8.37 (s, 1 H), 7.78 (dd, 1 H, J = 9.2, 0.8 Hz), 7.72 (dd, 1 H, J = 9.2, 1.6 Hz), 7.54-7.48 (m, 2 H), 7.31-7.27 (m, 1 H), 7.25 (br d, 1 H, J = 8.0 Hz), 7.13-7.08 (m, 2 H), 7.06 (d, 1 H, J = 8.0 Hz), 4.30 (s, 2 H), 2.64 (s, 3 H) | 417.15 |

Biological Data

The biological activity of the compounds of the invention may be assessed using the following assays:

Cell-Free Assay for Evaluating Inhibition of ALK5 Kinase Phosphorylation

ALK5 protein was expressed in Sf9 insect cells as human recombinant GST-fusion protein using the baculovirus expression system. Expressed protein was purified by affinity chromatography using GSH-agarose (Sigma-Aldrich). Kinase assay was performed in 96-well FlashPlates™ from Perkin Elmer (Boston, Mass., USA) in a 50 μL reaction volume. The reaction cocktail was pipetted in four steps in the following order: 20 μL of assay buffer (standard buffer), 5 μL of ATP solution in H₂O, 5 μL of each test compounds of formula (I) in 10% DMSO, 10 μL of GSK3 (14-27) (200 ng)/10 μL of ALK5 solution (1 ng) (premixed). The reaction cocktail contained 60 mM HEPES-NaOH, pH 7.5, 3 mM MgCl₂, 3 mM MnCl₂, 3 Na₃VO₄, 1.2 mM DTT, 50 μg/mL PEG₂₀₀₀₀, 1 μM [γ-$^{33}$P]-ATP (approximately 2.5×10⁵ cpm per well), 200 ng/10 μL GSK3 (14-27), and 1 ng/10 μL ALK5. The reaction cocktail was incubated at 30° C. for 60 min. The reaction was stopped with 50 μL of 2% (v/v) H₃PO₄, and plates were aspirated and washed two times with 200 μL 0.9% (w/v) NaCl. Assay was performed with a BeckmanCoulter Biomek 2000 robotic system. Incorporation of $^{33}$P$_i$ (counting of "cpm") was determined with a microplate scintillation counter (Microbeta, Wallac).

Compounds of formula (I) typically exhibited IC₅₀ values of less than 1 μM; some exhibited IC₅₀ values of less than 0.1 μM; and some even exhibited IC₅₀ values less than 10 nM, which is shown in the table 2.

TABLE 2

| Example | IC₅₀ (nM) |
|---|---|
| 1 | 13.10 |
| 2 | 6.68 |
| 5 | 9.41 |
| 6 | 17.40 |
| 7 | 8.96 |
| 8 | 9.84 |
| 9 | 6.39 |
| 10 | 9.41 |
| 12 | 6.16 |
| 14 | 10.70 |
| 15 | 12.30 |
| 16 | 7.54 |
| 17 | 14.60 |
| 18 | 6.54 |
| 20 | 4.53 |
| 22 | 17.10 |
| 23 | 13.90 |
| 24 | 9.07 |
| 26 | 15.60 |
| 27 | 18.00 |
| 28 | 17.40 |
| 29 | 14.30 |
| 30 | 10.60 |
| 31 | 8.01 |
| 33 | 14.20 |
| 34 | 16.20 |
| 35 | 46.00 |
| 36 | 14.20 |
| 37 | 11.90 |
| 40 | 29.60 |
| 42 | 14.40 |
| 43 | 14.30 |
| 44 | 48.10 |
| 45 | 57.50 |
| 46 | 44.20 |
| 47 | 14.40 |
| 48 | 24.10 |
| 49 | 15.30 |
| 50 | 50.70 |
| 51 | 12.30 |
| 52 | 23.40 |
| 53 | 60.10 |
| 54 | 9.93 |
| 55 | 6.70 |
| 58 | 39.60 |
| 59 | 19.50 |
| 60 | 4.83 |
| 63 | 32.10 |

TABLE 2-continued

| Example | IC$_{50}$ (nM) |
|---|---|
| 64 | 20.60 |
| 65 | 29.70 |
| 66 | 9.14 |
| 67 | 54.60 |
| 68 | 11.00 |
| 69 | 24.50 |
| 70 | 12.80 |
| 71 | 59.10 |
| 72 | 16.60 |
| 73 | 78.00 |
| 74 | 39.50 |
| 75 | 15.40 |
| 76 | 39.00 |
| 77 | 15.30 |
| 78 | 15.10 |
| 79 | 46.60 |
| 138 | 9.40 |
| 139 | 23.20 |
| 140 | 49.80 |
| 141 | 118.00 |
| 142 | 153.00 |
| 143 | 19.80 |
| 144 | 25.10 |
| 145 | 12.40 |
| 147 | 40.00 |
| 148 | 13.10 |
| 149 | 25.40 |
| 150 | 23.90 |
| 151 | 22.50 |
| 152 | 20.70 |

Cell-Free Assay for Evaluating Inhibition of ALK4 Kinase Phosphorylation

Inhibition of the ALK4 kinase phosphorylation by test compounds of formula (I) can be determined in a similar manner to that described above for ALK5 inhibition except that GST-tagged ALK4 (Invitrogen Corporation) and RBER-CHKtide are used in place of the GST-tagged ALK5 and GSK3 (14-27).

Compounds of formula (I) typically exhibited IC$_{50}$ values of less than 1 μM; some exhibited IC$_{50}$ values of less than 0.1 μM; and some even exhibited IC$_{50}$ values less than 10 nM.

Kinase Selectivity Profiling

Kinase assays were performed in 96-well FlashPlates™ from Perkin Elmer in a 50 reaction volume. The reaction cocktail was pipetted in four steps in the following order: 15 of ATP solution in H$_2$O, 20 μL of assay buffer (standard buffer), 5 μL of Example 2 in 10% DMSO, 10 μL of enzyme/substrate mixture in H$_2$O. The reaction cocktail contained 70 mM HEPES-NaOH, pH 7.5, 3 mM MnCl$_2$, 3 μM Na$_3$VO$_4$, 1.2 mM DTT, 1 μM [γ-$^{33}$P]-ATP (approximately 6×10$^5$ cpm per well), protein kinase (variable amounts), and substrate (variable amounts). The reaction cocktails were incubated at 30° C. for 60 min. The reaction was stopped with 50 μL of 2% (v/v) H$_3$PO$_4$, and plates were aspirated and washed two times with 200 μL 0.9% (w/v) NaCl. ALL assays were performed with a BeckmanCoulter Biomek 2000/SL robotic system. Incorporation of $^{33}$P$_i$ (counting of "cpm") was determined with a microplate scintillation counter.

TABLE 3

| protein kinase | IC$_{50}$ (μM) | % inhibition at 10 μM | % inhibition at 1 μM |
|---|---|---|---|
| ALK5 | 0.00668 | | |
| ALK4 | 0.0173 | | |
| P38α | 1.720 | | |
| VEGF-R1 | 0.391 | | |
| VEGF-R2 | 0.097 | | |
| VEGF-R3 | 0.257 | | |
| ALK1 | | 66 | 20 |
| ALK2 | | 71 | 17 |
| ALK3 | | 27 | −6 |
| AKT1 | | 3 | 0 |
| CDK1/CycA | | 2 | 5 |
| CHK1 | | 5 | −2 |
| DAPK1 | | 11 | 5 |
| EGF-R wt | | 43 | −8 |
| ERK1 | | 66 | 17 |
| GSK3α | | 15 | 10 |
| MEK1 wt | | 47 | 14 |
| MET wt | | 12 | −5 |
| MST1 | | 3 | −7 |
| PAK1 | | −3 | −7 |
| PDGFRα wt | | 91 | 53 |
| PDGFRβ | | 87 | 47 |
| PKA | | 18 | −7 |
| PKCα | | 4 | −9 |
| ROCK1 | | 9 | 3 |
| RPS6KA1 | | 14 | 6 |
| STK23 | | −1 | −4 |

Assay for Evaluating Cellular Inhibition of TGF-β Signaling

HaCaT-3TP-Luc stable cells or 4T1-3TP-Luc stable cells that have p3TP-Luc (neo) expression plasmid were seeded at 2.5×10$^6$ cells/well or 5×10$^8$ cells/well in 96-well plate, respectively. Cells were concomitantly treated with TGF-β1 (2 ng/mL) in 0.2% FBS in the presence or absence of each test compounds of formula (I) at approximately 60-70% confluence for 24 h at 37° C. in 5% CO$_2$. Cell lysates were prepared using Luciferase Assay System (Promega) according to the manufacturer's instruction, and luminescence was measured by a luminometer, Micro Lumat Plus (Berthold, Germany).

Compounds of formula (I) typically exhibited IC$_{50}$ values of less than 1 μM; some exhibited IC$_{50}$ values of less than 0.1 μM; and some even exhibited IC$_{50}$ values of less than 10 nM.

Immunofluorescence Assay

MCF10A cells were plated on the cover glass in 6-well plate at 2×10$^5$ cells/well. After 12 h, when cells were attached, 10% FBS medium was changed to 0.5% FBS medium. Twenty-four hours later, cells were treated with TGF-β1 (2 ng/mL) with or without Example 2 (1 μM) for 2 h. Then, cells were fixed with 4% formaldehyde solution for 30 min at room temperature and quenched with quenching solution (50 mM NH$_4$Cl in PBS) for 15 min. After being washed three times with PBS, cells were incubated with blocking/permeabilization solution (1% BSA and 0.1% Triton X-100 in PBS) for 1 h at room temperature and incubated with anti-Smad2/3 antibody (BD Biosciences, Franklin Lakes, N.J., USA) overnight at 4° C. Fluorescence was visualized by Cy3-conjugated goat anti-mouse IgG (Jackson ImmunoResearch Laboratories, Bar Harbor, Me., USA). Nuclei of the same cells were stained with DAPI solution. Cells were analyzed using the LSM 510 META laser confocal microscopy system (Carl Zeiss, Germany).

Example 2 suppressed TGF-β1-induced Smad2/3 nuclear translocation in MCF10A cells.

Wound Healing Assay

MCF10A cells were seeded at 2×10$^5$ cells/well in 6-well plate. When each well was occupied by cells over 80% of the area, 10% FBS was changed to 0.2% FBS. After 24 h, wound was made by a plastic pipette tip, and then cells were treated with TGF-β1 (2 ng/mL) with or without Example 2 (1 μM) for 16 h. Wound area change from 0 to 16 h was calculated based on Image J program (National Institutes of Health, MD, USA) based on phase-contrast images of cells taken by microscope.

Example 2 suppressed TGF-β1-induced cell migration in MCF10A cells.

Matrigel Invasion Assay

The upper surface of Transwells (6.5 mm diameter, 8 μm pore size; Corning, Lowell, Mass., USA) were coated with 20 μL diluted Matrigel (BD Biosciences). 4T1 cells were seeded at 4×10$^4$ cells/well on the upper chamber of transwell in serum free medium with or without TGF-β1 (2 ng/mL) in the presence or absence of Example 2. The lower chamber was filled with 10% FBS with TGF-β1 (2 ng/mL) in the presence or absence of Example 2. After incubation for 20 h at 37° C. in 5% CO$_2$, the cells remaining on the upper surface of the membrane were removed with a cotton swab, and DAPI-stained cells remaining on the bottom surface were observed using fluorescence microscopy. Average cell number per view field was obtained from 5 random fields.

Example 2 suppressed TGF-β1-induced cell invasion in matrigel invasion assay.

Cell Growth Study

Either 4T1 cells or MCF10A cells were seeded in 96-well plate at 5×10$^3$ cells per well. After cells were attached, cells were treated with Example 2 dissolved in DMSO in 0.2% serum medium. After incubation for four days, cell viability was determined by SRB assay.

Example 2 showed no effect on 4T1 cell growth and slightly increased MCF10A cell growth without significance, thus, suggesting that the anti-metastatic effect of Example 2 were not due to the primary tumor growth inhibition Anti-Metastatic Effect on BALB/c 4T1 Xenografted Mice Model Female BALB/c mice were purchased from Orient Bio Inc. (Seoul, Korea). Animals were maintained in a temperature-controlled room (22° C.) and supplied with food and water ad libitum. 4T1 cells (1.2×10$^4$ cells) were suspended in PBS and implanted into the left #4 mammary fat pad of five to six-week-old female BALB/c mice (day 0). In Experiment 1, treatment was started after tumor implantation (day 0). Example 3 (13.6 or 27.3 mg/kg) dissolved in water was given to mice orally BID five consecutive days per week for four weeks. In Experiment 2, treatment was started on day 4. Example 2 (5, 10, 20, or 40 mg/kg) dissolved in artificial gastric fluid formulation was given to mice orally five consecutive days per week for three weeks. In Experiment 3, treatment was started on day 4. Example 2 (5, 10, 20, or 40 mg/kg) dissolved in artificial gastric fluid formulation was given to mice orally every other day (three times per week) for 24 days. In Experiment 4, 4T1 cells (1×10$^4$ cells) were suspended in PBS and implanted into the left #4 mammary fat pad of ten-week-old female BALB/c mice (day 0). Treatment was started on day 10. Example 61 (43.6 mg/kg) dissolved in saline was given to mice intraperitoneally every other day for 2.5 weeks. In all Experiments, mice were sacrificed at 24 to 72 h after the last dosing, and 15% India ink solution (Hardy Diagnostics) in PBS was immediately injected into the trachea. The India ink-stained lungs were isolated and destained with Feket's solution (60% ethanol, 3% formaldehyde, and 4% acetic acid in PBS) for at least 20 min. Number of metastatic nodule was counted on the surface of left lobe of lung, and picture of lung was taken with digital camera. The tumor size was measured using calipers, and the tumor volume was calculated by using the following equation:

$$\text{Tumor volume} = (0.5236) \times (\text{width})^2 \times (\text{length})$$

Examples 2, 3, and 61 significantly reduced the number of metastastic nodules on the lung.

In Experiment 3, Western blot analysis was performed to examine the effect of Example 2 on the Smad2 phosphorylation in tumor tissues. Either vehicle buffer (4 mM HCl, 1 mg/mL BSA) or TGF-β1 (50 ng/mouse) in vehicle buffer was given to mice intravenously at 2 h before mice were sacrificed. Tumor tissues from mice were lysed in RIPA buffer [50 mM Tris, pH 7.5, 150 mM NaCl, 0.1% sodium dodecyl sulfate, 0.5% sodium deoxycholate, 1% NP-40, 1 mM NaF, 1 mM Na$_3$VO$_4$, 1 mM PMSF, a protease inhibitor cocktail (1 tablet of Roche Diagnostics GmbH protease inhibitor cocktail/10 mL) (Roche)] for 20 min on ice. Lysates were cleared by centrifugation at 13000 rpm at 4° C. for 20 min. Protein content of supernatants was determined using Micro-BCA (bicinchoninic acid) protein assay kit (Thermo Scientific). Lysates containing 20-50 μg total protein were separated by electrophoresis on polyacrylamide gel and then electrophoretically transferred to polyvinylidene difluoride transfer membranes (Millipore, Billerica, Mass., USA). Membranes were blocked with 5% BSA (Sigma-Aldrich) in PBS containing 0.5% Tween-20 (PBST) for 1 h and incubated overnight at 4° C. with one of following antibodies: anti-phospho-Smad2 (Millipore), anti-Smad2/3 (BD Transduction Laboratories, NJ, USA), or anti-β-actin (Sigma-Aldrich) in PBST containing 1% BSA. Membranes were washed three times with PBST and incubated with either horseradish peroxidase (HRP)-conjugated goat anti-mouse antibody or HRP-conjugated goat anti-rabbit antibody (SantaCruz Biotechnology, Santa Cruz, Calif., USA) at room temperature for 1 h. Bound antibodies were detected using Western Blotting Luminol Reagent (SantaCruz Biotechnology). Band intensities were analyzed using a densitometer LAS-3000 imager (FUJIFILM, Tokyo, Japan).

Example 2 suppressed TGF-β1-induced Smad2 phosphorylation in tumor tissues.

Anti-metastatic Effect on MMTV/c-Neu mice breast cancer model MMTV/c-Neu female transgenic mice were purchased from Jackson Laboratory (Bar Harbor, Me., USA). Animals were maintained in a temperature-controlled SPF room (22° C.) and supplied with food and water ad libitum. In Experiment 1, Example 61 (43.6 mg/kg) dissolved in saline was given to thirty two-week-old MMTV/c-Neu mice intraperitoneally every other day for three weeks. In Experiment 2, Example 3 (43.6 mg/kg) dissolved in saline was given to thirty two-week-old MMTV/c-Neu mice intraperitoneally every other day for ten weeks. Mice were sacrificed at 24 h after the last dosing, and tissues of mammary tumor and lung were analyzed by hematoxylin and eosin (H&E) staining To analyse β-casein mRNA level in tissues of mammary tumor and lung, total RNAs were isolated from these tissues using TRIzol reagent (Invitrogen Corporation) and RNeasy Mini kit (Qiagen) according to the manufacturer's instruction. The cDNAs were synthesized from 2 μg of total RNAs using random primer (Invitrogen Corporation) by MMLV RTase (Invitrogen Corporation) for 1 h at 37° C. and subjected to PCR amplification using Taq polymerase (Promega) and following gene-specific primers: mouse GAPDH (forward) 5'-ATG TGT CCG TCG TGG ATC TGA-3' and (reverse) 5'-TTG AAG TCG CAG GAG ACA ACC-3', mouse β-casein (forward) 5'-TCC CAC AAA ACA TCC AGC C-3' and (reverse) 5'-ACG GAA TGT TGT GGA GTG G-3'. Amplified DNA was analyzed by agarose gel electrophoresis.

Example 61 significantly reduced the number of metastastic lesions in the lung. Significant level of β-casein (a mammary differentiation marker) mRNA was detected in the lung of MMTV/c-Neu mice. Examples 3 and 61 significantly inhibited β-casein mRNA expression level in the lung, demonstrating their anti-metastatic effect.

Activity of MMP-9 and MMP-2 in the primary mammary tumor was measured by gelatin zymography. Tumor tissues from mice (30 mg) was lysed in 500 μL RIPA buffer (50 mM Tris, 150 mM NaCl, 0.1% sodium dodecyl sulfate, 0.5% sodium deoxycholate, 1% NP-40, protease inhibitor without EDTA) for 10-20 min on ice. Lysates were cleared by centrifugation at 13000 rpm at 4° C. for 10 min. Protein content of supernatants was determined using Micro-BCA protein assay kit (Thermo Scientific). Loading samples were prepared by adding loading buffer (0.5 M Tris, pH 6.8, 50% glycerol, 10% SDS, and 1% bromophenol blue solution) into lysates containing 15 μg of total protein. Loading samples were heated at 60° C. for 5 min and separated by electrophoresis on 10% polyacrylamide gel containing 0.2% gelatin. Gel was washed twice with washing buffer [2.5% Triton-X100, 0.05 M Tris-HCl, pH 7.5, and 0.1 M NaCl] for 30 min at room temperature. Then, the gel was incubated in incubation buffer [0.05 M Tris-HCl, pH 7.5, 0.15 M NaCl, 0.01 M $CaCl_2$, 0.02% $NaN_3$, and 1 μM $ZnCl_2$] at 37° C. for 16-18 h with shaking Gel was stained by 0.5% Coomassie blue 8250 solution containing 5% methanol and 10% acetic acid for 2-4 h at room temperature and destained twice by destaining solution (5% methanol and 10% acetic acid) for 30 min at room temperature. Gel image was obtained using a densitometer LAS-3000 imager (FUJIFILM) in cybergreen mode.

Example 3 significantly inhibited activity of MMP-9 and MMP-2 in the primary mammary tumor.

Anti-Fibrotic Effect on Bile Duct-Ligated Liver Fibrosis Model

Six-week-old male Sprague-Dawley (SD) rats were purchased from Orient Bio Inc. In Experiment 1, SD rats weighing 180-200 g were randomly divided into five experimental groups: sham-operated control rats (n=5), sham-operated rats treated with Example 3 (43.6 mg/kg, n=5), bile duct-ligated (BDL) rats (n=10), BDL rats treated with either 21.8 or 43.6 mg/kg of Example 3 (n=10). In Experiment 2, SD rats weighing 180-200 g were randomly divided into five experimental groups: sham-operated control rats (n=5), BDL rats (n=10), BDL rats treated with either 5, 10, or 20 mg/kg of Example 2 (n=10). For BDL, the animals were anesthetized with zoletil (20 mg/kg) and xylazine (10 mg/kg), and the common bile duct was exposed and double-ligated using 3-0 silk. The first ligature was placed below the junction of the hepatic duct, and the second was placed above the entrance of the pancreatic duct. The common bile duct was then cut between the double ligatures. In sham-operated rats, an incision was made in the abdomen and then closed without any treatment. Treatment was started within 2 h after surgical procedure. Either Example 3 dissolved in saline (Experiment 1) or Example 2 dissolved in artificial gastric fluid formulation (Experiment 2) was given to rats orally three times per week for four weeks starting from BDL surgery. Animals were maintained in a temperature controlled room (at 21° C.) and supplied with autoclaved food and water. At 48 h after the last dosing, animals were killed, and the serum, spleens and livers were removed. The livers were sagittally sliced into several parts, snap frozen in liquid nitrogen, and kept at −70° C. A part of livers was immersed into 10% neutral buffered-formalin for histopathological examinations. All experimental procedures were conducted in accordance with our institutional guidelines. The activity of serum alanine aminotransferase (ALT) and aspartate aminotransferase (AST) was determined using a spectrophotometric enzyme assay kit (Asan Pharm. Co., Ltd., Hwaseong-si, Korea) according to the manufacturer's instruction. Automated instrument was also used to assay general serum biochemistry. Liver specimens were fixed in 10% neutral buffered-formalin prior to routine processing in paraffin-embedded blocks. Sections (5 μm thick) were cut and stained using hematoxylin and eosin (H&E), and examined by light microscopy. Liver tissues were lysed in RIPA buffer [50 mM Tris, pH 7.5, 150 mM NaCl, 1 mM EDTA, 0.1% sodium dodecyl sulfate, 0.5% sodium deoxycholate, 1% NP-40, 50 mM NaF, 1 mM $Na_3VO_4$, 1 mM PMSF, a protease inhibitor cocktail (1 tablet of Roche Diagnostics GmbH protease inhibitor cocktail/10 mL) (Roche)] for 20 min on ice. Lysates were cleared by centrifugation at 13000 rpm at 4° C. for 20 min. Protein content of supernatants was determined using Micro-BCA protein assay kit (Thermo Scientific). Lysates containing 20-60 μg total protein were separated by electrophoresis on 6-10% sodium dodecyl sulfate-polyacrylamide gel and then transferred to nitrocellulose (Whatman®, Germany) or polyvinylidene difluoride membranes (Millipore). Membranes were blocked with 5% BSA (Sigma-Aldrich) or 5% nonfat dry milk solution for 1 h and incubated overnight at 4° C. with one of following antibodies: rabbit antiphospho-Smad3 (Cell Signaling Technology, Beverly, Mass., USA), rabbit anti-α-SMA (Millipore), mouse anti-fibronectin, mouse anti-vimentin (BD Biosciences), or mouse anti-β-actin (Sigma-Aldrich). Membranes were washed three times with Tris-buffered saline and incubated with either HRP-conjugated goat anti-rabbit antibody or HRP-conjugated goat anti-mouse antibody (SantaCruz Biotechnology) at room temperature for 1 h. Bound antibodies were detected using an ECL kit (GE Healthcare, Princeton, N.J., USA). Band intensities were analyzed using a densitometer LAS-3000 imager (FUJIFILM).

BDL rats showed body weight loss and organ (liver and spleen) weight increase compared with sham-operated control rats. Examples 2 and 3 recovered body weight loss and decreased organ (liver and spleen) weight in BDL rats. A significant increase in serum ALT and AST was observed in BDL rats as compared with sham-operated animals. Examples 2 and 3 improved serum ALT and AST in BDL rats. Examples 3 inhibited Smad signaling and suppressed α-SMA, fibronectin, and vimentin in BDL rat liver. Examples 2 suppressed α-SMA and fibronectin in BDL rat liver. BDL rat livers showed typical histological changes characterized by central±central architecture disruption and bridge fibrosis formation compared with that of normal rat livers. Examples 2 and 3 greatly abolished BDL-induced histological change.

TABLE 4

| | | | Organ weight | | |
| --- | --- | --- | --- | --- | --- |
| Groups (mg/kg) | Body weight (g) | Liver (g) | Spleen (g) | Liver/Body (%) | Spleen/Body (%) |
| Sham vehicle | 357 ± 5.2 | 11.7 ± 0.36 | 0.78 ± 0.06 | 3.28 ± 0.07 | 0.22 ± 0.02 |
| Example 3 (43.6) | 354 ± 12.2## | 11.8 ± 0.71 | 0.81 ± 0.04 | 3.34 ± 0.12 | 0.23 ± 0.01 |

TABLE 4-continued

| | | | Organ weight | | | |
|---|---|---|---|---|---|---|
| Groups (mg/kg) | | Body weight (g) | Liver (g) | Spleen (g) | Liver/Body (%) | Spleen/Body (%) |
| BDL | vehicle | 308 ± 6.1** | 22.8 ± 1.30** | 2.01 ± 0.14** | 7.43 ± 0.44** | 0.65 ± 0.04** |
| | Example 3 (21.8) | 340 ± 0.6# | 16.4 ± 0.72**,## | 1.30 ± 0.07** | 4.85 ± 0.26**,## | 0.39 ± 0.03**,## |
| | Example 3 (43.6) | 335 ± 8.4 | 16.1 ± 0.57**,## | 1.19 ± 0.09** | 4.84 ± 0.26**,## | 0.36 ± 0.03**,## |

Data represents the mean ± S.E. (n = 5-8).
**p < 0.01 vs. sham.
p < 0.05 vs. BDL.
p < 0.01 vs. BDL.

TABLE 5

| | | | Organ weight | | | |
|---|---|---|---|---|---|---|
| Groups (mg/kg) | | Body weight (g) | Liver (g) | Spleen (g) | Liver/Body (%) | Spleen/Body (%) |
| Sham | vehicle | 345 ± 6.3 | 12.1 ± 0.77 | 0.83 ± 0.05 | 3.51 ± 0.21 | 0.24 ± 0.02 |
| BDL | vehicle | 315 ± 16.1* | 20.3 ± 2.45** | 2.54 ± 0.29** | 6.39 ± 0.51** | 0.80 ± 0.05** |
| | Example 2 (5) | 324 ± 7.3 | 17.5 ± 1.82 | 2.00 ± 0.28** | 5.46 ± 0.62 | 0.63 ± 0.09** |
| | Example 2 (10) | 312 ± 10.4 | 15.8 ± 1.88 | 1.57 ± 0.12# | 5.08 ± 0.60 | 0.51 ± 0.05# |
| | Example 2 (20) | 312 ± 8.4* | 15.2 ± 1.80 | 1.50 ± 0.16# | 4.88 ± 0.63 | 0.48 ± 0.05# |

Data represents the mean ± S.E. (n = 5-8).
*p < 0.05 vs. sham.
**p < 0.01 vs. sham.
p < 0.05 vs. BDL.

Anti-Fibrotic Effect on Bleomycin-Induced Lung Fibrosis Model

Six-week-old male ICR mice were purchased from Orient Bio Inc. Mice weighing 31-35 g were randomly divided into five experimental groups: sham-operated control mice (saline, n=6), bleomycin (BLM)-treated mice (n=10), BLM-treated mice treated with either 5, 10, or 20 mg/kg of Example 2 (n=10). For the induction of lung fibrosis, mice were anesthetized with zoletil (10 mg/kg) and xylazine (5 mg/kg) and were given BLM (given as BLM sulfate, 1 mg/kg) (MBcell, Los Angeles, Calif., USA) dissolved in 60 µL of saline once on day 0 through intratracheal instillation. Example 2 dissolved in artificial gastric fluid formulation was given to mice orally five times per week for two weeks starting from day 7. Animals were maintained in a temperature controlled room (at 21° C.) and supplied with autoclaved food and water. At three weeks post-surgery, animals were killed, and the lungs were removed. The lungs were sagittally sliced into several parts, snap frozen in liquid nitrogen, and kept at −70° C. A part of lungs was immersed into 10% neutral buffered-formalin for histopathological examinations. All experimental procedures were conducted in accordance with our institutional guidelines. Lung specimens were fixed in 10% neutral buffered-formalin prior to routine processing in paraffin-embedded blocks. Sections (5 µm thick) were cut, stained using hematoxylin and eosin (H&E), and examined by light microscopy. Lung tissues were lysed in RIPA buffer [50 mM Tris, pH 7.5, 150 mM NaCl, 1 mM EDTA, 0.1% sodium dodecyl sulfate, 0.5% sodium deoxycholate, 1% NP-40, 50 mM NaF, 1 mM Na$_3$VO$_4$, 1 mM PMSF, a protease inhibitor cocktail (1 tablet of Roche Diagnostics GmbH protease inhibitor cocktail/10 mL) (Roche)] for 20 min on ice. Lysates were cleared by centrifugation at 13000 rpm at 4° C. for 20 min. Protein content of supernatants was determined using Micro-BCA protein assay kit (Thermo Scientific). Lysates containing 20-50 µg total protein were separated by electrophoresis on 6-10% sodium dodecyl sulfate-polyacrylamide gel and then transferred to nitrocellulose (Whatman®). Membranes were blocked with 5% nonfat dry milk solution for 1 h and incubated overnight at 4° C. with either rabbit anti-α-SMA (Millipore) or mouse anti-fibronectin (BD Biosciences). Membranes were washed three times with Tris-buffered saline and incubated with either HRP-conjugated goat anti-rabbit antibody or HRP-conjugated goat anti-mouse antibody (SantaCruz Biotechnology) at room temperature for 1 h. Bound antibodies were detected using an ECL kit (GE Healthcare). Band intensities were analyzed using a densitometer LAS-3000 imager (FUJIFILM).

BLM-induced fibrotic lungs showed the elevated levels of α-SMA and fibronectin compared with those of sham-operated animals. Example 2 suppressed α-SMA and fibronectin in BLM-induced fibrotic lung. Lung tissues from the BLM-treated mice showed typical histology that pulmonary interalveolar septa became thickened and infiltrated by inflammatory cells with collagen depositions in the interstitium disclosed. Example 2 greatly reduced BLM-induced histological changes at all dose levels tested.

What is claimed is:

1. A method of inhibiting TGF-β or activin signaling pathways or both in a human, comprising administering to the human in need of treatment, a therapeutically effective amount of the one or more compounds of formula (I) or a pharmaceutically acceptable salt thereof, wherein the compound of the formula (I) has the structure:

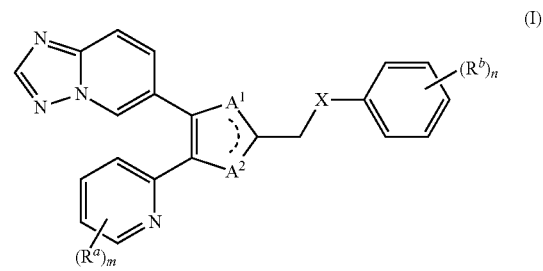

wherein:
  each $R^a$ is independently H, halo, $C_{1-6}$alkyl, $C_{1-6}$haloalkyl, $C_{3-6}$cycloalkyl, OH, —O—$C_{1-6}$alkyl, —O—$C_{1-6}$haloalkyl, —O—$C_{3-6}$cycloalkyl, $NH_2$, —NH—$C_{1-6}$alkyl, —NH—$C_{1-6}$haloalkyl, —NH—$C_{3-6}$cycloalkyl, —S—$C_{1-6}$alkyl, —S—$C_{1-6}$haloalkyl, —S—$C_{3-6}$cycloalkyl, CN, or $NO_2$;
  m is 0, 1, 2, 3, or 4;
  one of $A^1$ and $A^2$ is N and the other is $NR^1$, wherein $R^1$ is H, OH, $C_{1-6}$alkyl, $C_{1-6}$haloalkyl, or $C_{3-6}$cycloalkyl;
  X is —$NR^2$—, —O—, or —S—, wherein $R^2$ is H or $C_{1-3}$alkyl;
  each $R^b$ is independently H, halo, $C_{1-6}$alkyl, $C_{1-6}$haloalkyl, $C_{3-6}$cycloalkyl, $C_{2-6}$alkenyl, $C_{2-6}$alkynyl, —$(CH_2)_q$—$OR^3$, —$(CH_2)_q$—$NR^3R^4$, —$(CH_2)_q$—$SR^3$, —$(CH_2)_q$—$NO_2$, —$(CH_2)_q$—CONHOH, —$(CH_2)_q$—CN, —$(CH_2)_q$—$COR^3$, —$(CH_2)_q$—$CO_2R^3$, —$(CH_2)_q$—$CONR^3R^4$, —$(CH_2)_q$-tetrazole, —$(CH_2)_q$—CH=CH—CN, —$(CH_2)_q$—CH=CH—$CO_2R^3$, —$(CH_2)_q$—CH=CH—$CONR^3R^4$, —$(CH_2)_q$—CH=CH-tetrazole, —$(CH_2)_q$—$NHCOR^3$, —$(CH_2)_q$—$NHCO_2R^3$, —$(CH_2)_q$—$CONHSO_2R^3$, —$(CH_2)_q$—$NHSO_2R^3$, —$(CH_2)_q$—C≡C—CN, —$(CH_2)_q$—C≡C—$CO_2R^3$, —$(CH_2)_q$—C≡C—$CONR^3R^4$, —$(CH_2)_q$—C≡C-tetrazole, —$(CH_2)_q$—$SOR^5$, —$(CH_2)_q$—$SO_2R^5$, or —$(CH_2)_r$—$(OR^3)_2$, wherein $R^3$ and $R^4$ are independently H, $C_{1-6}$alkyl, $C_{1-6}$haloalkyl, or $C_{3-6}$cycloalkyl; or taken together with the nitrogen atom to which they are attached form a mono-cyclic ring such as imidazole, pyrrolidine, piperidine, morpholine, piperazine and homopiperazine; $R^5$ is $C_{1-6}$alkyl, $C_{1-6}$haloalkyl, or $C_{3-6}$cycloalkyl; q is 0, 1, 2, 3, or 4; and r is 1, 2, 3, or 4;
  n is 0, 1, 2, 3, 4, or 5; or a pharmaceutically acceptable salt thereof.

2. A method of treating a metastasis of breast cancer tumor cells in a human, comprising administering to the human in need of treatment, a therapeutically effective amount of one or more compounds of formula (I) or a pharmaceutically acceptable salt thereof, wherein the compound of the formula (I) has the structure:

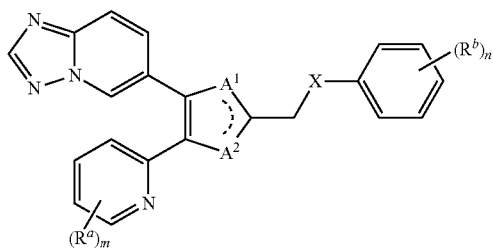

(I)

wherein:
  each $R^a$ is independently H, halo, $C_{1-6}$alkyl, $C_{1-6}$haloalkyl, $C_{3-6}$cycloalkyl, OH, —O—$C_{1-6}$alkyl, —O—$C_{1-6}$haloalkyl, —O—$C_{3-6}$cycloalkyl, $NH_2$, —NH—$C_{1-6}$alkyl, —NH—$C_{1-6}$haloalkyl, —NH—$C_{3-6}$cycloalkyl, —S—$C_{1-6}$alkyl, —S—$C_{1-6}$haloalkyl, —S—$C_{3-6}$cycloalkyl, CN, or $NO_2$;
  m is 0, 1, 2, 3, or 4;
  one of $A^1$ and $A^2$ is N and the other is $NR^1$, wherein $R^1$ is H, OH, $C_{1-6}$alkyl, $C_{1-6}$ haloalkyl, or $C_{3-6}$cycloalkyl;
  X is —$NR^2$—, —O—, or —S—, wherein $R^2$ is H or $C_{1-3}$alkyl;
  each $R^b$ is independently H, halo, $C_{1-6}$alkyl, $C_{1-6}$haloalkyl, $C_{3-6}$cycloalkyl, $C_{2-6}$alkenyl, $C_{2-6}$alkynyl, —$(CH_2)_q$—$OR^3$, —$(CH_2)_q$—$NR^3R^4$, —$(CH_2)_q$—$SR^3$, —$(CH_2)_q$—$NO_2$, —$(CH_2)_q$—CONHOH, —$(CH_2)_q$—CN, —$(CH_2)_q$—$COR^3$, —$(CH_2)_q$—$CO_2R^3$, —$(CH_2)_q$—$CONR^3R^4$, —$(CH_2)_q$-tetrazole, —$(CH_2)_q$—CH=CH—CN, —$(CH_2)_q$—CH=CH—$CO_2R^3$, —$(CH_2)_q$—CH=CH—$CONR^3R^4$, —$(CH_2)_q$—CH=CH-tetrazole, —$(CH_2)_q$—$NHCOR^3$, —$(CH_2)_q$—$NHCO_2R^3$, —$(CH_2)_q$—$CONHSO_2R^3$, —$(CH_2)_q$—$NHSO_2R^3$, —$(CH_2)_q$—C≡C—CN, —$(CH_2)_q$—C≡C—$CO_2R^3$, —$(CH_2)_q$—C≡C—$CONR^3R^4$, —$(CH_2)_q$—C≡C-tetrazole, —$(CH_2)_q$—$SOR^5$, —$(CH_2)_q$—$SO_2R^5$, or —$(CH_2)$—$(OR^3)_2$, wherein $R^3$ and $R^4$ are independently H, $C_{1-6}$alkyl, $C_{1-6}$haloalkyl, or $C_{3-6}$cycloalkyl; or taken together with the nitrogen atom to which they are attached form a mono-cyclic ring such as imidazole, pyrrolidine, piperidine, morpholine, piperazine and homopiperazine; $R^5$ is $C_{1-6}$alkyl, $C_{1-6}$haloalkyl, or $C_{3-6}$cycloalkyl; q is 0, 1, 2, 3, or 4; and r is 1, 2, 3, or 4;
  n is 0, 1, 2, 3, 4, or 5; or a pharmaceutically acceptable salt thereof.

3. A method for treating liver fibrosis due to all etiologies, pulmonary fibrosis, wound healing and breast cancer, comprising administering to a human in need of treatment, a therapeutically effective amount of one or more compounds of formula (I) or a pharmaceutically acceptable salt thereof, wherein the compound of the formula (I) has the structure:

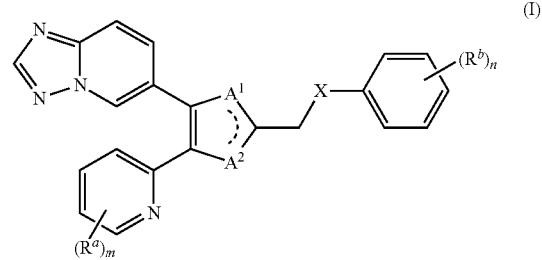

(I)

CONR³R⁴, —(CH₂)_q—C≡C-tetrazole, —(CH₂)_q—SOR⁵, —(CH₂)_q—SO₂R⁵, or —(CH₂)—(OR³)₂, wherein R³ and R⁴ are independently H, C₁₋₆alkyl, C₁₋₆haloalkyl, or C₃₋₆cycloalkyl; or taken together with the nitrogen atom to which they are attached form a mono-cyclic ring such as imidazole, pyrrolidine, piperidine, morpholine, piperazine and homopiperazine; R⁵ is C₁₋₆alkyl, C₁₋₆haloalkyl, or C₃₋₆cycloalkyl; q is 0, 1, 2, 3, or 4; and r is 1, 2, 3, or 4;

n is 0, 1, 2, 3, 4, or 5; or a pharmaceutically acceptable salt thereof.

4. The method of claim 1, wherein the compound is

N-((4-([1,2,4]triazolo[1,5-a]pyridin-6-yl)-5-(6-methylpyridin-2-yl)-1H-imidazol-2-yl)methyl)aniline;
N-((4-([1,2,4]triazolo[1,5-a]pyridin-6-yl)-5-(6-methylpyridin-2-yl)-1H-imidazol-2-yl)methyl)-2-fluoroaniline;
N-((4-([1,2,4]triazolo[1,5-a]pyridin-6-yl)-5-(6-methylpyridin-2-yl)-1H-imidazol-2-yl)methyl)-3-fluoroaniline;
N-((4-([1,2,4]triazolo[1,5-a]pyridin-6-yl)-5-(6-methylpyridin-2-yl)-1H-imidazol-2-yl)methyl)-4-fluoroaniline;
N-((4-([1,2,4]triazolo[1,5-a]pyridin-6-yl)-5-(6-methylpyridin-2-yl)-1H-imidazol-2-yl)methyl)-2,3-difluoroaniline;
N-((4-([1,2,4]triazolo[1,5-a]pyridin-6-yl)-5-(6-methylpyridin-2-yl)-1H-imidazol-2-yl)methyl)-3,4-difluoroaniline;
N-((4-([1,2,4]triazolo[1,5-a]pyridin-6-yl)-5-(6-methylpyridin-2-yl)-1H-imidazol-2-yl)methyl)-3,5-difluoroaniline;
N-((4-([1,2,4]triazolo[1,5-a]pyridin-6-yl)-5-(6-methylpyridin-2-yl)-1H-imidazol-2-yl)methyl)-2-chloroaniline;
N-((4-([1,2,4]triazolo[1,5-a]pyridin-6-yl)-5-(6-methylpyridin-2-yl)-1H-imidazol-2-yl)methyl)-3-chloroaniline;
N-((4-([1,2,4]triazolo[1,5-a]pyridin-6-yl)-5-(6-methylpyridin-2-yl)-1H-imidazol-2-yl)methyl)-4-chloroaniline;
N-((4-([1,2,4]triazolo[1,5-a]pyridin-6-yl)-5-(6-methylpyridin-2-yl)-1H-imidazol-2-yl)methyl)-2,3-dichloroaniline;
N-((4-([1,2,4]triazolo[1,5-a]pyridin-6-yl)-5-(6-methylpyridin-2-yl)-1H-imidazol-2-yl)methyl)-3,4-dichloroaniline;
N-((4-([1,2,4]triazolo[1,5-a]pyridin-6-yl)-5-(6-methylpyridin-2-yl)-1H-imidazol-2-yl)methyl)-3,5-dichloroaniline;
N-((4-([1,2,4]triazolo[1,5-a]pyridin-6-yl)-5-(6-methylpyridin-2-yl)-1H-imidazol-2-yl)methyl)-2-bromoaniline;
N-((4-([1,2,4]triazolo[1,5-a]pyridin-6-yl)-5-(6-methylpyridin-2-yl)-1H-imidazol-2-yl)methyl)-3-bromoaniline;
N-((4-([1,2,4]triazolo[1,5-a]pyridin-6-yl)-5-(6-methylpyridin-2-yl)-1H-imidazol-2-yl)methyl)-4-bromoaniline;
N-((4-([1,2,4]triazolo[1,5-a]pyridin-6-yl)-5-(6-methylpyridin-2-yl)-1H-imidazol-2-yl)methyl)-2-methylaniline;
N-((4-([1,2,4]triazolo[1,5-a]pyridin-6-yl)-5-(6-methylpyridin-2-yl)-1H-imidazol-2-yl)methyl)-3-methylaniline;
N-((4-([1,2,4]triazolo[1,5-a]pyridin-6-yl)-5-(6-methylpyridin-2-yl)-1H-imidazol-2-yl)methyl)-4-methylaniline;
N-((4-([1,2,4]triazolo[1,5-a]pyridin-6-yl)-5-(6-methylpyridin-2-yl)-1H-imidazol-2-yl)methyl)-2,3-dimethylaniline;
N-((4-([1,2,4]triazolo[1,5-a]pyridin-6-yl)-5-(6-methylpyridin-2-yl)-1H-imidazol-2-yl)methyl)-3,4-dimethylaniline;
N-((4-([1,2,4]triazolo[1,5-a]pyridin-6-yl)-5-(6-methylpyridin-2-yl)-1H-imidazol-2-yl)methyl)-3,5-dimethylaniline;
N-((4-([1,2,4]triazolo[1,5-a]pyridin-6-yl)-5-(6-methylpyridin-2-yl)-1H-imidazol-2-yl)methyl)-2-ethylaniline;
N-((4-([1,2,4]triazolo[1,5-a]pyridin-6-yl)-5-(6-methylpyridin-2-yl)-1H-imidazol-2-yl)methyl)-3-ethylaniline;
N-((4-([1,2,4]triazolo[1,5-a]pyridin-6-yl)-5-(6-methylpyridin-2-yl)-1H-imidazol-2-yl)methyl)-2-isopropylaniline;
N-((4-([1,2,4]triazolo[1,5-a]pyridin-6-yl)-5-(6-methylpyridin-2-yl)-1H-imidazol-2-yl)methyl)-3-isopropylaniline;
N-((4-([1,2,4]triazolo[1,5-a]pyridin-6-yl)-5-(6-methylpyridin-2-yl)-1H-imidazol-2-yl)methyl)-4-isopropylaniline;
N-((4-([1,2,4]triazolo[1,5-a]pyridin-6-yl)-5-(6-methylpyridin-2-yl)-1H-imidazol-2-yl)methyl)-2-vinylaniline;
N-((4-([1,2,4]triazolo[1,5-a]pyridin-6-yl)-5-(6-methylpyridin-2-yl)-1H-imidazol-2-yl)methyl)-3-vinylaniline;
N-((4-([1,2,4]triazolo[1,5-a]pyridin-6-yl)-5-(6-methylpyridin-2-yl)-1H-imidazol-2-yl)methyl)-4-vinylaniline;
N-((4-([1,2,4]triazolo[1,5-a]pyridin-6-yl)-5-(6-methylpyridin-2-yl)-1H-imidazol-2-yl)methyl)-3-ethynylaniline;
N-((4-([1,2,4]triazolo[1,5-a]pyridin-6-yl)-5-(6-methylpyridin-2-yl)-1H-imidazol-2-yl)methyl)-2-methoxyaniline;
N-((4-([1,2,4]triazolo[1,5-a]pyridin-6-yl)-5-(6-methylpyridin-2-yl)-1H-imidazol-2-yl)methyl)-3-methoxyaniline;
N-((4-([1,2,4]triazolo[1,5-a]pyridin-6-yl)-5-(6-methylpyridin-2-yl)-1H-imidazol-2-yl)methyl)-4-methoxyaniline;
N-((4-([1,2,4]triazolo[1,5-a]pyridin-6-yl)-5-(6-methylpyridin-2-yl)-1H-imidazol-2-yl)methyl)-2,3-dimethoxyaniline;
N-((4-([1,2,4]triazolo[1,5-a]pyridin-6-yl)-5-(6-methylpyridin-2-yl)-1H-imidazol-2-yl)methyl)-3,4-dimethoxyaniline;
N-((4-([1,2,4]triazolo[1,5-a]pyridin-6-yl)-5-(6-methylpyridin-2-yl)-1H-imidazol-2-yl)methyl)-3,5-dimethoxyaniline;
N-((4-([1,2,4]triazolo[1,5-a]pyridin-6-yl)-5-(6-methylpyridin-2-yl)-1H-imidazol-2-yl)methyl)-2-(methoxymethyl)aniline;
N-((4-([1,2,4]triazolo[1,5-a]pyridin-6-yl)-5-(6-methylpyridin-2-yl)-1H-imidazol-2-yl)methyl)-3-(methoxymethyl)aniline;
N-((4-([1,2,4]triazolo[1,5-a]pyridin-6-yl)-5-(6-methylpyridin-2-yl)-1H-imidazol-2-yl)methyl)-4-(methoxymethyl)aniline;
N-((4-([1,2,4]triazolo[1,5-a]pyridin-6-yl)-5-(6-methylpyridin-2-yl)-1H-imidazol-2-yl)methyl)-2-(trifluoromethoxy)aniline;
N-((4-([1,2,4]triazolo[1,5-a]pyridin-6-yl)-5-(6-methylpyridin-2-yl)-1H-imidazol-2-yl)methyl)-3-(trifluoromethoxy)aniline;
N-((4-([1,2,4]triazolo[1,5-a]pyridin-6-yl)-5-(6-methylpyridin-2-yl)-1H-imidazol-2-yl)methyl)-4-(trifluoromethoxy)aniline;
N-((4-([1,2,4]triazolo[1,5-a]pyridin-6-yl)-5-(6-methylpyridin-2-yl)-1H-imidazol-2-yl)methyl)-2-(methylthio)aniline;
N-((4-([1,2,4]triazolo[1,5-a]pyridin-6-yl)-5-(6-methylpyridin-2-yl)-1H-imidazol-2-yl)methyl)-3-(methylthio)aniline;
N-((4-([1,2,4]triazolo[1,5-a]pyridin-6-yl)-5-(6-methylpyridin-2-yl)-1H-imidazol-2-yl)methyl)-4-(methylthio)aniline;

2-((4-([1,2,4]triazolo[1,5-a]pyridin-6-yl)-5-(6-methylpyridin-2-yl)-1H-imidazol-2-yl)methylamino)benzonitrile;

3-((4-([1,2,4]triazolo[1,5-a]pyridin-6-yl)-5-(6-methylpyridin-2-yl)-1H-imidazol-2-yl)methylamino)benzonitrile;

4-((4-([1,2,4]triazolo[1,5-a]pyridin-6-yl)-5-(6-methylpyridin-2-yl)-1H-imidazol-2-yl)methylamino)benzonitrile;

3-((4-([1,2,4]triazolo[1,5-a]pyridin-6-yl)-5-(6-methylpyridin-2-yl)-1H-imidazol-2-yl)methylamino)phthalonitrile;

2-((4-([1,2,4]triazolo[1,5-a]pyridin-6-yl)-5-(6-methylpyridin-2-yl)-1H-imidazol-2-n yl)methylamino)benzamide;

3-((4-([1,2,4]triazolo[1,5-a]pyridin-6-yl)-5-(6-methylpyridin-2-yl)-1H-imidazol-2-yl)methylamino)benzamide;

4-((4-([1,2,4]triazolo[1,5-a]pyridin-6-yl)-5-(6-methylpyridin-2-yl)-1H-imidazol-2-yl)methylamino)benzamide;

2-(3-((4-([1,2,4]triazolo[1,5-a]pyridin-6-yl)-5-(6-methylpyridin-2-yl)-1H-imidazol-2-yl)methylamino)phenyl)acetonitrile;

2-(4-((4-([1,2,4]triazolo[1,5-a]pyridin-6-yl)-5-(6-methylpyridin-2-yl)-1H-imidazol-2-yl)methylamino)phenyl)acetonitrile;

1-(3-((4-([1,2,4]triazolo[1,5-a]pyridin-6-yl)-5-(6-methylpyridin-2-yl)-1H-imidazol-2-yl)methylamino)phenyl)ethanone;

1-(4-((4-([1,2,4]triazolo[1,5-a]pyridin-6-yl)-5-(6-methylpyridin-2-yl)-1H-imidazol-2-yl)methylamino)phenyl)ethanone;

Methyl 3-((4-([1,2,4]triazolo[1,5-a]pyridin-6-yl)-5-(6-methylpyridin-2-yl)-1H-imidazol-2-yl)methylamino)benzoate;

Methyl 4-((4-([1,2,4]triazolo[1,5-a]pyridin-6-yl)-5-(6-methylpyridin-2-yl)-1H-imidazol-2-yl)methylamino)benzoate;

N-(2-((4-([1,2,4]triazolo[1,5-a]pyridin-6-yl)-5-(6-methylpyridin-2-yl)-1H-imidazol-2-yl)methylamino)phenyl)acetamide;

N-(3-((4-([1,2,4]triazolo[1,5-a]pyridin-6-yl)-5-(6-methylpyridin-2-yl)-1H-imidazol-2-yl)methylamino)phenyl)acetamide;

N-(4-((4-([1,2,4]triazolo[1,5-a]pyridin-6-yl)-5-(6-methylpyridin-2-yl)-1H-imidazol-2-yl)methylamino)phenyl)acetamide;

N-(2-((4-([1,2,4]triazolo[1,5-a]pyridin-6-yl)-5-(6-methylpyridin-2-yl)-1H-imidazol-2-yl)methylamino)phenyl)methanesulfonamide;

N-(3-((4-([1,2,4]triazolo[1,5-a]pyridin-6-yl)-5-(6-methylpyridin-2-yl)-1H-imidazol-2-yl)methylamino)phenyl)methanesulfonamide;

N-(4-((4-([1,2,4]triazolo[1,5-a]pyridin-6-yl)-5-(6-methylpyridin-2-yl)-1H-imidazol-2-yl)methylamino)phenyl)methanesulfonamide;

$N^1$-((4-([1,2,4]triazolo[1,5-a]pyridin-6-yl)-5-(6-methylpyridin-2-yl)-1H-imidazol-2-yl)methyl)-$N^2$,$N^2$-dimethylbenzene-1,2-diamine;

$N^1$-((4-([1,2,4]triazolo[15-a]pyridin-6-yl)-5-(6-methylpyridin-2-yl)-1H-imidazol-2-yl)methyl)-$N^3$,$N^3$-dimethylbenzene-1,3-diamine;

N-((4-([1,2,4]triazolo[1,5-a]pyridin-6-yl)-5-(6-methylpyridin-2-yl)-1H-imidazol-2-yl)methyl)-2-(pyrrolidin-1-yl)aniline;

N-((4-([1,2,4]triazolo[1,5-a]pyridin-6-yl)-5-(6-methylpyridin-2-yl)-1H-imidazol-2-yl)methyl)-2-morpholinoaniline;

N-((4-([1,2,4]triazolo[1,5-a]pyridin-6-yl)-5-(6-methylpyridin-2-yl)-1H-imidazol-2-yl)methyl)-3-morpholinoaniline;

$N^3$-((4-([1,2,4]triazolo[1,5-a]pyridin-6-yl)-5-(6-methylpyridin-2-yl)-1H-imidazol-2-yl)methyl)-4-fluoro-$N^1$,$N^1$-dimethylbenzene-1,3-diamine;

3-((4-([1,2,4]triazolo[1,5-a]pyridin-6-yl)-5-(6-methylpyridin-2-yl)-1H-imidazol-2-yl)methylamino)-5-(dimethylamino)benzonitrile;

3-((4-([1,2,4]triazolo[1,5-a]pyridin-6-yl)-5-(6-methylpyridin-2-yl)-1H-imidazol-2-yl)methylamino)-4-(dimethylamino)benzonitrile;

N-((4-([1,2,4]triazolo[1,5-a]pyridin-6-yl)-5-(6-methylpyridin-2-yl)-1H-imidazol-2-yl)methyl)-2-((dimethylamino)methyl)aniline;

N-((4-([1,2,4]triazolo[1,5-a]pyridin-6-yl)-5-(6-methylpyridin-2-yl)-1H-imidazol-2-yl)methyl)-3-((dimethylamino)methyl)aniline;

N-((4-([1,2,4]triazolo[1,5-a]pyridin-6-yl)-5-(6-methylpyridin-2-yl)-1H-imidazol-2-yl)methyl)-2-(pyrrolidin-1-ylmethyl)aniline;

N-((4-([1,2,4]triazolo[1,5-a]pyridin-6-yl)-5-(6-methylpyridin-2-yl)-1H-imidazol-2-yl)methyl)-3-(pyrrolidin-1-ylmethyl)aniline;

N-((4-([1,2,4]triazolo[1,5-a]pyridin-6-yl)-5-(6-methylpyridin-2-yl)-1H-imidazol-2-yl)methyl)-2-(morpholinomethyl)aniline;

N-((4-([1,2,4]triazolo[1,5-a]pyridin-6-yl)-5-(6-methylpyridin-2-yl)-1H-imidazol-2-yl)methyl)-3-(morpholinomethyl)aniline;

N-((4-([1,2,4]triazolo[1,5-a]pyridin-6-yl)-5-(6-methylpyridin-2-yl)-1H-imidazol-2-yl)methyl)-5-((dimethylamino)methyl)-2-fluoroaniline;

N-((4-([1,2,4]triazolo[1,5-a]pyridin-6-yl)-5-(6-methylpyridin-2-yl)-1H-imidazol-2-yl)methyl)-3-((dimethylamino)methyl)-2-fluoroaniline;

N-((4-([1,2,4]triazolo[1,5-a]pyridin-6-yl)-5-(6-methylpyridin-2-yl)-1H-imidazol-2-yl)methyl)-2-fluoro-3-(pyrrolidin-1-ylmethyl)aniline;

N-((4-([1,2,4]triazolo[1,5-a]pyridin-6-yl)-5-(6-methylpyridin-2-yl)-1H-imidazol-2-yl)methyl)-2-fluoro-3-(morpholinomethyl)aniline;

3-((4-([1,2,4]triazolo[1,5-a]pyridin-6-yl)-5-(6-methylpyridin-2-yl)-1H-imidazol-2-yl)methylamino)-4-((dimethylamino)methyl)benzonitrile;

3-((4-([1,2,4]triazolo[1,5-a]pyridin-6-yl)-5-(6-methylpyridin-2-yl)-1H-imidazol-2-yl)methylamino)-2-((dimethylamino)methyl)benzonitrile;

3-((4-([1,2,4]triazolo[1,5-a]pyridin-6-yl)-5-(6-methylpyridin-2-yl)-1H-imidazol-2-yl)methylamino)-5-((dimethylamino)methyl)benzonitrile;

3-((4-([1,2,4]triazolo[1,5-a]pyridin-6-yl)-5-(6-methylpyridin-2-yl)-1H-imidazol-2-yl)methylamino)-4-(pyrrolidin-1-ylmethyl)benzonitrile;

3-((4-([1,2,4]triazlo[1,5-a]pyridin-6-yl)-5-(6-methylpyridin-2-yl)-1H-imidazol-2-yl)methylamino)-2-(pyrrolidin-1-ylmethyl)benzonitrile;

3-((4-([1,2,4]triazolo[1,5-a]pyridin-6-yl)-5-(6-methylpyridin-2-yl)-1H-imidazol-2-yl)methylamino)-5-(pyrrolidin-1-ylmethyl)benzonitrile;

3-((4-([1,2,4]triazolo[1,5-a]pyridin-6-yl)-5-(6-methylpyridin-2-yl)-1H-imidazol-2-yl)methylamino)-4-(morpholinomethyl)benzonitrile;

3-((4-([1,2,4]triazolo[1,5-a]pyridin-6-yl)-5-(6-methylpyridin-2-yl)-1H-imidazol-2-yl)methylamino)-2-(morpholinomethyl)benzonitrile;
3-((4-([1,2,4]triazolo[1,5-a]pyridin-6-yl)-5-(6-methylpyridin-2-yl)-1H-imidazol-2-yl)methylamino)-5-(morpholinomethyl)benzonitrile;
N-((4-([1,2,4]triazolo[1,5-a]pyridin-6-yl)-5-(6-methylpyridin-2-yl)-1H-imidazol-2-yl)methyl)-2-(2-(dimethylamino)ethylaniline;
N-((4-([1,2,4]triazolo[1,5-a]pyridin-6-yl)-5-(6-methylpyridin-2-yl)-1H-imidazol-2-yl)methyl)-3-(2-(dimethylamino)ethylaniline;
3-((4-([1,2,4]triazolo[1,5-a]pyridin-6-yl)-5-(6-ethylpyridin-2-yl)-1H-imidazol-2-yl)methylamino)benzonitrile;
N-((4-([1,2,4]triazolo[1,5-a]pyridin-6-yl)-5-(6-ethylpyridin-2-yl)-1H-imidazol-2-yl)methyl)-2-fluoroaniline;
N-((4-([1,2,4]triazolo[1,5-a]pyridin-6-yl)-5-(6-methylpyridin-2-yl)-1H-imidazol-2-yl)methyl)-2-fluoro-N-methylaniline;
3-((4-([1,2,4]triazolo[1,5-a]pyridin-6-yl)-5-(6-methylpyridin-2-yl)-1H-imidazol-2-yl)methyl)(methyl)amino)benzonitrile;
3-((4-([1,2,4]triazolo[1,5-a]pyridin-6-yl)-5-(6-methylpyridin-2-yl)-1H-imidazol-2-yl)methyl)(methyl)amino)benzamide;
6-(5-(6-methylpyridin-2-yl)-2-(phenoxymethyl)-1H-imidazol-4-yl)-[1,2,4]triazolo[1,5-a]pyridine;
6-(2-((2-fluorophenoxy)methyl)-5-(6-methylpyridin-2-yl)-1H-imidazol-4-yl)-[1,2,4]triazolo[1,5-a]pyridine;
3-((4-([1,2,4]triazolo[1,5-a]pyridin-6-yl)-5-(6-methylpyridin-2-yl)-1H-imidazol-2-yl)methoxy)benzonitrile;
3-((4-([1,2,4]triazolo[1,5-a]pyridin-6-yl)-5-(6-methylpyridin-2-yl)-1H-imidazol-2-yl)methoxy)benzamide;
6-(5-(6-methylpyridin-2-yl)-2-(phenylthiomethyl)-1H-imidazol-4-yl)-[1,2,4]triazolo[1,5-a]pyridine;
6-(2-((2-fluorophenylthio)methyl)-5-(6-methylpyridin-2-yl)-1H-imidazol-4-yl)-[1,2,4]triazolo[1,5-a]pyridine, and or pharmaceutically acceptable salts thereof.

5. The method of claim 2, wherein the compound is
N-((4-([1,2,4]triazolo[1,5-a]pyridin-6-yl)-5-(6-methylpyridin-2-yl)-1H-imidazol-2-yl)methyl)aniline;
N-((4-([1,2,4]triazolo[1,5-a]pyridin-6-yl)-5-(6-methylpyridin-2-yl)-1H-imidazol-2-yl)methyl)-2-fluoroaniline;
N-((4-([1,2,4]triazolo[1,5-a]pyridin-6-yl)-5-(6-methylpyridin-2-yl)-1H-imidazol-2-yl)methyl)-3-fluoroaniline;
N-((4-([1,2,4]triazolo[1,5-a]pyridin-6-yl)-5-(6-methylpyridin-2-yl)-1H-imidazol-2-yl)methyl)-4-fluoroaniline;
N-((4-([1,2,4]triazolo[1,5-a]pyridin-6-yl)-5-(6-methylpyridin-2-yl)-1H-imidazol-2-yl)methyl)-2,3-difluoroaniline;
N-((4-([1,2,4]triazolo[1,5-a]pyridin-6-yl)-5-(6-methylpyridin-2-yl)-1H-imidazol-2-yl)methyl)-3,4-difluoroaniline;
N-((4-([1,2,4]triazolo[1,5-a]pyridin-6-yl)-5-(6-methylpyridin-2-yl)-1H-imidazol-2-yl)methyl)-3,5-difluoroaniline;
N-((4-([1,2,4]triazolo[1,5-a]pyridin-6-yl)-5-(6-methylpyridin-2-yl)-1H-imidazol-2-yl)methyl)-2-chloroaniline;
N-((4-([1,2,4]triazolo[1,5-a]pyridin-6-yl)-5-(6-methylpyridin-2-yl)-1H-imidazol-2-yl)methyl)-3-chloroaniline;
N-((4-([1,2,4]triazolo[1,5-a]pyridin-6-yl)-5-(6-methylpyridin-2-yl)-1H-imidazol-2-yl)methyl)-4-chloroaniline;
N-((4-([1,2,4]triazolo[1,5-a]pyridin-6-yl)-5-(6-methylpyridin-2-yl)-1H-imidazol-2-yl)methyl)-2,3-dichloroaniline;
N-((4-([1,2,4]triazolo[1,5-a]pyridin-6-yl)-5-(6-methylpyridin-2-yl)-1H-imidazol-2-yl)methyl)-3,4-dichloroaniline;
N-((4-([1,2,4]triazolo[1,5-a]pyridin-6-yl)-5-(6-methylpyridin-2-yl)-1H-imidazol-2-yl)methyl)-3,5-dichloroaniline;
N-((4-([1,2,4]triazolo[1,5-a]pyridin-6-yl)-5-(6-methylpyridin-2-yl)-1H-imidazol-2-yl)methyl)-2-bromoaniline;
N-((4-([1,2,4]triazolo[1,5-a]pyridin-6-yl)-5-(6-methylpyridin-2-yl)-1H-imidazol-2-yl)methyl)-3-bromoaniline;
N-((4-([1,2,4]triazolo[1,5-a]pyridin-6-yl)-5-(6-methylpyridin-2-yl)-1H-imidazol-2-yl)methyl)-4-bromoaniline;
N-((4-([1,2,4]triazolo[1,5-a]pyridin-6-yl)-5-(6-methylpyridin-2-yl)-1H-imidazol-2-yl)methyl)-2-methylaniline;
N-((4-([1,2,4]triazolo[1,5-a]pyridin-6-yl)-5-(6-methylpyridin-2-yl)-1H-imidazol-2-yl)methyl)-3-methylaniline;
N-((4-([1,2,4]triazolo[1,5-a]pyridin-6-yl)-5-(6-methylpyridin-2-yl)-1H-imidazol-2-yl)methyl)-4-methylaniline;
N-((4-([1,2,4]triazolo[1,5-a]pyridin-6-yl)-5-(6-methylpyridin-2-yl)-1H-imidazol-2-yl)methyl)-2,3-dimethylaniline;
N-((4-([1,2,4]triazolo[1,5-a]pyridin-6-yl)-5-(6-methylpyridin-2-yl)-1H-imidazol-2-yl)methyl)-3,4-dimethylaniline;
N-((4-([1,2,4]triazolo[1,5-a]pyridin-6-yl)-5-(6-methylpyridin-2-yl)-1H-imidazol-2-yl)methyl)-3,5-dimethylaniline;
N-((4-([1,2,4]triazolo[1,5-a]pyridin-6-yl)-5-(6-methylpyridin-2-yl)-1H-imidazol-2-yl)methyl)-2-ethylaniline;
N-((4-([1,2,4]triazolo[1,5-a]pyridin-6-yl)-5-(6-methylpyridin-2-yl)-1H-imidazol-2-yl)methyl)-3-ethylaniline;
N-((4-([1,2,4]triazolo[1,5-a]pyridin-6-yl)-5-(6-methylpyridin-2-yl)-1H-imidazol-2-yl)methyl)-2-isopropylaniline;
N-((4-([1,2,4]triazolo[1,5-a]pyridin-6-yl)-5-(6-methylpyridin-2-yl)-1H-imidazol-2-yl)methyl)-3-isopropylaniline;
N-((4-([1,2,4]triazolo[1,5-a]pyridin-6-yl)-5-(6-methylpyridin-2-yl)-1H-imidazol-2-yl)methyl)-4-isopropylaniline;
N-((4-([1,2,4]triazolo[1,5-a]pyridin-6-yl)-5-(6-methylpyridin-2-yl)-1H-imidazol-2-yl)methyl)-2-vinylaniline;
N-((4-([1,2,4]triazolo[1,5-a]pyridin-6-yl)-5-(6-methylpyridin-2-yl)-1H-imidazol-2-yl)methyl)-3-vinylaniline;
N-((4-([1,2,4]triazlo[1,5-a]pyridin-6-yl)-5-(6-methylpyridin-2-yl)-1H-imidazol-2-yl)methyl)-4-vinylaniline;
N-((4-([1,2,4]triazolo[1,5-a]pyridin-6-yl)-5-(6-methylpyridin-2-yl)-1H-imidazol-2-yl)methyl)-3-ethynylaniline;
N-((4-([1,2,4]triazolo[1,5-a]pyridin-6-yl)-5-(6-methylpyridin-2-yl)-1H-imidazol-2-yl)methyl)-2-methoxyaniline;
N-((4-([1,2,4]triazolo[1,5-a]pyridin-6-yl)-5-(6-methylpyridin-2-yl)-1H-imidazol-2-yl)methyl)-3-methoxyaniline;
N-((4-([1,2,4]triazolo[1,5-a]pyridin-6-yl)-5-(6-methylpyridin-2-yl)-1H-imidazol-2-yl)methyl)-4-methoxyaniline;
N-((4-([1,2,4]triazolo[1,5-a]pyridin-6-yl)-5-(6-methylpyridin-2-yl)-1H-imidazol-2-yl)methyl)-2,3-dimethoxyaniline;
N-((4-([1,2,4]triazolo[1,5-a]pyridin-6-yl)-5-(6-methylpyridin-2-yl)-1H-imidazol-2-yl)methyl)-3,4-dimethoxyaniline;
N-((4-([1,2,4]triazolo[1,5-a]pyridin-6-yl)-5-(6-methylpyridin-2-yl)-1H-imidazol-2-yl)methyl)-3,5-dimethoxyaniline;

N-((4-([1,2,4]triazolo[1,5-a]pyridin-6-yl)-5-(6-methylpyridin-2-yl)-1H-imidazol-2-yl)methyl)-2-(methoxymethyl)aniline;
N-((4-([1,2,4]triazolo[1,5-a]pyridin-6-yl)-5-(6-methylpyridin-2-yl)-1H-imidazol-2-yl)methyl)-3-(methoxymethyl)aniline;
N-((4-([1,2,4]triazolo[1,5-a]pyridin-6-yl)-5-(6-methylpyridin-2-yl)-1H-imidazol-2-yl)methyl)-4-(methoxymethyl)aniline;
N-((4-([1,2,4]triazolo[1,5-a]pyridin-6-yl)-5-(6-methylpyridin-2-yl)-1H-imidazol-2-yl)methyl)-2-(trifluoromethoxy)aniline;
N-((4-([1,2,4]triazolo[1,5-a]pyridin-6-yl)-5-(6-methylpyridin-2-yl)-1H-imidazol-2-yl)methyl)-3-(trifluoromethoxy)aniline;
N-((4-([1,2,4]triazolo[1,5-a]pyridin-6-yl)-5-(6-methylpyridin-2-yl)-1H-imidazol-2-yl)methyl)-4-(trifluoromethoxy)aniline;
N-((4-([1,2,4]triazolo[1,5-a]pyridin-6-yl)-5-(6-methylpyridin-2-yl)-1H-imidazol-2-yl)methyl)-2-(methylthio)aniline;
N-((4-([1,2,4]triazolo[1,5-a]pyridin-6-yl)-5-(6-methylpyridin-2-yl)-1H-imidazol-2-yl)methyl)-3-(methylthio)aniline;
N-((4-([1,2,4]triazolo[1,5-a]pyridin-6-yl)-5-(6-methylpyridin-2-yl)-1H-imidazol-2-yl)methyl)-4-(methylthio)aniline;
2-((4-([1,2,4]triazolo[1,5-a]pyridin-6-yl)-5-(6-methylpyridin-2-yl)-1H-imidazol-2-yl)methylamino)benzonitrile;
3-((4-([1,2,4]triazolo[1,5-a]pyridin-6-yl)-5-(6-methylpyridin-2-yl)-1H-imidazol-2-yl)methylamino)benzonitrile;
4-((4-([1,2,4]triazolo[1,5-a]pyridin-6-yl)-5-(6-methylpyridin-2-yl)-1H-imidazol-2-yl)methylamino)benzonitrile;
3-((4-([1,2,4]triazolo[1,5-a]pyridin-6-yl)-5-(6-methylpyridin-2-yl)-1H-imidazol-2-yl)methylamino)phthalonitrile;
2-((4-([1,2,4]triazolo[1,5-a]pyridin-6-yl)-5-(6-methylpyridin-2-yl)-1H-imidazol-2-yl)methylamino)benzamide;
3-((4-([1,2,4]triazolo[1,5-a]pyridin-6-yl)-5-(6-methylpyridin-2-yl)-1H-imidazol-2-yl)methylamino)benzamide;
4-((4-([1,2,4]triazolo[1,5-a]pyridin-6-yl)-5-(6-methylpyridin-2-yl)-1H-imidazol-2-yl)methylamino)benzamide;
2-(3-((4-([1,2,4]triazolo[1,5-a]pyridin-6-yl)-5-(6-methylpyridin-2-yl)-1H-imidazol-2-yl)methylamino)phenyl)acetonitrile;
2-(4-((4-([1,2,4]triazolo[1,5-a]pyridin-6-yl)-5-(6-methylpyridin-2-yl)-1H-imidazol-2-yl)methylamino)phenyl)acetonitrile;
1-(3-((4-([1,2,4]triazolo[1,5-a]pyridin-6-yl)-5-(6-methylpyridin-2-yl)-1H-imidazol-2-yl)methylamino)phenyl)ethanone;
1-(4-((4-([1,2,4]triazolo[1,5-a]pyridin-6-yl)-5-(6-methylpyridin-2-yl)-1H-imidazol-2-yl)methylamino)phenyl)ethanone;
Methyl 3-((4-([1,2,4]triazolo[1,5-a]pyridin-6-yl)-5-(6-methylpyridin-2-yl)-1H-imidazol-2-yl)methylamino)benzoate;
Methyl 4-((4-([1,2,4]triazolo[1,5-a]pyridin-6-yl)-5-(6-methylpyridin-2-yl)-1H-imidazol-2-yl)methylamino)benzoate;
N-(2-((4-([1,2,4]triazolo[1,5-a]pyridin-6-yl)-5-(6-methylpyridin-2-yl)-1H-imidazol-2-yl)methylamino)phenyl)acetamide;
N-(3-((4-([1,2,4]triazolo[1,5-a]pyridin-6-yl)-5-(6-methylpyridin-2-yl)-1H-imidazol-2-yl)methylamino)phenyl)acetamide;
N-(4-((4-([1,2,4]triazolo[1,5-a]pyridin-6-yl)-5-(6-methylpyridin-2-yl)-1H-imidazol-2-yl)methylamino)phenyl)acetamide;
N-(2-((4-([1,2,4]triazolo[1,5-a]pyridin-6-yl)-5-(6-methylpyridin-2-yl)-1H-imidazol-2-yl)methylamino)phenyl)methanesulfonamide;
N-(3-((4-([1,2,4]triazolo[1,5-a]pyridin-6-yl)-5-(6-methylpyridin-2-yl)-1H-imidazol-2-yl)methylamino)phenyl)methanesulfonamide;
N-(4-((4-([1,2,4]triazolo[1,5-a]pyridin-6-yl)-5-(6-methylpyridin-2-yl)-1H-imidazol-2-yl)methylamino)phenyl)methanesulfonamide;
$N^1$-((4-([1,2,4]triazolo[1,5-a]pyridin-6-yl)-5-(6-methylpyridin-2-yl)-1H-imidazol-2-yl)methyl)-$N^2$,$N^2$-dimethylbenzene-1,2-diamine;
$N^1$-((4-([1,2,4]triazolo[1,5-a]pyridin-6-yl)-5-(6-methylpyridin-2-yl)-1H-imidazol-2-yl)methyl)-$N^3$,$N^3$-dimethylbenzene-1,3-diamine;
N-((4-([1,2,4]triazolo[1,5-a]pyridin-6-yl)-5-(6-methylpyridin-2-yl)-1H-imidazol-2-yl)methyl)-2-(pyrrolidin-1-yl)aniline;
N-((4-([1,2,4]triazolo[1,5-a]pyridin-6-yl)-5-(6-methylpyridin-2-yl)-1H-imidazol-2-yl)methyl)-2-morpholinoaniline;
N-((4-([1,2,4]triazolo[1,5-a]pyridin-6-yl)-5-(6-methylpyridin-2-yl)-1H-imidazol-2-yl)methyl)-3-morpholinoaniline;
$N^3$-((4-([1,2,4]triazolo[1,5-a]pyridin-6-yl)-5-(6-methylpyridin-2-yl)-1H-imidazol-2-yl)methyl)-4-fluoro-N',N'-dimethylbenzene-1,3-diamine;
3-((4-([1,2,4]triazolo[1,5-a]pyridin-6-yl)-5-(6-methylpyridin-2-yl)-1H-imidazol-2-yl)methylamino)-5-(dimethylamino)benzonitrile;
3-((4-([1,2,4]triazolo[1,5-a]pyridin-6-yl)-5-(6-methylpyridin-2-yl)-1H-imidazol-2-yl)methylamino)-4-(dimethylamino)benzonitrile;
N-((4-([1,2,4]triazolo[1,5-a]pyridin-6-yl)-5-(6-methylpyridin-2-yl)-1H-imidazol-2-yl)methyl)-2-((dimethylamino)methyl)aniline;
N-((4-([1,2,4]triazolo[1,5-a]pyridin-6-yl)-5-(6-methylpyridin-2-yl)-1H-imidazol-2-yl)methyl)-3-((dimethylamino)methyl)aniline;
N-((4-([1,2,4]triazolo[1,5-a]pyridin-6-yl)-5-(6-methylpyridin-2-yl)-1H-imidazol-2-yl)methyl)-2-(pyrrolidin-1-ylmethyl)aniline;
N-((4-([1,2,4]triazolo[1,5-a]pyridin-6-yl)-5-(6-methylpyridin-2-yl)-1H-imidazol-2-yl)methyl)-3-(pyrrolidin-1-ylmethyl)aniline;
N-((4-([1,2,4]triazolo[1,5-a]pyridin-6-yl)-5-(6-methylpyridin-2-yl)-1H-imidazol-2-yl)methyl)-2-(morpholinomethyl)aniline;
N-((4-([1,2,4]triazolo[1,5-a]pyridin-6-yl)-5-(6-methylpyridin-2-yl)-1H-imidazol-2-yl)methyl)-3-(morpholinomethyl)aniline;
N-((4-([1,2,4]triazolo[1,5-a]pyridin-6-yl)-5-(6-methylpyridin-2-yl)-1H-imidazol-2-yl)methyl)-5-((dimethylamino)methyl)-2-fluoroaniline;
N-((4-([1,2,4]triazolo[1,5-a]pyridin-6-yl)-5-(6-methylpyridin-2-yl)-1H-imidazol-2-yl)methyl)-3-((dimethylamino)methyl)-2-fluoroaniline;

N-((4-([1,2,4]triazolo[1,5-a]pyridin-6-yl)-5-(6-methylpyridin-2-yl)-1H-imidazol-2-yl)methyl)-2-fluoro-3-(pyrrolidin-1-ylmethyl)aniline;
N-((4-([1,2,4]triazolo[1,5-a]pyridin-6-yl)-5-(6-methylpyridin-2-yl)-1H-imidazol-2-yl)methyl)-2-fluoro-3-(morpholinomethyl)aniline;
3-((4-([1,2,4]triazolo[1,5-a]pyridin-6-yl)-5-(6-methylpyridin-2-yl)-1H-imidazol-2-yl)methylamino)-4-((dimethylamino)methyl)benzonitrile;
3-((4-([1,2,4]triazolo[1,5-a]pyridin-6-yl)-5-(6-methylpyridin-2-yl)-1H-imidazol-2-yl)methylamino)-2-((dimethylamino)methyl)benzonitrile;
3-((4-([1,2,4]triazolo[1,5-a]pyridin-6-yl)-5-(6-methylpyridin-2-yl)-1H-imidazol-2-yl)methylamino)-5-((dimethylamino)methyl)benzonitrile;
3-((4-([1,2,4]triazolo[1,5-a]pyridin-6-yl)-5-(6-methylpyridin-2-yl)-1H-imidazol-2-yl)methylamino)-4-(pyrrolidin-1-ylmethyl)benzonitrile;
3-((4-([1,2,4]triazolo[1,5-a]pyridin-6-yl)-5-(6-methylpyridin-2-yl)-1H-imidazol-2-yl)methylamino)-2-(pyrrolidin-1-ylmethyl)benzonitrile;
3-((4-([1,2,4]triazolo[1,5-a]pyridin-6-yl)-5-(6-methylpyridin-2-yl)-1H-imidazol-2-yl)methylamino)-5-(pyrrolidin-1-ylmethyl)benzonitrile;
3-((4-([1,2,4]triazolo[1,5-a]pyridin-6-yl)-5-(6-methylpyridin-2-yl)-1H-imidazol-2-yl)methylamino)-4-(morpholinomethyl)benzonitrile;
3-((4-([1,2,4]triazlo[1,5-a]pyridin-6-yl)-5-(6-methylpyridin-2-yl)-1H-imidazol-2-yl)methylamino)-2-(morpholinomethyl)benzonitrile;
3-((4-([1,2,4]triazolo[1,5-a]pyridin-6-yl)-5-(6-methylpyridin-2-yl)-1H-imidazol-2-yl)methylamino)-5-(morpholinomethyl)benzonitrile;
N-((4-([1,2,4]triazolo[1,5-a]pyridin-6-yl)-5-(6-methylpyridin-2-yl)-1H-imidazol-2-yl)methyl)-2-(2-(dimethylamino)ethylaniline;
N-((4-([1,2,4]triazolo[1,5-a]pyridin-6-yl)-5-(6-methylpyridin-2-yl)-1H-imidazol-2-yl)methyl)-3-(2-(dimethylamino)ethylaniline;
3-((4-([1,2,4]triazolo[1,5-a]pyridin-6-yl)-5-(6-ethylpyridin-2-yl)-1H-imidazol-2-yl)methylamino)benzonitrile;
N-((4-([1,2,4]triazolo[1,5-a]pyridin-6-yl)-5-(6-ethylpyridin-2-yl)-1H-imidazol-2-yl)methyl)-2-fluoroaniline;
N-((4-([1,2,4]triazolo[1,5-a]pyridin-6-yl)-5-(6-methylpyridin-2-yl)-1H-imidazol-2-yl)methyl)-2-fluoro-N-methylaniline;
3-((4-([1,2,4]triazolo[1,5-a]pyridin-6-yl)-5-(6-methylpyridin-2-yl)-1H-imidazol-2-yl)methyl)(methyl)amino)benzonitrile;
3-((4-([1,2,4]triazolo[1,5-a]pyridin-6-yl)-5-(6-methylpyridin-2-yl)-1H-imidazol-2-yl)methyl)(methyl)amino)benzamide;
6-(5-(6-methylpyridin-2-yl)-2-(phenoxymethyl)-1H-imidazol-4-yl)-[1,2,4]triazolo[1,5-a]pyridine;
6-(2-((2-fluorophenoxy)methyl)-5-(6-methylpyridin-2-yl)-1H-imidazol-4-yl)-[1,2,4]triazolo[1,5-a]pyridine;
3-((4-([1,2,4]triazolo[1,5-a]pyridin-6-yl)-5-(6-methylpyridin-2-yl)-1H-imidazol-2-yl)methoxy)benzonitrile;
3-((4-([1,2,4]triazolo[1,5-a]pyridin-6-yl)-5-(6-methylpyridin-2-yl)-1H-imidazol-2-yl)methoxy)benzamide;
6-(5-(6-methylpyridin-2-yl)-2-(phenylthiomethyl)-1H-imidazol-4-yl)-[1,2,4]triazolo[1,5-a]pyridine;
6-(2-((2-fluorophenylthio)methyl)-5-(6-methylpyridin-2-yl)-1H-imidazol-4-yl)-[1,2,4]triazolo[1,5-a]pyridine, or pharmaceutically acceptable salts thereof.

6. The method of claim 3, wherein the compound is
N-((4-([1,2,4]triazolo[1,5-a]pyridin-6-yl)-5-(6-methylpyridin-2-yl)-1H-imidazol-2-yl)methyl)aniline;
N-((4-([1,2,4]triazolo[1,5-a]pyridin-6-yl)-5-(6-methylpyridin-2-yl)-1H-imidazol-2-yl)methyl)-2-fluoroaniline;
N-((4-([1,2,4]triazolo[1,5-a]pyridin-6-yl)-5-(6-methylpyridin-2-yl)-1H-imidazol-2-yl)methyl)-3-fluoroaniline;
N-((4-([1,2,4]triazolo[1,5-a]pyridin-6-yl)-5-(6-methylpyridin-2-yl)-1H-imidazol-2-yl)methyl)-4-fluoroaniline;
N-((4-([1,2,4]triazolo[1,5-a]pyridin-6-yl)-5-(6-methylpyridin-2-yl)-1H-imidazol-2-yl)methyl)-2,3-difluoroaniline;
N-((4-([1,2,4]triazolo[1,5-a]pyridin-6-yl)-5-(6-methylpyridin-2-yl)-1H-imidazol-2-yl)methyl)-3,4-difluoroaniline;
N-((4-([1,2,4]triazolo[1,5-a]pyridin-6-yl)-5-(6-methylpyridin-2-yl)-1H-imidazol-2-yl)methyl)-3,5-difluoroaniline;
N-((4-([1,2,4]triazolo[1,5-a]pyridin-6-yl)-5-(6-methylpyridin-2-yl)-1H-imidazol-2-yl)methyl)-2-chloroaniline;
N-((4-([1,2,4]triazolo[1,5-a]pyridin-6-yl)-5-(6-methylpyridin-2-yl)-1H-imidazol-2-yl)methyl)-3-chloroaniline;
N-((4-([1,2,4]triazolo[1,5-a]pyridin-6-yl)-5-(6-methylpyridin-2-yl)-1H-imidazol-2-yl)methyl)-4-chloroaniline;
N-((4-([1,2,4]triazolo[1,5-a]pyridin-6-yl)-5-(6-methylpyridin-2-yl)-1H-imidazol-2-yl)methyl)-2,3-dichloroaniline;
N-((4-([1,2,4]triazolo[1,5-a]pyridin-6-yl)-5-(6-methylpyridin-2-yl)-1H-imidazol-2-yl)methyl)-3,4-dichloroaniline;
N-((4-([1,2,4]triazolo[1,5-a]pyridin-6-yl)-5-(6-methylpyridin-2-yl)-1H-imidazol-2-yl)methyl)-3,5-dichloroaniline;
N-((4-([1,2,4]triazolo[1,5-a]pyridin-6-yl)-5-(6-methylpyridin-2-yl)-1H-imidazol-2-yl)methyl)-2-bromoaniline;
N-((4-([1,2,4]triazolo[1,5-a]pyridin-6-yl)-5-(6-methylpyridin-2-yl)-1H-imidazol-2-yl)methyl)-3-bromoaniline;
N-((4-([1,2,4]triazolo[1,5-a]pyridin-6-yl)-5-(6-methylpyridin-2-yl)-1H-imidazol-2-yl)methyl)-4-bromoaniline;
N-((4-([1,2,4]triazolo[1,5-a]pyridin-6-yl)-5-(6-methylpyridin-2-yl)-1H-imidazol-2-yl)methyl)-2-methylaniline;
N-((4-([1,2,4]triazolo[1,5-a]pyridin-6-yl)-5-(6-methylpyridin-2-yl)-1H-imidazol-2-yl)methyl)-3-methylaniline;
N-((4-([1,2,4]triazolo[1,5-a]pyridin-6-yl)-5-(6-methylpyridin-2-yl)-1H-imidazol-2-yl)methyl)-4-methylaniline;
N-((4-([1,2,4]triazolo[1,5-a]pyridin-6-yl)-5-(6-methylpyridin-2-yl)-1H-imidazol-2-yl)methyl)-2,3-dimethylaniline;
N-((4-([1,2,4]triazolo[1,5-a]pyridin-6-yl)-5-(6-methylpyridin-2-yl)-1H-imidazol-2-yl)methyl)-3,4-dimethylaniline;
N-((4-([1,2,4]triazolo[1,5-a]pyridin-6-yl)-5-(6-methylpyridin-2-yl)-1H-imidazol-2-yl)methyl)-3,5-dimethylaniline;
N-((4-([1,2,4]triazolo[1,5-a]pyridin-6-yl)-5-(6-methylpyridin-2-yl)-1H-imidazol-2-yl)methyl)-2-ethylaniline;
N-((4-([1,2,4]triazolo[1,5-a]pyridin-6-yl)-5-(6-methylpyridin-2-yl)-1H-imidazol-2-yl)methyl)-3-ethylaniline;
N-((4-([1,2,4]triazolo[1,5-a]pyridin-6-yl)-5-(6-methylpyridin-2-yl)-1H-imidazol-2-yl)methyl)-2-isopropylaniline;
N-((4-([1,2,4]triazolo[1,5-a]pyridin-6-yl)-5-(6-methylpyridin-2-yl)-1H-imidazol-2-yl)methyl)-3-isopropylaniline;
N-((4-([1,2,4]triazolo[1,5-a]pyridin-6-yl)-5-(6-methylpyridin-2-yl)-1H-imidazol-2-yl)methyl)-4-isopropylaniline;

N-((4-([1,2,4]triazolo[1,5-a]pyridin-6-yl)-5-(6-methylpyridin-2-yl)-1H-imidazol-2-yl)methyl)-2-vinylaniline;
N-((4-([1,2,4]triazolo[1,5-a]pyridin-6-yl)-5-(6-methylpyridin-2-yl)-1H-imidazol-2-yl)methyl)-3-vinylaniline;
N-((4-([1,2,4]triazolo[1,5-a]pyridin-6-yl)-5-(6-methylpyridin-2-yl)-1H-imidazol-2-yl)methyl)-4-vinylaniline;
N-((4-([1,2,4]triazolo[1,5-a]pyridin-6-yl)-5-(6-methylpyridin-2-yl)-1H-imidazol-2-yl)methyl)-3-ethynylaniline;
N-((4-([1,2,4]triazolo[1,5-a]pyridin-6-yl)-5-(6-methylpyridin-2-yl)-1H-imidazol-2-yl)methyl)-2-methoxyaniline;
N-((4-([1,2,4]triazolo[1,5-a]pyridin-6-yl)-5-(6-methylpyridin-2-yl)-1H-imidazol-2-yl)methyl)-3-methoxyaniline;
N-((4-([1,2,4]triazolo[1,5-a]pyridin-6-yl)-5-(6-methylpyridin-2-yl)-1H-imidazol-2-yl)methyl)-4-methoxyaniline;
N-((4-([1,2,4]triazolo[1,5-a]pyridin-6-yl)-5-(6-methylpyridin-2-yl)-1H-imidazol-2-yl)methyl)-2,3-dimethoxyaniline;
N-((4-([1,2,4]triazolo[1,5-a]pyridin-6-yl)-5-(6-methylpyridin-2-yl)-1H-imidazol-2-yl)methyl)-3,4-dimethoxyaniline;
N-((4-([1,2,4]triazolo[1,5-a]pyridin-6-yl)-5-(6-methylpyridin-2-yl)-1H-imidazol-2-yl)methyl)-3,5-dimethoxyaniline;
N-((4-([1,2,4]triazolo[1,5-a]pyridin-6-yl)-5-(6-methylpyridin-2-yl)-1H-imidazol-2-yl)methyl)-2-(methoxymethyl)aniline;
N-((4-([1,2,4]triazolo[1,5-a]pyridin-6-yl)-5-(6-methylpyridin-2-yl)-1H-imidazol-2-yl)methyl)-3-(methoxymethyl)aniline;
N-((4-([1,2,4]triazolo[1,5-a]pyridin-6-yl)-5-(6-methylpyridin-2-yl)-1H-imidazol-2-yl)methyl)-4-(methoxymethyl)aniline;
N-((4-([1,2,4]triazolo[1,5-a]pyridin-6-yl)-5-(6-methylpyridin-2-yl)-1H-imidazol-2-yl)methyl)-2-(trifluoromethoxy)aniline;
N-((4-([1,2,4]triazolo[1,5-a]pyridin-6-yl)-5-(6-methylpyridin-2-yl)-1H-imidazol-2-yl)methyl)-3-(trifluoromethoxy)aniline;
N-((4-([1,2,4]triazolo[1,5-a]pyridin-6-yl)-5-(6-methylpyridin-2-yl)-1H-imidazol-2-yl)methyl)-4-(trifluoromethoxy)aniline;
N-((4-([1,2,4]triazolo[1,5-a]pyridin-6-yl)-5-(6-methylpyridin-2-yl)-1H-imidazol-2-yl)methyl)-2-(methylthio)aniline;
N-((4-([1,2,4]triazolo[1,5-a]pyridin-6-yl)-5-(6-methylpyridin-2-yl)-1H-imidazol-2-yl)methyl)-3-(methylthio)aniline;
N-((4-([1,2,4]triazolo[1,5-a]pyridin-6-yl)-5-(6-methylpyridin-2-yl)-1H-imidazol-2-yl)methyl)-4-(methylthio)aniline;
2-((4-([1,2,4]triazolo[1,5-a]pyridin-6-yl)-5-(6-methylpyridin-2-yl)-1H-imidazol-2-yl)methylamino)benzonitrile;
3-((4-([1,2,4]triazolo[1,5-a]pyridin-6-yl)-5-(6-methylpyridin-2-yl)-1H-imidazol-2-yl)methylamino)benzonitrile;
4-((4-([1,2,4]triazolo[1,5-a]pyridin-6-yl)-5-(6-methylpyridin-2-yl)-1H-imidazol-2-yl)methylamino)benzonitrile;
3-((4-([1,2,4]triazolo[1,5-a]pyridin-6-yl)-5-(6-methylpyridin-2-yl)-1H-imidazol-2-yl)methylamino)phthalonitrile;
2-((4-([1,2,4]triazolo[1,5-a]pyridin-6-yl)-5-(6-methylpyridin-2-yl)-1H-imidazol-2-yl)methylamino)benzamide;
3-((4-([1,2,4]triazolo[1,5-a]pyridin-6-yl)-5-(6-methylpyridin-2-yl)-1H-imidazol-2-yl)methylamino)benzamide;
4-((4-([1,2,4]triazolo[1,5-a]pyridin-6-yl)-5-(6-methylpyridin-2-yl)-1H-imidazol-2-yl)methylamino)benzamide;
2-(3-((4-([1,2,4]triazolo[1,5-a]pyridin-6-yl)-5-(6-methylpyridin-2-yl)-1H-imidazol-2-yl)methylamino)phenyl)acetonitrile;
2-(4-((4-([1,2,4]triazolo[1,5-a]pyridin-6-yl)-5-(6-methylpyridin-2-yl)-1H-imidazol-2-yl)methylamino)phenyl)acetonitrile;
1-(3-((4-([1,2,4]triazolo[1,5-a]pyridin-6-yl)-5-(6-methylpyridin-2-yl)-1H-imidazol-2-yl)methylamino)phenyl)ethanone;
1-(4-((4-([1,2,4]triazolo[1,5-a]pyridin-6-yl)-5-(6-methylpyridin-2-yl)-1H-imidazol-2-yl)methylamino)phenyl)ethanone;
Methyl 3-((4-([1,2,4]triazolo[1,5-a]pyridin-6-yl)-5-(6-methylpyridin-2-yl)-1H-imidazol-2-yl)methylamino)benzoate;
Methyl 4-((4-([1,2,4]triazolo[1,5-a]pyridin-6-yl)-5-(6-methylpyridin-2-yl)-1H-imidazol-2-yl)methylamino)benzoate;
N-(2-((4-([1,2,4]triazolo[1,5-a]pyridin-6-yl)-5-(6-methylpyridin-2-yl)-1H-imidazol-2-yl)methylamino)phenyl)acetamide;
N-(3-((4-([1,2,4]triazolo[15-a]pyridin-6-yl)-5-(6-methylpyridin-2-yl)-1H-imidazol-2-yl)methylamino)phenyl)acetamide;
N-(4-((4-([1,2,4]triazolo[1,5-a]pyridin-6-yl)-5-(6-methylpyridin-2-yl)-1H-imidazol-2-yl)methylamino)phenyl)acetamide;
N-(2-((4-([1,2,4]triazolo[1,5-a]pyridin-6-yl)-5-(6-methylpyridin-2-yl)-1H-imidazol-2-yl)methylamino)phenyl)methanesulfonamide;
N-(3-((4-([1,2,4]triazolo[1,5-a]pyridin-6-yl)-5-(6-methylpyridin-2-yl)-1H-imidazol-2-yl)methylamino)phenyl)methanesulfonamide;
N-(4-((4-([1,2,4]triazolo[1,5-a]pyridin-6-yl)-5-(6-methylpyridin-2-yl)-1H-imidazol-2-yl)methylamino)phenyl)methanesulfonamide;
$N^1$-((4-([1,2,4]triazolo[1,5-a]pyridin-6-yl)-5-(6-methylpyridin-2-yl)-1H-imidazol-2-yl)methyl)-$N^2,N^2$-dimethylbenzene-1,2-diamine;
$N^1$-((4-([1,2,4]triazolo[1,5-a]pyridin-6-yl)-5-(6-methylpyridin-2-yl)-1H-imidazol-2-yl)methyl)-$N^3,N^3$-dimethylbenzene-1,3-diamine;
N-((4-([1,2,4]triazolo[1,5-a]pyridin-6-yl)-5-(6-methylpyridin-2-yl)-1H-imidazol-2-yl)methyl)-2-(pyrrolidin-1-yl)aniline;
N-((4-([1,2,4]triazolo[1,5-a]pyridin-6-yl)-5-(6-methylpyridin-2-yl)-1H-imidazol-2-yl)methyl)-2-morpholinoaniline;
N-((4-([1,2,4]triazolo[1,5-a]pyridin-6-yl)-5-(6-methylpyridin-2-yl)-1H-imidazol-2-yl)methyl)-3-morpholinoaniline;
$N^3$-((4-([1,2,4]triazolo[1,5-a]pyridin-6-yl)-5-(6-methylpyridin-2-yl)-1H-imidazol-2-yl)methyl)-4-fluoro-N,N'-dimethylbenzene-1,3-diamine;
3-((4-([1,2,4]triazolo[1,5-a]pyridin-6-yl)-5-(6-methylpyridin-2-yl)-1H-imidazol-2-yl)methylamino)-5-(dimethylamino)benzonitrile;

3-((4-([1,2,4]triazolo[1,5-a]pyridin-6-yl)-5-(6-methylpyridin-2-yl)-1H-imidazol-2-yl)methylamino)-4-(dimethylamino)benzonitrile;
N-((4-([1,2,4]triazolo[1,5-a]pyridin-6-yl)-5-(6-methylpyridin-2-yl)-1H-imidazol-2-yl)methyl)-2-((dimethylamino)methyl)aniline;
N-((4-([1,2,4]triazolo[1,5-a]pyridin-6-yl)-5-(6-methylpyridin-2-yl)-1H-imidazol-2-yl)methyl)-3-((dimethylamino)methyl)aniline;
N-((4-([1,2,4]triazolo[1,5-a]pyridin-6-yl)-5-(6-methylpyridin-2-yl)-1H-imidazol-2-yl)methyl)-2-(pyrrolidin-1-ylmethyl)aniline;
N-((4-([1,2,4]triazolo[1,5-a]pyridin-6-yl)-5-(6-methylpyridin-2-yl)-H-imidazol-2-yl)methyl)-3-(pyrrolidin-1-ylmethyl)aniline;
N-((4-([1,2,4]triazolo[1,5-a]pyridin-6-yl)-5-(6-methylpyridin-2-yl)-1H-imidazol-2-yl)methyl)-2-(morpholinomethyl)aniline;
N-((4-([1,2,4]triazolo[1,5-a]pyridin-6-yl)-5-(6-methylpyridin-2-yl)-1H-imidazol-2-yl)methyl)-3-(morpholinomethyl)aniline;
N-((4-([1,2,4]triazolo[1,5-a]pyridin-6-yl)-5-(6-methylpyridin-2-yl)-1H-imidazol-2-yl)methyl)-5-((dimethylamino)methyl)-2-fluoroaniline;
N-((4-([1,2,4]triazolo[1,5-a]pyridin-6-yl)-5-(6-methylpyridin-2-yl)-1H-imidazol-2-yl)methyl)-3-((dimethylamino)methyl)-2-fluoroaniline;
N-((4-([1,2,4]triazolo[1,5-a]pyridin-6-yl)-5-(6-methylpyridin-2-yl)-1H-imidazol-2-yl)methyl)-2-fluoro-3-(pyrrolidin-1-ylmethyl)aniline;
N-((4-([1,2,4]triazolo[1,5-a]pyridin-6-yl)-5-(6-methylpyridin-2-yl)-1H-imidazol-2-yl)methyl)-2-fluoro-3-(morpholinomethyl)aniline;
3-((4-([1,2,4]triazolo[1,5-a]pyridin-6-yl)-5-(6-methylpyridin-2-yl)-1H-imidazol-2-yl)methylamino)-4-((dimethylamino)methyl)benzonitrile;
3-((4-([1,2,4]triazolo[1,5-a]pyridin-6-yl)-5-(6-methylpyridin-2-yl)-1H-imidazol-2-yl)methylamino)-2-((dimethylamino)methyl)benzonitrile;
3-((4-([1,2,4]triazolo[1,5-a]pyridin-6-yl)-5-(6-methylpyridin-2-yl)-1H-imidazol-2-yl)methylamino)-5-((dimethylamino)methyl)benzonitrile;
3-((4-([1,2,4]triazolo[1,5-a]pyridin-6-yl)-5-(6-methylpyridin-2-yl)-1H-imidazol-2-yl)methylamino)-4-(pyrrolidin-1-ylmethyl)benzonitrile;
3-((4-([1,2,4]triazolo[1,5-a]pyridin-6-yl)-5-(6-methylpyridin-2-yl)-1H-imidazol-2-yl)methylamino)-2-(pyrrolidin-1-ylmethyl)benzonitrile;
3-((4-([1,2,4]triazolo[1,5-a]pyridin-6-yl)-5-(6-methylpyridin-2-yl)-1H-imidazol-2-yl)methylamino)-5-(pyrrolidin-1-ylmethyl)benzonitrile;
3-((4-([1,2,4]triazolo[1,5-a]pyridin-6-yl)-5-(6-methylpyridin-2-yl)-1H-imidazol-2-yl)methylamino)-4-(morpholinomethyl)benzonitrile;
3-((4-([1,2,4]triazolo[1,5-a]pyridin-6-yl)-5-(6-methylpyridin-2-yl)-1H-imidazol-2-yl)methylamino)-2-(morpholinomethyl)benzonitrile;
3-((4-([1,2,4]triazolo[1,5-a]pyridin-6-yl)-5-(6-methylpyridin-2-yl)-1H-imidazol-2-yl)methylamino)-5-(morpholinomethyl)benzonitrile;
N-((4-([1,2,4]triazolo[1,5-a]pyridin-6-yl)-5-(6-methylpyridin-2-yl)-1H-imidazol-2-yl)methyl)-2-(2-(dimethylamino)ethylaniline;
N-((4-([1,2,4]triazolo[1,5-a]pyridin-6-yl)-5-(6-methylpyridin-2-yl)-1H-imidazol-2-yl)methyl)-3-(2-(dimethylamino)ethylaniline;
3-((4-([1,2,4]triazolo[1,5-a]pyridin-6-yl)-5-(6-ethylpyridin-2-yl)-1H-imidazol-2-yl)methylamino)benzonitrile;
N-((4-([1,2,4]triazolo[1,5-a]pyridin-6-yl)-5-(6-ethylpyridin-2-yl)-1H-imidazol-2-yl)methyl)-2-fluoroaniline;
N-((4-([1,2,4]triazolo[1,5-a]pyridin-6-yl)-5-(6-methylpyridin-2-yl)-1H-imidazol-2-yl)methyl)-2-fluoro-N-methylaniline;
3-((4-([1,2,4]triazolo[1,5-a]pyridin-6-yl)-5-(6-methylpyridin-2-yl)-1H-imidazol-2-yl)methyl)(methyl)amino)benzonitrile;
3-((4-([1,2,4]triazolo[1,5-a]pyridin-6-yl)-5-(6-methylpyridin-2-yl)-1H-imidazol-2-yl)methyl)(methyl)amino)benzamide;
6-(5-(6-methylpyridin-2-yl)-2-(phenoxymethyl)-1H-imidazol-4-yl)-[1,2,4]triazolo[1,5-a]pyridine;
6-(2-((2-fluorophenoxy)methyl)-5-(6-methylpyridin-2-yl)-1H-imidazol-4-yl)-[1,2,4]triazolo[1,5-a]pyridine;
3-((4-([1,2,4]triazolo[1,5-a]pyridin-6-yl)-5-(6-methylpyridin-2-yl)-1H-imidazol-2-yl)methoxy)benzonitrile;
3-((4-([1,2,4]triazolo[1,5-a]pyridin-6-yl)-5-(6-methylpyridin-2-yl)-1H-imidazol-2-yl)methoxy)benzamide;
6-(5-(6-methylpyridin-2-yl)-2-(phenylthiomethyl)-1H-imidazol-4-yl)-[1,2,4]triazolo[1,5-a]pyridine;
6-(2-((2-fluorophenylthio)methyl)-5-(6-methylpyridin-2-yl)-1H-imidazol-4-yl)-[1,2,4]triazolo[1,5-a]pyridine,
or pharmaceutically acceptable salts thereof.

\* \* \* \* \*